(12) United States Patent
Domb et al.

(10) Patent No.: US 10,137,225 B2
(45) Date of Patent: Nov. 27, 2018

(54) CRYSTALLINE COATING AND RELEASE OF BIOACTIVE AGENTS

(71) Applicant: Yissum Research Development Company of the Hebrew University of Jerusalem Ltd., Jerusalem (IL)

(72) Inventors: Abraham Jacob Domb, Jerusalem (IL); Shady Farah, Kfar-Yassif (IL)

(73) Assignee: Yissum Research Development Company of the Hebrew University of Jerusalem Ltd., Jerusalem (IL)

( * ) Notice: Subject to any disclaimer, the term of this patent is extended or adjusted under 35 U.S.C. 154(b) by 0 days.

(21) Appl. No.: 15/361,426

(22) Filed: Nov. 27, 2016

(65) Prior Publication Data

US 2017/0072114 A1   Mar. 16, 2017

Related U.S. Application Data

(63) Continuation of application No. PCT/IL2015/050553, filed on May 27, 2015.

(60) Provisional application No. 62/003,092, filed on May 27, 2014.

(51) Int. Cl.
| | | |
|---|---|---|
| *B05D 3/10* | (2006.01) | |
| *C09D 5/16* | (2006.01) | |
| *A61K 9/00* | (2006.01) | |
| *A61L 31/10* | (2006.01) | |
| *A61L 31/04* | (2006.01) | |
| *A61L 31/08* | (2006.01) | |
| *A61L 31/16* | (2006.01) | |
| *C09D 105/08* | (2006.01) | |
| *A61F 2/915* | (2013.01) | |
| *A61L 29/08* | (2006.01) | |
| *A61L 29/16* | (2006.01) | |

(52) U.S. Cl.
CPC .............. *A61L 31/10* (2013.01); *A61F 2/915* (2013.01); *A61L 29/085* (2013.01); *A61L 29/16* (2013.01); *A61L 31/042* (2013.01); *A61L 31/08* (2013.01); *A61L 31/16* (2013.01); *C09D 105/08* (2013.01); *A61F 2002/91575* (2013.01); *A61F 2002/91583* (2013.01); *A61F 2250/0067* (2013.01); *A61L 2300/204* (2013.01); *A61L 2300/21* (2013.01); *A61L 2300/416* (2013.01); *A61L 2300/61* (2013.01); *A61L 2300/63* (2013.01); *A61L 2420/02* (2013.01); *A61L 2420/08* (2013.01)

(58) Field of Classification Search
None
See application file for complete search history.

(56) References Cited

U.S. PATENT DOCUMENTS

| | | | |
|---|---|---|---|
| 7,282,213 B2 | 10/2007 | Schroeder et al. | |
| 2002/0119178 A1 | 8/2002 | Levesque et al. | |
| 2006/0210494 A1 | 9/2006 | Rabiei et al. | |
| 2007/0016284 A1* | 1/2007 | Pacetti | A61L 31/10 |
| | | | 623/1.46 |
| 2007/0134288 A1 | 6/2007 | Parsonage et al. | |
| 2007/0154554 A1 | 7/2007 | Burgermeister et al. | |
| 2007/0160641 A1* | 7/2007 | Jang | A61L 27/34 |
| | | | 424/423 |
| 2008/0097591 A1 | 4/2008 | Savage et al. | |
| 2008/0097618 A1 | 4/2008 | Baker et al. | |
| 2010/0093686 A1* | 4/2010 | Chappa | A61K 6/0017 |
| | | | 514/180 |
| 2012/0231037 A1* | 9/2012 | Levi | A61L 31/08 |
| | | | 424/400 |
| 2013/0053947 A1* | 2/2013 | Kangas | A61L 27/54 |
| | | | 623/1.42 |

FOREIGN PATENT DOCUMENTS

| | | |
|---|---|---|
| WO | WO 00/32238 | 6/2000 |
| WO | WO 2006/063021 | 6/2006 |
| WO | WO 2006/105362 | 10/2006 |
| WO | WO 2007/011707 | 1/2007 |
| WO | WO 2008/131131 | 10/2008 |
| WO | WO 2010/086863 | 8/2010 |
| WO | WO 2013/028208 | 2/2013 |
| WO | WO 2015/181826 | 12/2015 |

OTHER PUBLICATIONS

International Preliminary Report on Patentability dated Dec. 8, 2016 From the International Bureau of WIPO Re. Application No. PCT/IL2015/050553. (7 Pages).
International Search Report and the Written Opinion dated Sep. 21, 2015 From the International Searching Authority Re. Application No. PCT/IL2015/050553.
Levy et al. "Biodegradable Inflatable Balloon for Reducing Radiation Adverse Effects in Prostate Cancer", Journal of Biomedical Materials Research, Part B Applied Biomaterials, 91(2): 855-867, Nov. 2009.
Wessely et al. "Inhibition of Neointima Formation by a Novel Drug-Eluting Stent System That Allows for Dose-Adjustable, Multiple, and On-Site Stent Coating", Arteriosclerosis, Thrombosis, and Vascular Biology, 25(4): 748-753, Published Online Jan. 27, 2005.

* cited by examiner

*Primary Examiner* — Abigail Vanhorn

(57) ABSTRACT

Articles-of-manufacturing comprising an object having a surface and at least a first layer of a first therapeutically active agent being deposited onto at least a continuous portion of the surface, wherein at least 50 weight percents of the first layer is the first therapeutically active agent in a crystalline form are disclosed. Methods utilizing such articles-of-manufacturing for treating medical conditions are also disclosed. Processes of preparing the articles-of-manufacturing by contacting a surface of the object with a solution containing the therapeutically active agent, without cooling the surface to a temperature below a temperature of the solution, are also disclosed.

8 Claims, 91 Drawing Sheets
(66 of 91 Drawing Sheet(s) Filed in Color)

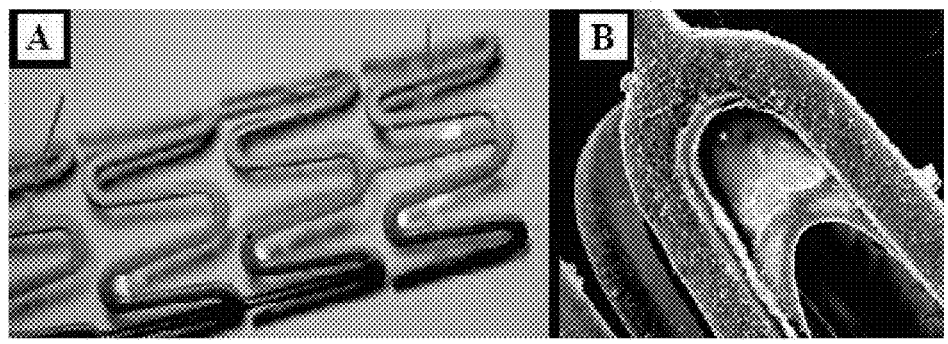
FIG. 21A    FIG. 21B
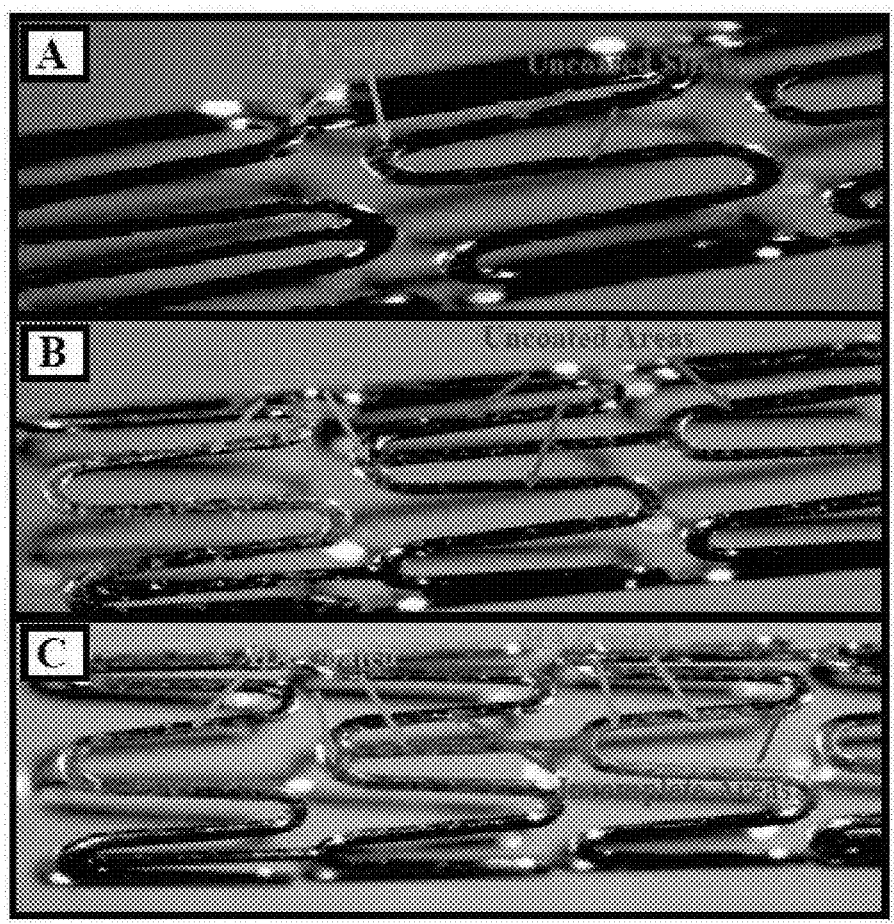
FIG. 22A
FIG. 22B
FIG. 22C

FIG. 41A
FIG. 41B
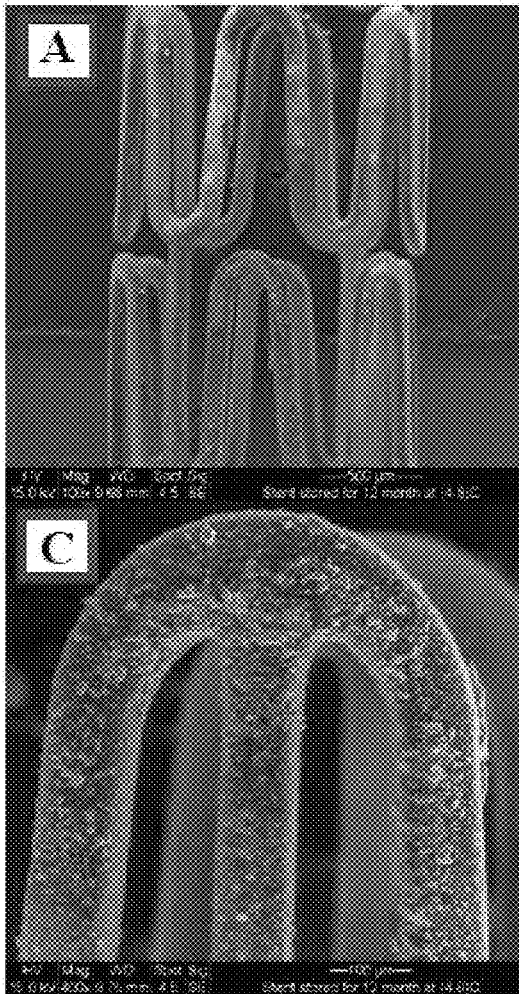
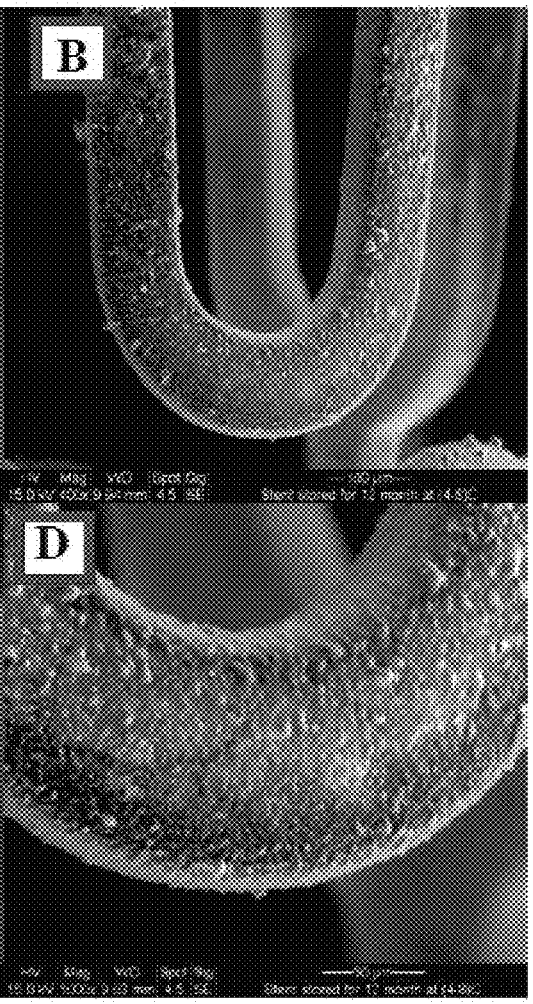
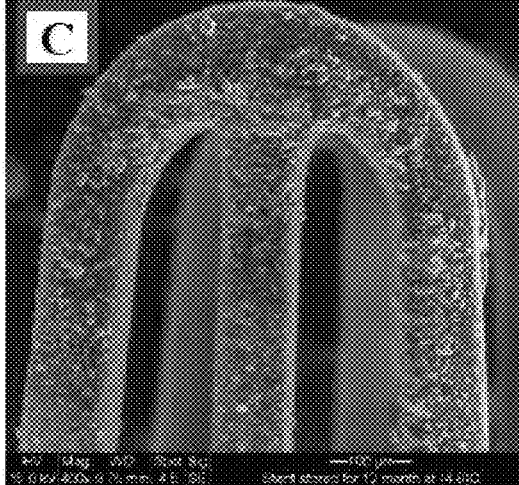
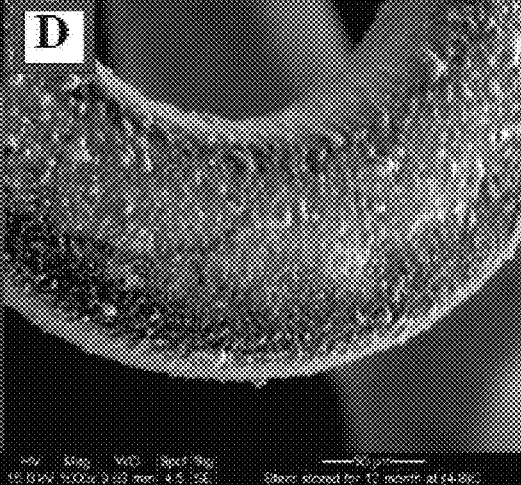
FIG. 41C
FIG. 41D

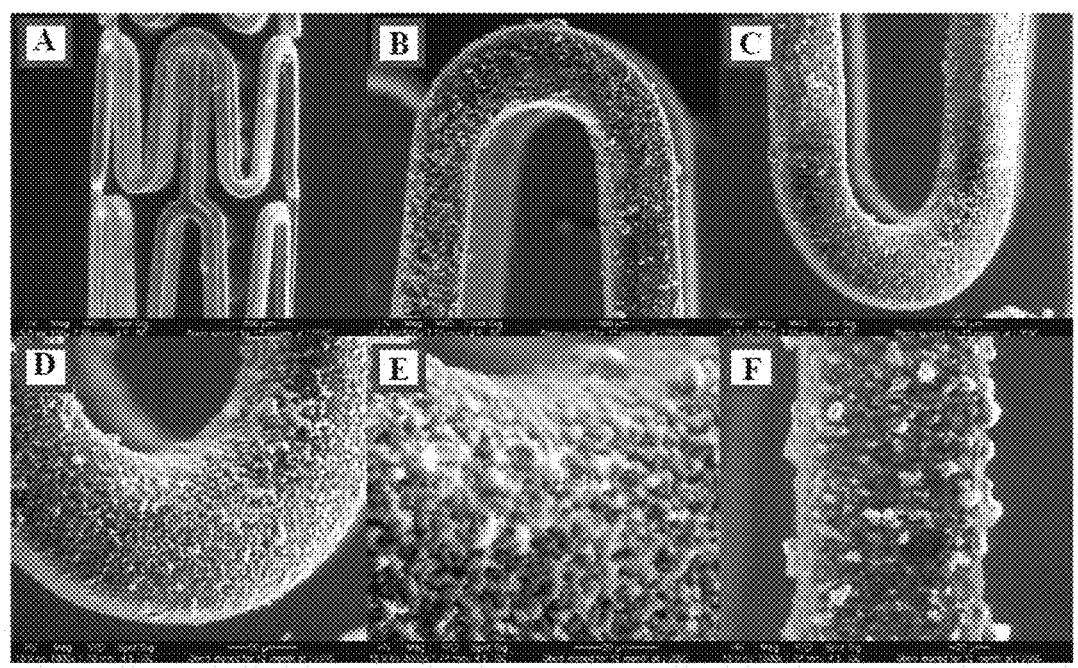
FIG. 42A  FIG. 42B  FIG. 42C
FIG. 42D  FIG. 42E  FIG. 42F
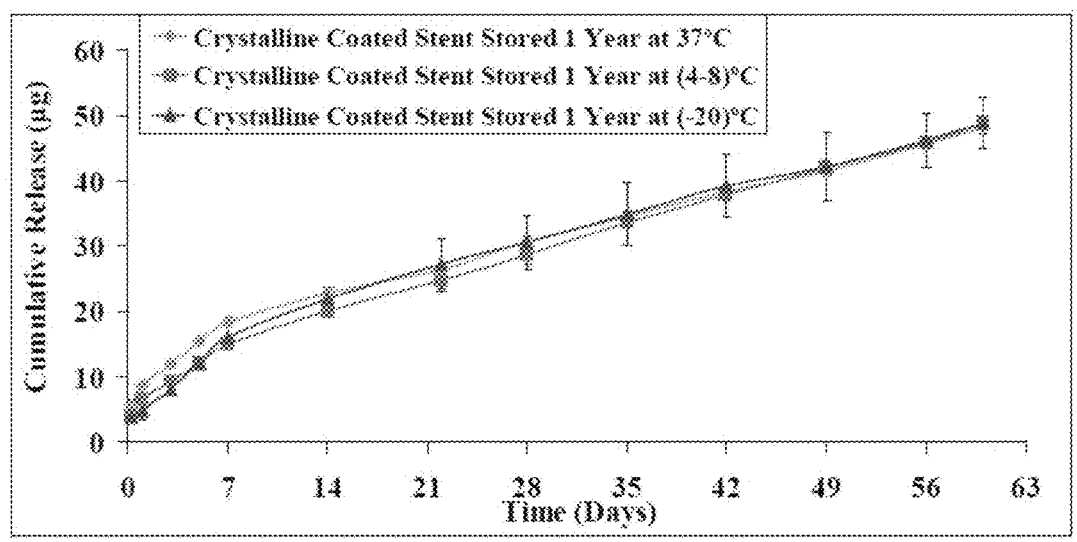
FIG. 43

FIG. 62A
FIG. 62B
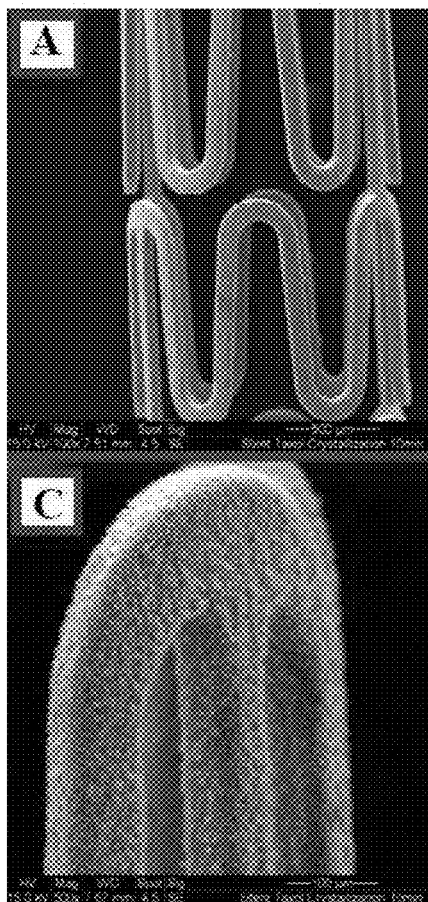
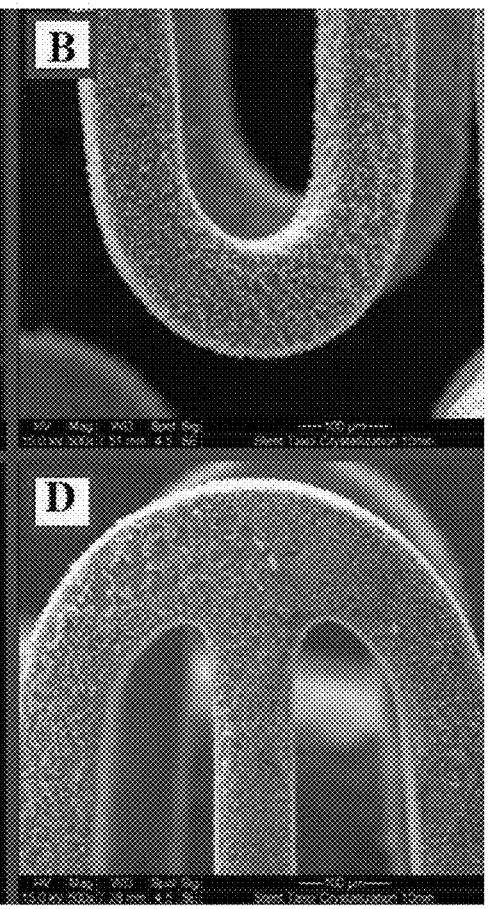
FIG. 62C
FIG. 62D

CRYSTALLINE COATING AND RELEASE OF BIOACTIVE AGENTS

RELATED APPLICATIONS

This application is a Continuation of PCT Patent Application No. PCT/IL2015/050553 having International filing date of May 27, 2015, which claims the benefit of priority under 35 USC § 119(e) of U.S. Provisional Patent Application No. 62/003,092 filed on May 27, 2014. The contents of the above applications are all incorporated by reference as if fully set forth herein in their entirety.

FIELD AND BACKGROUND OF THE INVENTION

The present invention, in some embodiments thereof, relates to surfaces having applied thereon therapeutically active agents and, more particularly, but not exclusively, to articles-of-manufacture such as medical devices having applied thereon a crystalline form of a therapeutically active agent.

Drug-eluting stents (DES) have become an accepted technology in intravascular intervention.

Examples of such drug-eluting stents are paclitaxel-eluting stents (TAXUS® stents, Boston Scientific), which inhibit the proliferation of SMCs, and sirolimus (rapamycin)-eluting stents (Cypher® stents, Cordis Corporation), which inhibit the inflammation response of the arterial wall. In these drug-eluting stents, a polymeric carrier is used for loading the anti-proliferative agent onto the stent. Unfortunately, such drug-eluting stents use polymers which are at least partially biostable, namely, remain stable and non-degradable under in vivo conditions, and can result in adverse effects, most commonly in-stent thrombosis. Consequently, DES patients are usually treated with anti-platelet therapy for a prolonged time period, which is also associated with adverse side effects and complications.

Development of drug-eluting stents devoid of polymeric carriers, or bearing a minimal amount of polymeric carriers, suffers from numerous limitations imposed by factors such as the poor adherence of therapeutically active agents to bare metal stents and the limited control of drug release (influenced, inter alia, by the drug's dissolution rate).

Manufacturing methodologies of drug-eluting stents are based mainly on mechanical processes such as spray and dip coating which tend to generate amorphous coatings that are poorly adhered to the surface, and have poor stability properties and fast drug release; related as a potential hazard [Levy et al., *J Biomed Mater Res B Appl Biomater* 2009, 91(1):441-451]. Moreover, many drugs in an amorphous phase, including rapamycin and paclitaxel, are chemically unstable, resulting in rapid degradation of the drug both under physiological conditions and under storage conditions, thus limiting their commercial and therapeutic value. Wessely et al. [*Arteriosclerosis, Thrombosis, and Vascular Biology* 2005, 25:748] teach a polymer-free stent coated with rapamycin by spray-coating the surface with a rapamycin solution, as well as a device for coating the stent before use.

WO 2010/086863 describes articles-of-manufacturing comprising a therapeutically active agent deposited onto a surface hereof, while at least a portion of the therapeutically active agent is in a crystalline form; as well as processes and apparatuses for preparing such articles-of-manufacturing by contacting a surface with a solution containing the therapeutically active agent, and cooling the surface to a temperature below a temperature of the solution.

Most of the studies conducted with crystalline drug in drug-eluting stents use polymeric carriers to facilitate adherence of crystalline drugs to surfaces.

WO 00/032238 teaches a stent having applied thereof a crystalline drug within or over a polymer coating which coats the stent.

WO 2006/063021 teaches a coating composition comprising a polymer and an active agent, wherein the active agent crystallizes following application of the coating composition.

U.S. Patent Application having Publication No. 20070154554 teaches a crystalline therapeutic agent encapsulated in a biocompatible polymer coating.

U.S. Pat. No. 7,282,213 teaches a method of applying a steroid to a surface of a medical device by depositing a solution of the steroid on the surface to form a crystalline coating, and heating the coating in order to form a coating that is better conformed to the surface.

WO 2006/105362 teaches antimicrobial metal-containing coatings.

U.S. patent applications having Publication Nos. 20080097618 and 20060210494 teach crystalline calcium phosphate coatings on medical devices. Additional background art includes WO 2007/011707 and U.S. patent applications having Publication Nos. 20020119178 and 20070134288.

SUMMARY OF THE INVENTION

According to an aspect of some embodiments of the invention, there is provided an article-of-manufacture comprising an object having a surface and at least a first layer of a first therapeutically active agent being deposited onto at least a continuous portion of the surface, wherein at least 50 weight percents of the first layer is the first therapeutically active agent in a crystalline form.

According to an aspect of some embodiments of the invention, there is provided an article-of-manufacture comprising an object having a surface and at least a first layer of a first therapeutically active agent being deposited onto at least a continuous portion of the surface, wherein at least 50 weight percents of the first layer is the first therapeutically active agent in a crystalline form, and wherein at least 50% of an area of the continuous portion of the surface is covered by the first layer.

According to an aspect of some embodiments of the invention, there is provided an article-of-manufacture comprising an object having a surface and at least a first layer of a first therapeutically active agent being deposited onto at least a continuous portion of the surface, wherein at least 50 weight percents of the first layer is the first therapeutically active agent in a crystalline form, and wherein at least 80% of an area of the continuous portion of the surface is covered by the first layer, and wherein an average density of the first therapeutically active agent on the continuous portion of the surface is no more than 6 µg/mm$^2$.

According to an aspect of some embodiments of the invention, there is provided an article-of-manufacture comprising an object having a surface, a first layer of a first therapeutically active agent and at least one additional layer comprising a second therapeutically active agent, the first layer and the additional layer being deposited onto at least a continuous portion of the surface, wherein at least 50 weight percents of the first layer is the first therapeutically active agent in a first crystalline form, wherein at least 50% of an area of the portion of the surface is covered by the first layer, and wherein the second therapeutically active agent is the first therapeutically active agent in an amorphous form and/or in a second crystalline form which is different than the first crystalline form, or the second therapeutically active agent is a different therapeutically active agent than the first therapeutically active agent.

According to an aspect of some embodiments of the invention, there is provided an article-of-manufacture comprising an object having a surface, a base layer applied onto the surface, at least one nucleating agent conjugated to the base layer, and a first layer of a first therapeutically active agent being deposited onto the base layer on at least a continuous portion of the surface, wherein at least 50 weight percents of the first layer is the first therapeutically active agent in a crystalline form.

According to an aspect of some embodiments of the invention, there is provided an article-of-manufacture comprising an object having a surface, a first layer of a first therapeutically active agent being deposited onto at least a continuous portion of the surface, and a coat layer comprising hyaluronic acid and coating at least the continuous portion of the first layer, wherein at least 50 weight percents of the first layer is the first therapeutically active agent in a crystalline form.

According to an aspect of some embodiments of the invention, there is provided a process of depositing at least a first layer of a first therapeutically active agent onto at least a continuous portion of a surface of an object, wherein at least 50 weight percents of the first layer is the first therapeutically active agent in a crystalline form, the process comprising contacting the surface of the object with a solution containing the first therapeutically active agent, so as to form the crystalline form of the first therapeutically active agent deposited on at least the continuous portion of the surface, wherein the surface is not cooled to a temperature below a temperature of the solution.

According to an aspect of some embodiments of the invention, there is provided a process of depositing at least a first layer of a first therapeutically active agent onto at least a continuous portion of a surface of an object, wherein at least 50 weight percents of the first layer is the first therapeutically active agent in a crystalline form, the process comprising:

seeding the surface of the object with crystals of the first therapeutically active agent, so as to obtain a seeded surface comprising the crystals; and contacting the seeded surface with a solution containing the first therapeutically active agent, so as to form the crystalline form of the first therapeutically active agent deposited on at least the continuous portion of the surface, wherein the surface is not cooled to a temperature below a temperature of the solution.

According to an aspect of some embodiments of the invention, there is provided a process of depositing a first layer of a first therapeutically active agent and at least one additional layer of a second therapeutically active agent onto at least a continuous portion of a surface of an object, wherein at least 50 weight percents of the first layer is the first therapeutically active agent in a first crystalline form, and wherein the second therapeutically active agent is the first therapeutically active agent in an amorphous form and/or in a second crystalline form which is different than the first crystalline form, or the second therapeutically active agent is a different therapeutically active agent than the first therapeutically active agent, the process comprising:

seeding the surface of the object with crystals of the first therapeutically active agent, so as to obtain a seeded surface comprising the crystals;

contacting the seeded surface with a solution containing the first therapeutically active agent, so as to form the first crystalline form of the therapeutically active agent deposited on at least the continuous portion of the surface, wherein the surface is not cooled to a temperature below a temperature of the solution; and forming the at least one additional layer, prior to the seeding and/or subsequent to contacting the seeded surface with the solution.

According to an aspect of some embodiments of the invention, there is provided a process of depositing a first layer of a first therapeutically active agent onto at least a continuous portion of a surface of an object, wherein at least 50 weight percents of the first layer is the first therapeutically active agent in a crystalline form, the process comprising:

seeding the surface of the object with crystals of the first therapeutically active agent, so as to obtain a seeded surface comprising the crystals;

contacting the seeded surface with a solution containing the first therapeutically active agent, so as to form the crystalline form of the first therapeutically active agent deposited on at least the continuous portion of the surface; and applying a top coat comprising hyaluronic acid onto the surface having the first therapeutically active agent deposited thereon.

According to an aspect of some embodiments of the invention, there is provided a process of depositing a first layer of a first therapeutically active agent onto at least a continuous portion of a surface of an object, wherein at least 50 weight percents of the first layer is the first therapeutically active agent in a crystalline form, the process comprising:

applying a base layer and at least one nucleating agent conjugated to the base layer onto at least a portion of the surface, so as to obtain a surface with a base layer applied thereon;

contacting the surface with the base layer applied thereon with a solution containing the first therapeutically active agent, so as to form the crystalline form of the first therapeutically active agent deposited on at least the continuous portion of the surface.

According to an aspect of some embodiments of the invention, there is provided a method of treating a subject having a medical condition in which implanting a medical device is beneficial, the method comprising:

implanting the medical device according to any of the respective embodiments described herein within the subject, thereby treating the medical condition.

According to some embodiments of the invention, the medical condition is selected from the group consisting of a cardiovascular disease, atherosclerosis, thrombosis, stenosis, restenosis, a cardiologic disease, a peripheral vascular disease, an orthopedic condition, a proliferative disease, an infectious disease, a transplantation-related disease, a degenerative disease, a cerebrovascular disease, a gastrointestinal disease, a hepatic disease, a neurological disease, an autoimmune disease, and an implant-related disease.

According to some embodiments of the invention, the article-of-manufacture further comprises at least one additional layer comprising a second therapeutically active agent being deposited onto at least the continuous portion of the surface, wherein the second therapeutically active agent is the first therapeutically active agent in an amorphous form and/or in a different crystalline form than in the first layer, or the second therapeutically active agent is a different therapeutically active agent than the first therapeutically active agent.

According to some embodiments of the invention, at least 80% of an area of the continuous portion of the surface is covered by the first layer.

According to some embodiments of the invention, the continuous portion optionally comprises regions at least 4 µm in diameter which are devoid of the first therapeutically active agent, wherein a concentration of such regions is less than 1 of such regions per $mm^2$.

According to some embodiments of the invention, at least 90 weight percents of the first layer is the first therapeutically active agent in a crystalline form.

According to some embodiments of the invention, at least 99 weight percents of the first layer is the first therapeutically active agent in a crystalline form.

According to some embodiments of the invention, an average thickness of the first layer is no more than 20 µm.

According to some embodiments of the invention, an average density of the first therapeutically active agent on the continuous portion of the surface is no more than 6 µg/$mm^2$.

According to some embodiments of the invention, the object is devoid of a water-insoluble polymeric carrier on the surface which envelops the first therapeutically active agent.

According to some embodiments of the invention, the first layer is deposited directly onto the surface.

According to some embodiments of the invention, the article-of-manufacture further comprises a base layer applied onto the surface, and at least one nucleating agent conjugated to the base layer, wherein the first layer is deposited onto the base layer.

According to some embodiments of the invention, at least 50% of an area of the continuous portion of the surface is covered by the first layer.

According to some embodiments of the invention, the at least one nucleating agent comprises the first therapeutically active agent.

According to some embodiments of the invention, the base layer is a non-polymeric layer.

According to some embodiments of the invention, the surface is a conductive or semi-conductive surface and the base layer comprises at least one aryl moiety and/or at least one thiol moiety being electrochemically attached to the surface.

According to some embodiments of the invention, the article-of-manufacture further comprises a coat layer coating at least a portion of the first layer.

According to some embodiments of the invention, the coat layer comprises a water-soluble material.

According to some embodiments of the invention, at least 20% of the coat layer dissolves within 1 hour under physiological conditions.

According to some embodiments of the invention, the coat layer comprises a polymeric substance selected from the group consisting of hyaluronic acid and a mixture of carboxymethylcellulose with a plasticizer.

According to some embodiments of the invention, the plasticizer is a polyalkylene glycol.

According to some embodiments of the invention, the polymeric substance is hyaluronic acid.

According to some embodiments of the invention, the first therapeutically active agent is selected from the group consisting of an anti-restenosis agent, an anti-thrombogenic agent, an anti-platelet agent, an anti-coagulant, a statin, a toxin, an antimicrobial agent, an analgesic, an anti-metabolic agent, a vasoactive agent, a vasodilator, a prostaglandin, a thrombin inhibitor, a vitamin, a cardiovascular agent, an antibiotic, a chemotherapeutic agent, an antioxidant, a phospholipid, an anti-proliferative agent, paclitaxel, rapamycin, tacrolimus and any combination thereof.

According to some embodiments of the invention, the first therapeutically active agent is rapamycin.

According to some embodiments of the invention, an amount of the first therapeutically active agent that is released upon subjecting the object to physiological conditions for 24 hours is less than 10 percents by weight.

According to some embodiments of the invention, an amount of the first therapeutically active agent that is released upon subjecting the object to physiological conditions for 28 days is less than 40 percents by weight.

According to some embodiments of the invention, an amount of the first therapeutically active agent that is released upon subjecting the object to physiological conditions for 90 days is less than 70 percents by weight.

According to some embodiments of the invention, an amount of the first therapeutically active agent that is released upon subjecting the object to physiological conditions for 28 days is no more than 70% of an amount of the first therapeutically active agent that is released upon subjecting the object to physiological conditions for 90 days.

According to some embodiments of the invention, at least 10% of the first therapeutically active agent that is released upon subjecting the object to physiological conditions for 90 days is released in a native form.

According to some embodiments of the invention, the crystalline form of the first therapeutically active agent comprises crystals having an average diameter in a range of from 400 nm to 5 µm.

According to some embodiments of the invention, the object is a medical device.

According to some embodiments of the invention, the object is an implantable medical device.

According to some embodiments of the invention, the implantable device is a stent.

According to some embodiments of the invention, the process further comprises depositing at least one additional layer comprising a second therapeutically active agent onto the surface, wherein the second therapeutically active agent is the first therapeutically active agent in an amorphous form and/or in a different crystalline form than in the first layer, or the second therapeutically active agent is a different therapeutically active agent than the first therapeutically active agent.

According to some embodiments of the invention, one of the abovementioned first layer and the abovementioned additional layer is overlying the other.

According to some embodiments of the invention, seeding comprises contacting the surface with a dispersion of the crystals of the first therapeutically active agent.

According to some embodiments of the invention, the process further comprises subjecting the dispersion in contact with the surface to sonication.

According to some embodiments of the invention, the sonication is characterized by a frequency in a range of from 20 to 180 kHz, and/or a duration in a range of from 1 to 50 minutes, optionally from 2.5 to 20 minutes.

According to some embodiments of the invention, the seeded surface comprises the crystals at a density in a range of from 0.03 µg/$mm^2$ to 3 µg/$mm^2$.

According to some embodiments of the invention, the crystals in the seeded surface have an average diameter of less than 1 μm.

According to some embodiments of the invention, the solution contains a mixture of a solvent and anti-solvent of the first therapeutically active agent.

According to some embodiments of the invention, a concentration of the first therapeutically active agent in the solution contacted with the seeded surface is no more than 1 mg/ml.

According to some embodiments of the invention, contacting the seeded surface with the solution is effected for a time period in a range of from 1 to 50 minutes, optionally from 2.5 to 20 minutes.

According to some embodiments of the invention, the process further comprises masking a portion of the surface, to thereby obtain a masked portion of the surface, such that the first therapeutically active agent is absent from a portion of the surface.

According to some embodiments of the invention, the process further comprises applying a top coat onto the surface having the first layer deposited thereon.

According to some embodiments of the invention, applying the top coat is effected by spray coating.

According to some embodiments of the invention, the object further comprises a base layer applied onto at least a portion of the surface, and at least one nucleating agent conjugated to the base layer, and the process further comprises, prior to seeding the surface, applying the base layer and the nucleating agent conjugated to the base layer onto the surface.

According to some embodiments of the invention, the surface is a conductive or semi-conductive surface, the base layer comprises at least one aryl moiety and/or at least one thiol moiety, and applying the base layer comprises electrochemically attaching the at least one aryl moiety and/or at least one thiol moiety to the surface.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1A:
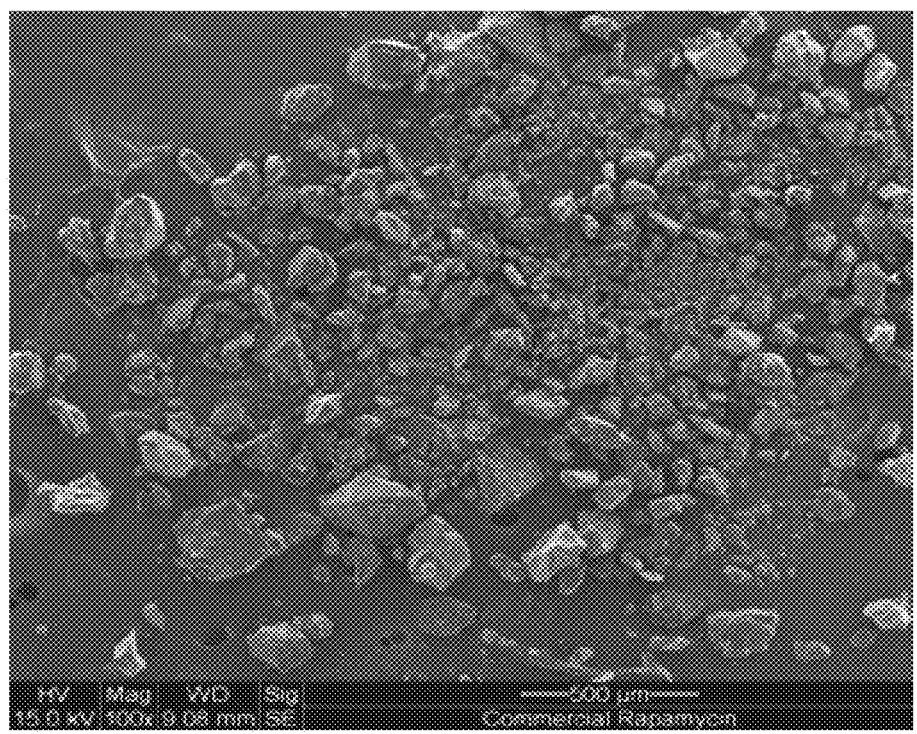
Figure 1B:
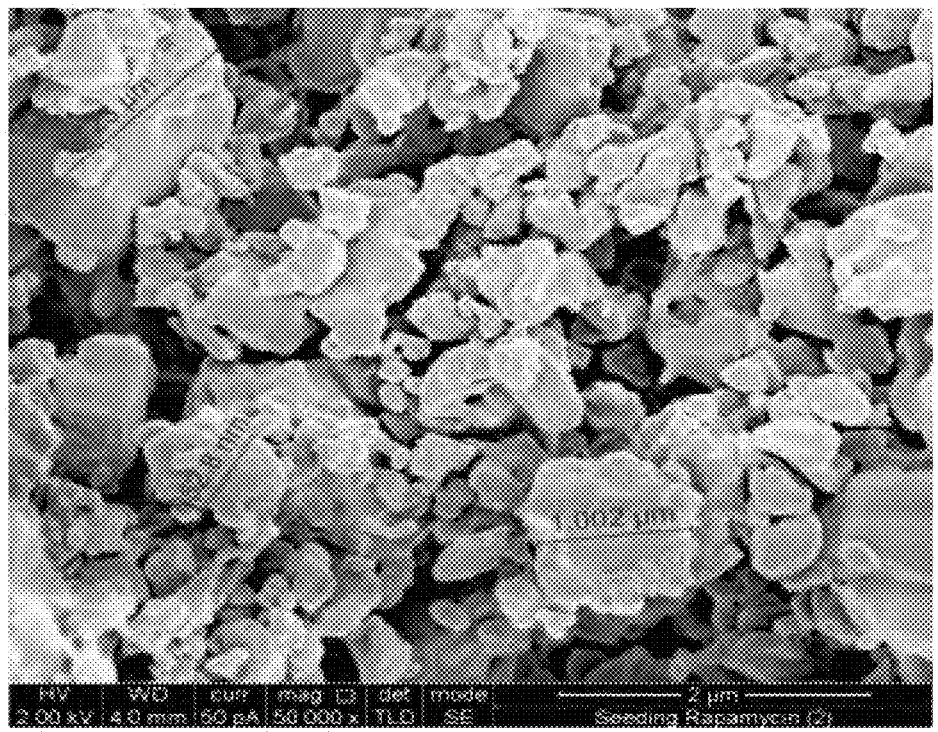
Figure 2A:
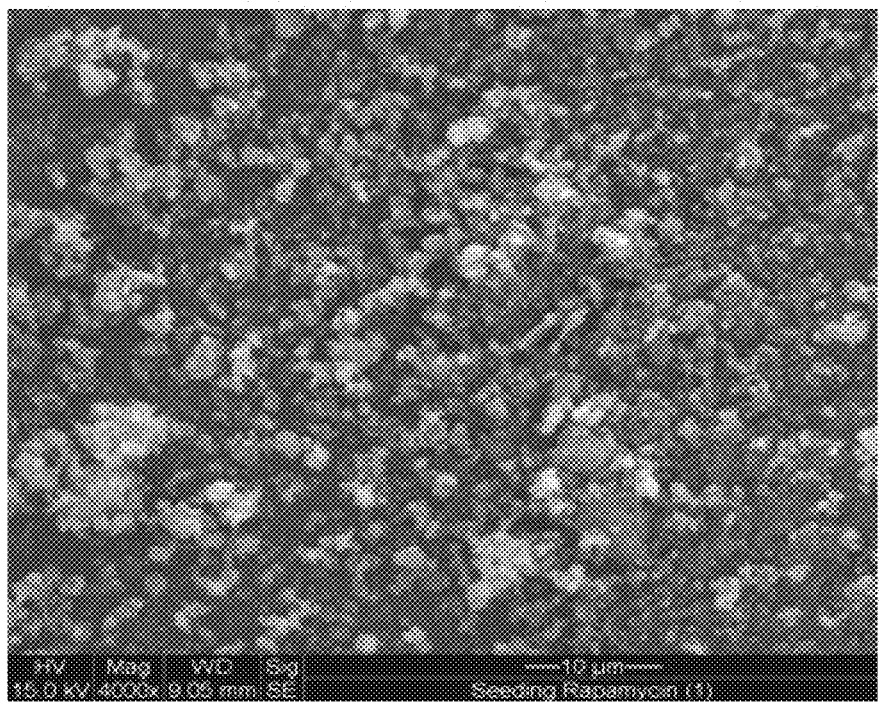
Figure 2B:
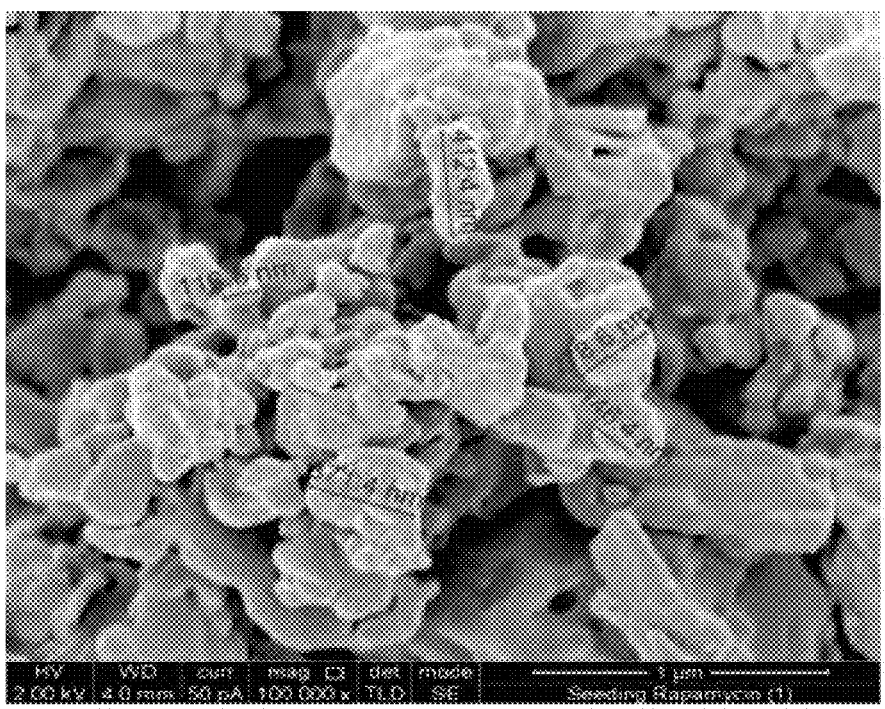
Figure 3:
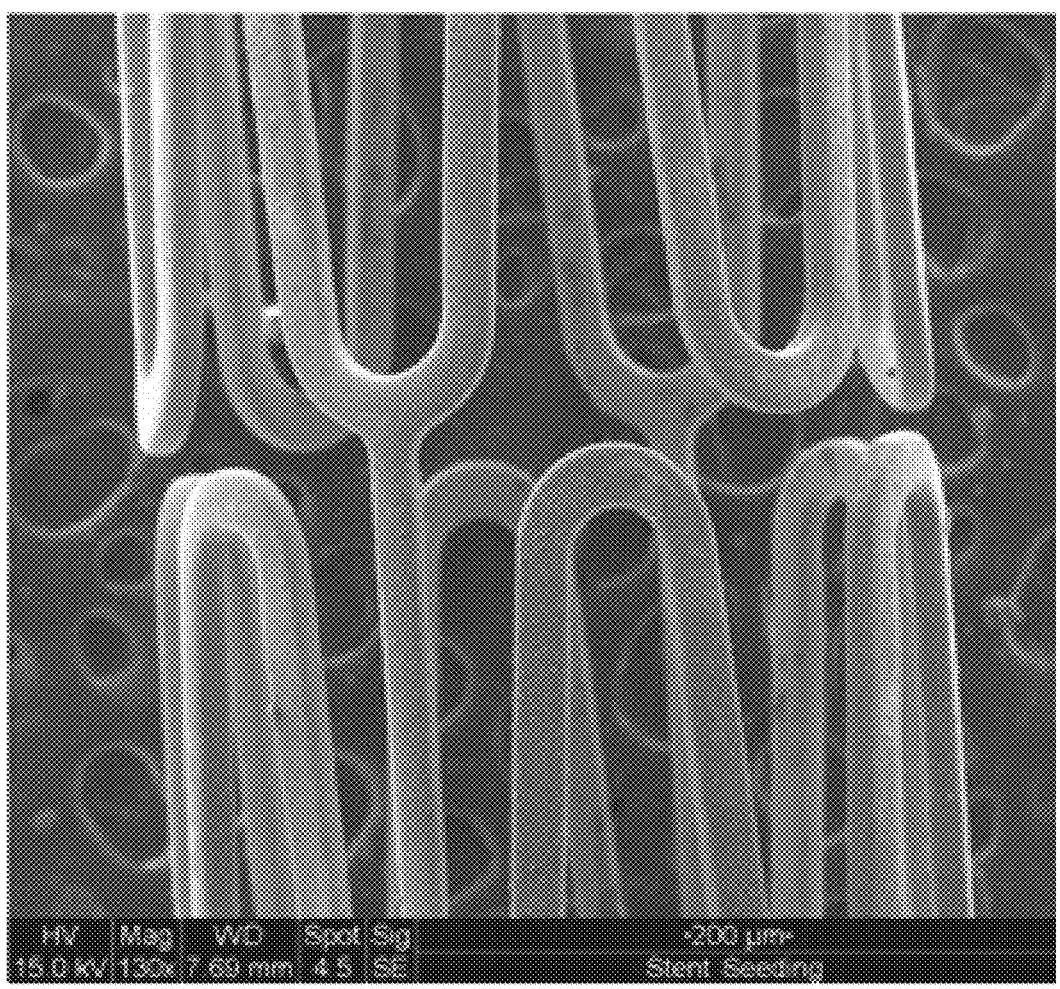
Figure 4:
Figure 5A:
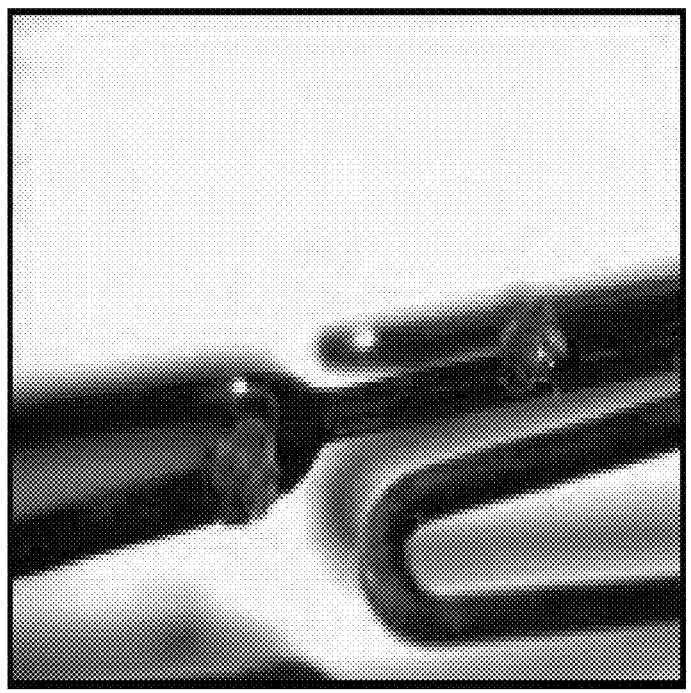
Figure 5B:
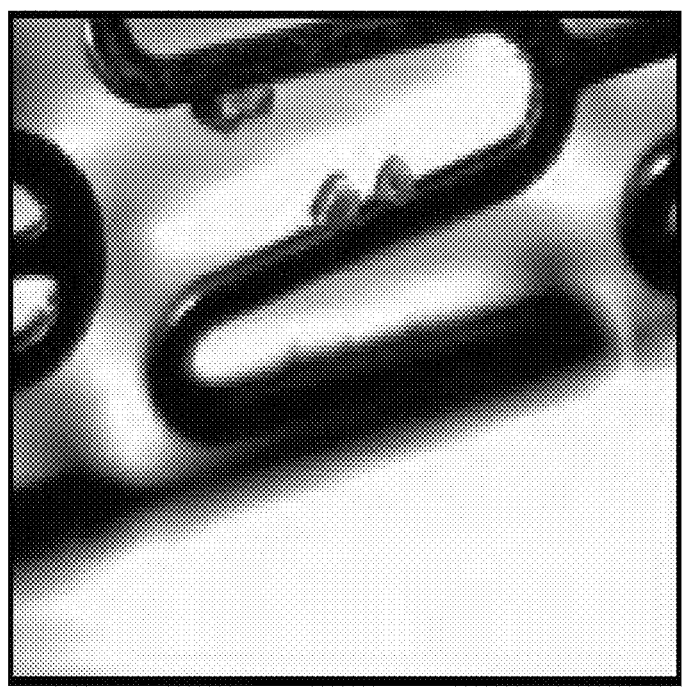
Figure 6A:
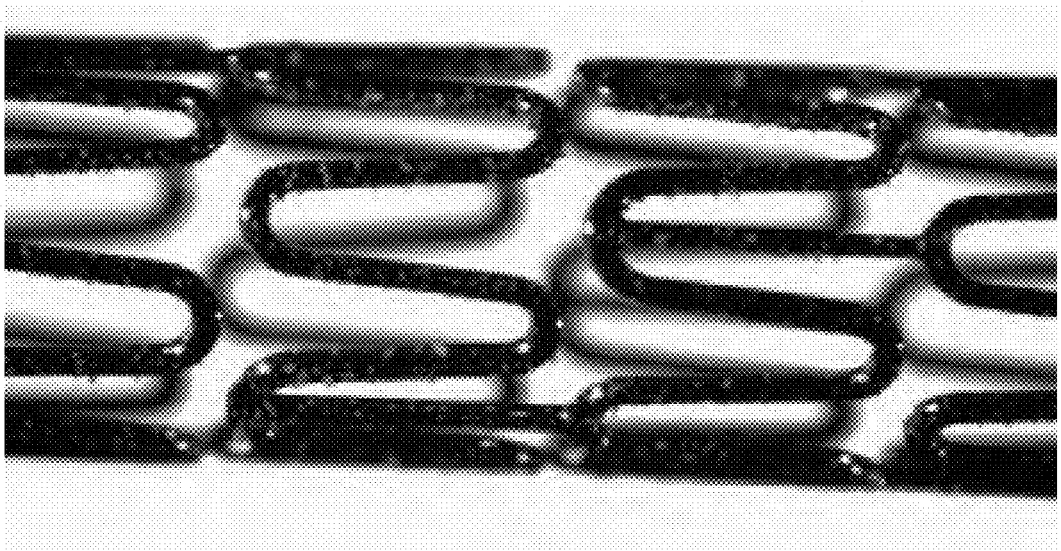
Figure 6B:
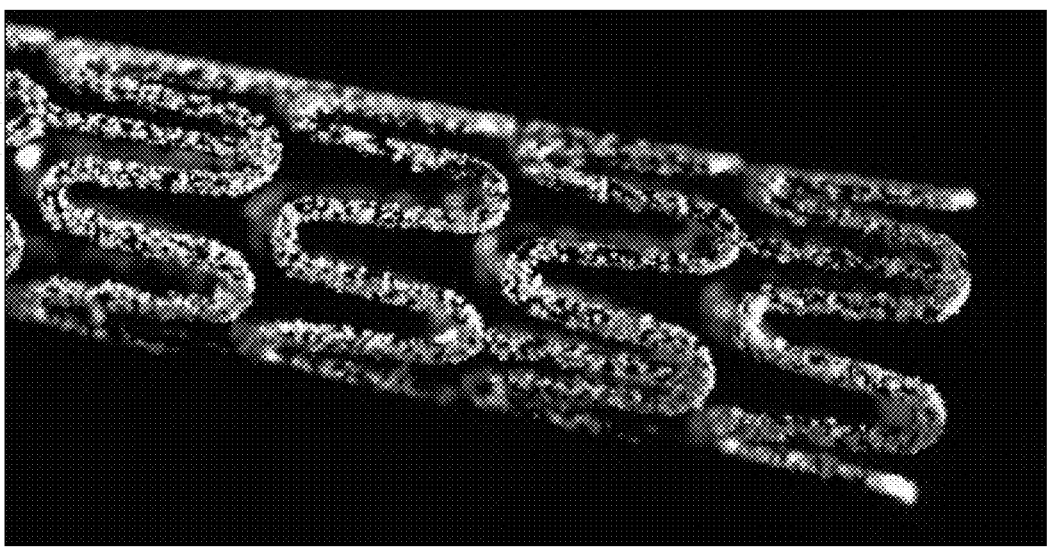
Figure 7A:
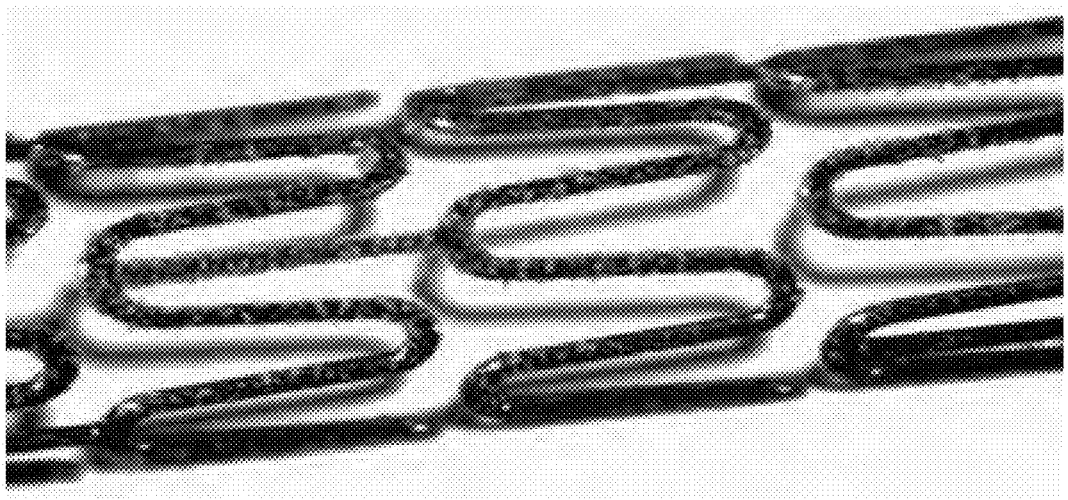
Figure 7B:
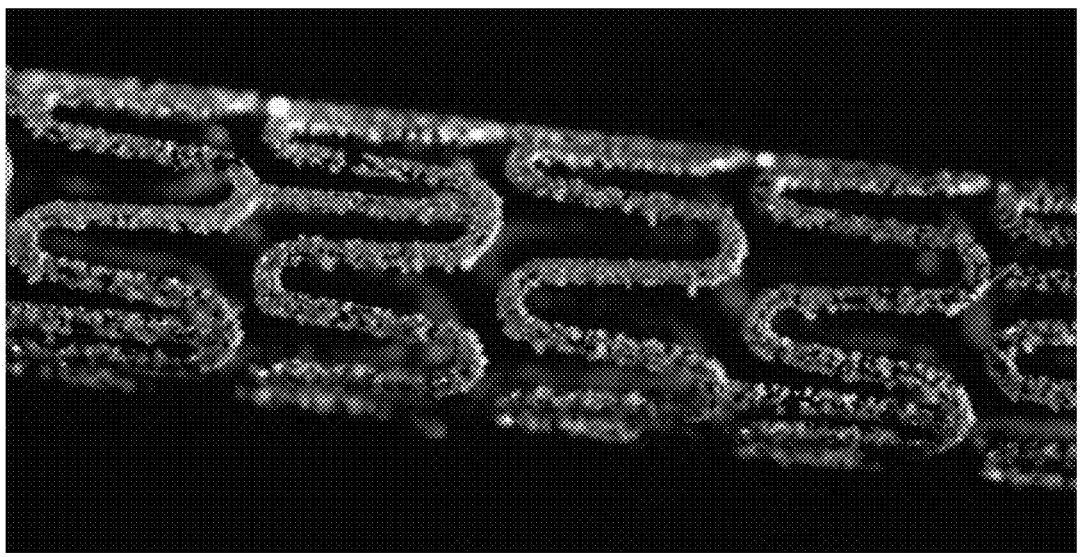
Figure 8A:
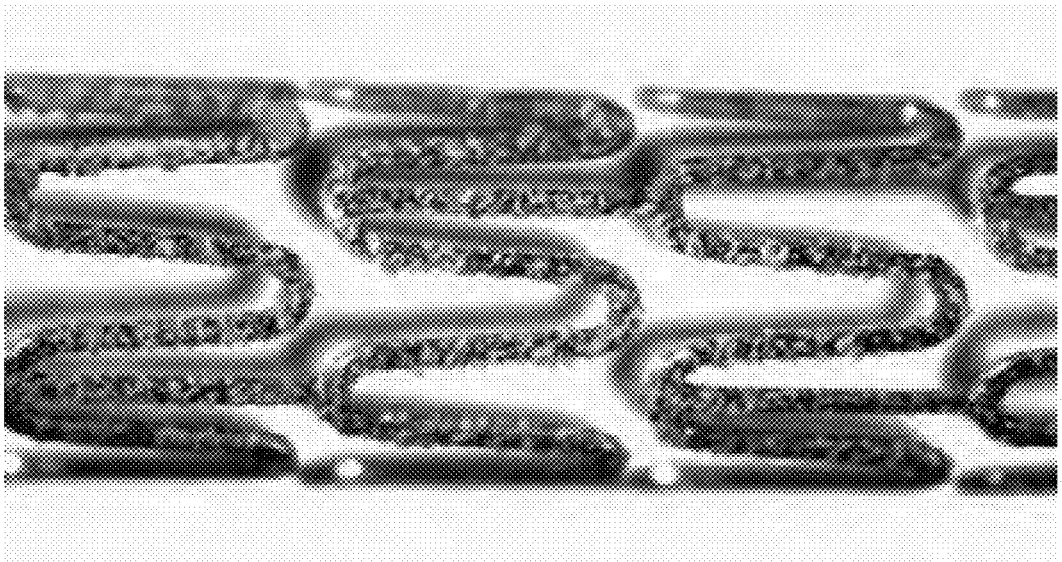
Figure 8B:
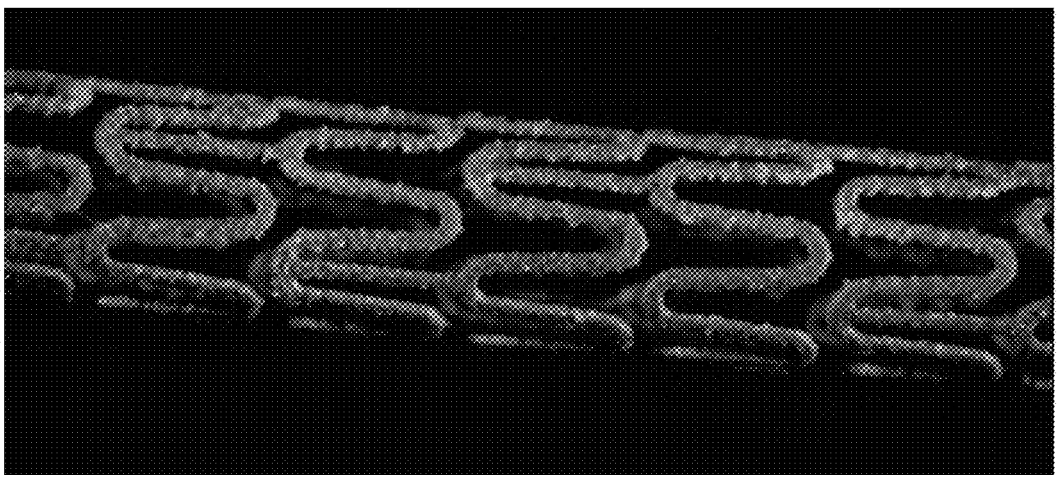
Figure 9:
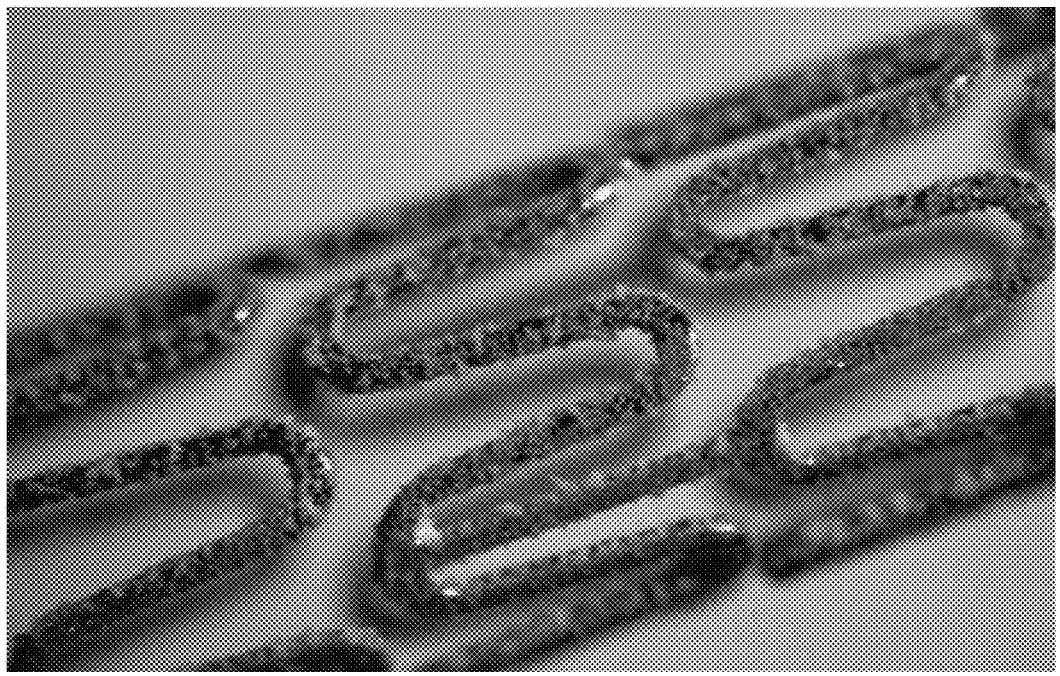
Figure 10:
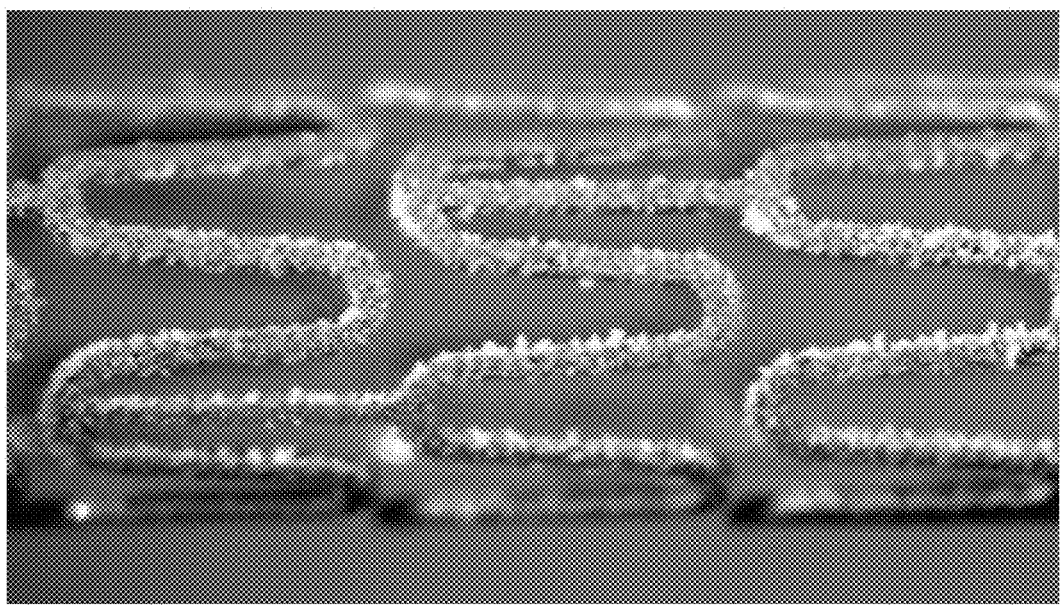
Figure 11:
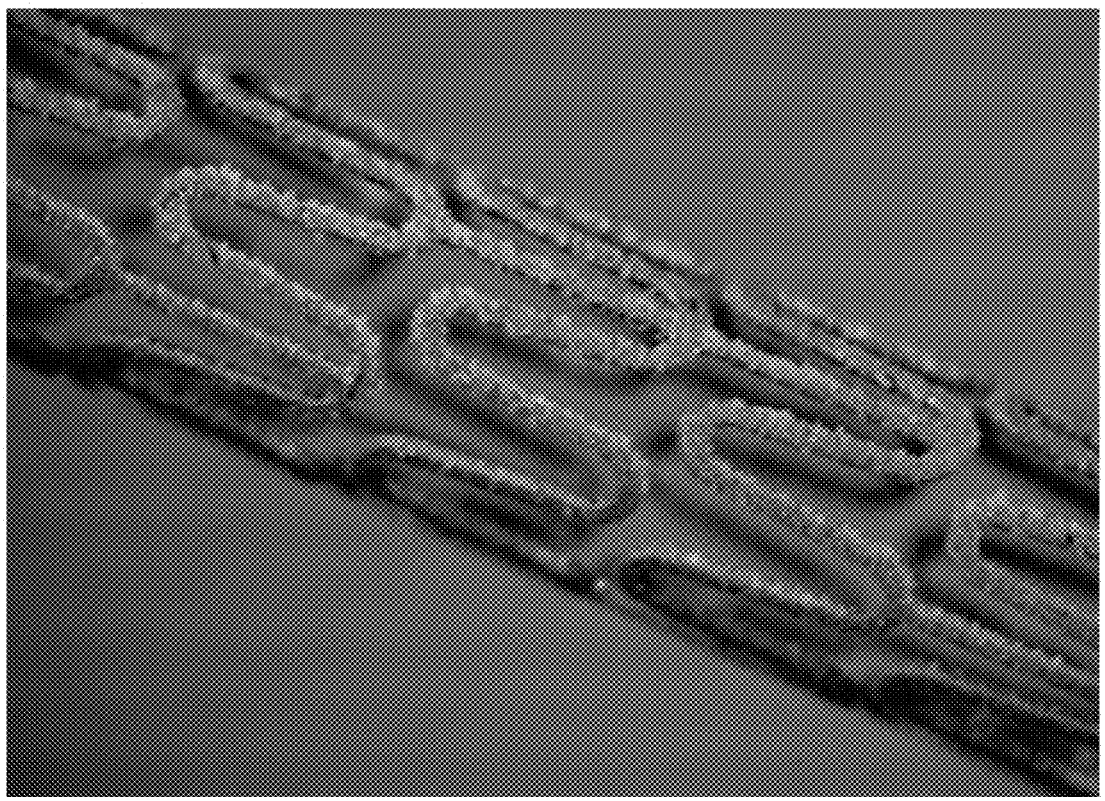
Figure 12:
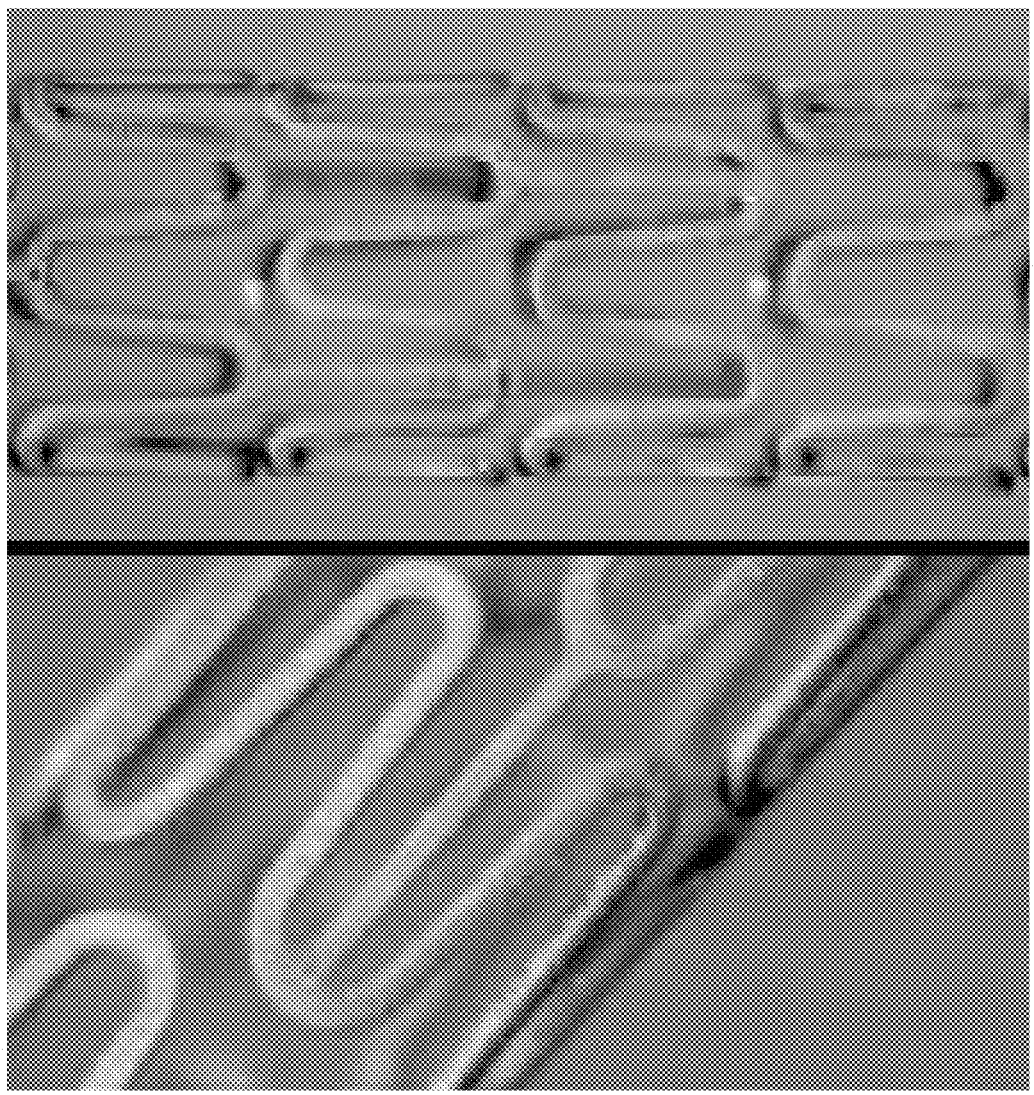
Figure 13:
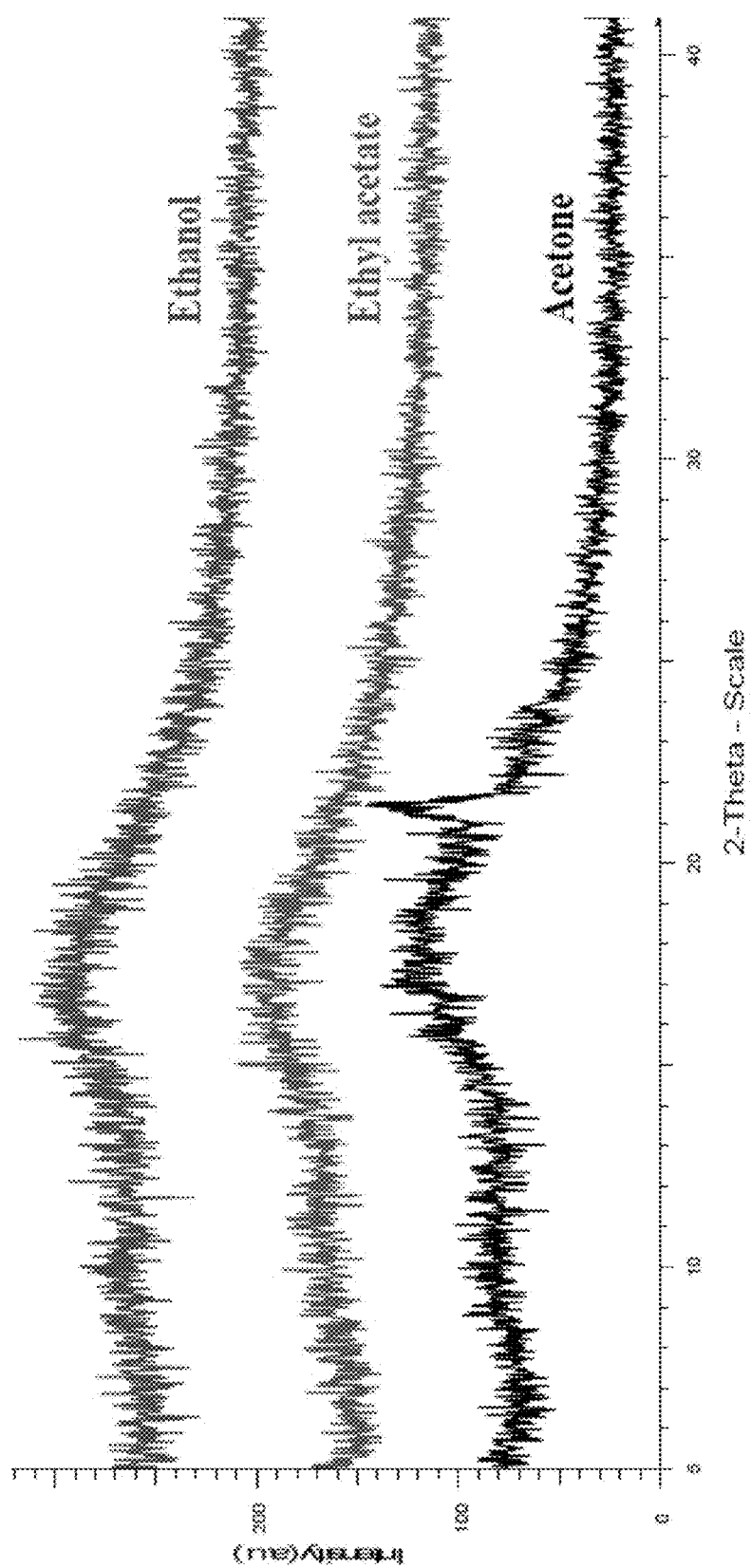
Figure 14:
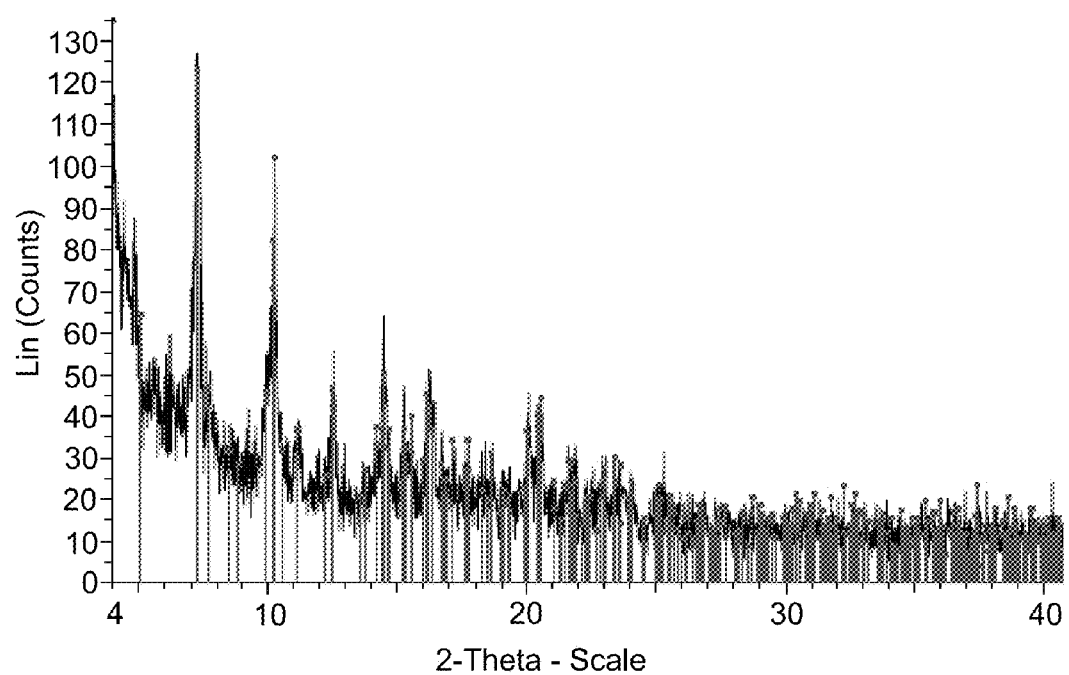
Figure 15:
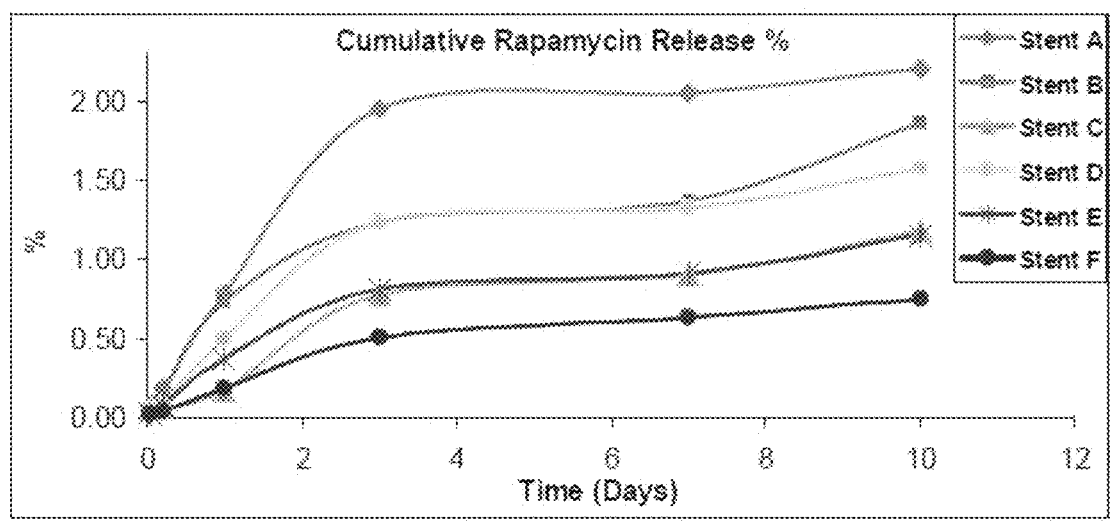
Figure 16:
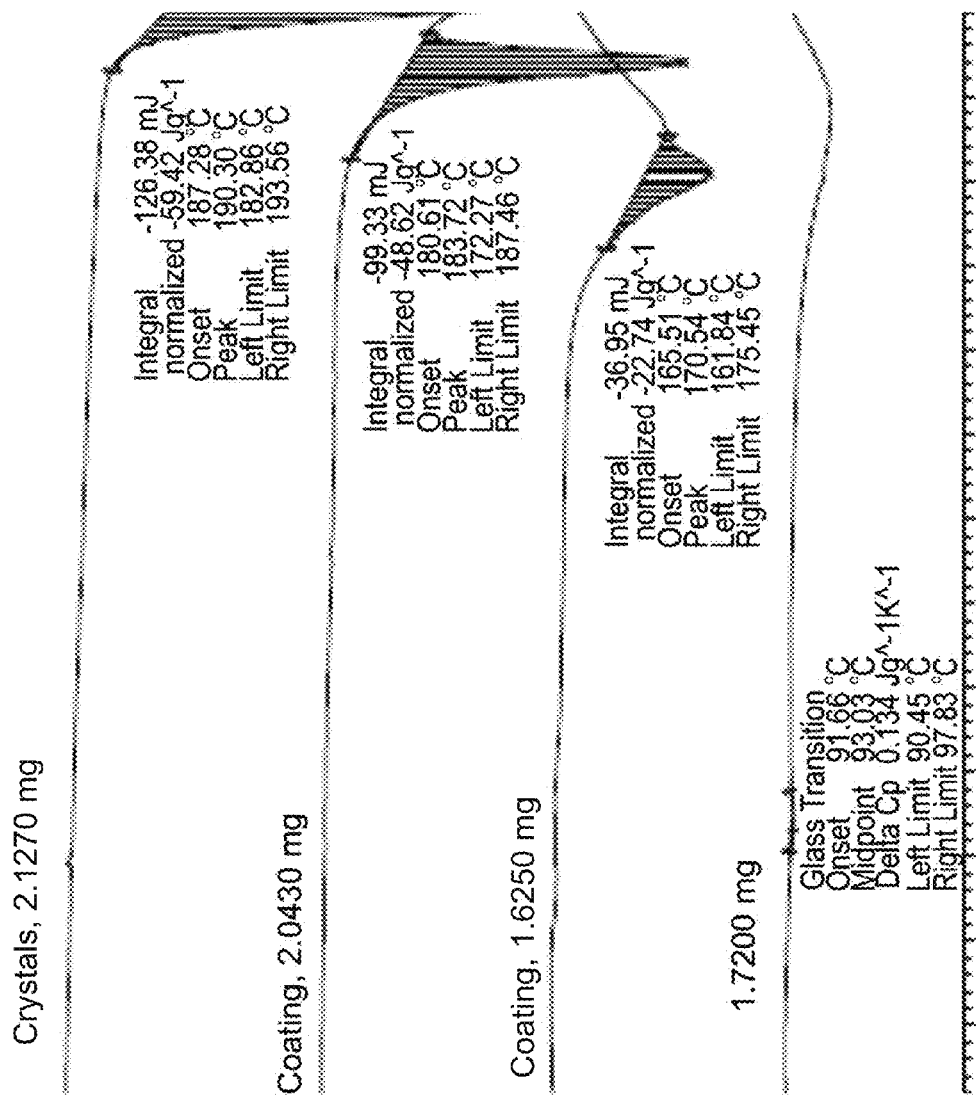
Figures 17A, 17B:
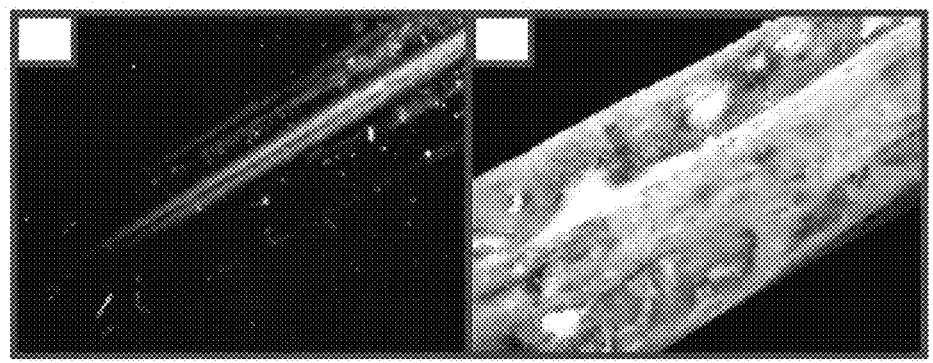
Figure 18A:
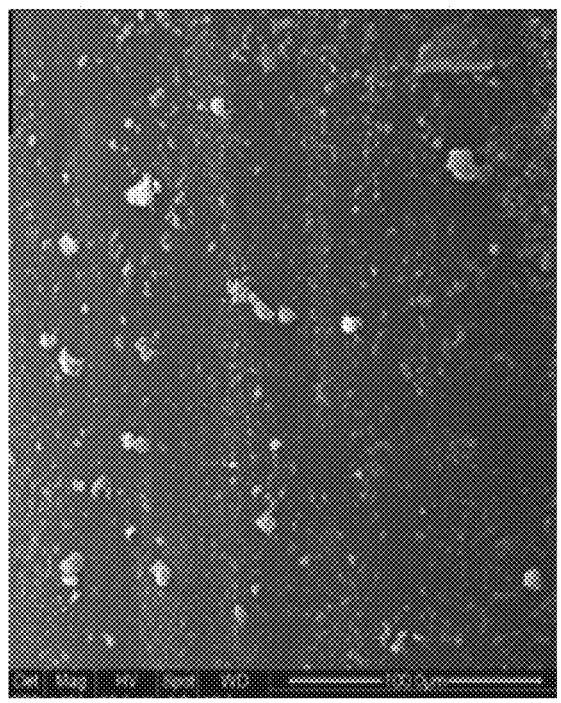
Figure 18B:
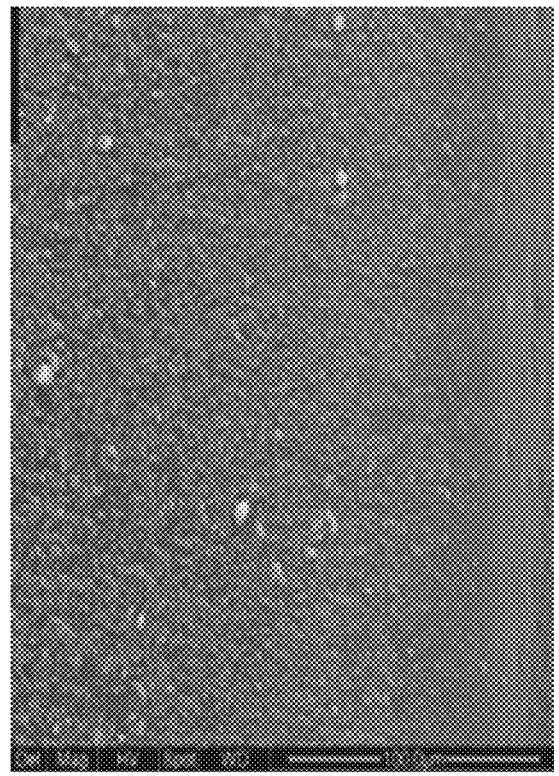
Figure 18C:
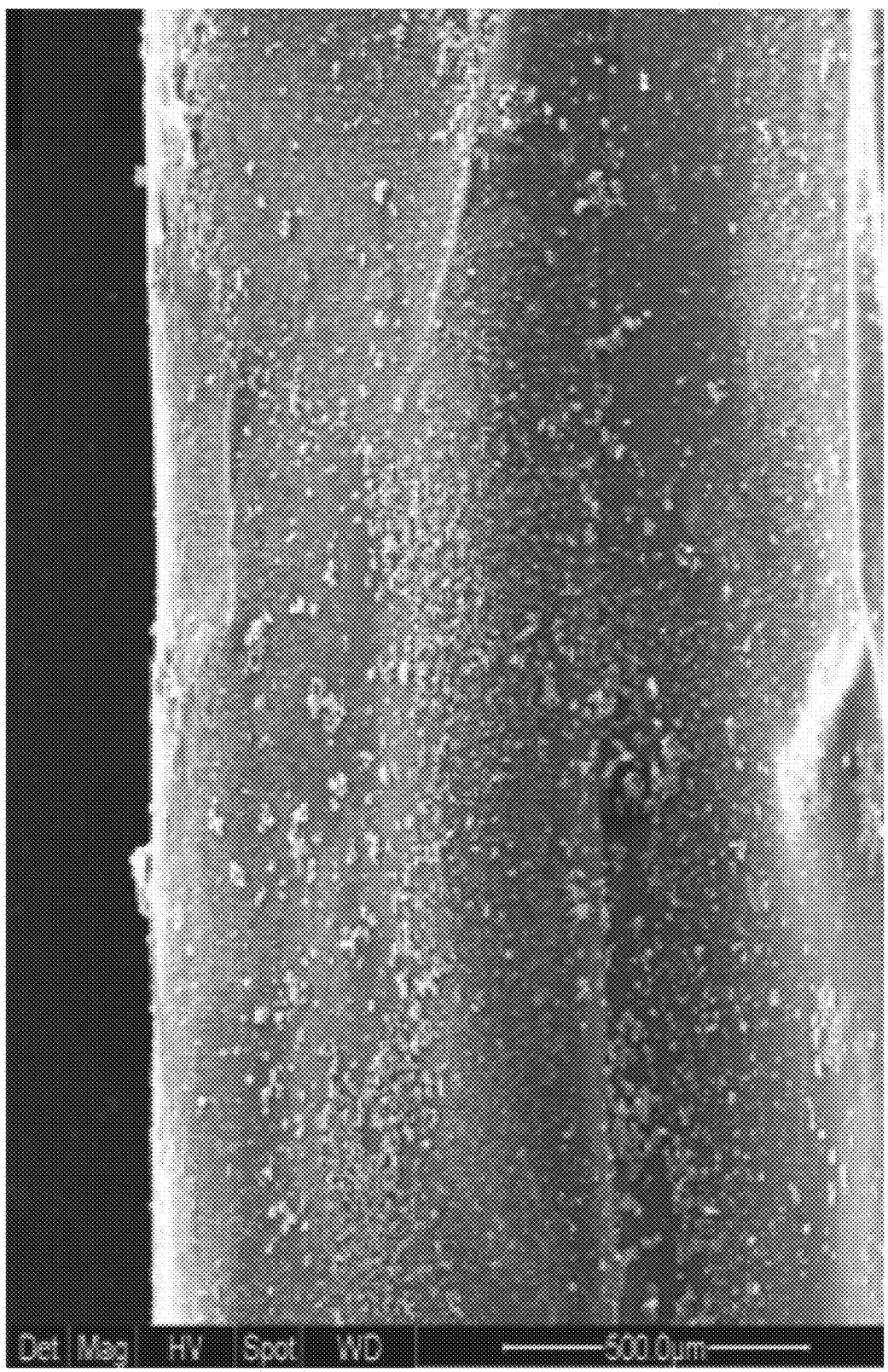
Figure 20A:
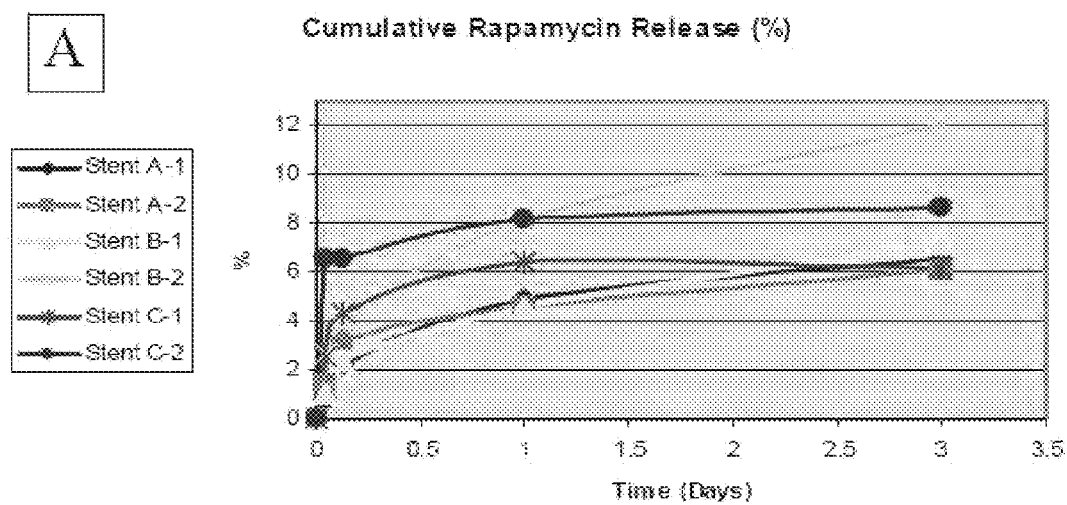
Figure 20B:
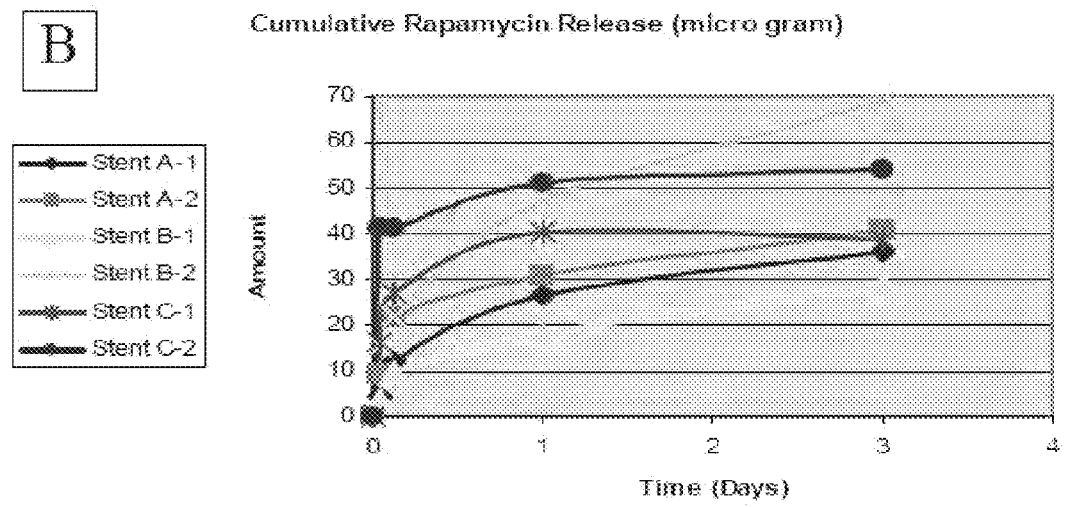
Figures 23A, 23B:
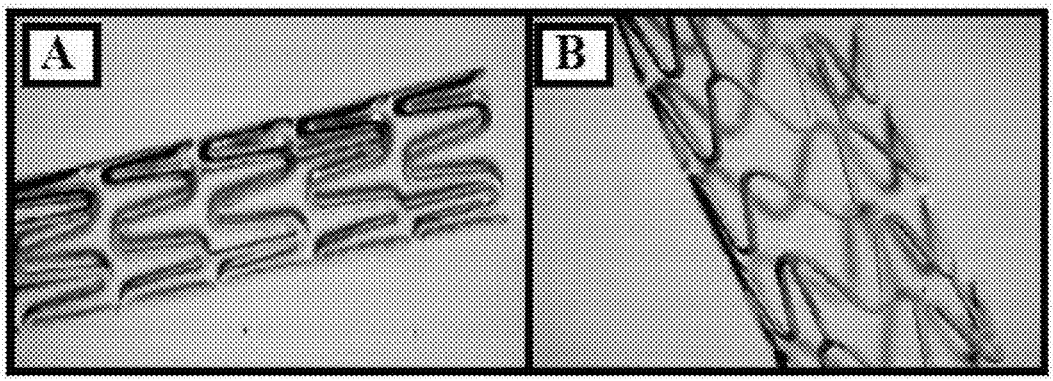
Figures 24A, 24B:
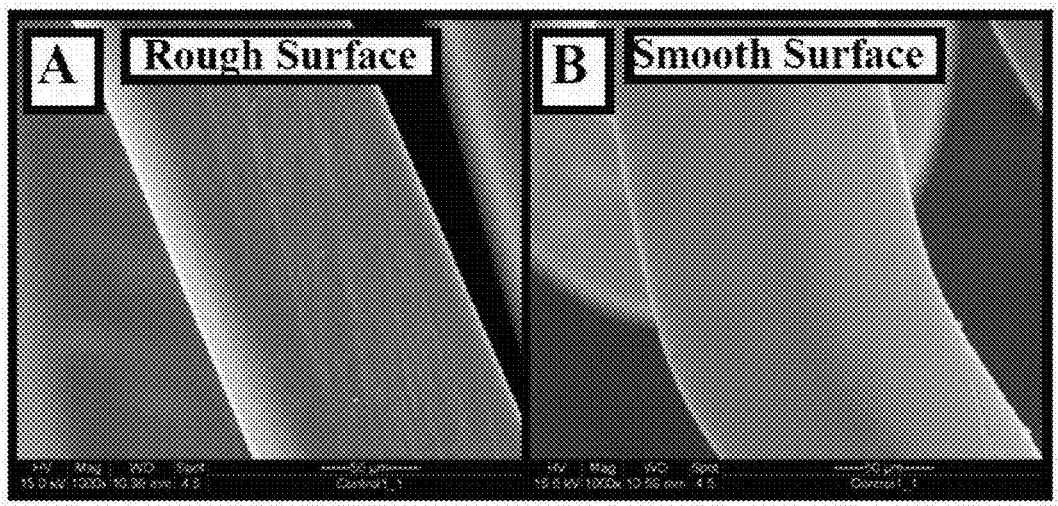
Figure 25A:
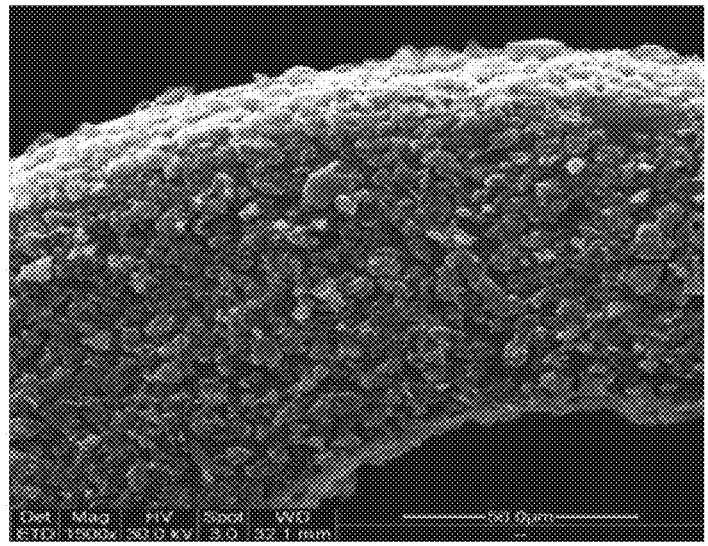
Figure 25B:
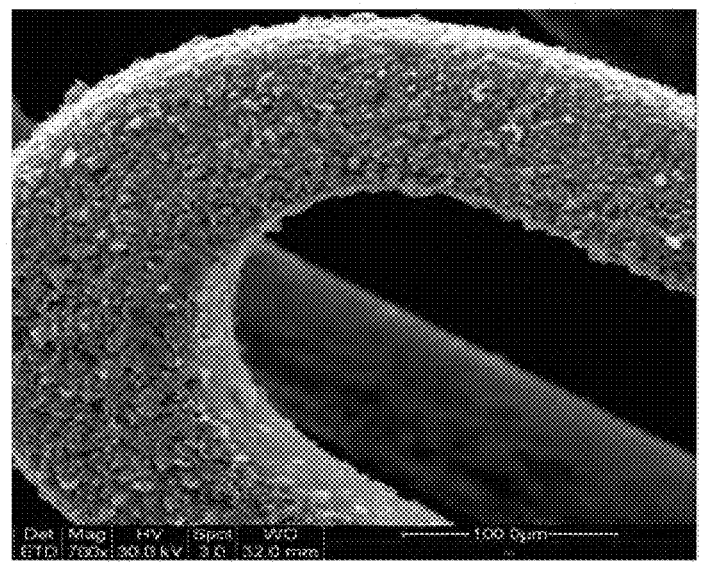
Figure 25C:
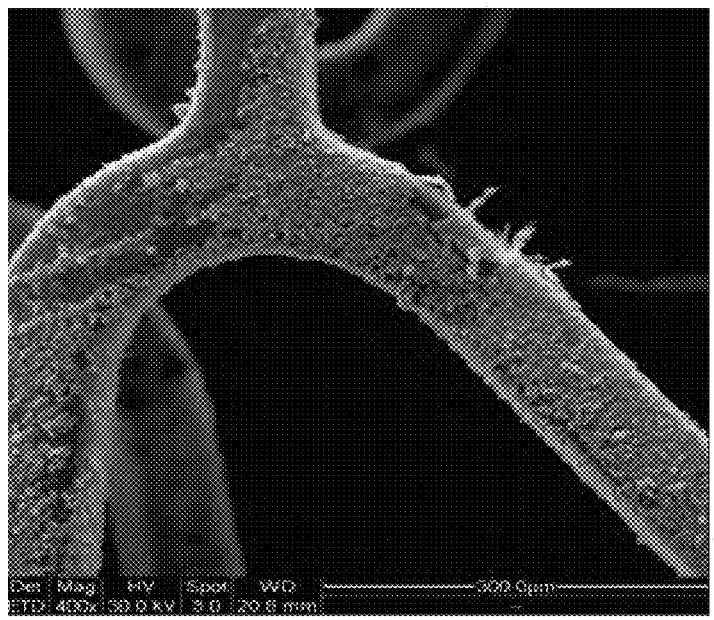
Figure 25D:
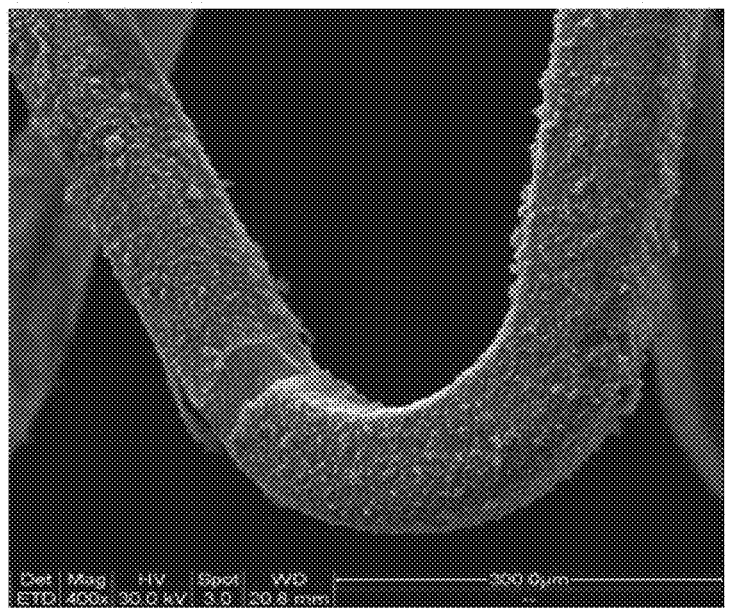
Figure 25E:
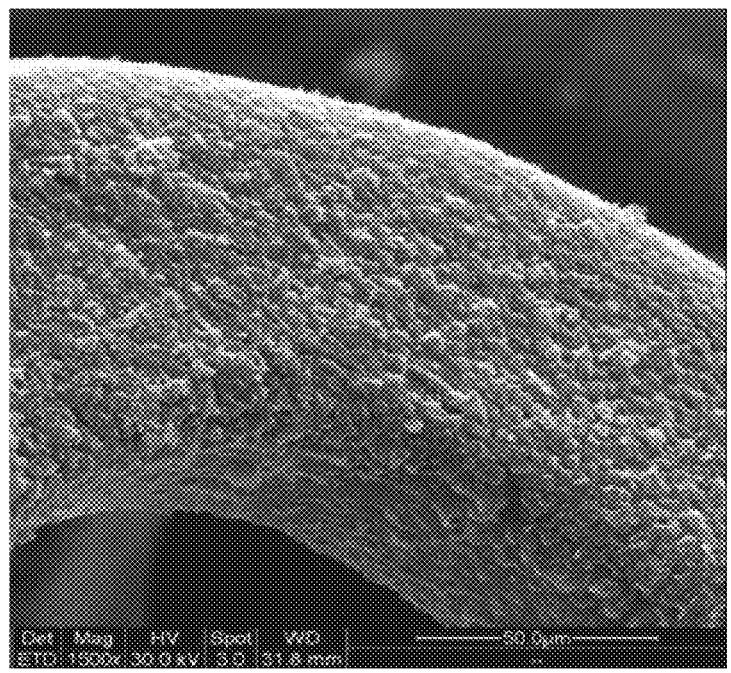
Figure 25F:
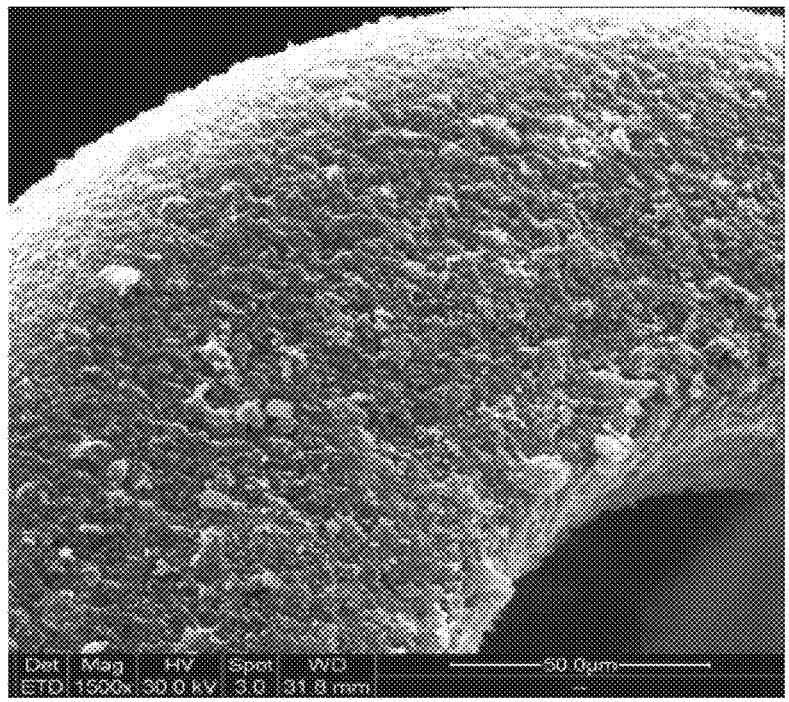
Figure 25G:
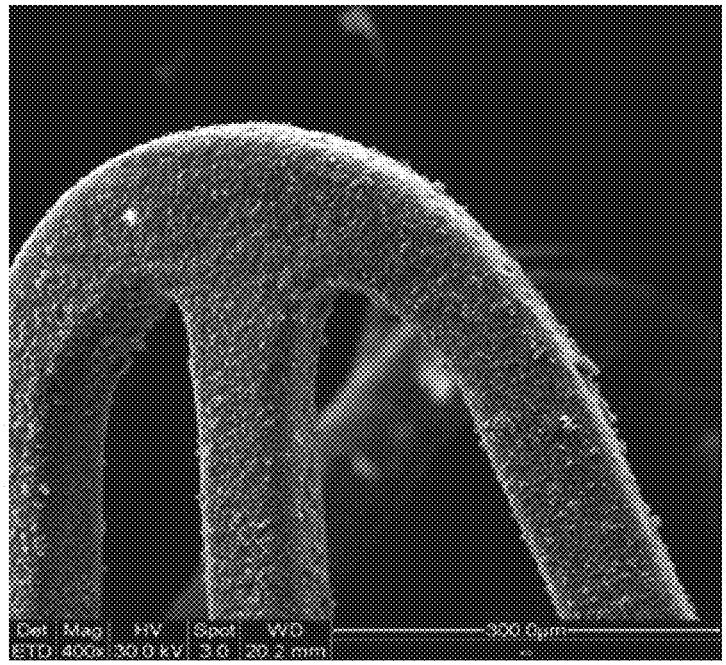
Figure 25H:
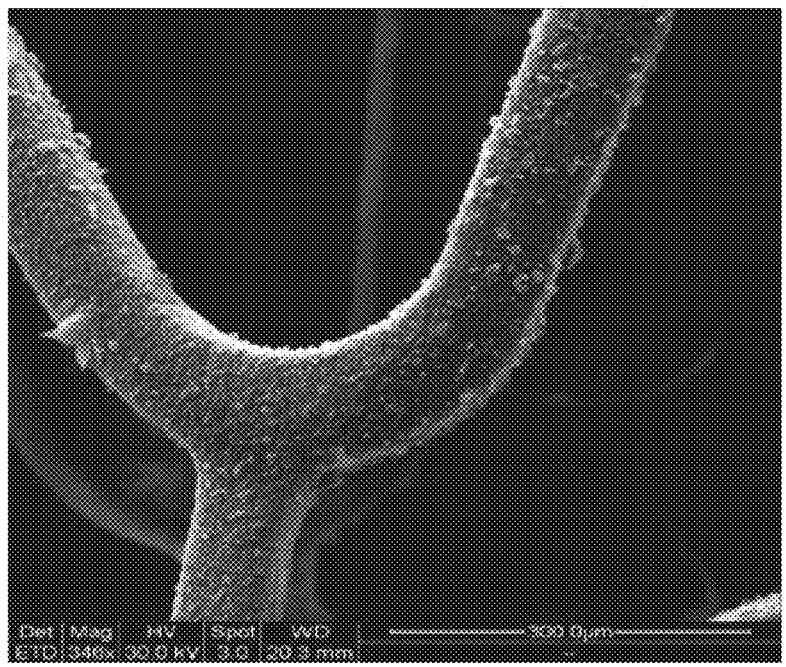
Figure 25I:
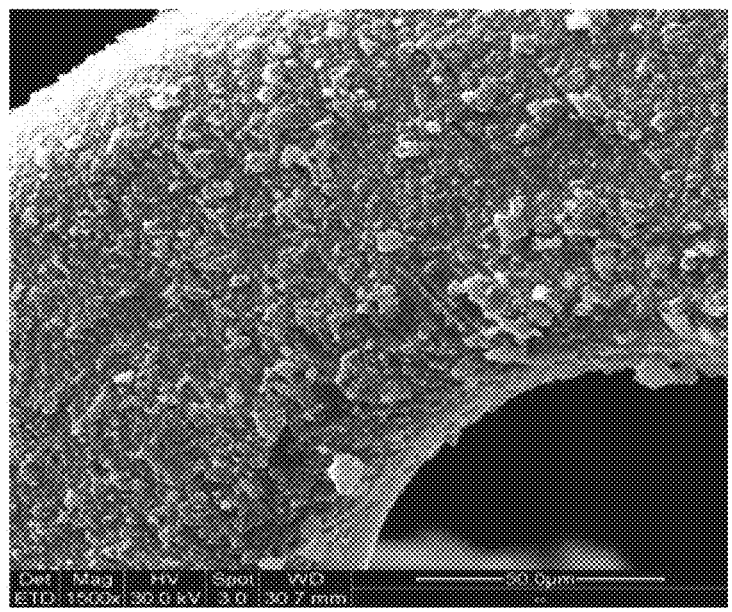
Figure 25J:
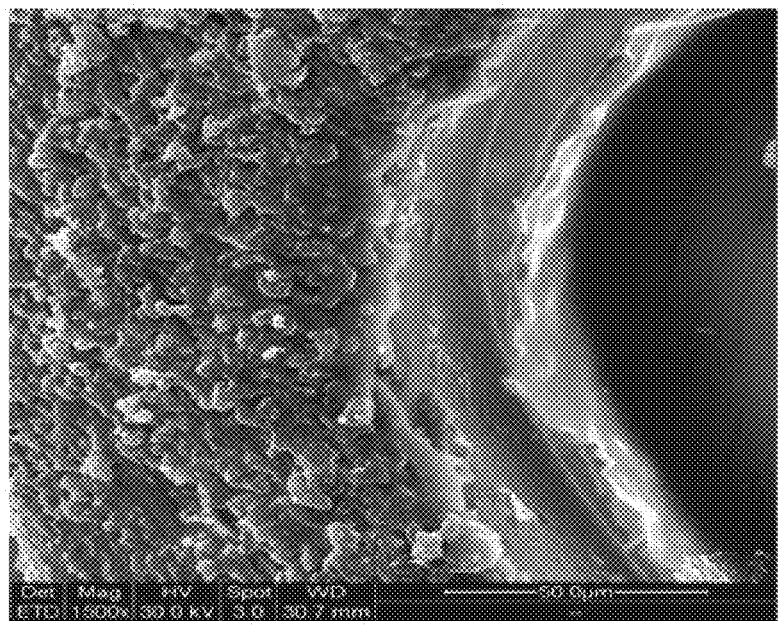
Figure 25K:
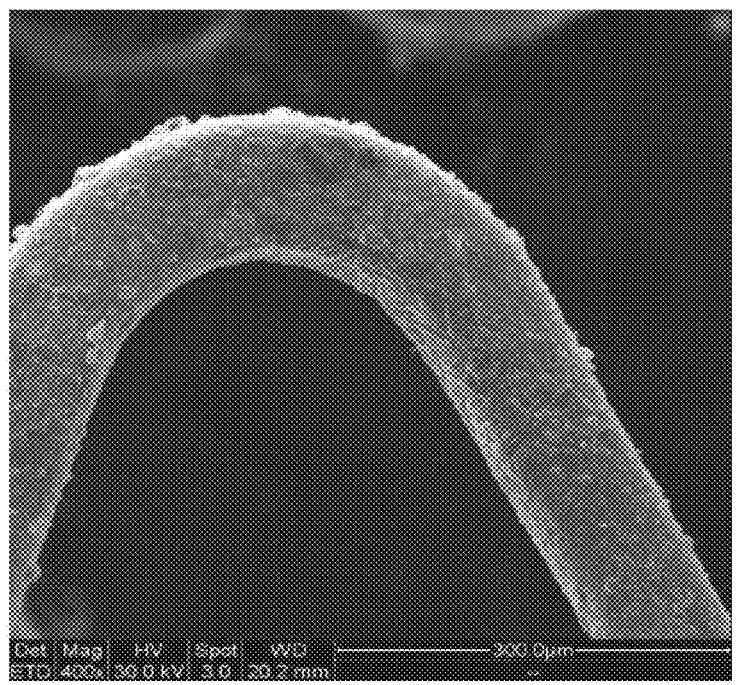
Figure 25L:
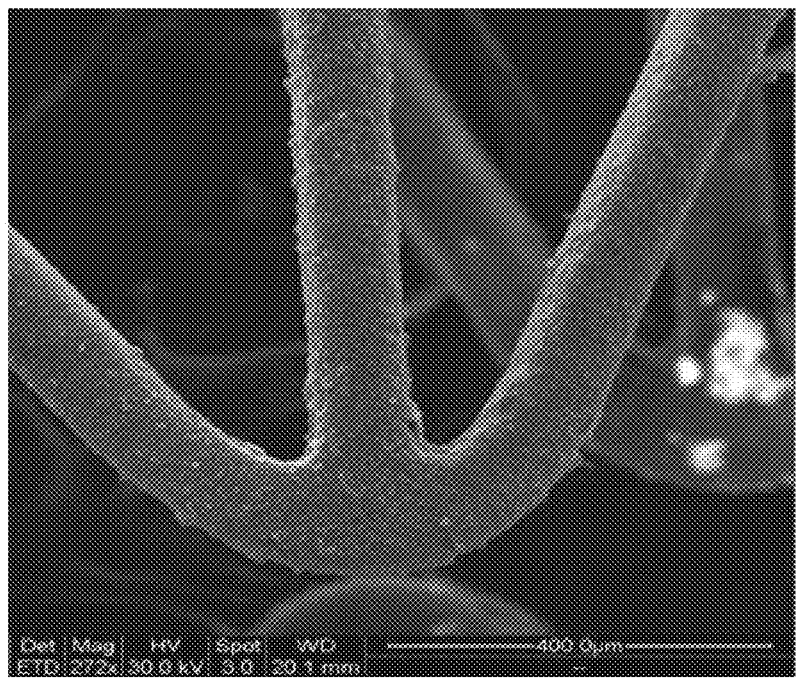
Figure 25M:
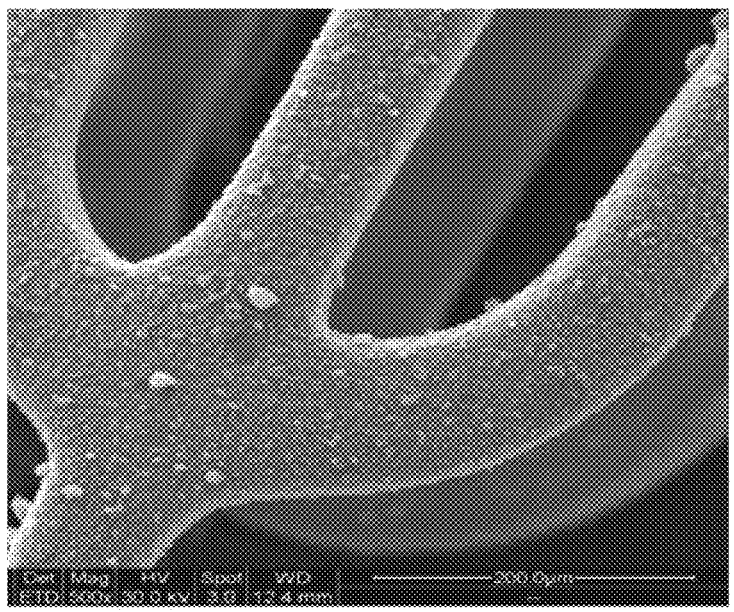
Figure 25N:
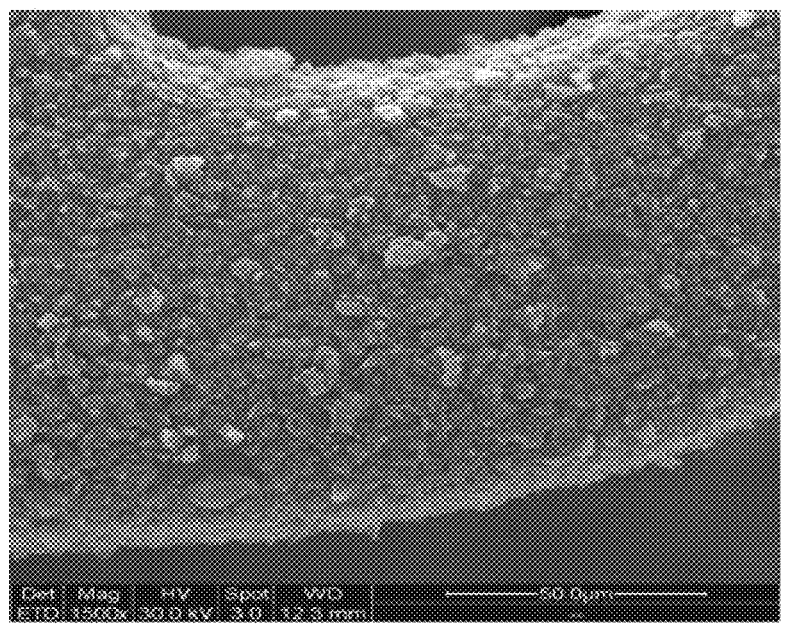
Figure 25O:
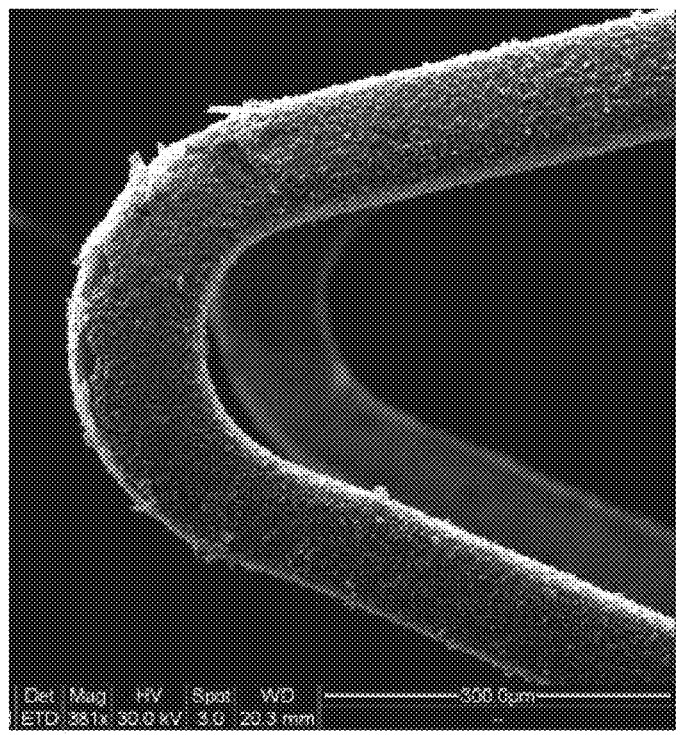
Figure 25P:
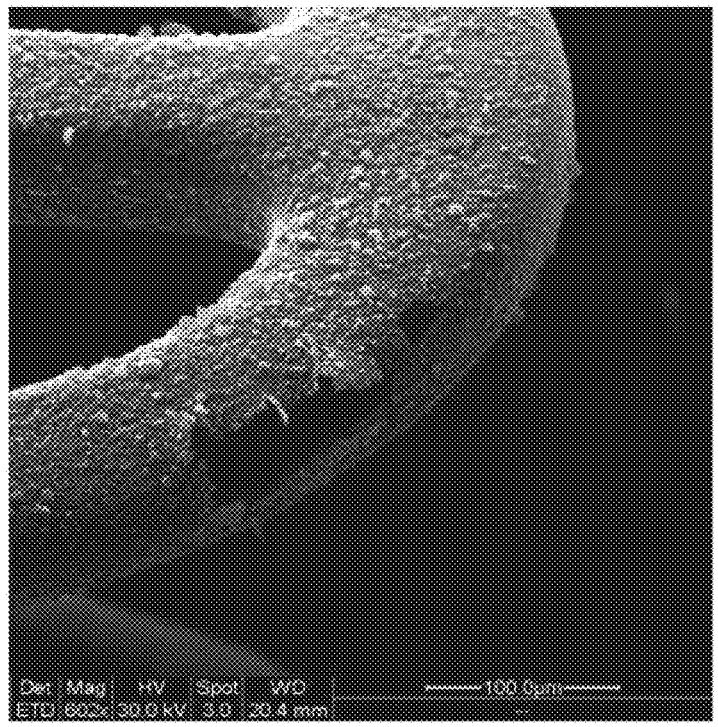
Figure 25Q:
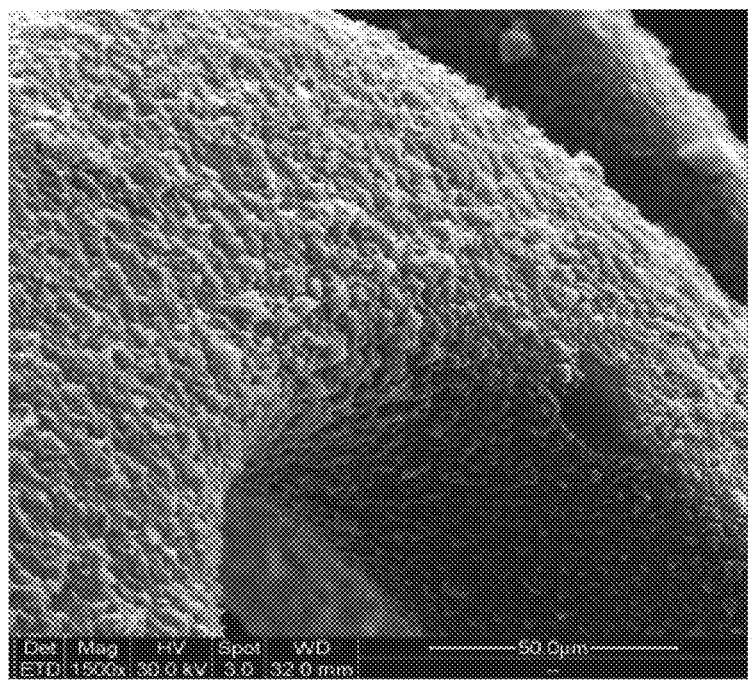
Figure 25R:
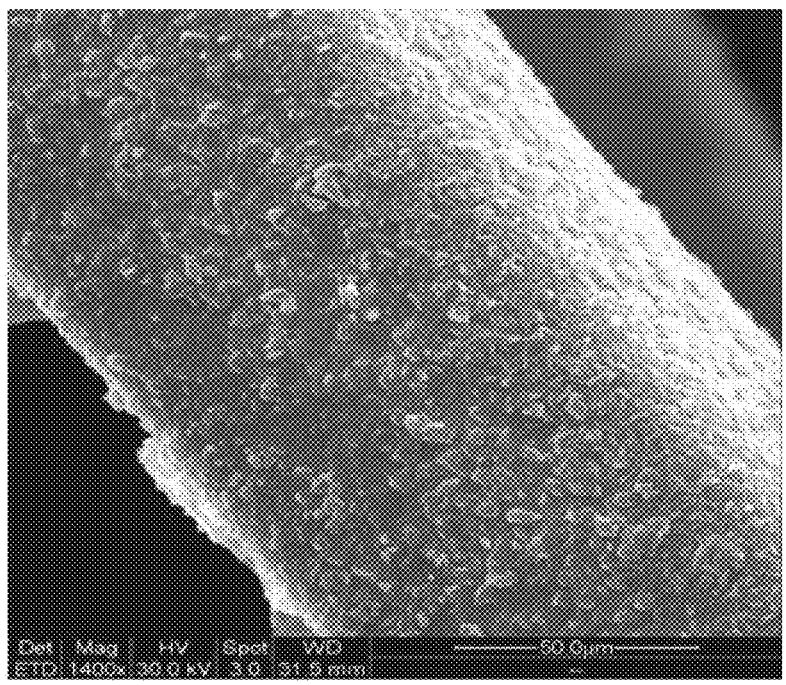
Figure 25S:
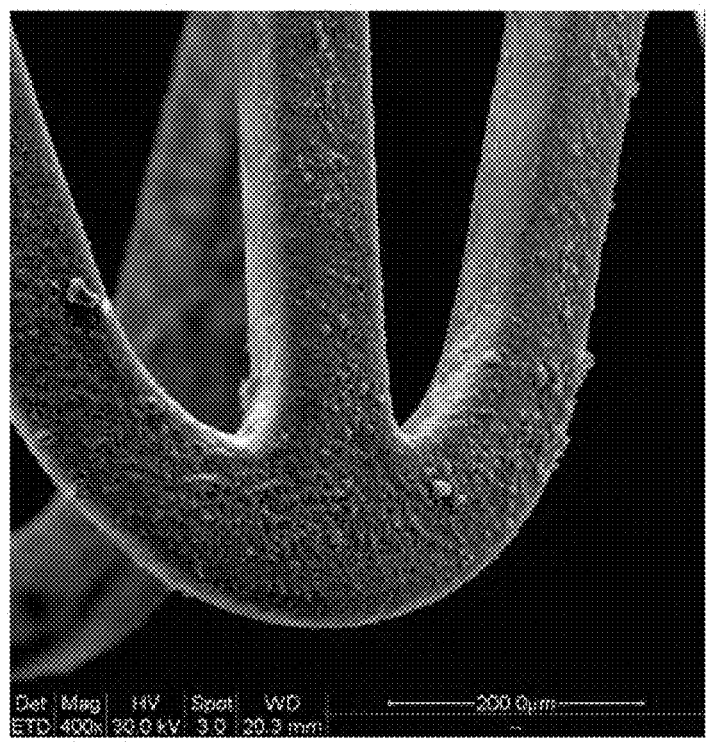
Figure 25T:
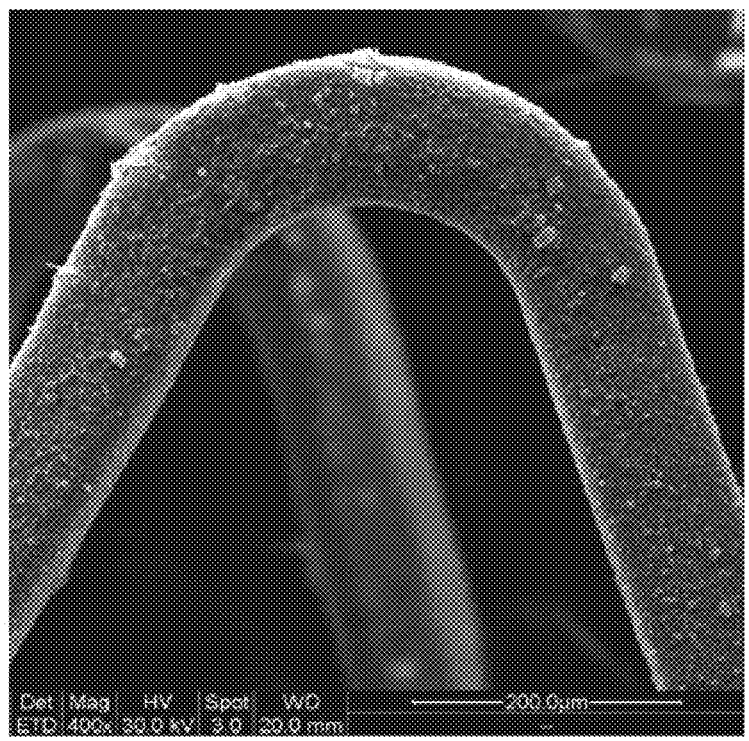
Figure 25U:
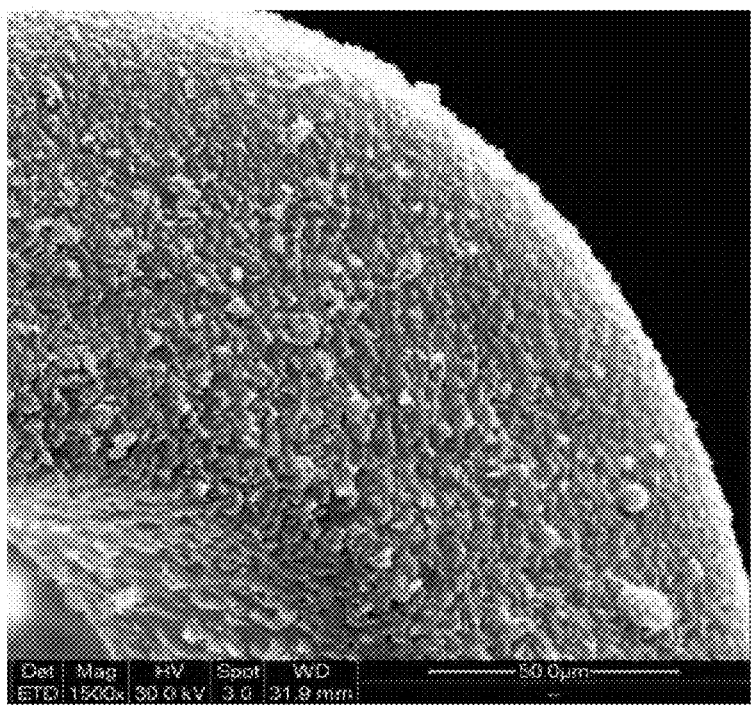
Figure 25V:
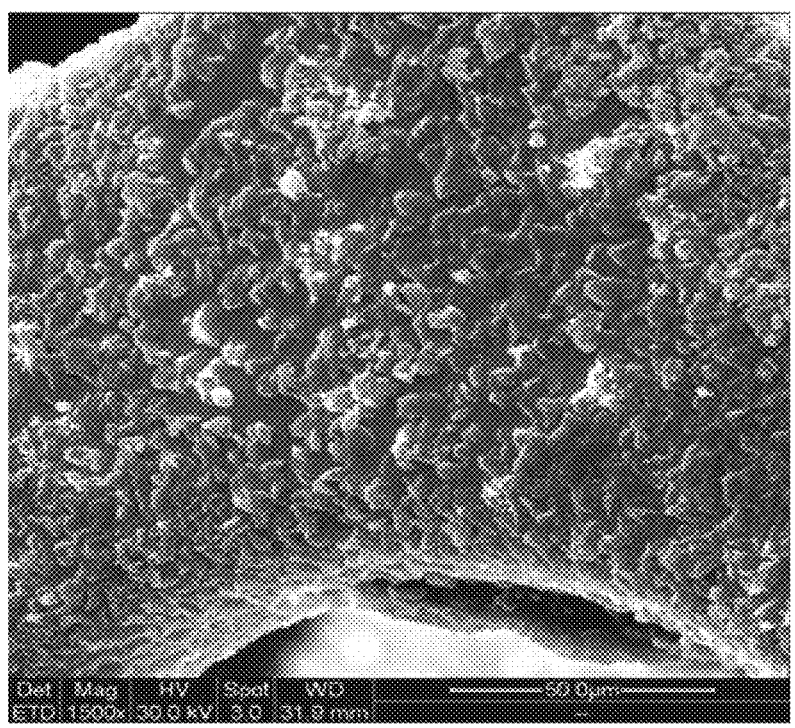
Figure 25W:
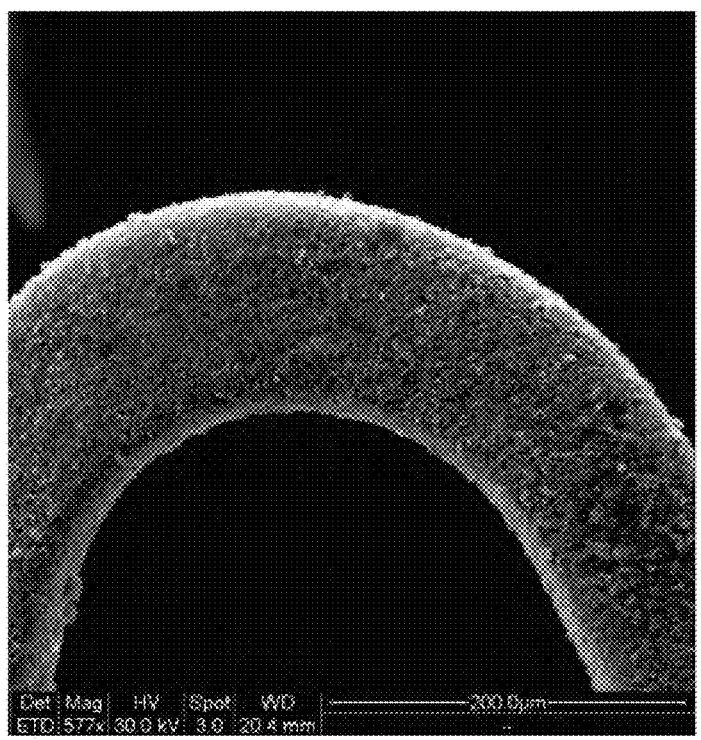
Figure 25X:
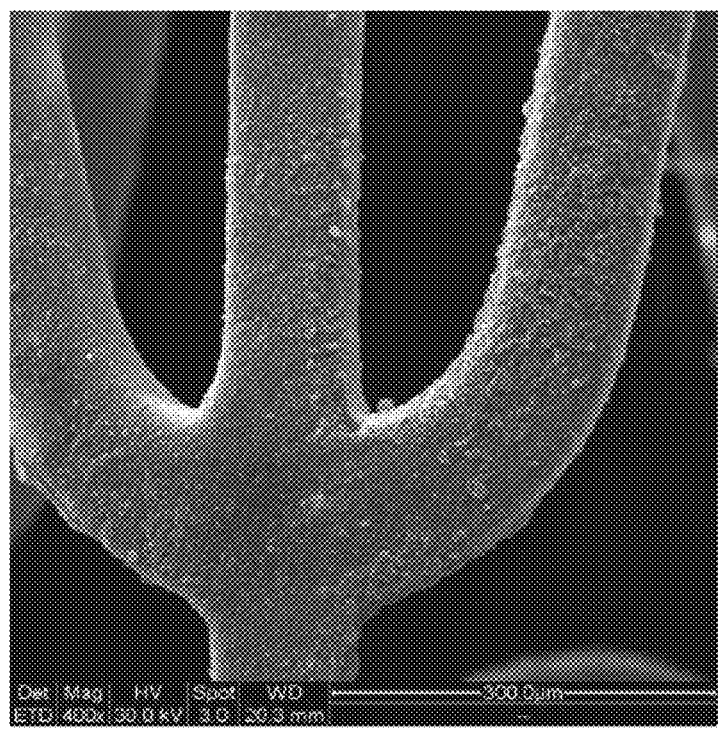
Figure 26A:
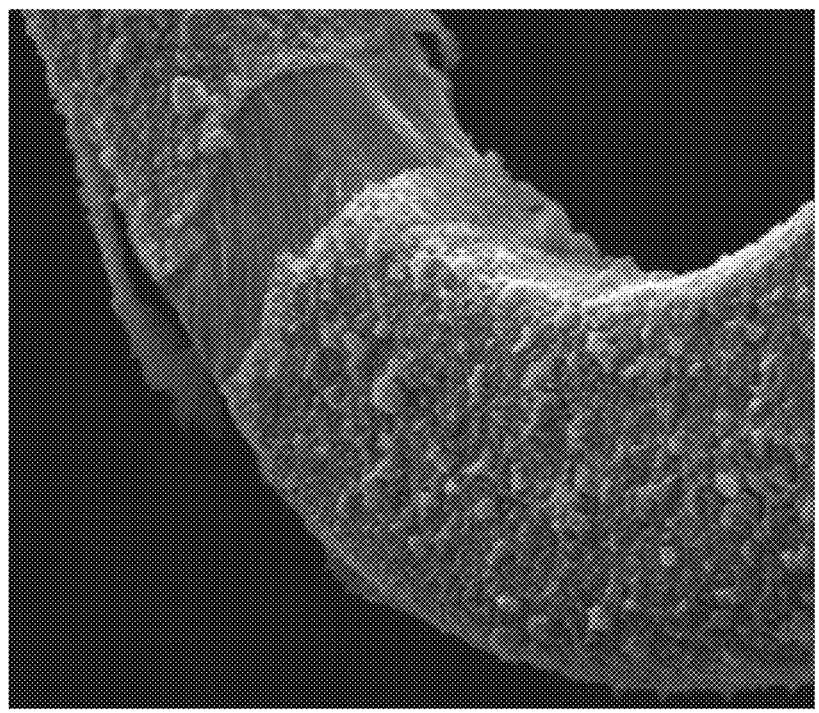
Figure 26B:
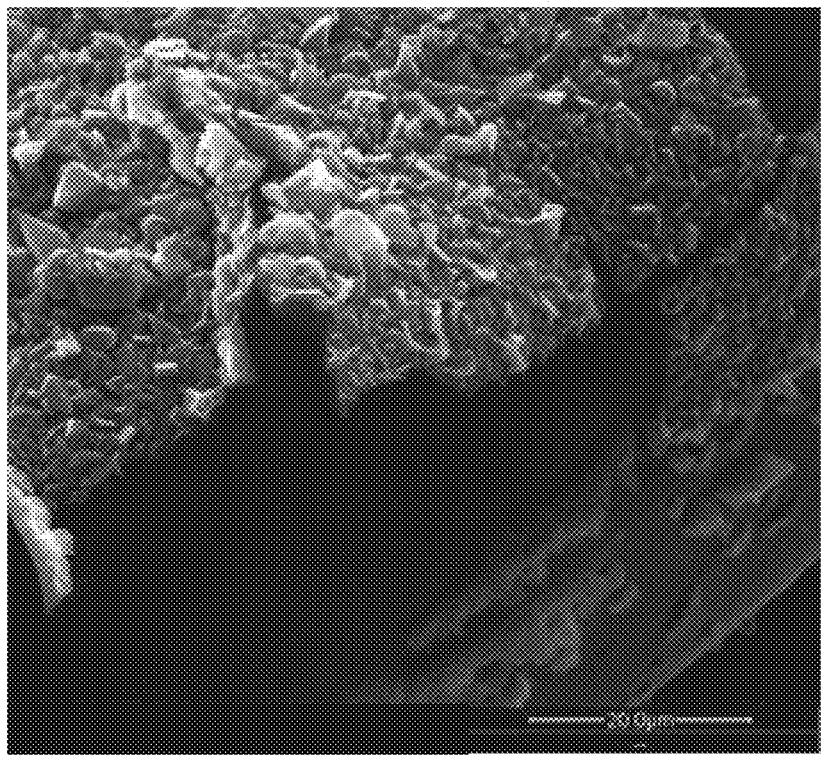
Figure 27:
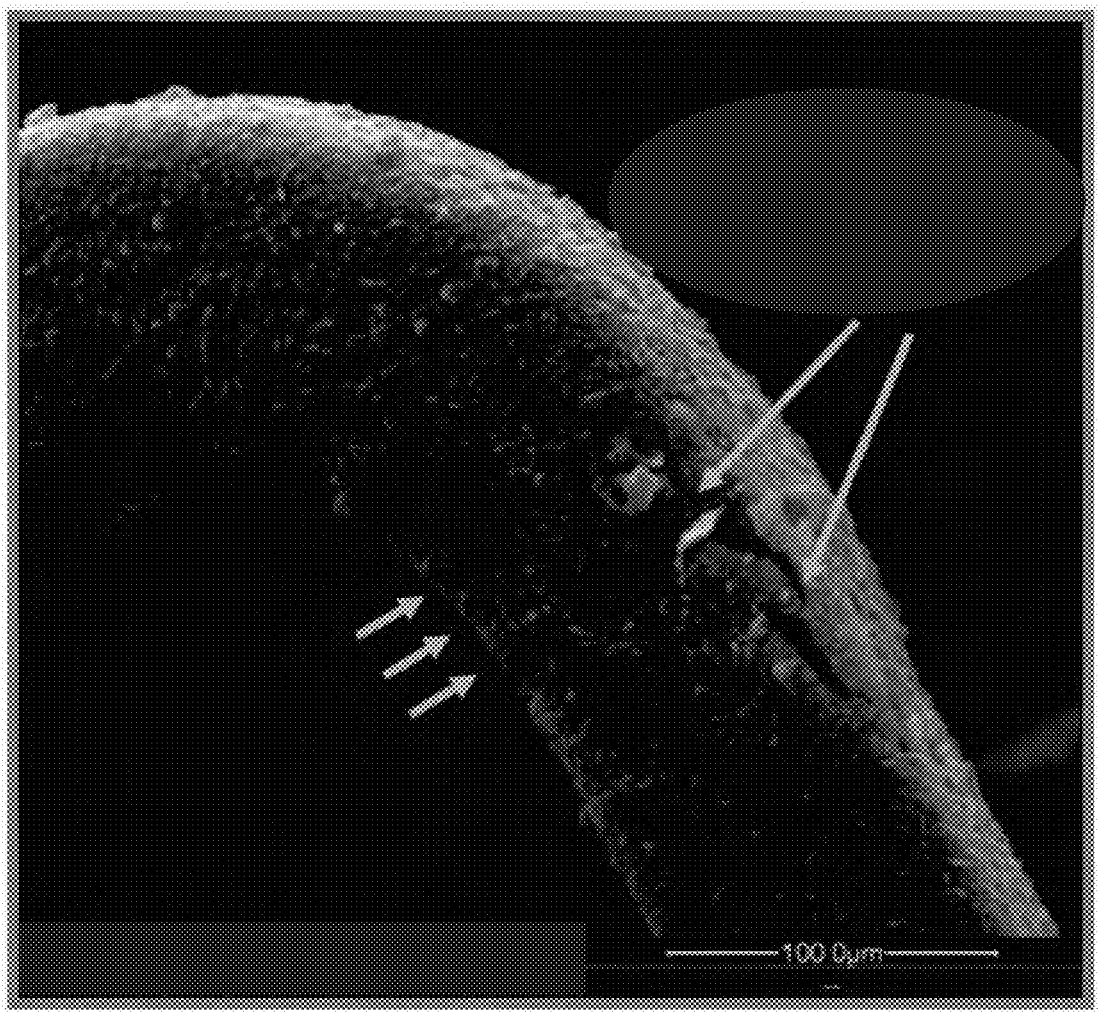
Figure 28A:
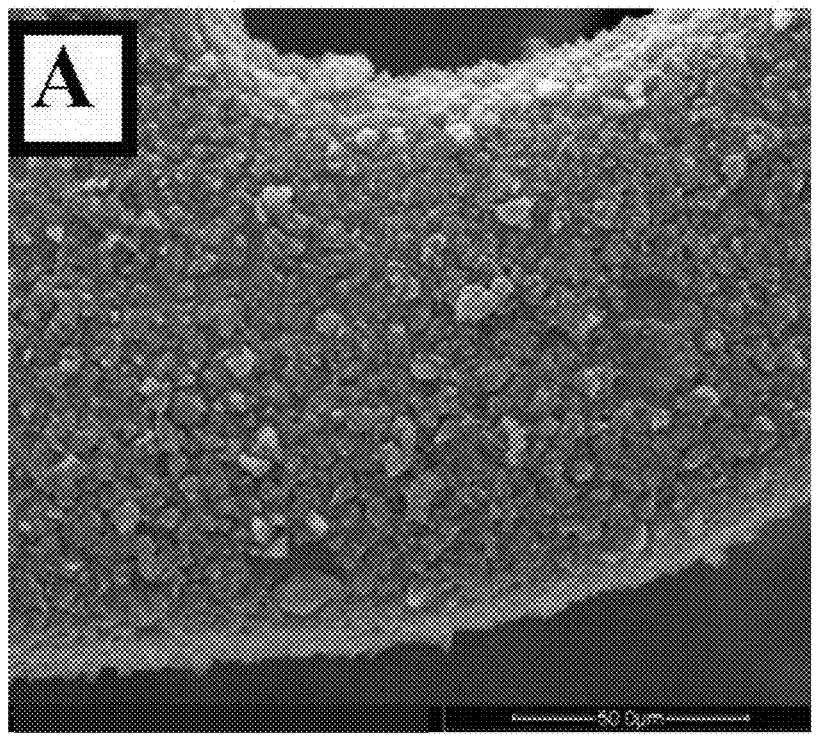
Figure 28B:
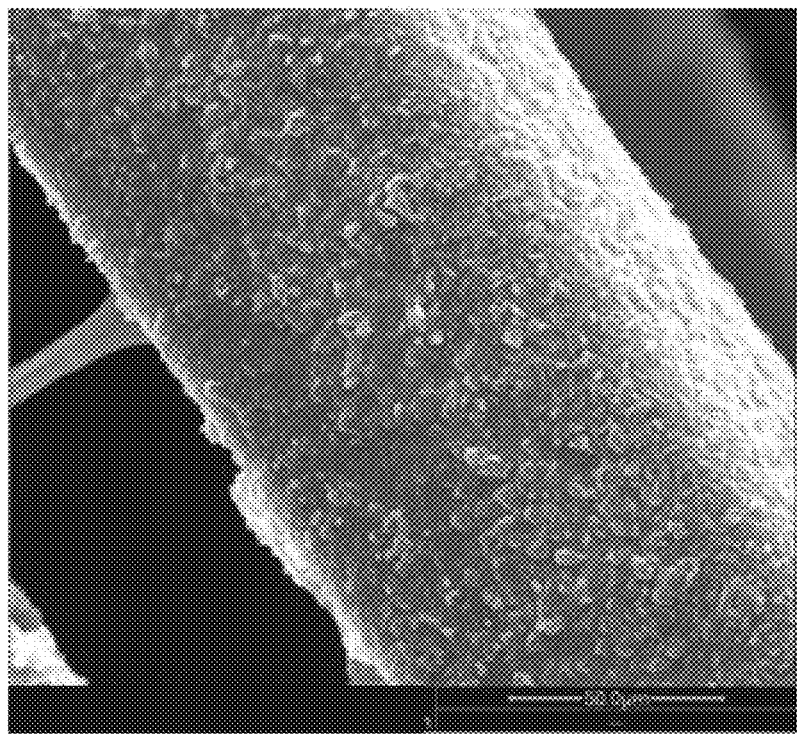
Figure 28C:
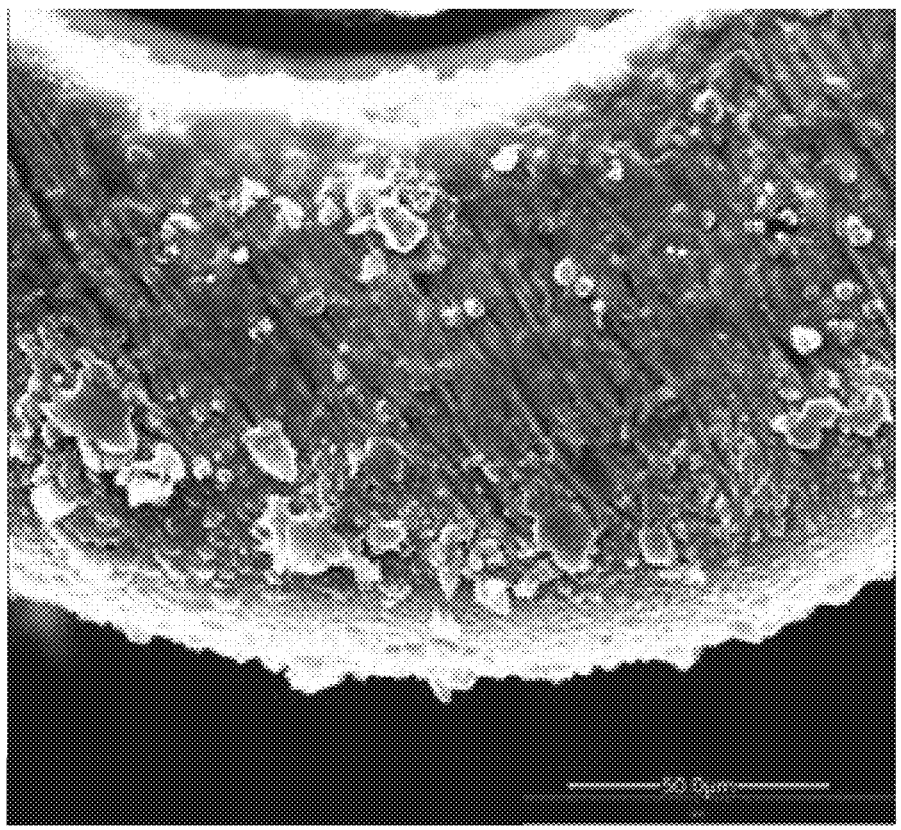
Figures 29A, 29B:
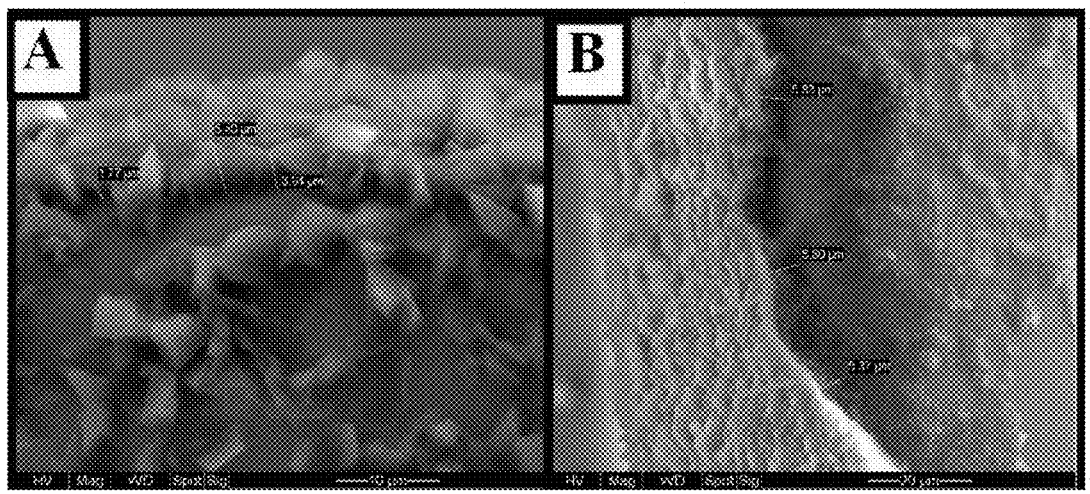
Figure 31A:
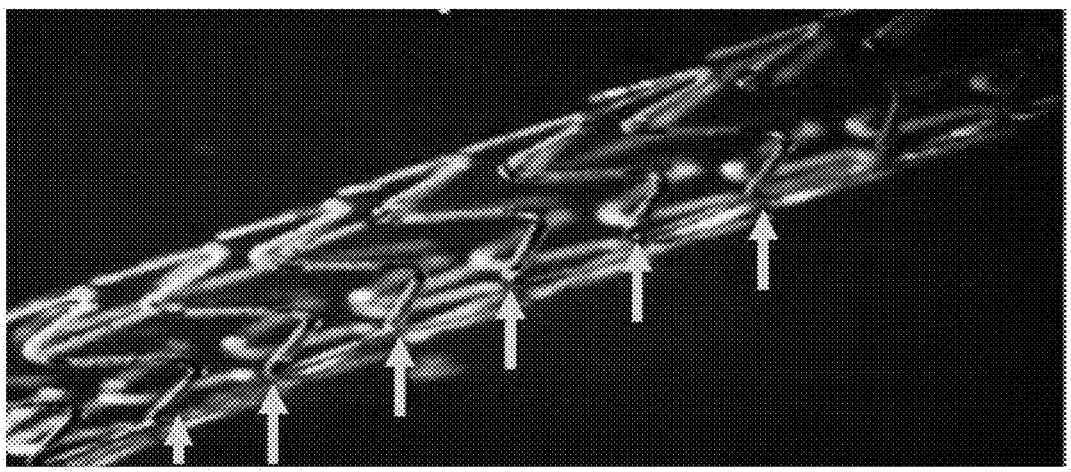
Figure 31B:
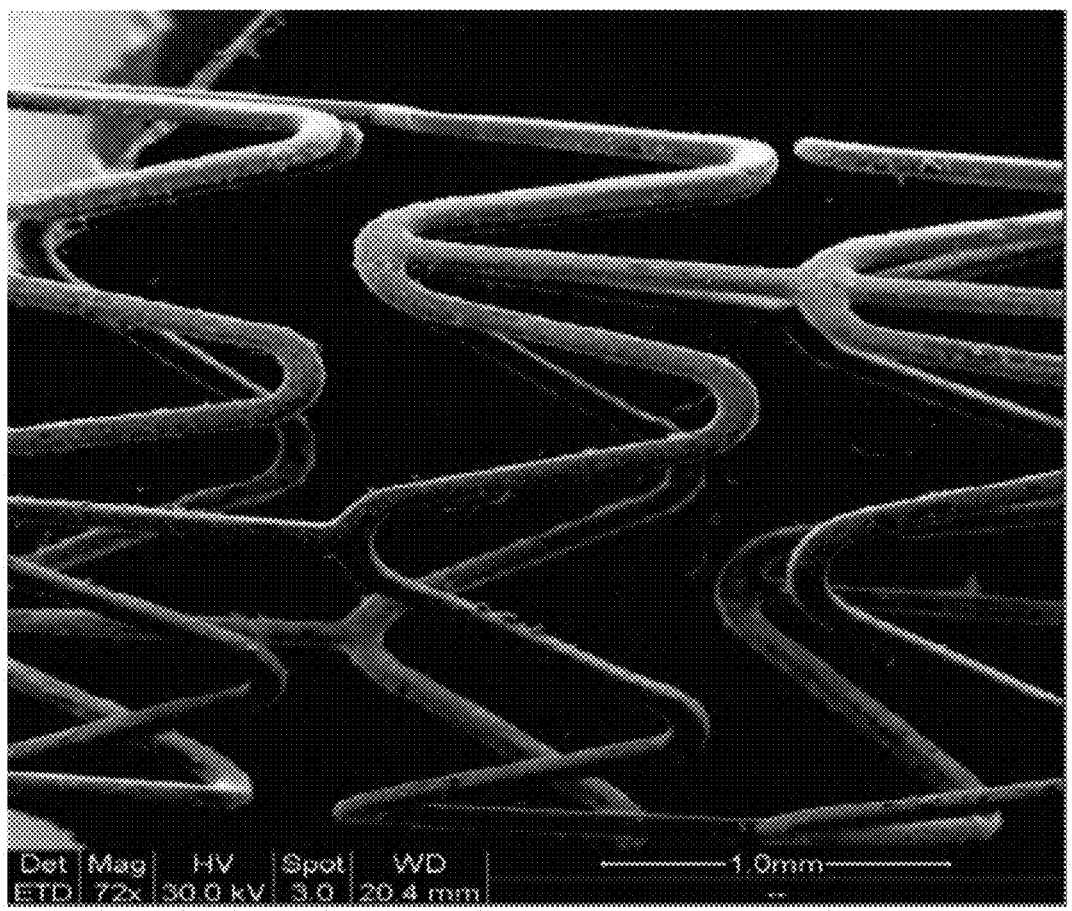
Figure 32A:
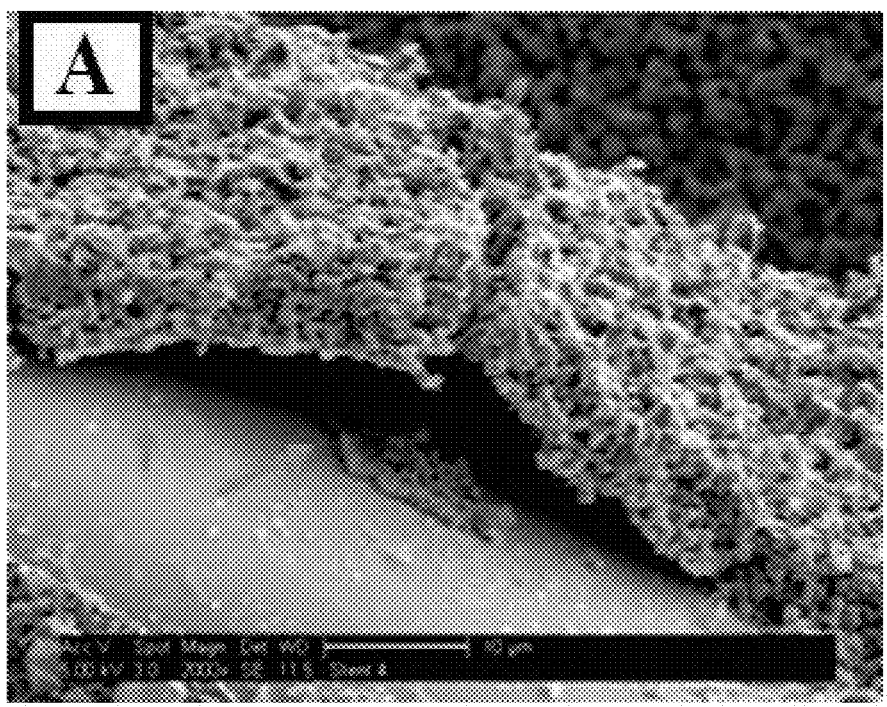
Figure 32B:
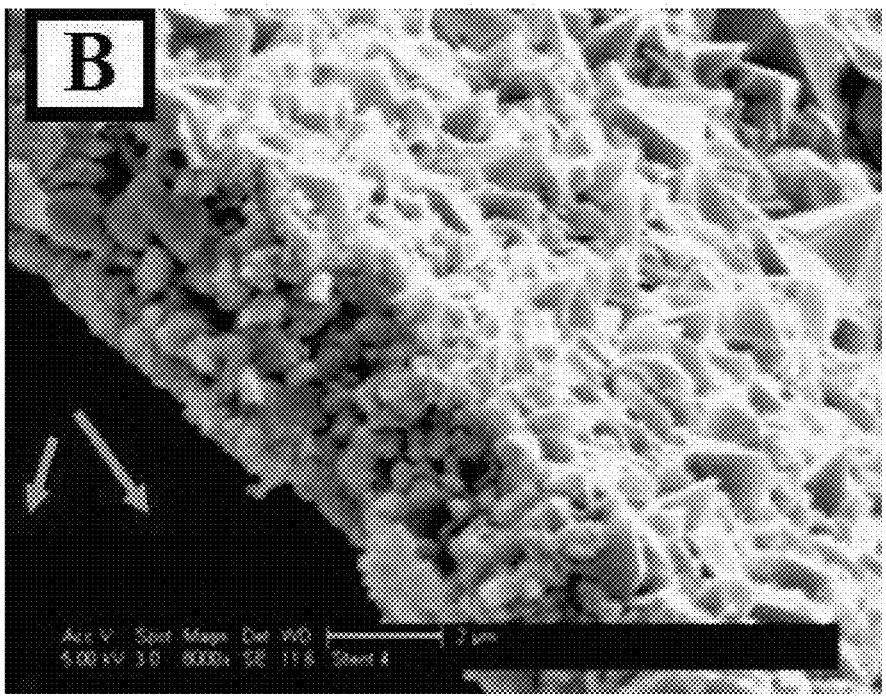
Figure 32C:
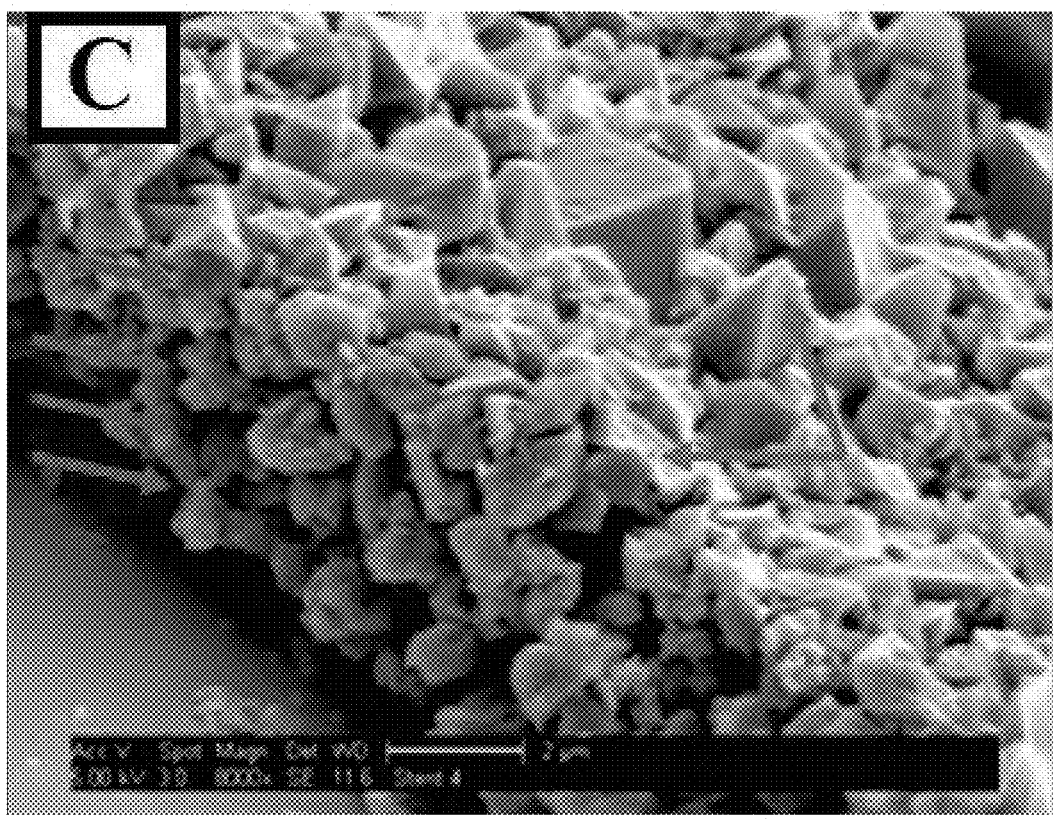
Figure 33A:
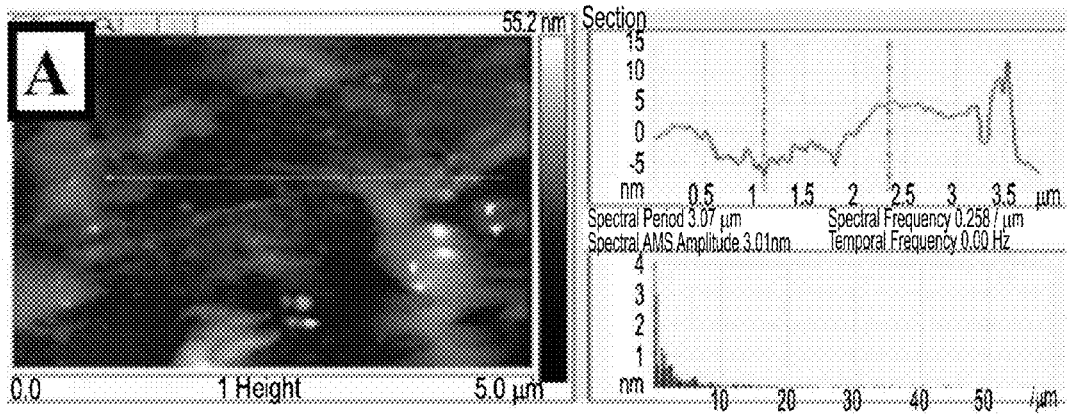
Figure 33B:
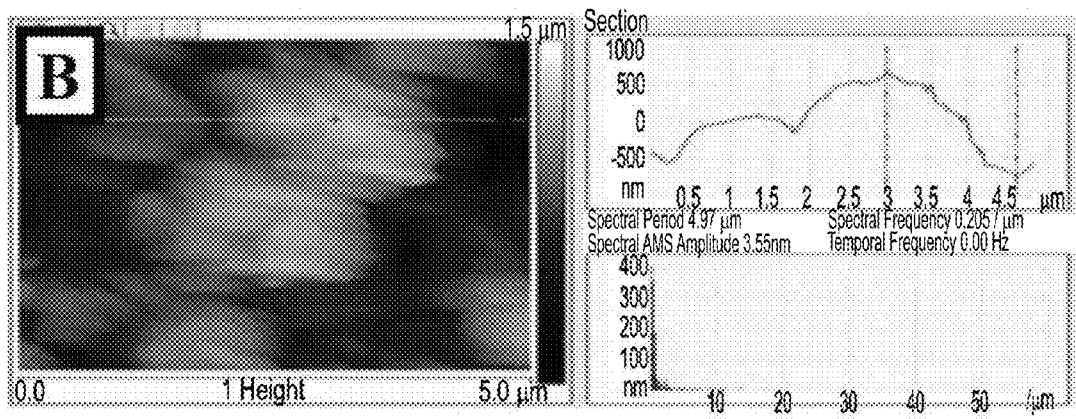
Figure 33C:
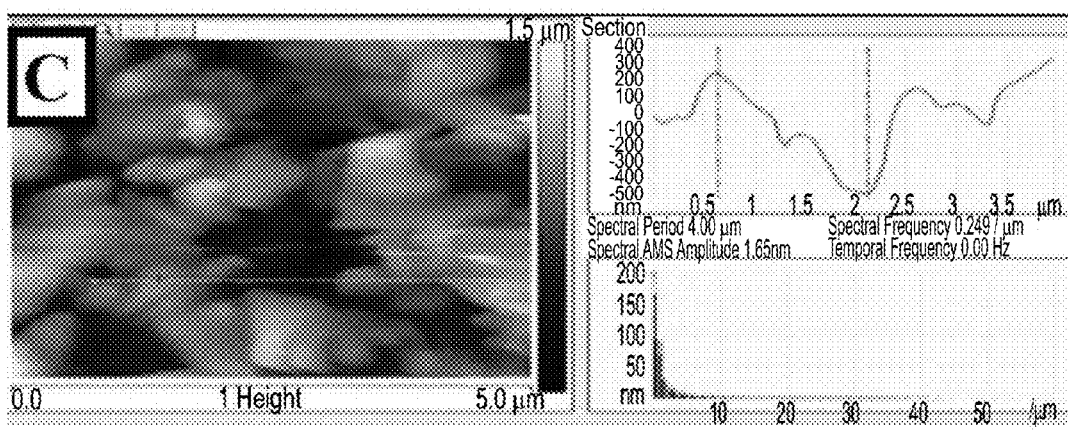
Figure 33D:
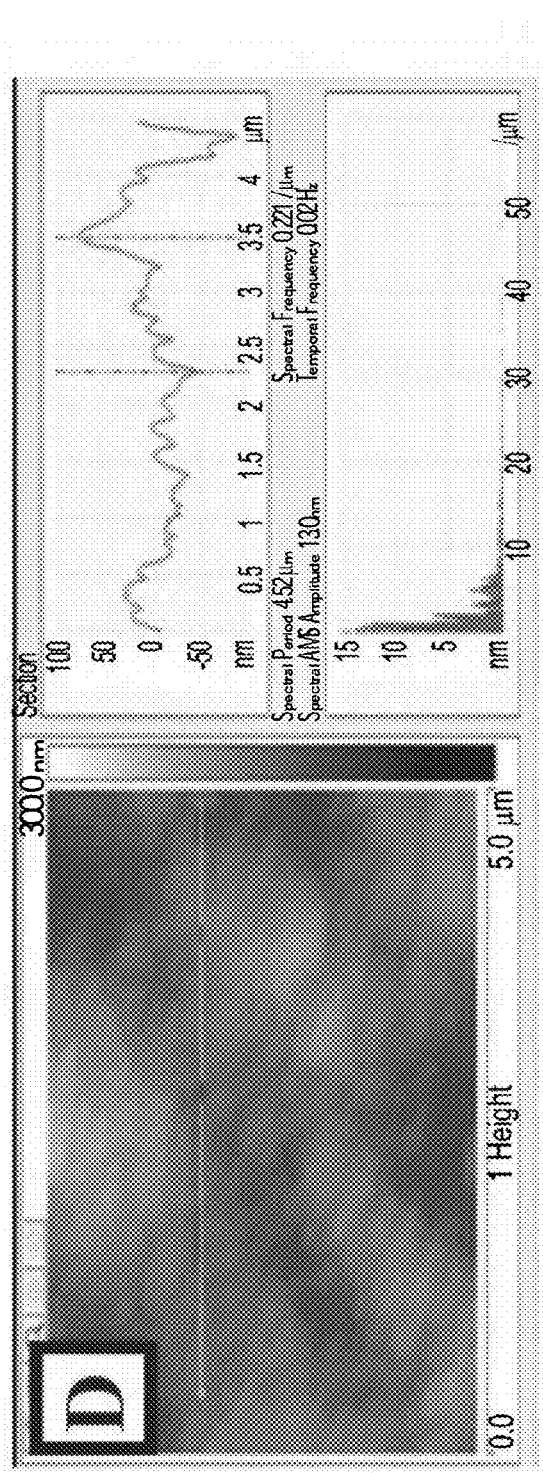
Figure 34:
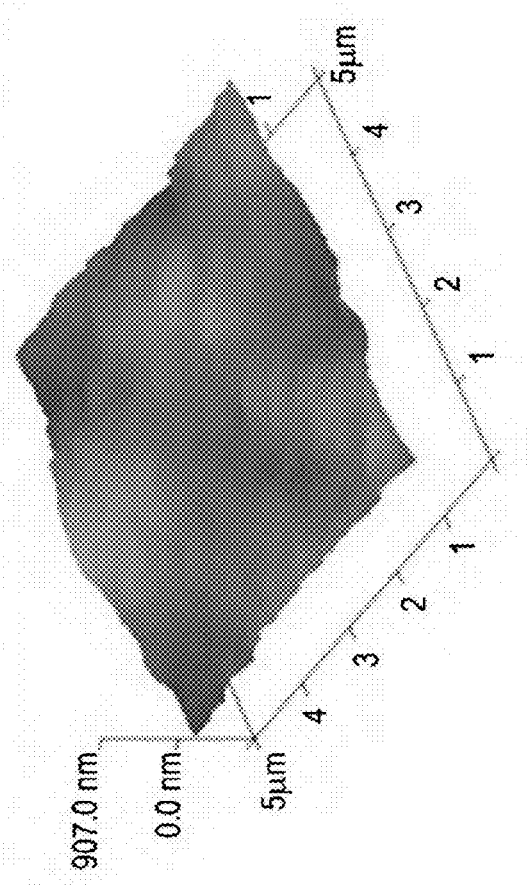
Figure 35:
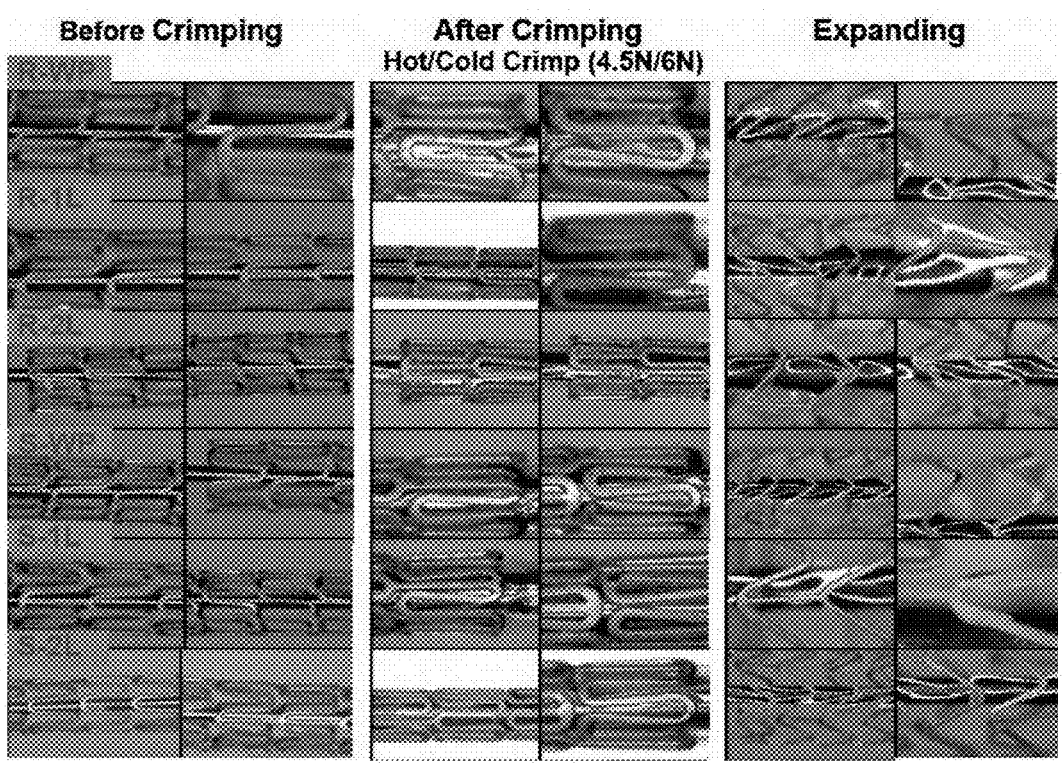
Figure 37A:
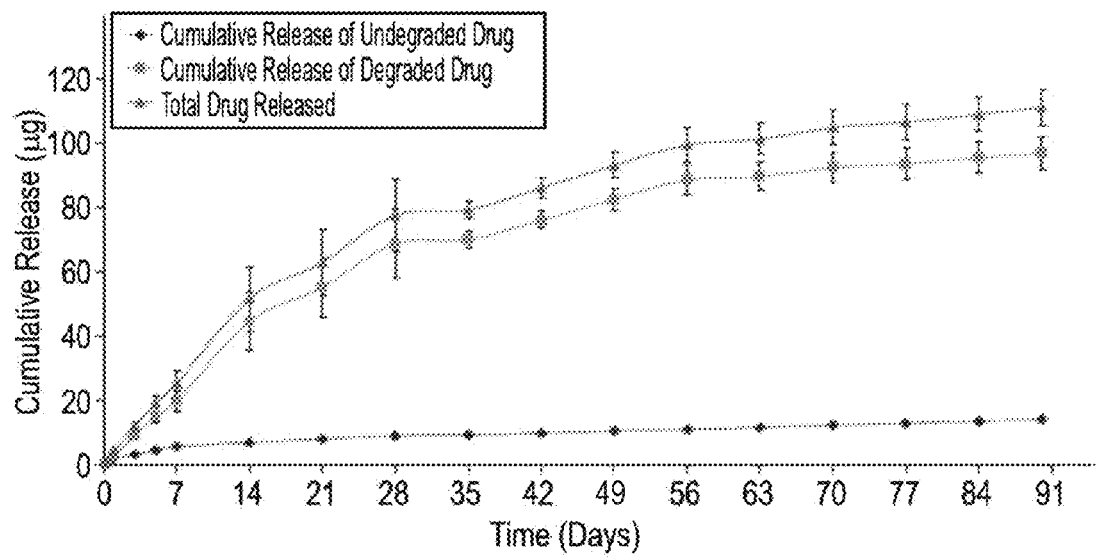
Figure 37B:
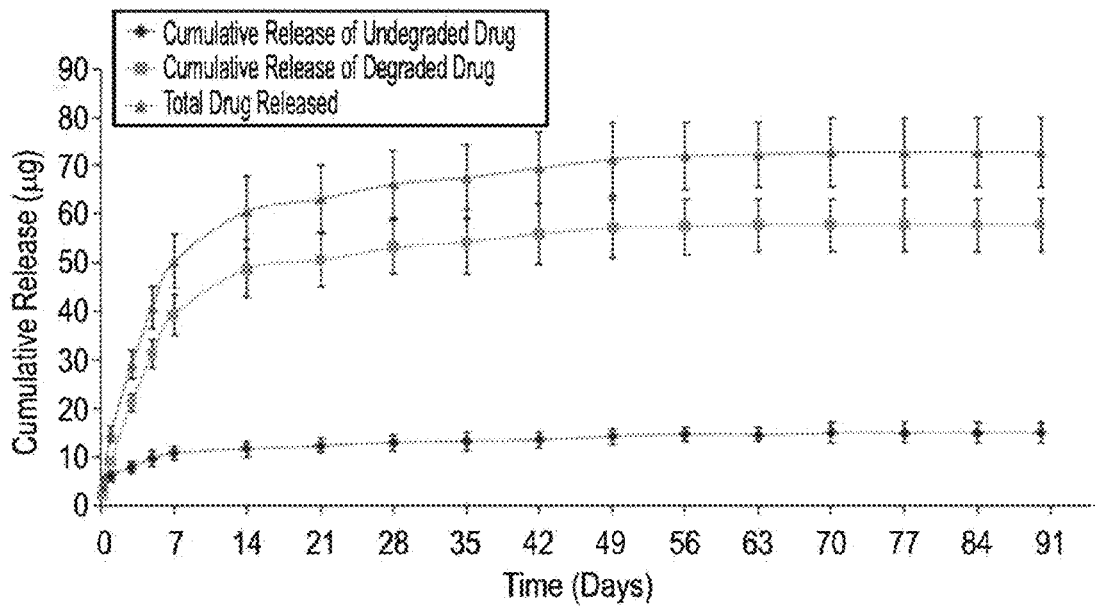
Figure 37C:
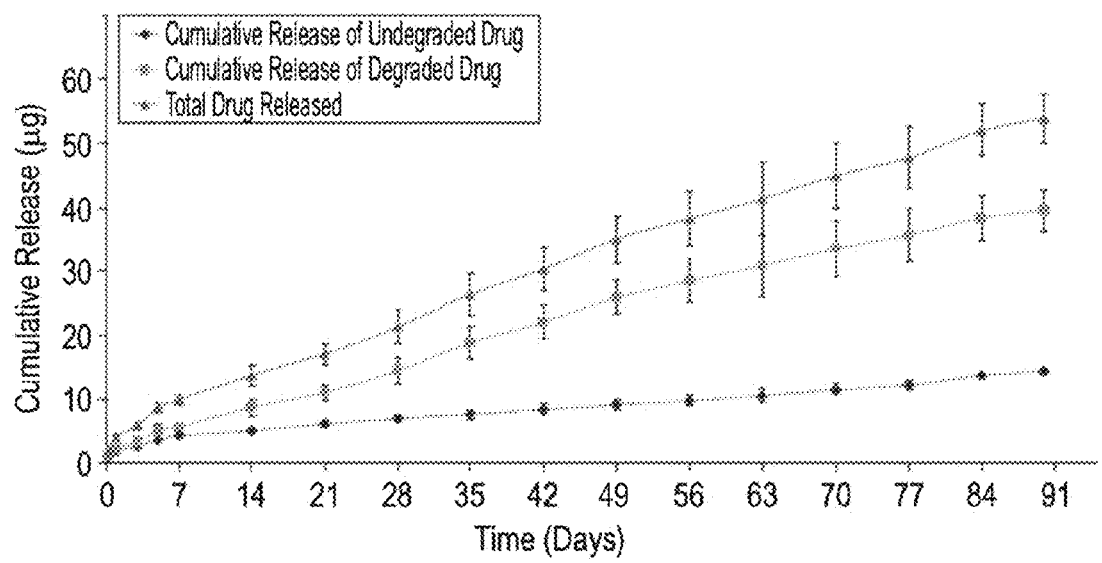
Figure 38A:
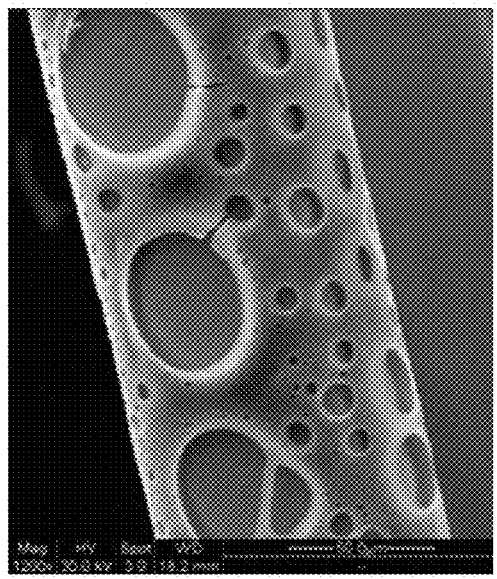
Figures 38B, 38C:
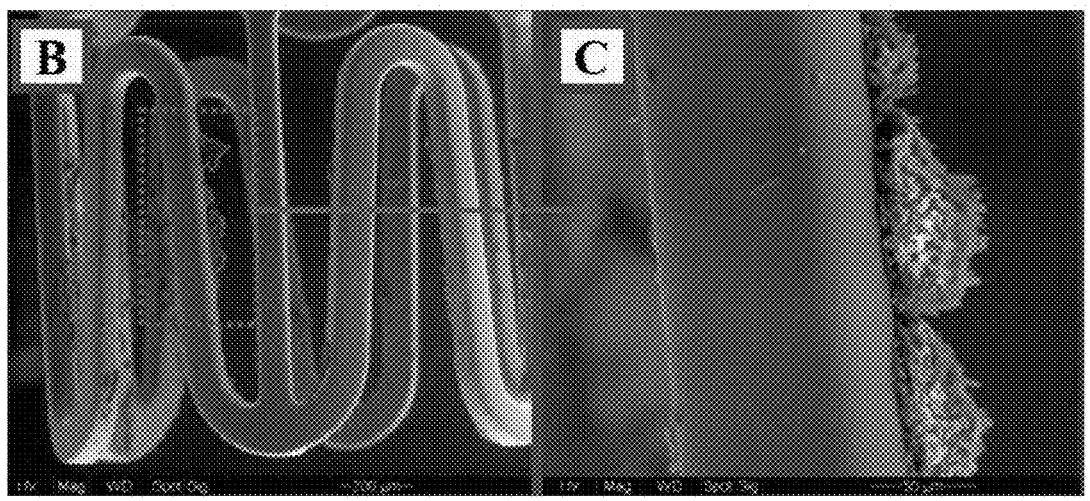
Figure 39:
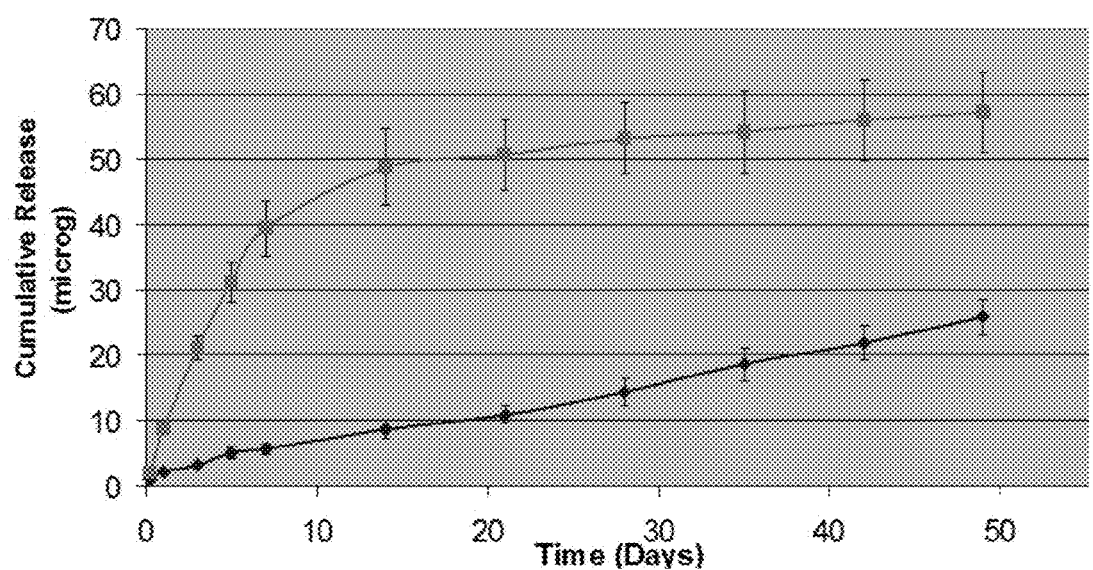
Figures 40A, 40B, 40C, 40D, 40E, 40F:
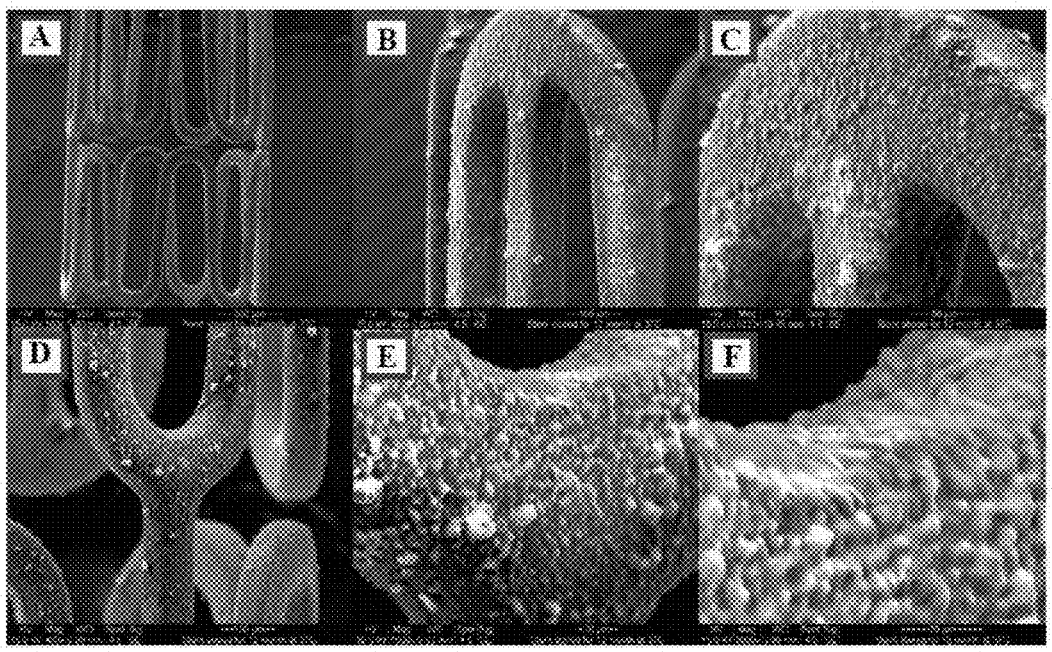
Figure 44A:
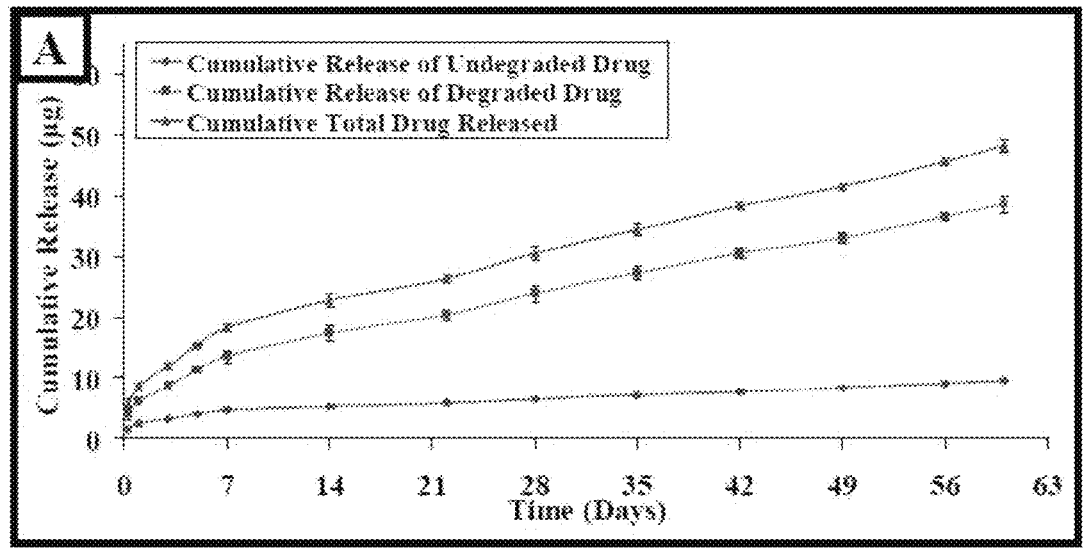
Figure 44B:
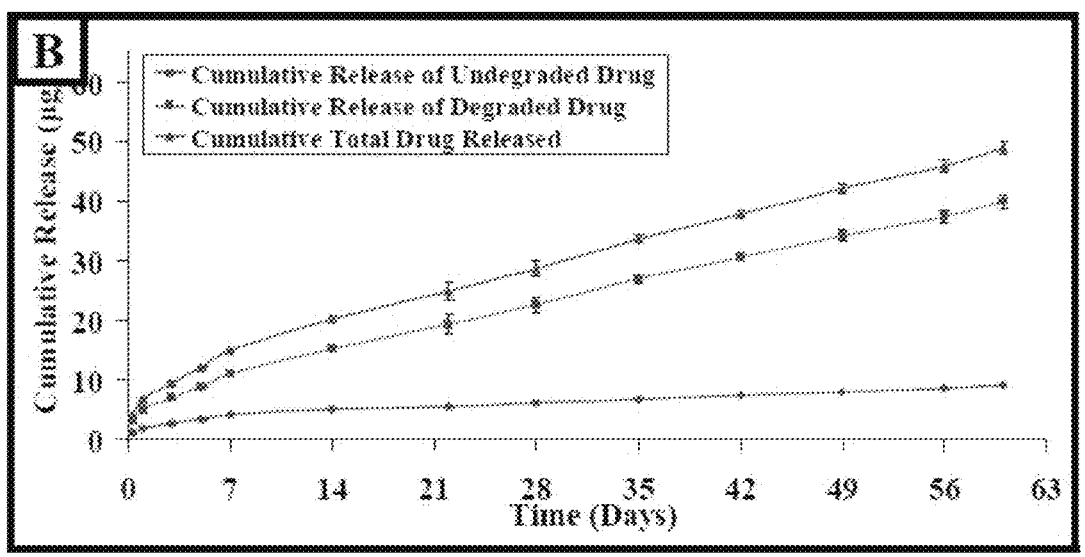
Figure 44C:
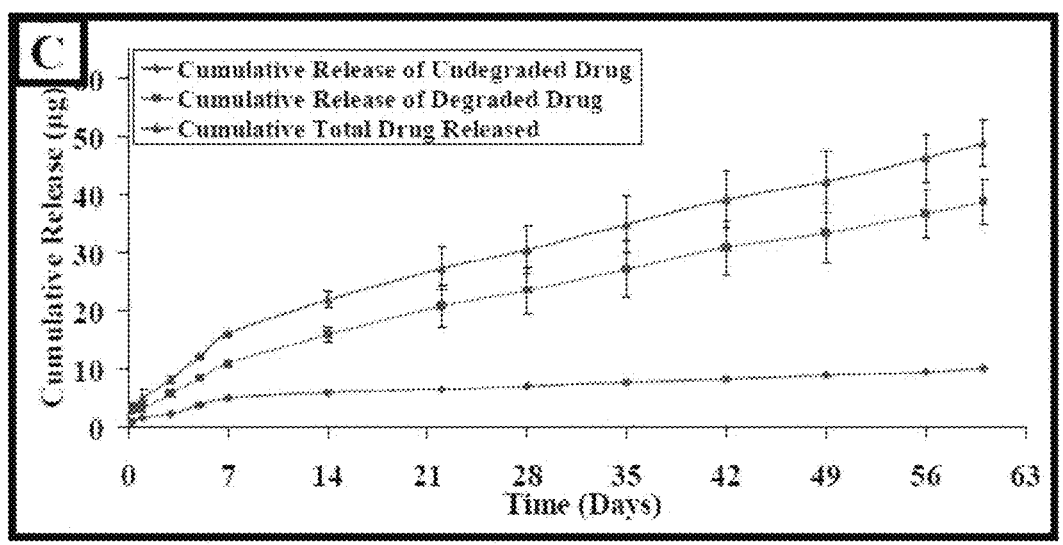
Figure 45:
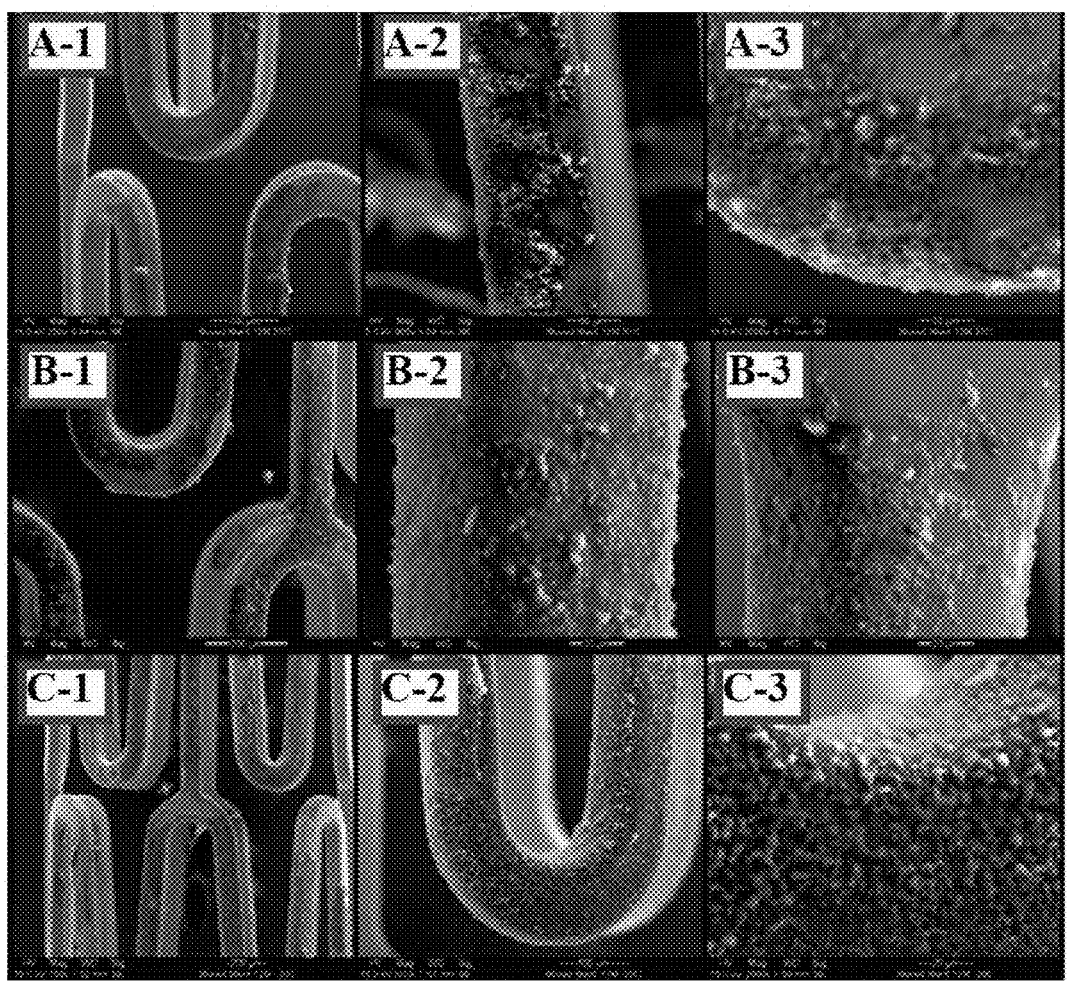
Figure 46A:
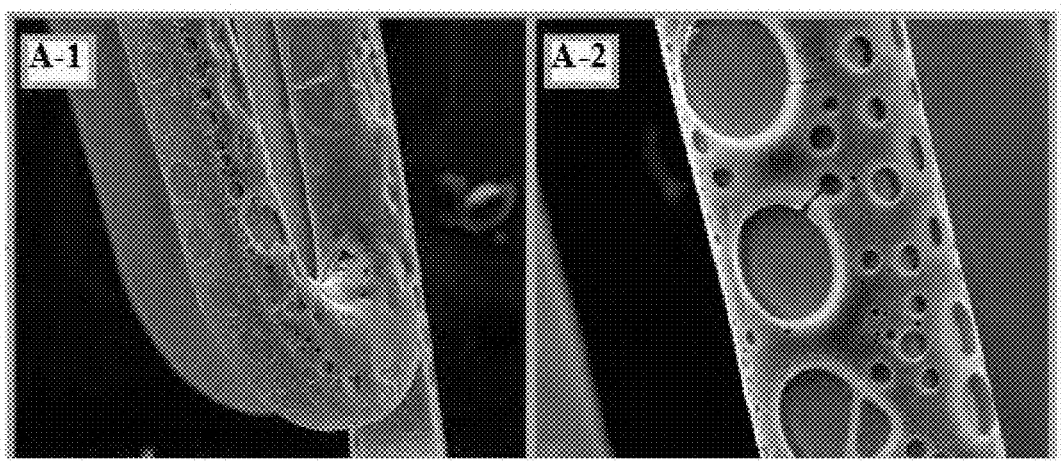
Figure 46B:
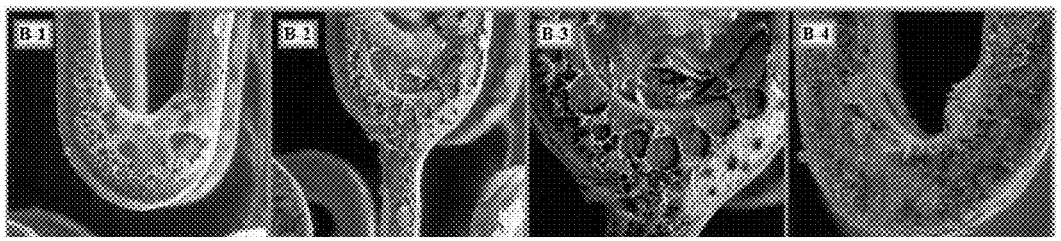
Figure 46C:
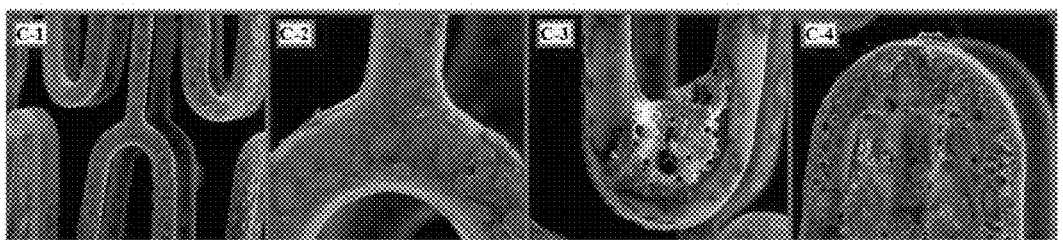
Figure 47A:
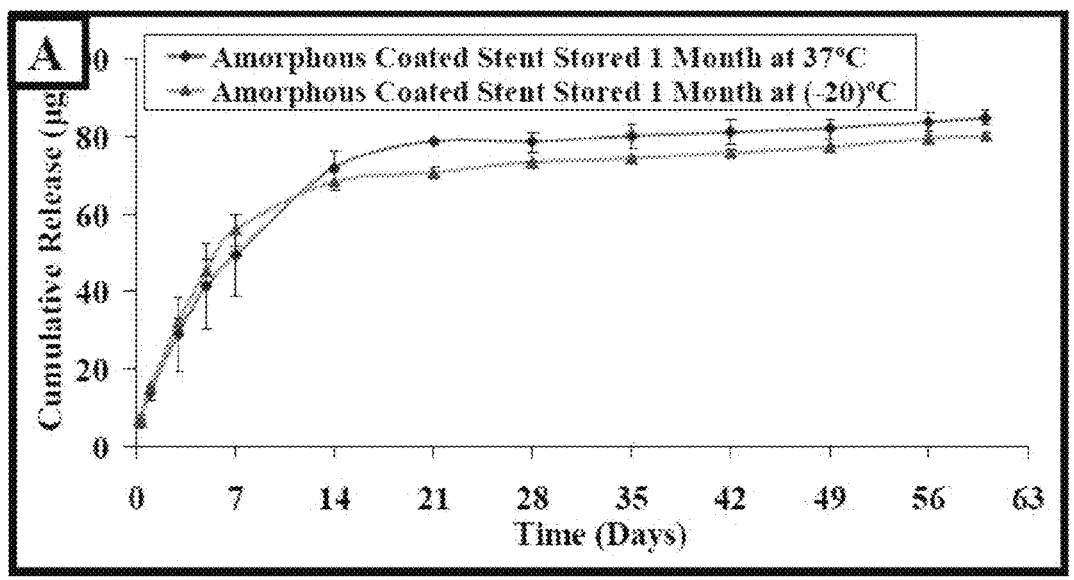
Figure 47B:
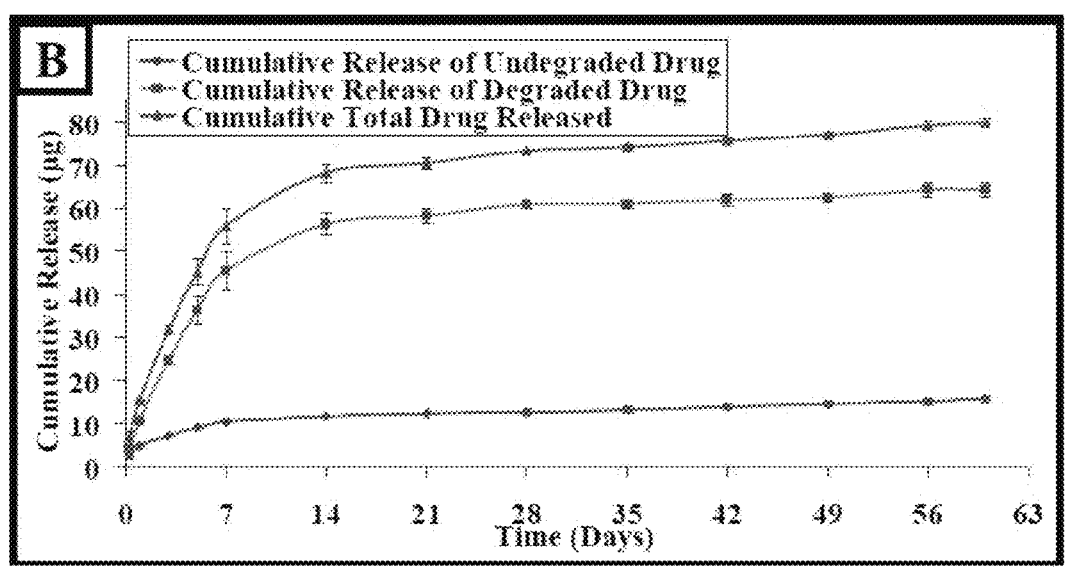
Figure 47C:
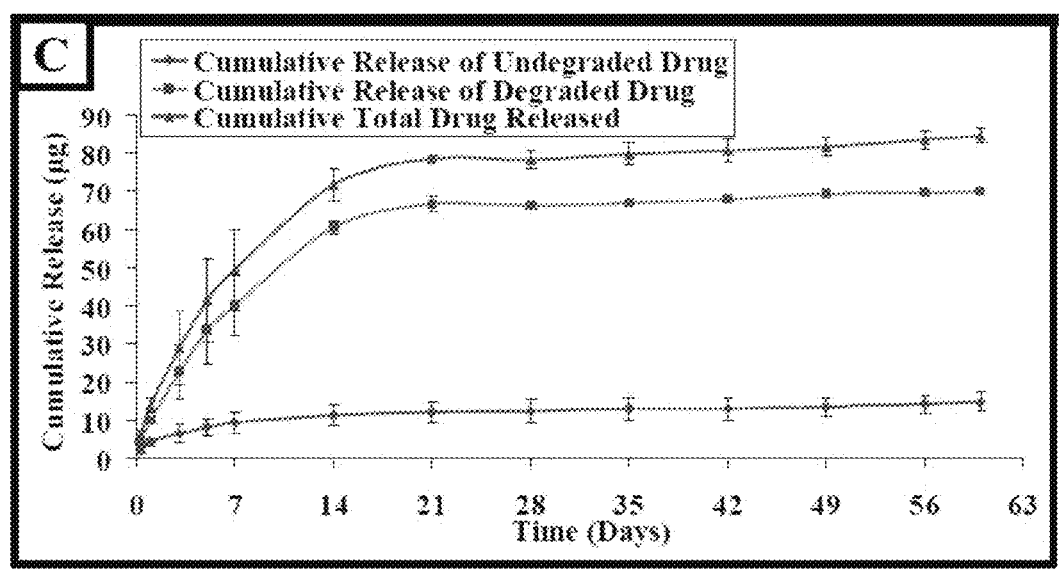
Figure 48:
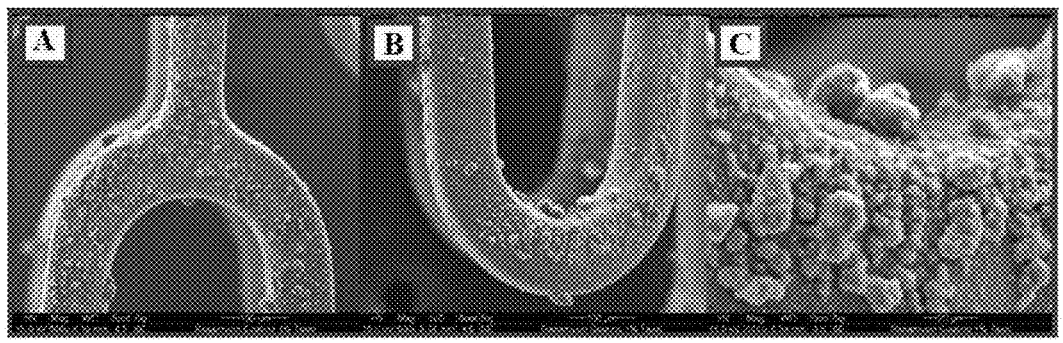
Figure 49:
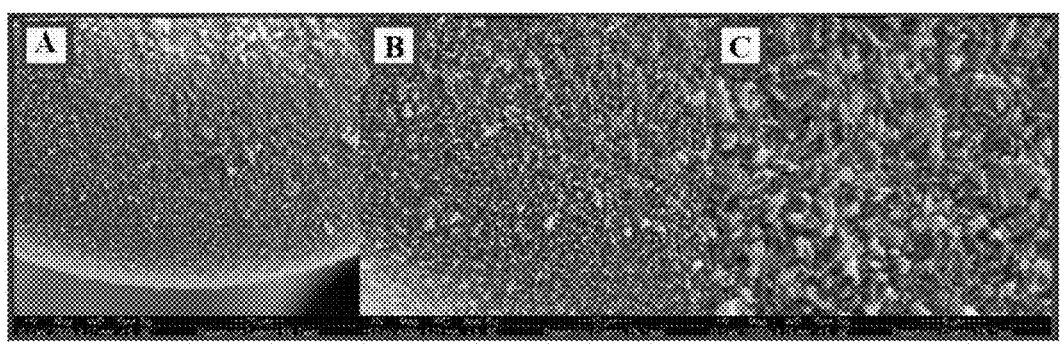
Figure 50:
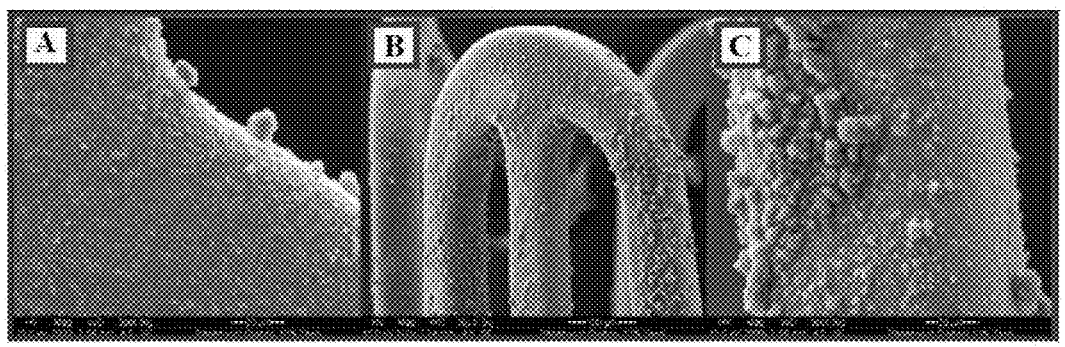
Figure 51:
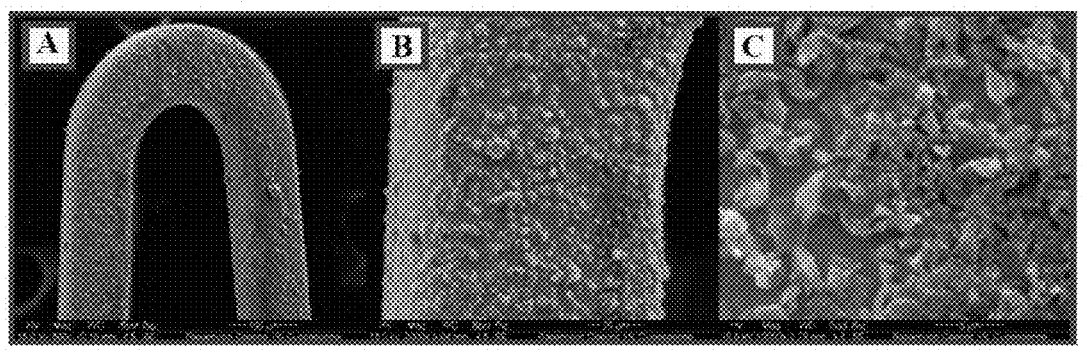
Figure 52:
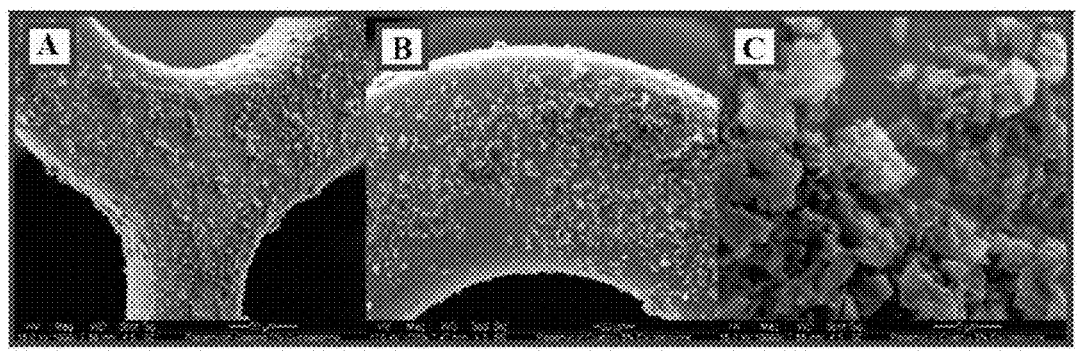
Figure 53:
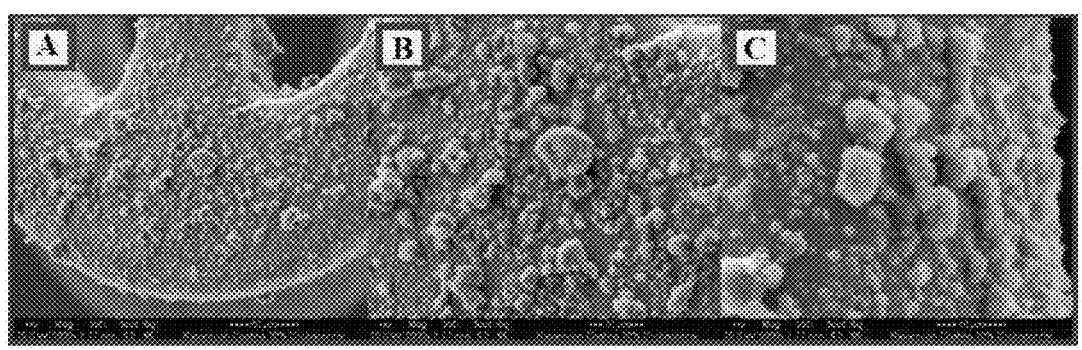
Figure 54A:
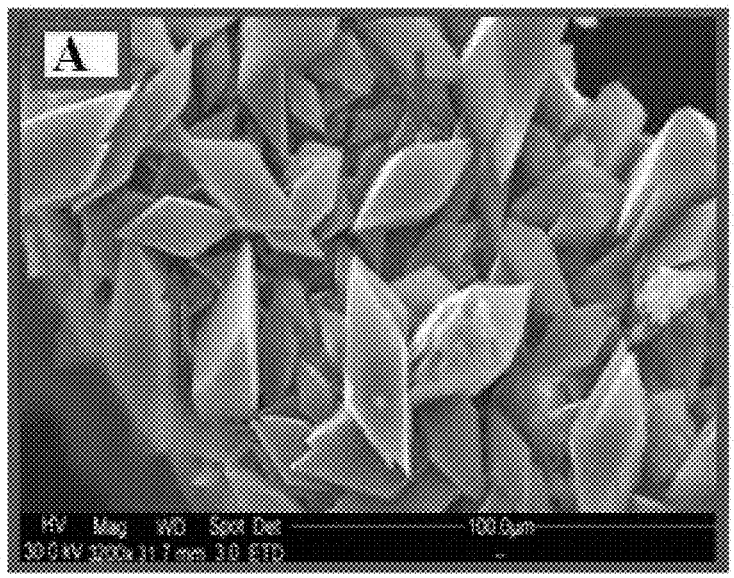
Figure 54B:
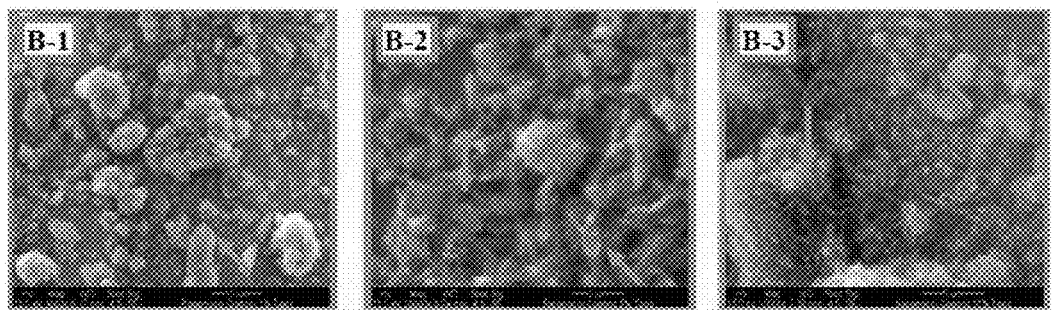
Figure 54C:
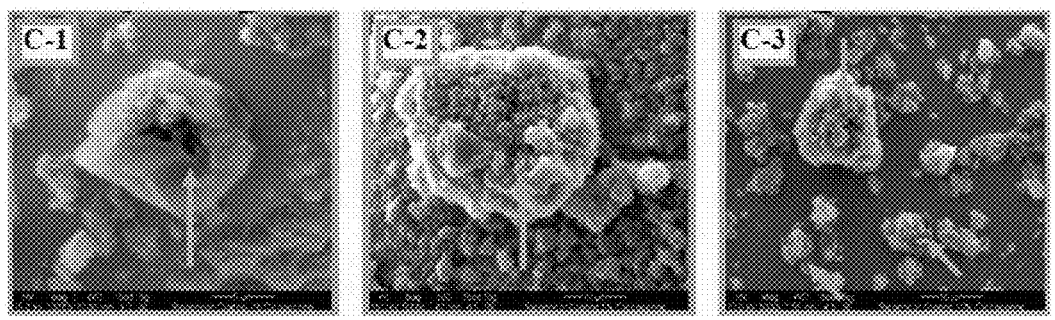
Figure 55A:
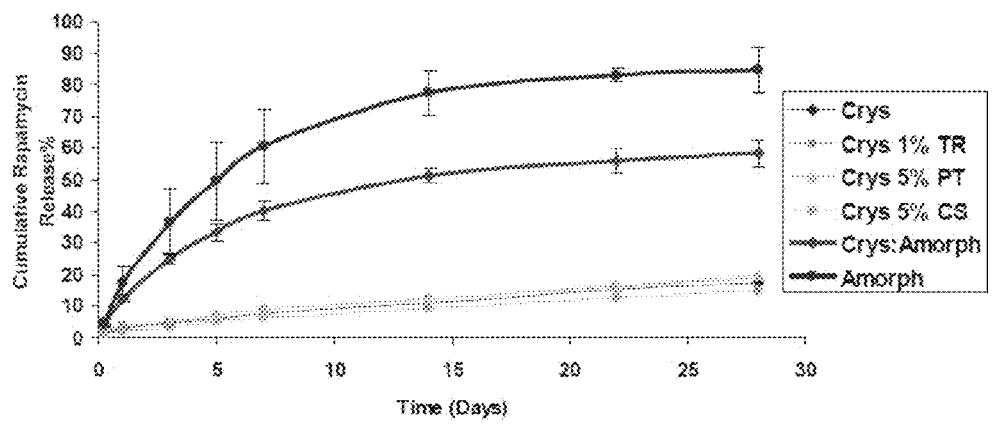
Figure 55B:
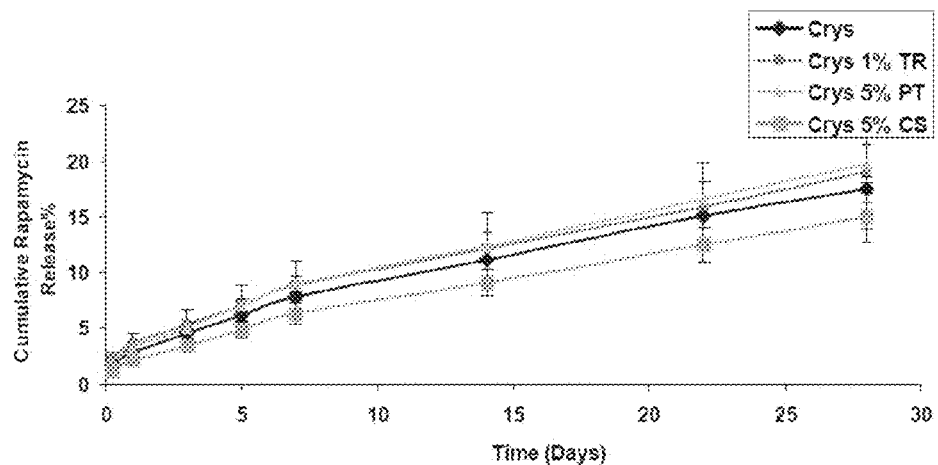
Figure 55C:
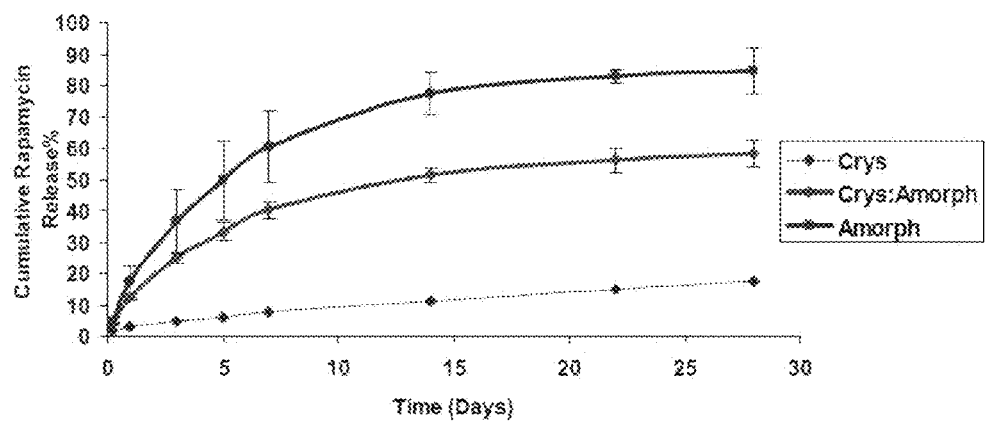
Figure 56A:
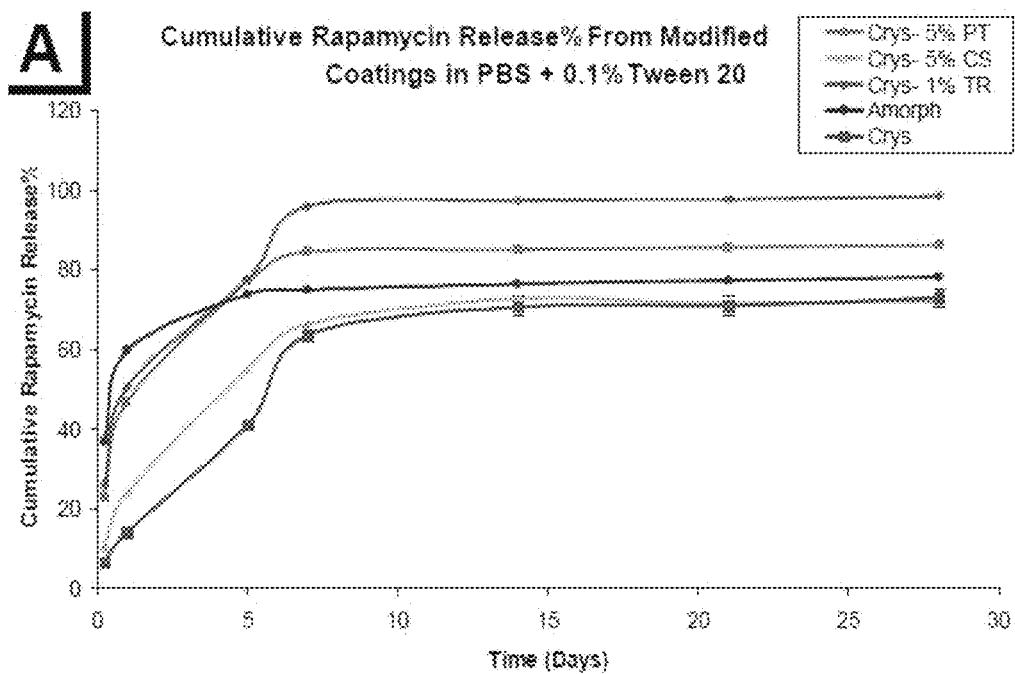
Figure 56B:
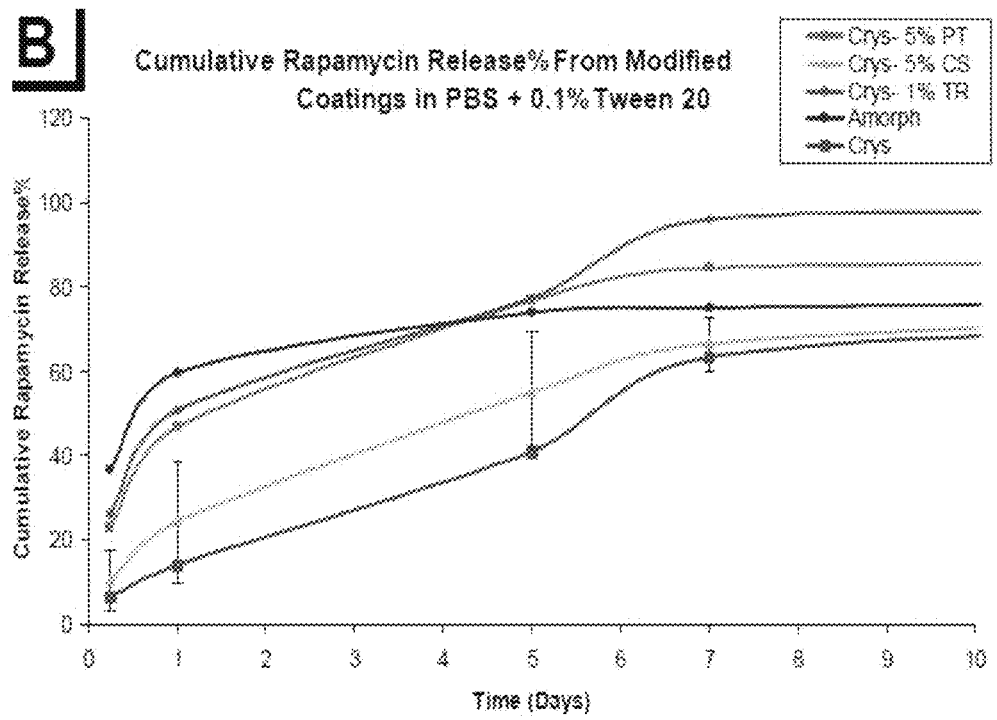
Figure 56C:
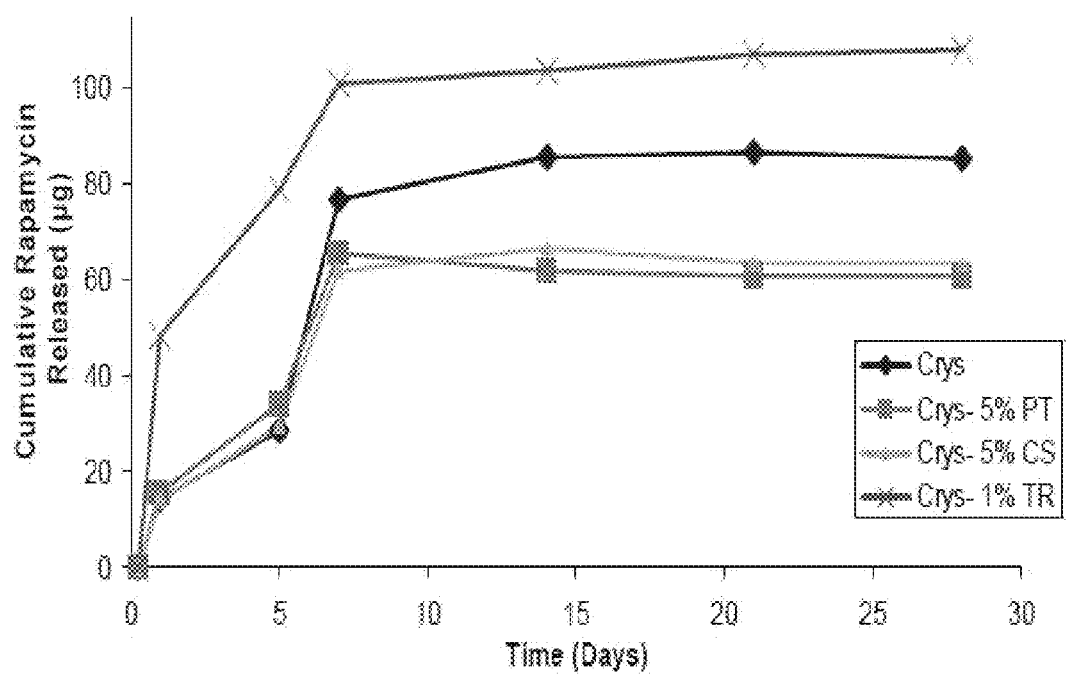
Figure 57A:
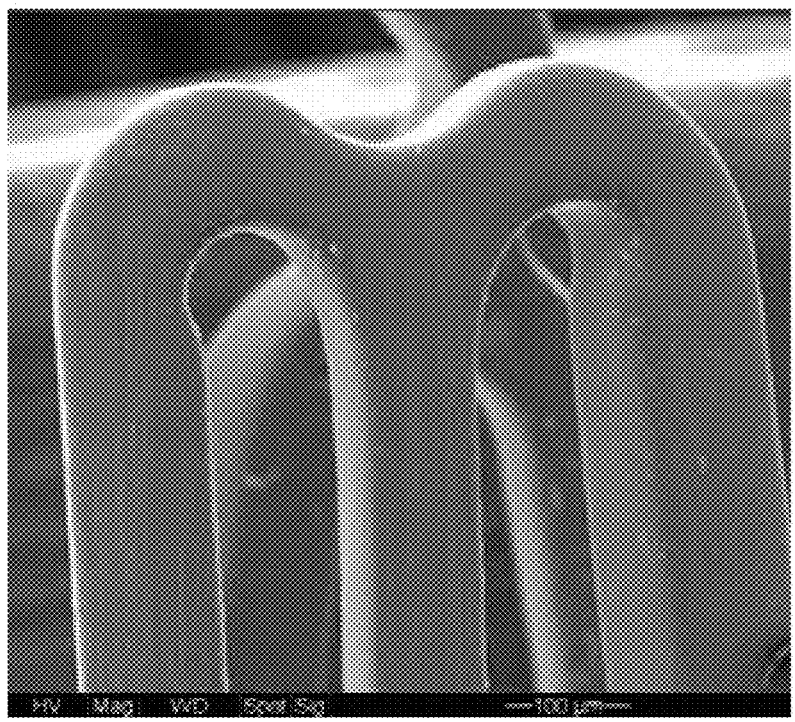
Figure 57B:
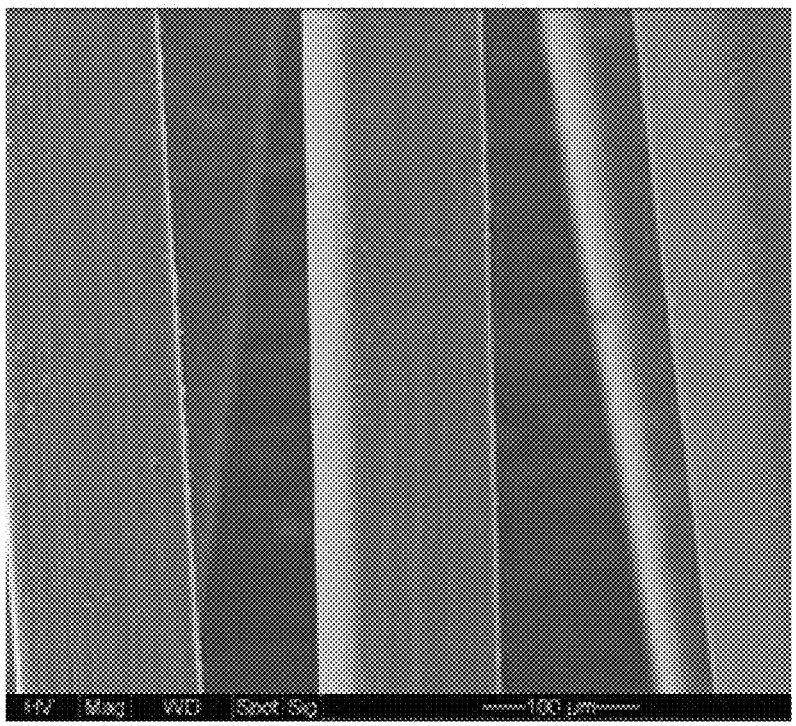
Figure 57C:
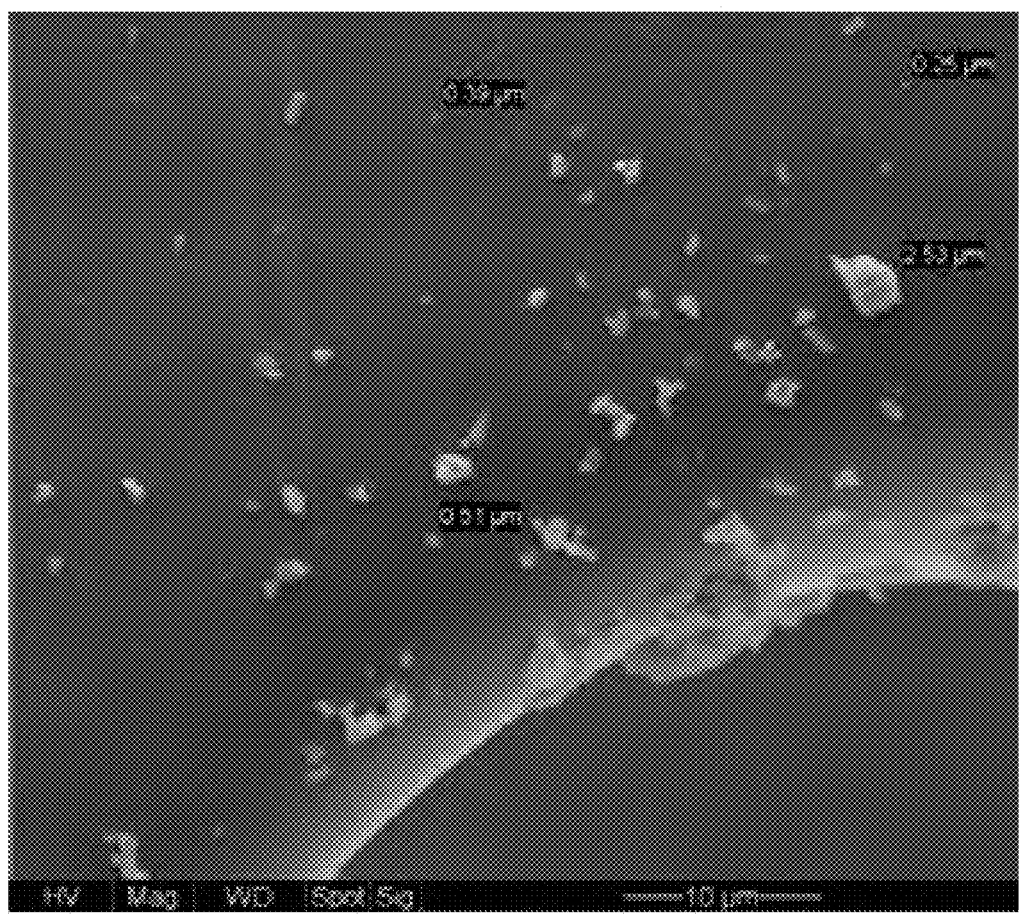
Figure 58A:
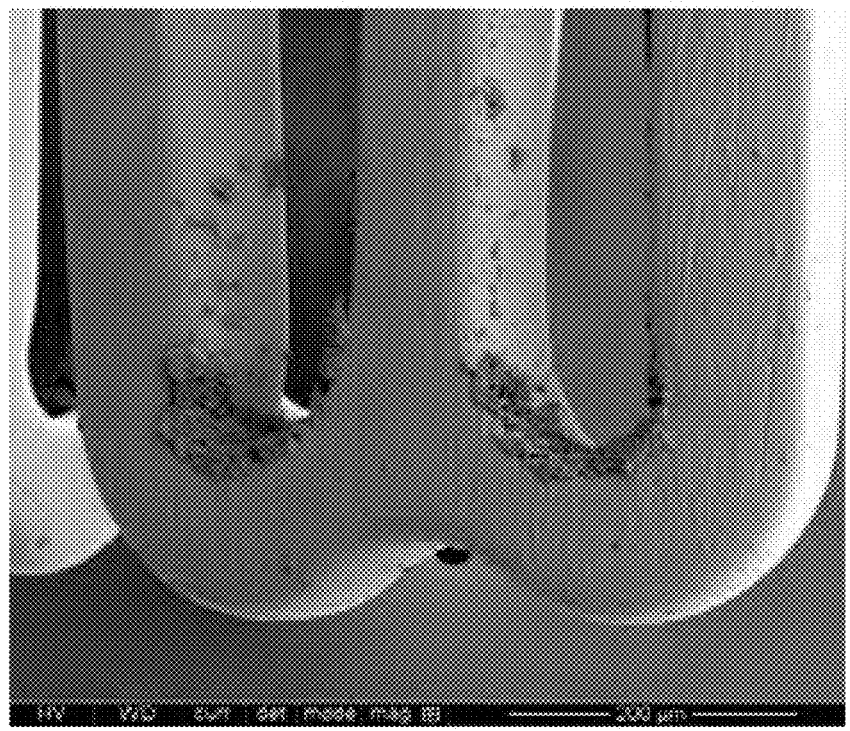
Figure 58B:
Figure 58C:
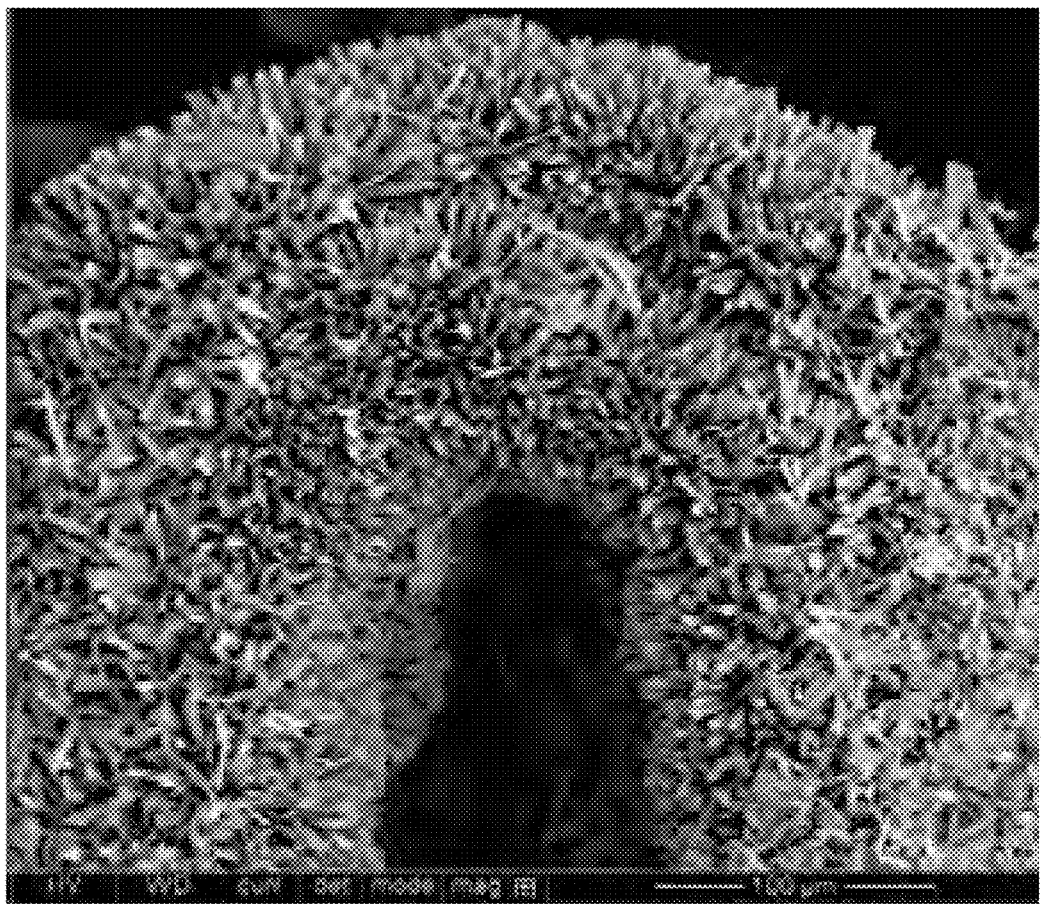
Figure 59A:
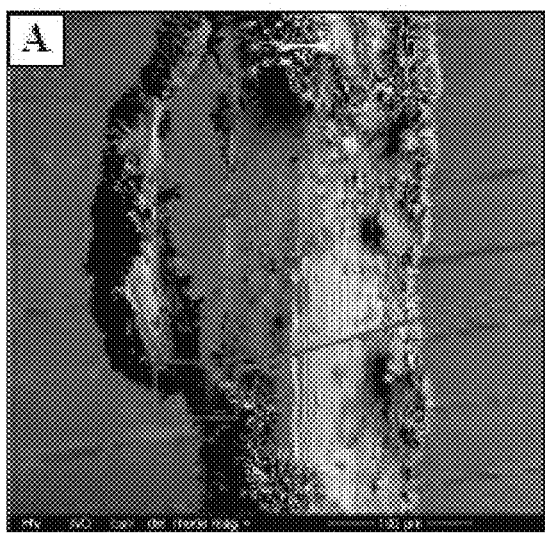
Figure 59B:
Figure 60A:
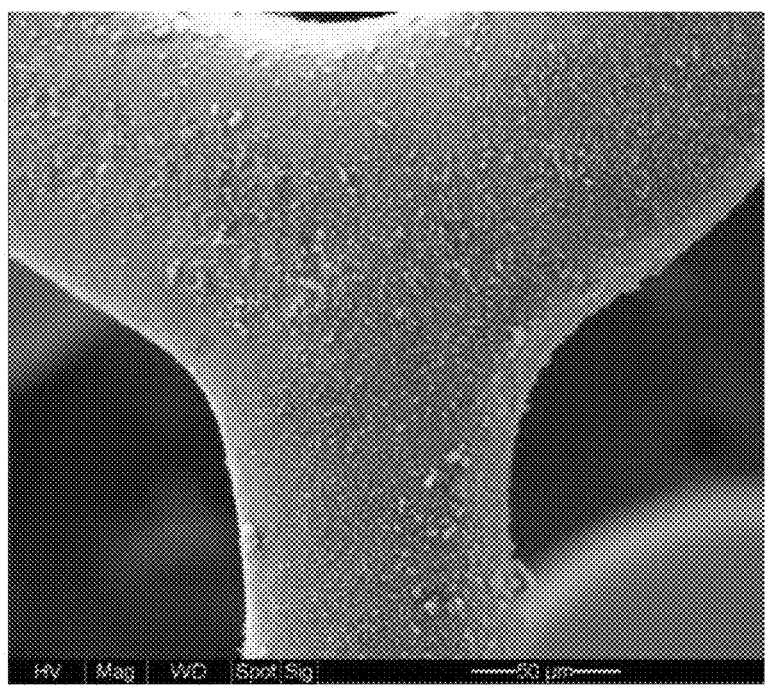
Figure 60B:
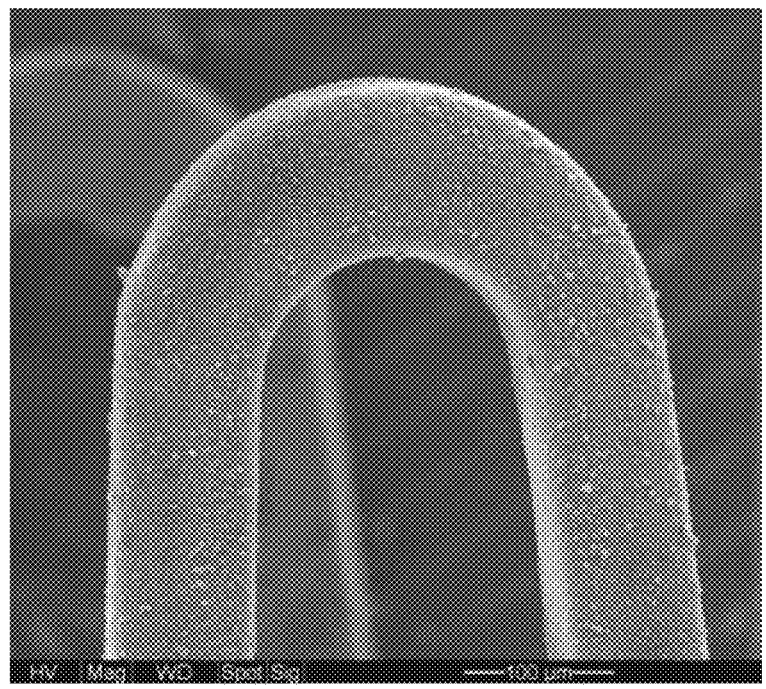
Figure 60C:
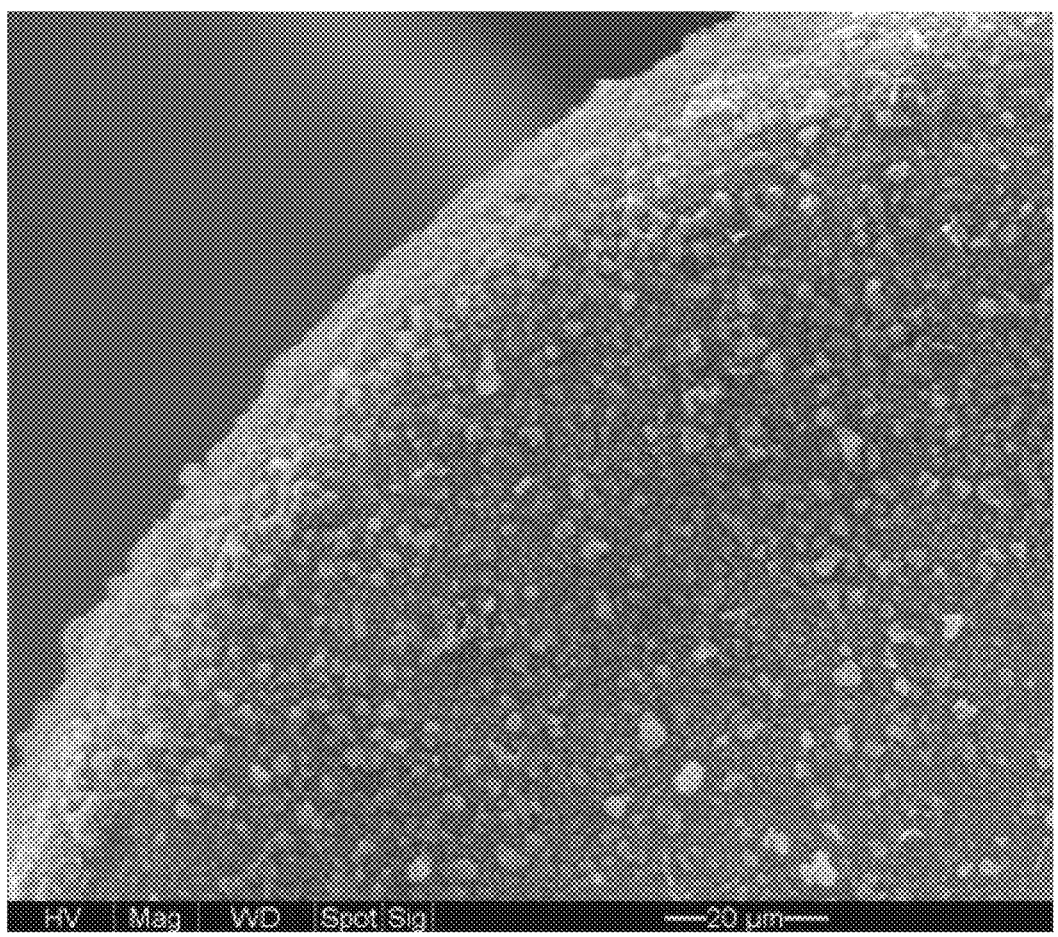
Figures 61A, 61B, 61C, 61D, 61E, 61F:
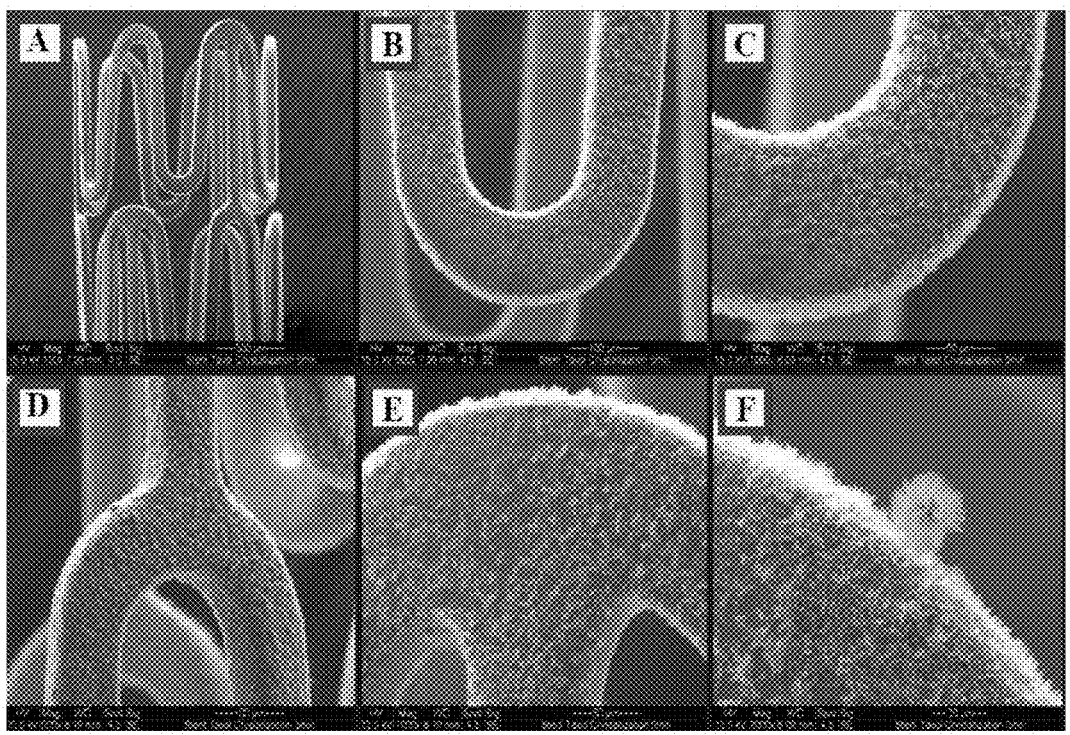
Figures 63A, 63B, 63C, 63D, 63E, 63F:
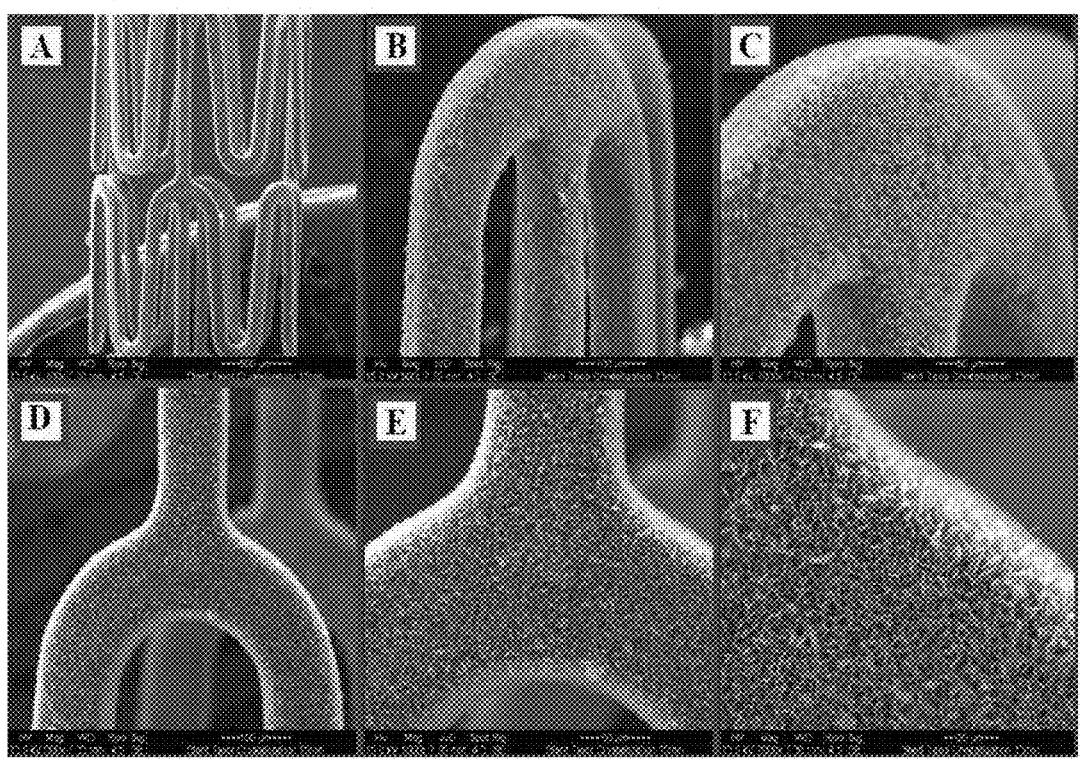
Figures 64A, 64B, 64C, 64D, 64E, 64F:
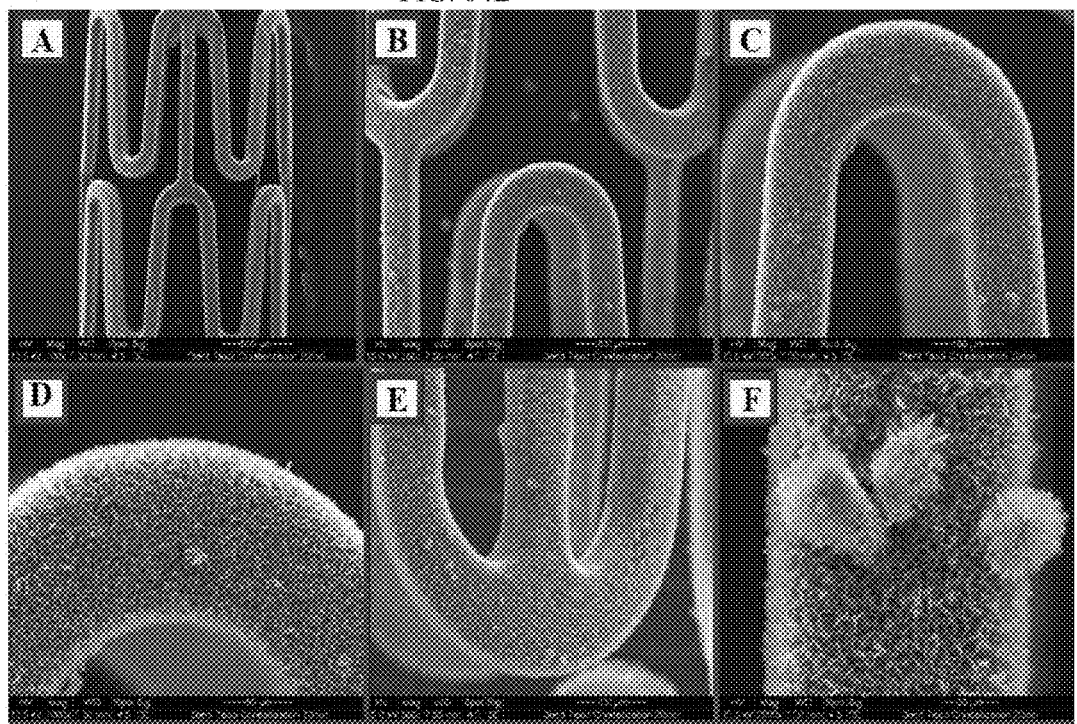
Figures 65A, 65B, 65C, 65D, 65E, 65F:
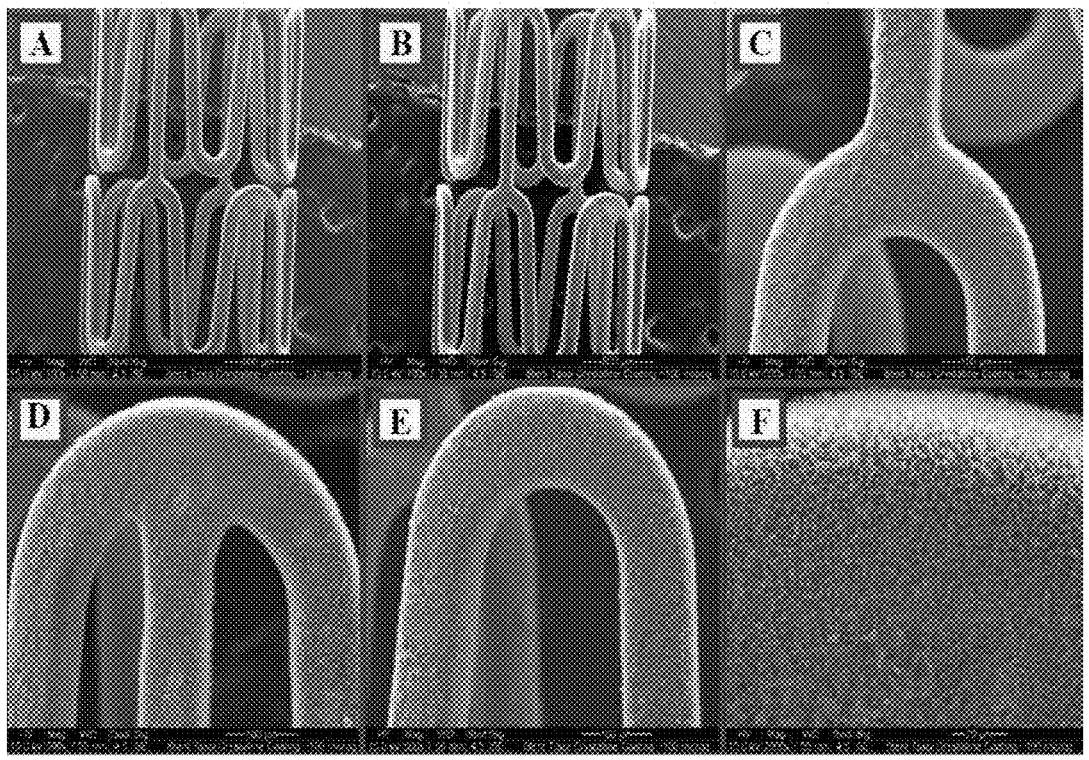
Figures 66A, 66B, 66C, 66D, 66E, 66F:
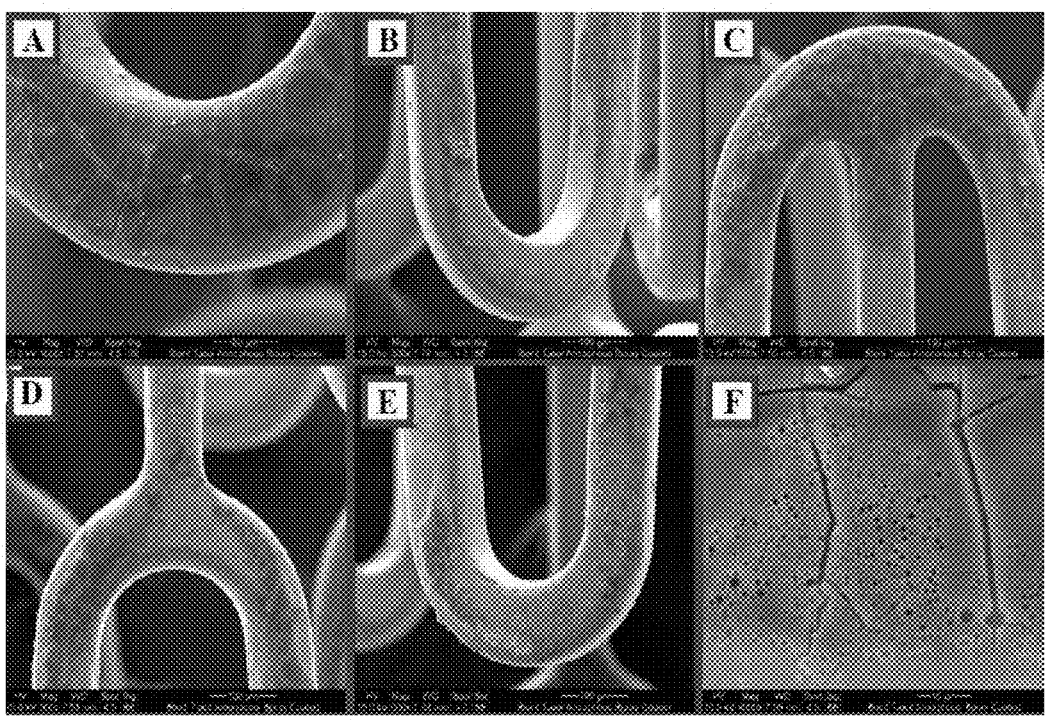
Figure 67A:
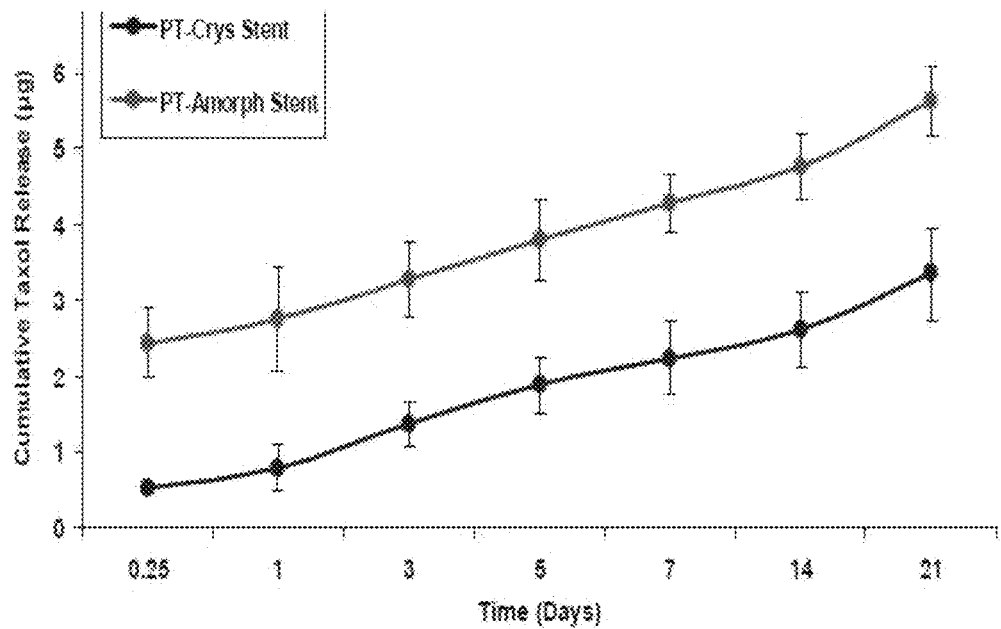
Figure 67B:
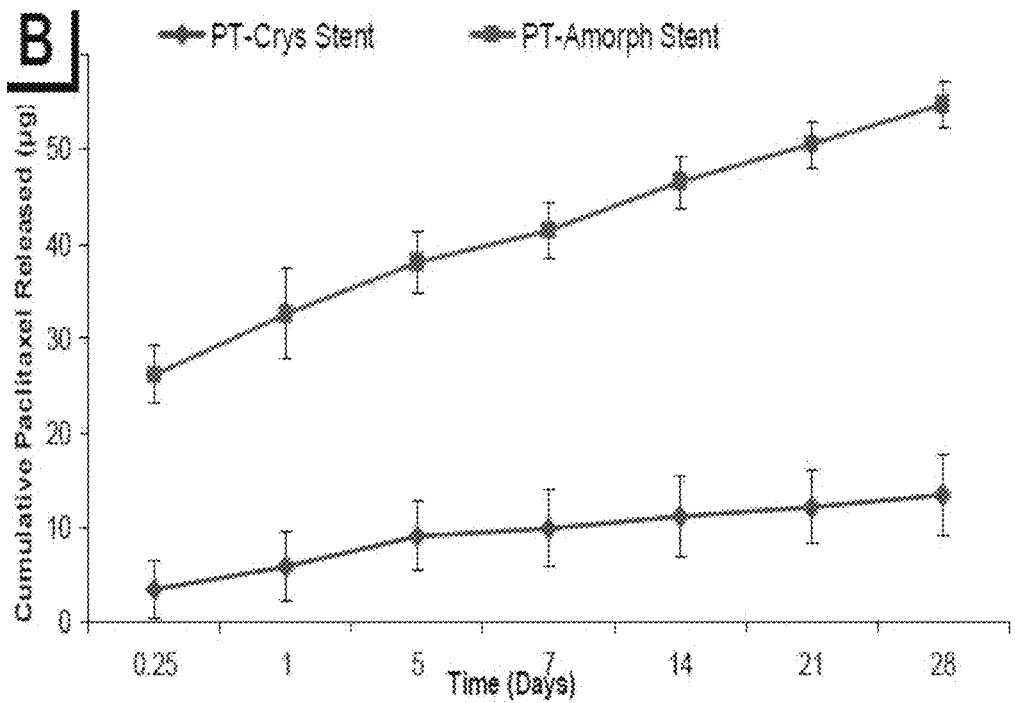
Figure 68:
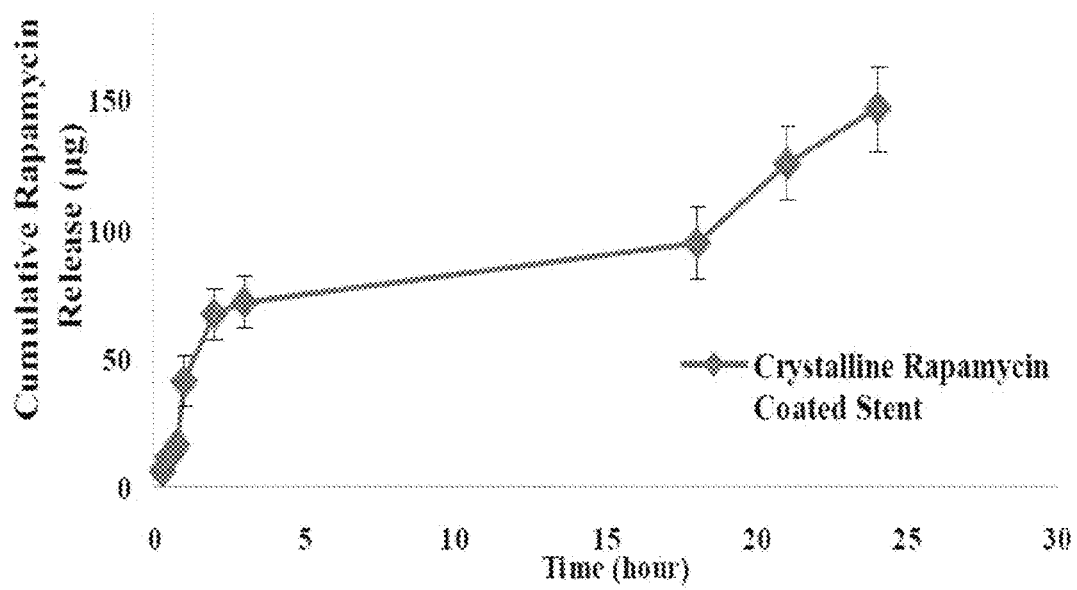
Figure 69A:
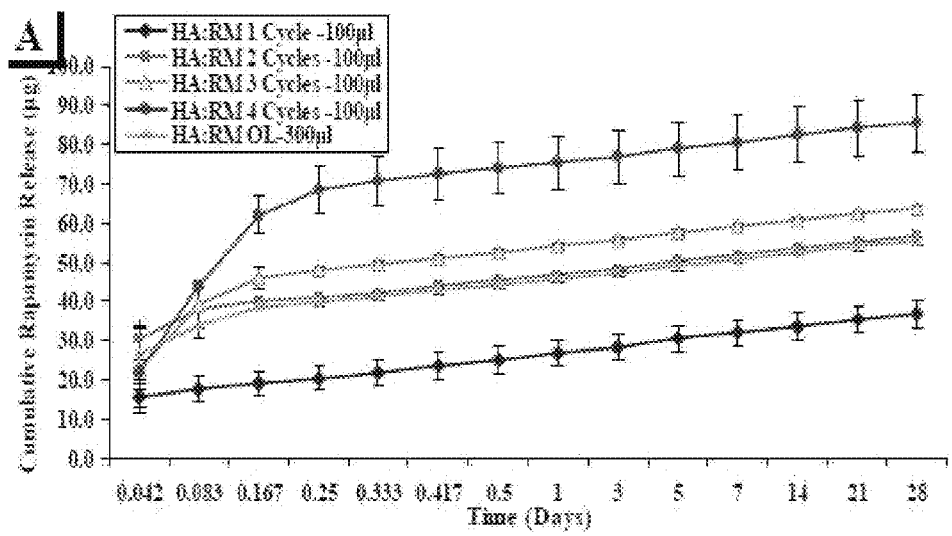
Figure 69B:
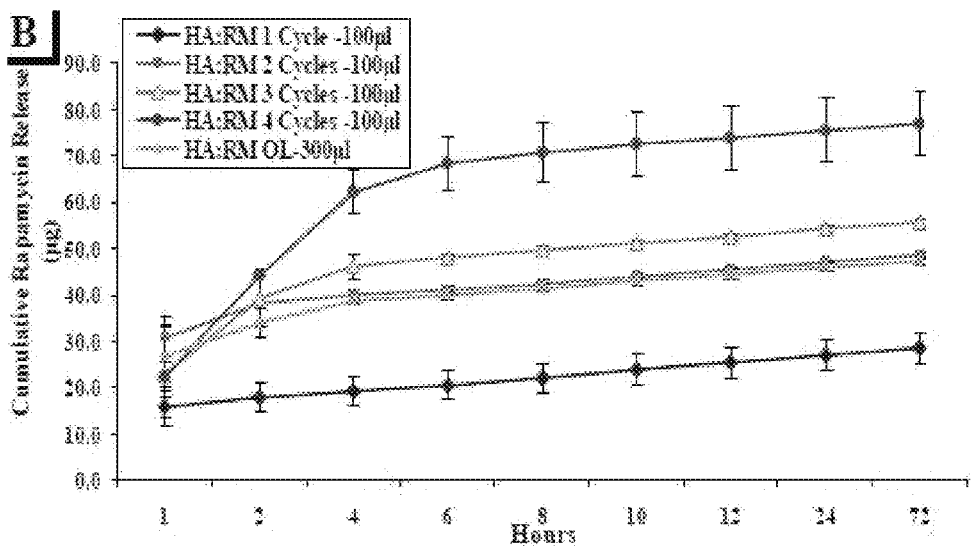
Figure 69C:
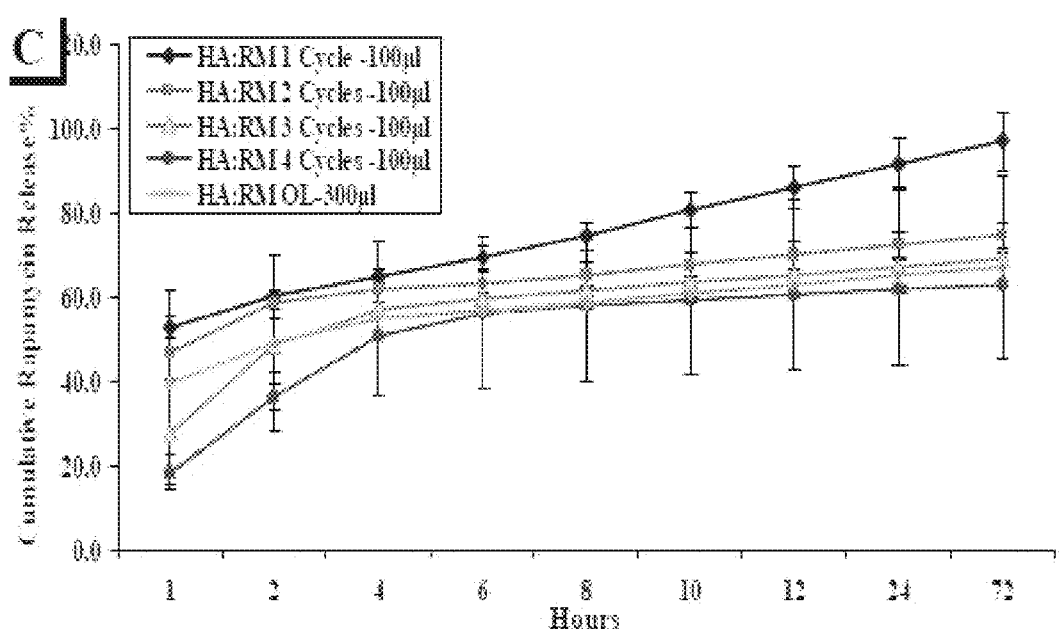
Figure 70A:
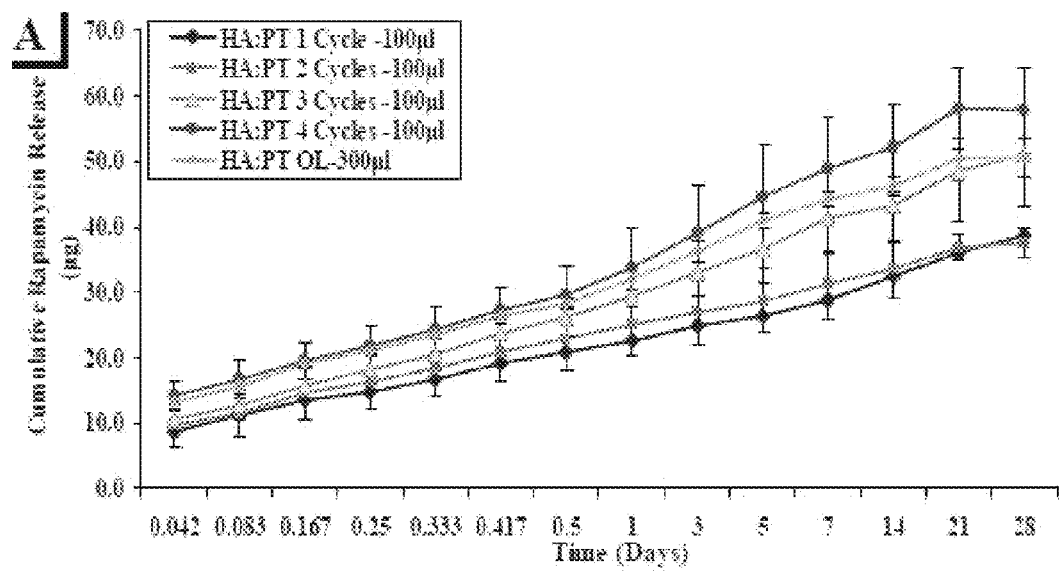
Figure 70B:
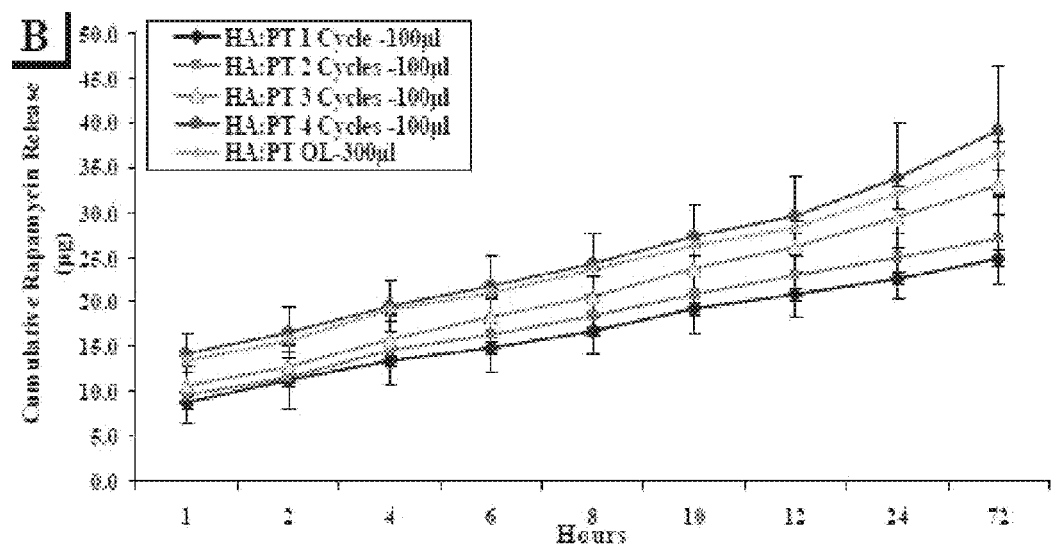
Figure 70C:
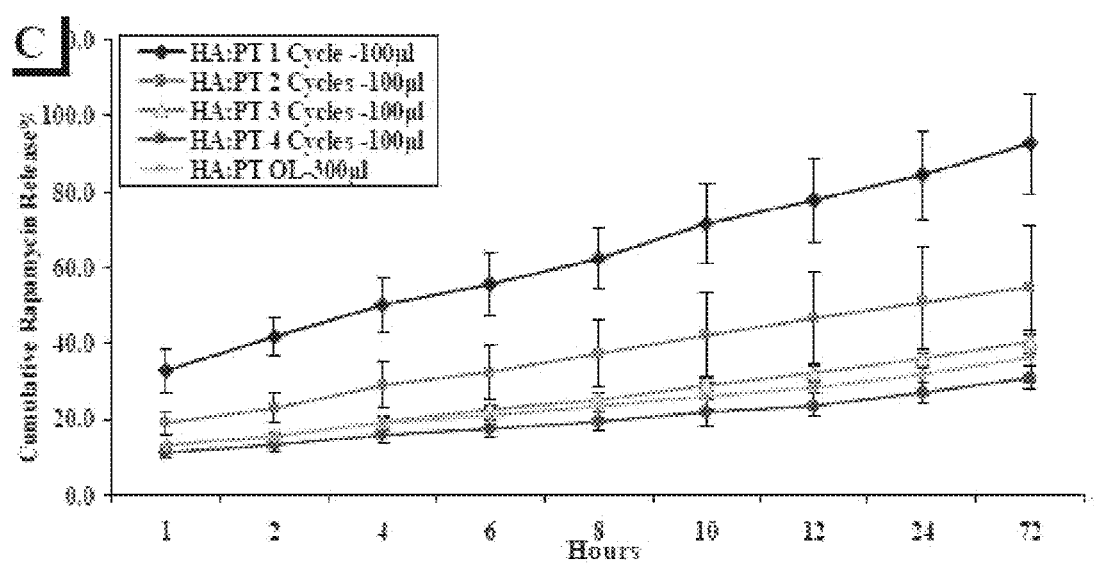
Figure 71A:
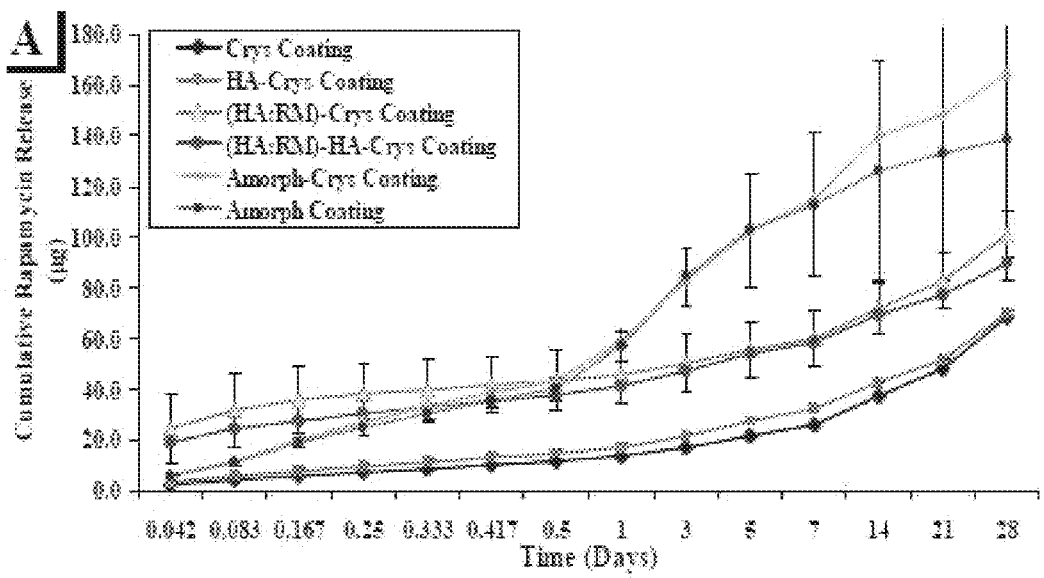
Figure 71B:
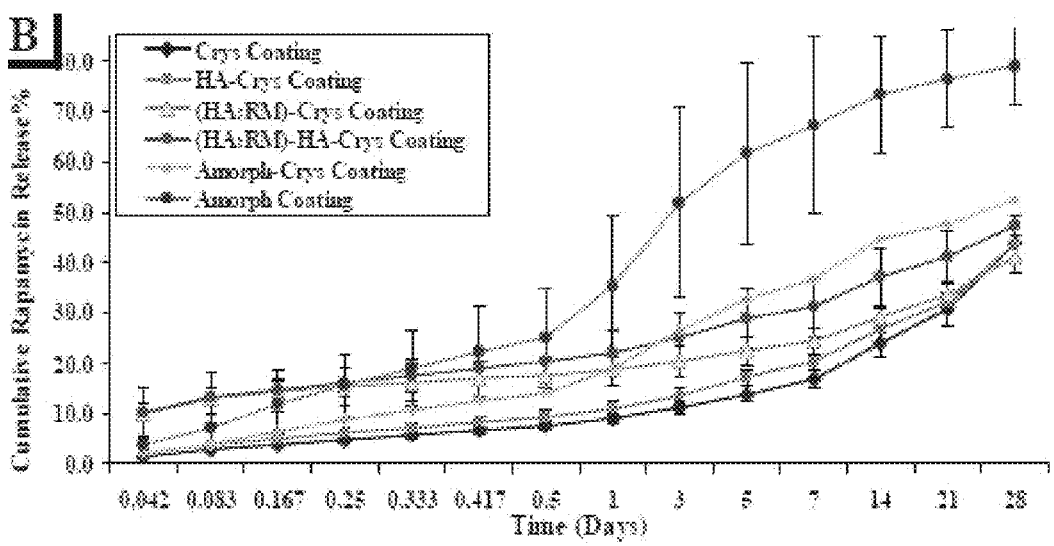
Figure 72:
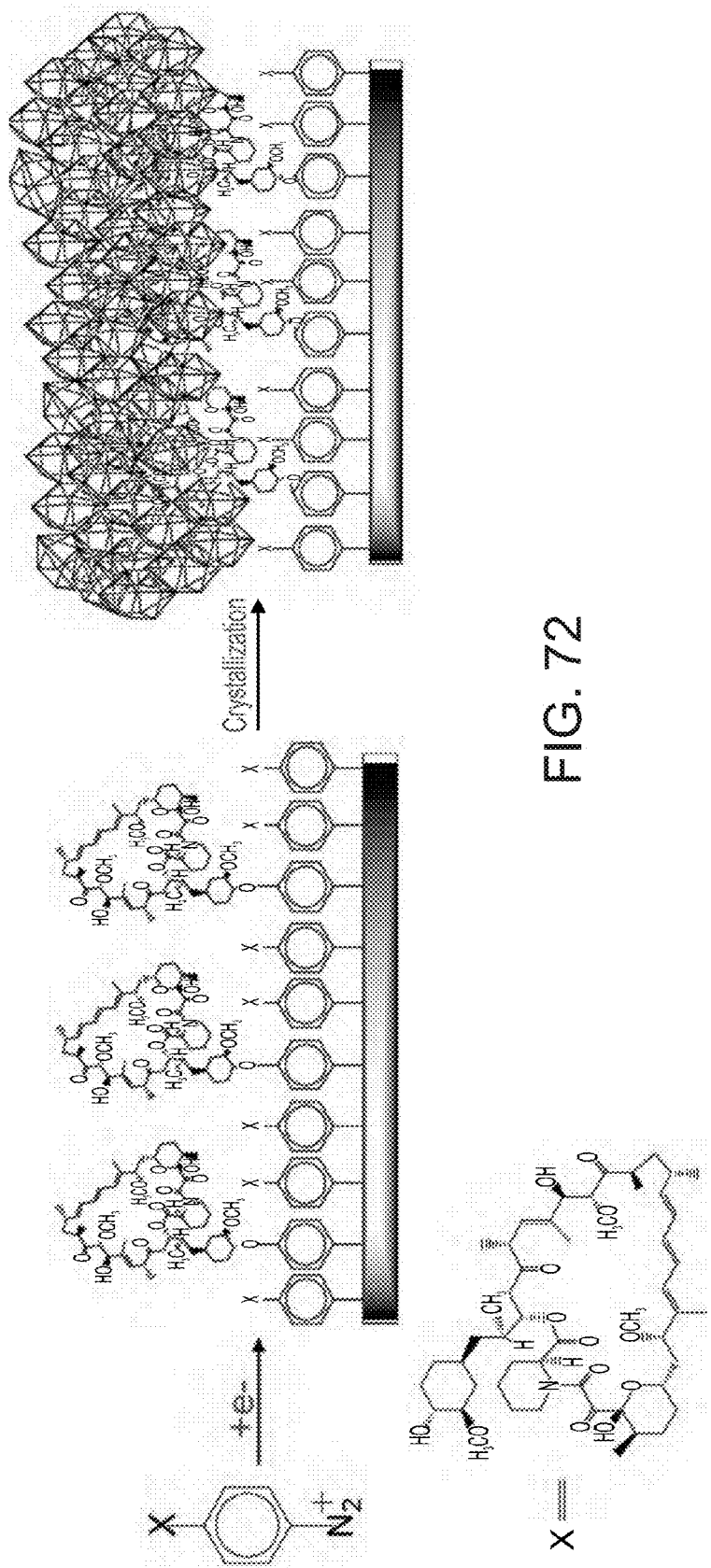
Figure 73A:
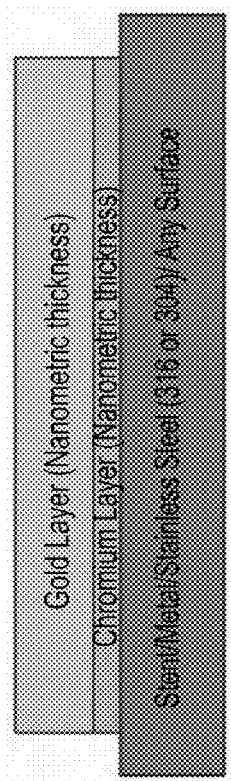
Figure 73B:
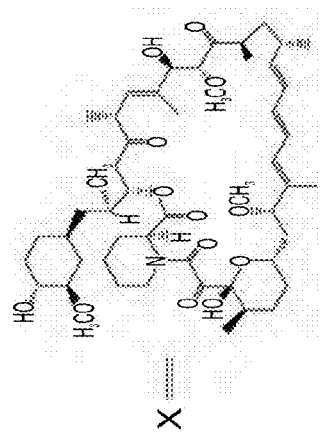
Figure 73B:
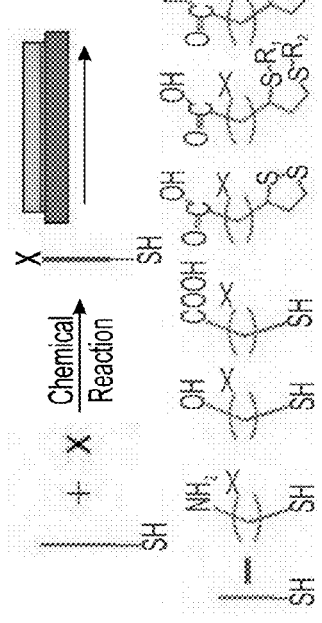
Figure 73C:
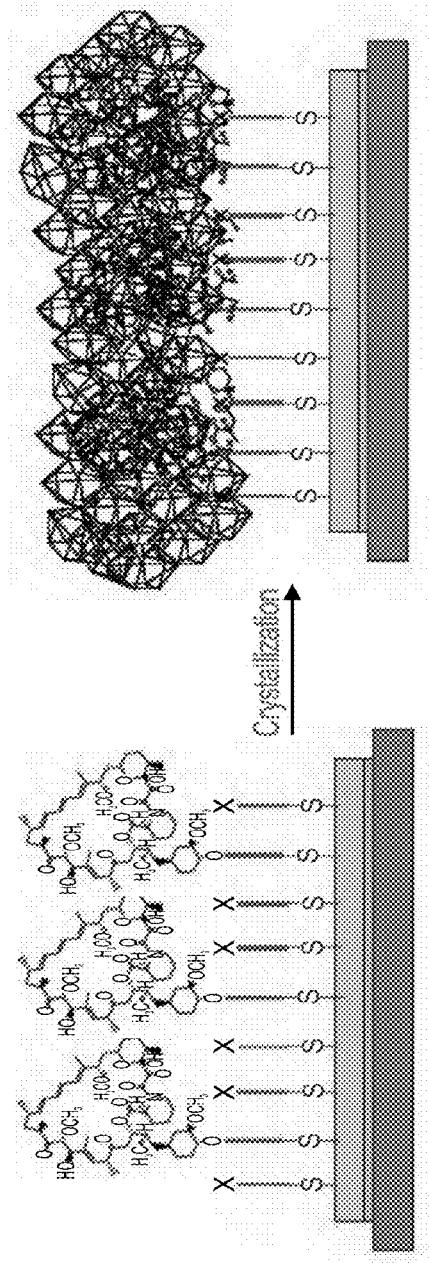

FIGS. 1A and 1B present scanning electron microscopy (SEM) images of rapamycin before (FIG. 1A) and after (FIG. 1B) grinding with a mortar and pestle for 3 minutes;

FIGS. 2A and 2B present scanning electron microscopy (SEM) images of finely ground rapamycin for use in seeding according to some embodiments of the invention;

FIG. 3 presents a scanning electron microscopy (SEM) image of a stent seeded with small rapamycin crystals according to some embodiments of the invention;

FIG. 4 presents a scanning electron microscopy (SEM) image of a stent coated with a continuous carpet of rapamycin crystals according to some embodiments of the invention;

FIGS. 5A and 5B present images of a stent with large, isolated rapamycin crystals deposited thereon;

FIGS. 6A and 6B present images of a stent seeded with rapamycin crystals by incubation in a rapamycin solution until the solution became turbid, with (FIG. 6B) and without (FIG. 6A) subsequent incubation of the seeded stent in a rapamycin solution for 1 hour in order to promote crystal growth according to exemplary embodiments of the invention;

FIGS. 7A and 7B present images of a stent seeded with rapamycin crystals by incubation in a turbid rapamycin dispersion for 5 minutes, with (FIG. 7B) and without (FIG. 7A) subsequent incubation of the seeded stent in a rapamycin solution for 1 hour in order to promote crystal growth according to exemplary embodiments of the invention;

FIGS. 8A and 8B present images of a stent seeded with rapamycin crystals by incubation in a turbid rapamycin dispersion for 15 minutes, with (FIG. 8B) and without (FIG. 8A) subsequent incubation of the seeded stent in a rapamycin solution for 1 hour in order to promote crystal growth according to exemplary embodiments of the invention;

FIG. 9 presents an image of a stent with a crystalline rapamycin coating formed by incubation of a seeded stent in a rapamycin solution for 10 minutes according to an exemplary embodiment of the invention;

FIG. 10 presents an image of a stent with a crystalline rapamycin coating formed by incubation of a seeded stent in a rapamycin solution for 20 minutes according to an exemplary embodiment of the invention;

FIG. 11 presents an image of a stent with a crystalline rapamycin coating formed by incubation of a seeded stent in a rapamycin solution for 30 minutes according to an exemplary embodiment of the invention;

FIG. 12 presents images (at different magnifications) of is a stent coated with a continuous layer of rapamycin crystals according to some embodiments of the invention;

FIG. 13 is a graph showing x-ray diffraction (XRD) spectra of amorphous rapamycin coatings on stents, prepared by evaporation of rapamycin solution containing ethanol, ethyl acetate or acetone as solvent;

FIG. 14 is a graph showing x-ray diffraction (XRD) spectra of a crystalline rapamycin coating on a stent according to some embodiments of the invention, as well as theoretical values (indicated by vertical lines) for cell unit parameters a=34.850; b=13.080; c=12.250 Å;

FIG. 15 is a graph showing cumulative rapamycin release (expressed as a percentage of total rapamycin) from exemplary stents coated with crystalline rapamycin according to some embodiments of the invention, upon incubation in phosphate buffer (pH 7.4, 37° C., with 0.02% sodium dodecyl sulfate);

FIG. 16 is a graph showing differential scanning calorimetry (DSC) spectra of commercial crystalline rapamycin (top spectrum), rapamycin from an exemplary seeded stent surface (second spectrum from top), an exemplary crystalline rapamycin stent coating (third spectrum from top), and an amorphous layer of rapamycin prepared by evaporation of a solution in ethanol (bottom spectrum);

FIGS. 17A and 17B present images of a stent insertion balloon before (FIG. 17A) and after (FIG. 17B) formation of a crystalline rapamycin coating according to some embodiments of the invention;

FIGS. 18A-18C present SEM images of a surface of a stent insertion balloon seeded with rapamycin crystals (FIG. 18A), and following formation of a crystalline rapamycin coating according to some embodiments of the invention, before (FIG. 18B) and after (FIG. 18C) inflation of the balloon;

FIGS. 19A-19F present images of exemplary stents coated with a crystalline rapamycin coating, without a top coat (FIGS. 19A and 19B), with a carboxymethylcellulose top coat (FIGS. 19C and 19D) and with a hyaluronic acid top coat (FIGS. 19E and 19F), before (FIGS. 19A, 19C and 19E) and after (FIGS. 19B, 19D and 19F) expansion of the stents;

FIGS. 20A and 20B are graphs showing cumulative release of rapamycin, expressed as a percentage of total rapamycin (FIG. 20A) or by rapamycin weight (FIG. 20B), from exemplary stents coated with crystalline rapamycin according to some embodiments of the invention, without a top coat (A-1 and A-2), with a carboxymethylcellulose top coat (B-1 and B-2) and with a hyaluronic acid top coat (C-1 and C-2), for non-expanded (A-1, B-1 and C-1) and expanded (A-2, B-2 and C-2) stents;

FIGS. 21A and 21B present a photographic image (FIG. 21A) and a SEM image (FIG. 21B) of a stent with a hyaluronic acid top coat according to some embodiments of the invention which comprises webbing between stent struts (indicated by arrows in FIG. 21A);

FIGS. 22A-22C present images of stents spray coated with one (FIG. 22A), two (FIG. 22B) or three (FIG. 22C) layers of 0.1% hyaluronic acid (HA) solution according to some embodiments of the invention;

FIGS. 23A and 23B present images of an exemplary stent coated with a crystalline rapamycin coating and a hyaluronic acid (HA) top coat (formed by spray coating an aqueous 0.3% HA solution with glycerol) according to some embodiments of the invention, before (FIG. 23A) and after (FIG. 23B) stent expansion;

FIGS. 24A and 24B present SEM images of surfaces of bare stents characterized by a rough (FIG. 24A) or smooth (FIG. 24B) surface;

FIGS. 25A-25X present SEM images of surfaces of rough stents (FIGS. 25A-25L) and smooth stent (FIGS. 25M-25X) coated with a crystalline rapamycin coating, with a single-layer (FIGS. 25E-25H and 25Q-25T) or double-layer (FIGS. 25I-25L and 25U-25X) hyaluronic acid top coat, or without a top coat (FIGS. 25A-25D and 25M-25P), for non-expanded (FIGS. 25A, 25B, 25E, 25F, 25I, 25J, 25M, 25N, 25Q, 25R, 25U and 25V) and expanded (FIGS. 25C, 25D, 25G, 25H, 25K, 25L, 25O, 25P, 25S, 25T, 25W and 25X) stents;

FIGS. 26A and 26B present SEM images of surfaces of a rough stent (FIG. 26A) and a smooth stent (FIG. 26B) coated with a crystalline rapamycin coating, following expansion of the stents;

FIG. 27 presents a SEM image of surfaces of surfaces of an exemplary stent coated with a crystalline rapamycin coating and a hyaluronic top coat, following expansion of the stent (arrows indicate cracks in the crystalline layer, wherein the crystalline layer does not peel away from the stent surface);

FIGS. 28A-28C present SEM images of surfaces of stents coated with a crystalline rapamycin coating, with a single-layer (FIG. 28B) or double-layer (FIG. 28C) hyaluronic acid top coat, or without a top coat (FIG. 28A);

FIGS. 29A and 29B present SEM images of a cross section of an exemplary crystalline rapamycin coating, with a single-layer hyaluronic acid top coat (FIG. 29B) and without a top coat (FIG. 29A);

FIGS. 30A-30F present SEM images of stents with a hyaluronic acid top coat according to some embodiments of the invention which comprises webbing attached to stent struts (indicated by arrows), before (FIGS. 30A and 30B) and after (FIGS. 30C-30F) stent expansion by balloon inflation;

FIGS. 31A and 31B present images of exemplary stents coated with a crystalline coating of about 750 µg (FIG. 31A) or about 100 µg (FIG. 31B) rapamycin per stent, following expansion of the stent (arrows indicate fractures in the crystalline layer coating);

FIGS. 32A-32C present SEM images of crystalline rapamycin coatings prepared on stent surfaces according to some embodiments of the invention (arrows indicate rapamycin seed crystals in FIG. 32A, and multiple strata of coating and protruding crystals in FIG. 32C);

FIGS. 33A-33D present atomic force microscopy topographical images (left panels; dark color indicates depth) and graphs showing topographical profile (right panels) of 5 µm×5 µm sections on surfaces of a bare stent (FIG. 33A), a stent seeded with rapamycin crystals (FIG. 33B), crystalline rapamycin coating on a stent (FIG. 33C) and a hyaluronic acid top coat applied over a crystalline rapamycin coating on a stent (FIG. 33D);

FIG. 34 presents an atomic force microscopy topographical image of a 5 µm×5 µm section on a surface of a stent with a hyaluronic acid top coat applied over a crystalline rapamycin coating, according to some embodiments of the invention;

FIG. 35 presents images of rough (R) and smooth (S) stents coated with a crystalline rapamycin coating, with a single-layer (1L) or double-layer (2L) hyaluronic acid top coat, or without a top coat (WP), before crimping, after crimping, and after expansion of crimped stents;

FIGS. 36A-36E present exemplary HPLC chromatograms of medium in which an amorphous rapamycin coating was incubated for 0 hours (FIG. 36A), 6 hours (FIG. 36B), 1 day (FIG. 36C), 3 days (FIG. 36D) and 7 days (FIG. 36E), showing a gradually decreasing signal (right arrow) associated with rapamycin, and a gradually increasing signal (left arrow) associated with degraded rapamycin (drug area refers to area of peak indicated by right arrow; buffer area refers to area of peaks indicated by left arrow and peaks associated with buffer);

FIGS. 37A-37C are graphs showing cumulative release of undegraded rapamycin, degraded rapamycin and total rapamycin from Cypher® stents (FIG. 37A) stents coated with amorphous rapamycin (FIG. 37B) and stents coated with an exemplary crystalline rapamycin coating according to some embodiments of the invention, as a function of time of incubation in phosphate buffer saline (pH 7.4, 37° C.);

FIGS. 38A-38C present SEM images of stents with an amorphous rapamycin coating, following incubation for 29 days in phosphate buffer saline (pH 7.4, 37° C.) (FIGS. 38B and 38C) and without incubation (FIG. 38C) (FIG. 38C presents enlarged view of rectangle in FIG. 38B);

FIG. 39 is a graph showing cumulative release of degraded rapamycin from stents coated with amorphous rapamycin (Amorph) and stents coated with an exemplary crystalline rapamycin coating (Crys) according to some embodiments of the invention, as a function of time of incubation in phosphate buffer saline (pH 7.4, 37° C.);

FIGS. 40A-40F present SEM images of stents with exemplary crystalline rapamycin coatings according to some embodiments of the invention, following storage for 1 year at 37° C.;

FIGS. 41A-41D present SEM images of stents with exemplary crystalline rapamycin coatings according to some embodiments of the invention, following storage for 1 year at 4-8° C.;

FIGS. 42A-42F present SEM images of stents with exemplary crystalline rapamycin coatings according to some embodiments of the invention, following storage for 1 year at −20° C.;

FIG. 43 is a graph showing cumulative release of total (degraded and undegraded) rapamycin from stents with exemplary crystalline rapamycin coatings according to some embodiments of the invention, as a function of time of incubation in phosphate buffer saline (pH 7.4, 37° C.), following storage of the stents for 1 year at 37, 4-8 or −20° C.;

FIGS. 44A-44C are graphs showing cumulative release of degraded rapamycin, undegraded rapamycin and total rapamycin from stents with exemplary crystalline rapamycin coatings according to some embodiments of the invention, as a function of time of incubation in phosphate buffer saline (pH 7.4, 37° C.), following storage of the stents for 1 year at 37° C. (FIG. 44A), 4-8° C. (FIG. 44B) or −20° C. (FIG. 44C);

FIG. 45 presents SEM images of stents with exemplary crystalline rapamycin coatings according to some embodiments of the invention, following storage for 1 year at 37° C. (A-1, A-2 and A-3), 4-8° C. (B-1, B-2 and B-3) or −20° C. (C-1, C-2 and C-3), followed by two months incubation in phosphate buffer saline (pH 7.4, 37° C.);

FIGS. 46A-46C presents SEM images of stents with spray-coated amorphous rapamycin coatings which are freshly prepared (FIG. 46A) or following storage for 1 month at 37° C. (FIG. 46C) or −20° C. (FIG. 46B);

FIGS. 47A-47C are graphs showing cumulative release of degraded rapamycin, undegraded rapamycin and total rapamycin from stents with spray-coated amorphous rapamycin coatings which are freshly prepared (FIG. 47A) or following storage for 1 month at 37° C. (FIG. 47C) or −20° C. (FIG. 47B), as a function of time of incubation in phosphate buffer saline (pH 7.4, 37° C.);

FIG. 48 presents SEM images of exemplary stent surfaces with rapamycin crystallized in the presence of 1% paclitaxel (w/w relative to rapamycin), according to some embodiments of the invention;

FIG. 49 presents SEM images of exemplary stent surfaces with rapamycin crystallized in the presence of 5% paclitaxel (w/w relative to rapamycin), according to some embodiments of the invention;

FIG. 50 presents SEM images of exemplary stent surfaces with rapamycin crystallized in the presence of 10% paclitaxel (w/w relative to rapamycin), according to some embodiments of the invention;

FIG. 51 presents SEM images of exemplary stent surfaces with rapamycin crystallized in the presence of 1% cyclosporin A (w/w relative to rapamycin), according to some embodiments of the invention;

FIG. 52 presents SEM images of exemplary stent surfaces with rapamycin crystallized in the presence of 5% cyclosporin A (w/w relative to rapamycin), according to some embodiments of the invention;

FIG. 53 presents SEM images of exemplary stent surfaces with rapamycin crystallized in the presence of 10% cyclosporin A (w/w relative to rapamycin), according to some embodiments of the invention;

FIGS. 54A-54C presents SEM images of exemplary stent surfaces with rapamycin crystallized in the presence of 1% (FIG. 54B; B-1), 5% (FIG. 54B; B-2) or 10% (FIG. 54B; B-3) paclitaxel, 1% (FIG. 54C; C-1), 5% (FIG. 54C; C-2) or 10% (FIG. 54C; C-3) cyclosporin A, or without paclitaxel or cyclosporin A (FIG. 54A), according to some embodiments of the invention (concentrations are w/w relative to rapamycin);

FIGS. 55A-55C are graphs showing cumulative release rapamycin from stents coated with rapamycin crystallized alone (Crys) or in the presence of 1% tacrolimus (TR) or 5% paclitaxel (PT) or cyclosporin A (CS), with crystalline rapamycin coated by amorphous rapamycin (Crys:Amorph), or with amorphous rapamycin alone (Amorph), as a function of time of incubation in phosphate buffer saline (pH 7.4, 37° C.) (concentrations are w/w relative to rapamycin);

FIGS. 56A-56C are graphs showing cumulative release of rapamycin from stents coated with rapamycin crystallized alone (Crys) or in the presence of 1% tacrolimus (TR) or 5% paclitaxel (PT) or cyclosporin A (CS), or with amorphous rapamycin (Amorph), as a function of time of incubation in phosphate buffer saline (pH 7.4, 37° C.) with 0.1% (w/v) TWEEN 20;

FIGS. 57A-57C present SEM images of exemplary stent surfaces seeded with paclitaxel crystals about 0.5-2.5 μm in size, according to some embodiments of the invention;

FIGS. 58A-58C present SEM images of exemplary stent surfaces coated with crystalline paclitaxel following incubation in a paclitaxel solution for 5 minutes (FIG. 58A), 20 minutes (FIG. 58B) or 60 minutes (FIG. 58C), according to some embodiments of the invention;

FIGS. 59A and 59B present SEM images of exemplary stent surfaces coated with crystalline paclitaxel according to some embodiments of the invention (FIG. 59B presents enlarged view of rectangle in FIG. 59A; arrows in FIG. 59B indicate connection points in crystal network);

FIGS. 60A-60C present SEM images of exemplary stent surfaces homogeneously seeded with paclitaxel crystals about 200-400 nm in size, according to some embodiments of the invention;

FIGS. 61A-61F present SEM images of exemplary stent surfaces coated with crystalline paclitaxel following incubation in a solution of paclitaxel in ethyl acetate/hexane (7:65 v/v ratio) for 5 minutes at 25° C., according to some embodiments of the invention;

FIGS. 62A-62D present SEM images of exemplary stent surfaces coated with crystalline paclitaxel following incubation in a solution of paclitaxel in ethyl acetate/hexane (7:65 v/v ratio) for 10 minutes at 25° C., according to some embodiments of the invention;

FIGS. 63A-63F present SEM images of exemplary stent surfaces coated with a continuous layer of crystalline paclitaxel following incubation in a solution of paclitaxel in ethyl acetate/hexane (7:65 v/v ratio) for 15 minutes at 25° C., according to some embodiments of the invention;

FIGS. 64A-64F present SEM images of exemplary stent surfaces coated with a continuous layer of crystalline paclitaxel following incubation in a solution of paclitaxel in ethyl acetate/hexane (7:65 v/v ratio) for 20 minutes at 25° C., according to some embodiments of the invention;

FIGS. 65A-65F present SEM images of exemplary stent surfaces coated with a continuous layer of about 100 μg crystalline paclitaxel per stent following incubation in a solution of paclitaxel in ethyl acetate/hexane (7:65 v/v ratio) for 15 minutes at 25° C., according to some embodiments of the invention;

FIGS. 66A-66F present SEM images of exemplary stent surfaces coated with a layer of about 100 μg amorphous paclitaxel per stent, prepared by spray coating a solution of paclitaxel in ethyl acetate;

FIGS. 67A and 67B are graphs showing cumulative release of paclitaxel (PT) from stents coated with about 100 μg of amorphous paclitaxel (Amorph) or crystalline paclitaxel (Crys), as a function of time of incubation in phosphate buffer saline (pH 7.4, 37° C.) with (FIG. 67B) or without (FIG. 67A) 0.1% (w/v) TWEEN 20;

FIG. 68 is a graph showing cumulative release of rapamycin in an in vitro simulation of in vivo elution (elution medium 2% sodium dodecyl sulfate, 10% acetonitrile, buffered to pH 4.5 with phosphate);

FIGS. 69A-69C are graphs showing cumulative release of rapamycin, expressed as a percentage of total rapamycin (FIG. 69C) or as rapamycin weight (FIGS. 69A and 69B), from exemplary stents with a crystalline rapamycin (RM) coating and a hyaluronic acid (HA) top coat prepared by 1, 2, 3 or 4 cycles of spray coating (100 μl HA solution per cycle) or by continuous spray coating (OL) of 300 μl HA solution, as a function of time of incubation in phosphate buffer saline (pH 7.4, 37° C.);

FIGS. 70A-70C are graphs showing cumulative release of paclitaxel, expressed as a percentage of total paclitaxel (FIG. 70C) or as paclitaxel weight (FIGS. 70A and 70B), from exemplary stents with a crystalline paclitaxel (PT) coating and a hyaluronic acid (HA) top coat prepared by 1, 2, 3 or 4 cycles of spray coating (100 μl HA solution per cycle) or by continuous spray coating (OL) of 300 μl HA solution, as a function of time of incubation in phosphate buffer saline (pH 7.4, 37° C.);

FIGS. 71A and 71B are graphs showing cumulative release of rapamycin, expressed as a percentage of total rapamycin (FIG. 71B) or as rapamycin weight (FIGS. 71A and 71B), from exemplary stents with a crystalline rapamycin (Crys) coating alone or with a top coat containing a layer of hyaluronic acid (HA), a mixture of hyaluronic acid and rapamycin (HA:RM) or amorphous rapamycin (Amorph-Crys), or with an amorphous rapamycin (Amorph) coating alone, as a function of time of incubation in phosphate buffer saline (pH 7.4, 37° C.);

FIG. 72 is a scheme showing an exemplary process according to some embodiments of the invention, wherein rapamycin (X) conjugated to an exemplary aryl diazonium compound is subjected to electrocoating (+e−), to obtain a base layer containing conjugated rapamycin, followed by crystallization or rapamycin on the base layer; and FIGS. 73A-73C depict an exemplary process according to some embodiments of the invention, wherein a gold layer applied on a chromium layer on a stent surface (FIG. 73A) is contacted with a thiol conjugated to rapamycin (X) (FIG. 73B) to obtain rapamycin (X) conjugated to an exemplary aryl diazonium compound is subjected to electrocoating (+e−), to obtain a base layer containing conjugated rapamycin, followed by crystallization or rapamycin on the base layer (FIG. 73C) (FIG. 73B further depicts exemplary thiols suitable for being conjugated to rapamycin).

DESCRIPTION OF SPECIFIC EMBODIMENTS OF THE INVENTION

The present invention, in some embodiments thereof, relates to surfaces having applied thereon therapeutically active agents and, more particularly, but not exclusively, to articles-of-manufacture such as medical devices having applied thereon a crystalline form of a therapeutically active agent.

As discussed hereinabove, current methodologies for manufacturing drug-eluting medical devices such as drug-eluting stents (DES) generally involve either deposition of a polymeric carrier in which the drug is dispersed, or direct deposition of the drug on the surface of the device. As further discussed hereinabove, the use of polymeric materials as drug carriers in drug-eluting devices is associated with adverse side effects, whereby the currently practiced technologies for direct deposition of drugs on the surfaces of medical devices are associated with poor adherence of the drug to the surface, and furthermore, typically result in deposition of an amorphous form of the drug. Both the poor adherence and the amorphous form of the drug result is a non-controllable release of the drug.

The present inventors have now devised and successfully practiced a novel methodology for depositing therapeutically active agents onto a surface, a methodology which is highly beneficial for coating medical devices. This methodology is based on depositing on an object's surface a crystalline form of the therapeutically active agent. This methodology surprisingly results in a well-adhered deposition of the therapeutically active agent onto the surface in the absence of temperature gradient driving crystallization on the surface (e.g., a gradient generated by cooling the surface), and is further characterized by a desirable and controllable release profile.

As described in detail in the Examples section that follows, the methodology presented herein is effected, in some embodiments thereof, by seeding a surface of the substrate with crystalline seeds and/or a base layer with a nucleating agent, followed by contact with a solution of a therapeutically active agent, so as to promote growth of a relatively homogenous and continuous crystalline layer of the agent on the surface in a gradual and controlled manner. As further demonstrated in the Examples section that follows, various parameters of the practiced methodology can be manipulated so as to affect the release profile of the therapeutically active agent.

Thus, using the methodology described herein, objects having deposited on a surface thereof a therapeutically active agent which is, at least in part, in a crystalline form thereof, are obtained. Using the methodology described herein circumvents the need to use a polymeric drug carrier in order to achieve the desirable characteristics of drug-eluting medical devices.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Referring now to the drawings, FIGS. 4, 12 and 32A-32B show that crystallization on a suitable seeded surface results in a continuous crystalline layer, and FIGS. 5A and 5B show that such a crystalline layer is not formed without seeding.

FIGS. 6A-6B show that development of a crystalline drug layer can be modulated according to time of incubation in a dispersion of crystalline drug (for seeding the surface). FIGS. 9-11 and 57A-65F show that development of crystalline layers of different drugs can be modulated according to time of incubation in a solution of the drug (for promoting crystal growth).

FIGS. 14 and 16 show that an exemplary crystalline rapamycin layer prepared as described herein exhibits high degree of crystallinity. In contrast, FIGS. 9 and 12 show that evaporation of various rapamycin solutions results in amorphous rapamycin.

FIG. 15 shows that drug release profiles depend on crystal size, which can be controlled based on crystallization conditions.

FIGS. 17A and 17B show that a stent insertion balloon can be coated by a crystalline rapamycin coating using exemplary procedures described herein. FIGS. 18A-18C show that the crystalline layer remains adhered to the balloon following inflation of the balloon.

FIGS. 19A-20B, 23A-23B, 25A-27 and 30A-31B show that top coats can protect crystalline drug layers on stent surfaces upon stent expansion. FIG. 35 shows that top coats can further protect crystalline drug layers on stent surfaces during stent crimping. FIGS. 28A-29B and 33A-34 show that top coats can substantially reduce roughness of surfaces coated with a crystalline coating.

FIGS. 36A-36E show that rapamycin is progressively degraded upon incubation in an aqueous environment.

FIGS. 37A-37C and 39 show that exemplary crystalline drug layers exhibit slow release and enhance chemical stability of the drug.

FIGS. 40A-46C show that exemplary crystalline rapamycin coatings remain substantially unchanged upon storage for 1 year at temperatures ranging from −20 to 37° C. FIGS. 47A-47C show that amorphous rapamycin is considerably less durable upon storage.

FIGS. 48-54C show that co-crystallization of a small proportion of an additional compound can considerably alter the development of a crystalline drug layer. FIGS. 55A-56C show that co-crystallization can be used to alter a drug release profile.

FIGS. 69A-71B show that the shape of a drug release profile can be controlled based on selected combinations of different types of layers.

FIGS. 72 and 73A-73C each depict an exemplary process for forming a base layer according to some embodiments of the invention.

According to an aspect of some embodiments of the invention, there is provided an article-of-manufacture comprising an object having a surface and at least a first layer of a therapeutically active agent being deposited onto at least a continuous portion of the surface. The first layer is characterized by crystallinity of the therapeutically active agent therein (also referred to herein as a "first therapeutically active agent"), whereby at least 50 weight percents of the first layer is the first therapeutically active agent in a crystalline form.

Herein, the phrase "at least a first layer" means that one or more additional layers may optionally be present in addition to the first layer described herein.

Herein, the phrase "continuous portion" encompasses a portion of a surface, the portion having any possible shape, provided that the portion encompasses all of the surface within the outer boundaries of the portion of the surface, for example, a continuous portion as defined herein does not include holes therein unless such holes are in the surface per se and not only in the given portion of the surface. The "continuous portion" of the surface, is used herein to describe a continuous, non-disrupted coating which is deposited on at least a section of the surface, and optionally on the entire surface.

In some embodiments of any of the embodiments described herein, the first layer is deposited directly onto the surface. By "directly" it is meant that the therapeutically active agent is deposited directly onto the surface, without an additional substance (e.g., a polymeric material) that mediates the binding the therapeutically active agent to the surface.

By "at least 50 weight percents of the first layer is the first therapeutically active agent in a crystalline form" it is meant that at least 50 weight percents of the therapeutically active agent in the first layer exhibits single-crystallinity, as defined herein.

In some embodiments of any of the embodiments described herein, at least 60 weight percents of the first layer is the first therapeutically active agent in a crystalline form.

In some embodiments of any of the embodiments described herein, at least 70 weight percents of the first layer is the first therapeutically active agent in a crystalline form.

In some embodiments of any of the embodiments described herein, at least 80 weight percents of the first layer is the first therapeutically active agent in a crystalline form.

In some embodiments of any of the embodiments described herein, at least 90 weight percents of the first layer is the first therapeutically active agent in a crystalline form.

In some embodiments of any of the embodiments described herein, at least 95 weight percents of the first layer is the first therapeutically active agent in a crystalline form.

In some embodiments of any of the embodiments described herein, at least 98 weight percents of the first layer is the first therapeutically active agent in a crystalline form.

In some embodiments of any of the embodiments described herein, at least 99 weight percents of the first layer is the first therapeutically active agent in a crystalline form.

As used herein, the phrases "crystalline form", "crystallized", "single-crystallinity" and any other grammatical deviation thereof, referring to a therapeutically active agent or a drug, are used interchangeably and describe a form of a solid or semi-solid matter in which the constituent atoms and/or molecules are arranged in the same 3-dimensional ordered, repeating pattern, thus forming a crystalline structure. The pattern can be detected and determined according to known methods used in the chemical arts, including, for example, visual identification of crystals (typically by their relatively simple geometric shapes) and identification of X-ray diffraction patterns. The portion of the therapeutically active agent that is not in a crystalline form is in an amorphous form. The degree (and type) of crystallinity may be determined according to any suitable method known to those skilled in the chemical arts, for example, the method described in Wang et al. [*Am. J. Biochem. Biotech.* 1:207-211, 2005].

As exemplified herein, crystalline layers according to some embodiments of the invention may cover a substantial portion of a surface or of a continuous portion of a surface.

In some embodiments of any of the embodiments described herein, at least 50% of an area of a continuous portion of the surface is covered by the first layer. In some such embodiments, the continuous portion has an area of at least 1 mm². In some such embodiments, the continuous portion has an area of at least 3 mm². In some such embodiments, the continuous portion has an area of at least 10 mm². In some such embodiments, the continuous portion has an area of at least 30 mm². In some such embodiments, the continuous portion has an area of at least 100 mm².

Herein, if a layer contains one or more holes therein, it is to be understood that the surface exposed by the holes is considered a part of the area of the continuous portion of the surface which encompasses the holes, but the holes are not considered part of the area of the layer, such that the layer with one or more holes is considered as covering less than 100% of the continuous portion of the surface.

In some embodiments of any of the embodiments described herein, at least 60% of an area of a continuous portion of the surface is covered by the first layer. In some such embodiments, the continuous portion has an area of at least 1 mm². In some such embodiments, the continuous portion has an area of at least 3 mm². In some such embodiments, the continuous portion has an area of at least 10 mm². In some such embodiments, the continuous portion has an area of at least 30 mm². In some such embodiments, the continuous portion has an area of at least 100 mm².

In some embodiments of any of the embodiments described herein, at least 70% of an area of a continuous portion of the surface is covered by the first layer. In some such embodiments, the continuous portion has an area of at least 1 mm². In some such embodiments, the continuous portion has an area of at least 3 mm². In some such embodiments, the continuous portion has an area of at least 10 mm². In some such embodiments, the continuous portion has an area of at least 30 mm². In some such embodiments, the continuous portion has an area of at least 100 mm².

In some embodiments of any of the embodiments described herein, at least 80% of an area of a continuous portion of the surface is covered by the first layer. In some such embodiments, the continuous portion has an area of at least 1 mm². In some such embodiments, the continuous portion has an area of at least 3 mm². In some such embodiments, the continuous portion has an area of at least 10 mm². In some such embodiments, the continuous portion has an area of at least 30 mm². In some such embodiments, the continuous portion has an area of at least 100 mm².

In some embodiments of any of the embodiments described herein, at least 90% of an area of a continuous portion of the surface is covered by the first layer. In some such embodiments, the continuous portion has an area of at least 1 mm². In some such embodiments, the continuous portion has an area of at least 3 mm². In some such embodiments, the continuous portion has an area of at least 10 mm². In some such embodiments, the continuous portion has an area of at least 30 mm². In some such embodiments, the continuous portion has an area of at least 100 mm².

As exemplified herein, crystalline layers according to some embodiments of the invention may be relatively continuous "carpets", having few or no substantial holes (e.g., regions at least 4 μm in diameter on the surface which are devoid of the first therapeutically active agent).

Herein, the a region is optionally determined to be "devoid of" a therapeutically active agent by determining an absence of material which is visible by scanning electron microscopy and comprises the therapeutically active agent, wherein the material is at least 100 nm in diameter.

Herein, a region "at least 4 μm in diameter" means that the region fully encompasses a circle having a diameter of 4 μm.

In some embodiments of any of the embodiments described herein, the continuous portion optionally comprises regions at least 4 μm in diameter which are devoid of the first therapeutically active agent, provided that a concentration of said regions is less than 2 of said regions per mm². In some such embodiments, a concentration of said regions is less than 1 of said regions per mm². In some such embodiments, a concentration of said regions is less than 0.5 of said regions per mm². In some such embodiments, a concentration of said regions is less than 0.25 of said regions per mm². In some such embodiments, a concentration of said regions is less than 0.1 of said regions per mm².

In some embodiments, the first layer is characterized by relatively thin dimensions and/or low amount of therapeutically active agent per area.

Without being bound by any particular theory, it is believed that such crystalline layers are advantageous in that they provide suitable doses of therapeutically active agent, are more durable than thicker layers, and/or are more controllable and reproducible than thicker layers.

In some embodiments of any of the embodiments described herein, an average thickness of the first layer according to any of the respective embodiments described herein is no more than 20 μm. In some such embodiments, at least 50% of an area of a continuous portion of the surface is covered by a first layer having the aforementioned average thickness. In some such embodiments, at least 60% of an area of a continuous portion of the surface is covered by a first layer having the aforementioned average thickness. In some such embodiments, at least 70% of an area of a continuous portion of the surface is covered by a first layer having the aforementioned average thickness. In some such embodiments, at least 80% of an area of a continuous portion of the surface is covered by a first layer having the aforementioned average thickness. In some such embodiments, at least 90% of an area of a continuous portion of the surface is covered by a first layer having the aforementioned average thickness. In some such embodiments, at least 95% of an area of a continuous portion of the surface is covered by a first layer having the aforementioned average thickness. In some such embodiments, at least 98% of an area of a continuous portion of the surface is covered by a first layer having the aforementioned average thickness. In some such embodiments, at least 99% of an area of a continuous portion of the surface is covered by a first layer having the aforementioned average thickness.

In some embodiments of any of the embodiments described herein, an average thickness of the first layer according to any of the respective embodiments described herein is no more than 10 μm. In some such embodiments, at least 50% of an area of a continuous portion of the surface is covered by a first layer having the aforementioned average thickness. In some such embodiments, at least 60% of an area of a continuous portion of the surface is covered by a first layer having the aforementioned average thickness. In some such embodiments, at least 70% of an area of a continuous portion of the surface is covered by a first layer having the aforementioned average thickness. In some such embodiments, at least 80% of an area of a continuous portion of the surface is covered by a first layer having the aforementioned average thickness. In some such embodiments, at least 90% of an area of a continuous portion of the surface is covered by a first layer having the aforementioned average thickness. In some such embodiments, at least 95% of an area of a continuous portion of the surface is covered by a first layer having the aforementioned average thickness. In some such embodiments, at least 98% of an area of a continuous portion of the surface is covered by a first layer having the aforementioned average thickness. In some such embodiments, at least 99% of an area of a continuous portion of the surface is covered by a first layer having the aforementioned average thickness.

In some embodiments of any of the embodiments described herein, an average thickness of the first layer according to any of the respective embodiments described herein is no more than 5 μm. In some such embodiments, at least 50% of an area of a continuous portion of the surface is covered by a first layer having the aforementioned average thickness. In some such embodiments, at least 60% of an area of a continuous portion of the surface is covered by a first layer having the aforementioned average thickness. In some such embodiments, at least 70% of an area of a continuous portion of the surface is covered by a first layer having the aforementioned average thickness. In some such embodiments, at least 80% of an area of a continuous portion of the surface is covered by a first layer having the aforementioned average thickness. In some such embodiments, at least 90% of an area of a continuous portion of the surface is covered by a first layer having the aforementioned average thickness. In some such embodiments, at least 95% of an area of a continuous portion of the surface is covered by a first layer having the aforementioned average thickness. In some such embodiments, at least 98% of an area of a continuous portion of the surface is covered by a first layer having the aforementioned average thickness. In some such embodiments, at least 99% of an area of a continuous portion of the surface is covered by a first layer having the aforementioned average thickness.

In some embodiments of any of the embodiments described herein, an average thickness of the first layer according to any of the respective embodiments described herein is no more than 2.5 μm. In some such embodiments, at least 50% of an area of a continuous portion of the surface is covered by a first layer having the aforementioned average thickness. In some such embodiments, at least 60% of an area of a continuous portion of the surface is covered by a first layer having the aforementioned average thickness. In some such embodiments, at least 70% of an area of a continuous portion of the surface is covered by a first layer having the aforementioned average thickness. In some such embodiments, at least 80% of an area of a continuous portion of the surface is covered by a first layer having the aforementioned average thickness. In some such embodiments, at least 90% of an area of a continuous portion of the surface is covered by a first layer having the aforementioned average thickness. In some such embodiments, at least 95% of an area of a continuous portion of the surface is covered by a first layer having the aforementioned average thickness. In some such embodiments, at least 98% of an area of a continuous portion of the surface is covered by a first layer having the aforementioned average thickness. In some such embodiments, at least 99% of an area of a continuous portion of the surface is covered by a first layer having the aforementioned average thickness.

In some embodiments of any of the embodiments described herein, an average density of the first therapeutically active agent on the continuous portion of the surface is no more than 6 $\mu g/mm^2$. In some such embodiments, at least 50% of an area of the continuous portion of the surface is covered by a first layer of the first therapeutically active agent. In some such embodiments, at least 60% of an area of the continuous portion of the surface is covered by a first layer of the first therapeutically active agent. In some such embodiments, at least 70% of an area of the continuous portion of the surface is covered by a first layer of the first therapeutically active agent. In some such embodiments, at least 80% of an area of the continuous portion of the surface is covered by a first layer of the first therapeutically active agent. In some such embodiments, at least 90% of an area of the continuous portion of the surface is covered by a first layer of the first therapeutically active agent. In some such embodiments, at least 95% of an area of the continuous portion of the surface is covered by a first layer of the first therapeutically active agent. In some such embodiments, at least 98% of an area of the continuous portion of the surface is covered by a first layer of the first therapeutically active agent. In some such embodiments, at least 99% of an area of the continuous portion of the surface is covered by a first layer of the first therapeutically active agent.

Herein, the term "average density", when denoted by units of mass per area, refers to an amount of material per area.

In some embodiments of any of the embodiments described herein, an average density of the first therapeutically active agent on the continuous portion of the surface is no more than 5 $\mu g/mm^2$. In some such embodiments, at least 50% of an area of the continuous portion of the surface is covered by a first layer of the first therapeutically active agent. In some such embodiments, at least 60% of an area of the continuous portion of the surface is covered by a first layer of the first therapeutically active agent. In some such embodiments, at least 70% of an area of the continuous portion of the surface is covered by a first layer of the first therapeutically active agent. In some such embodiments, at least 80% of an area of the continuous portion of the surface is covered by a first layer of the first therapeutically active agent. In some such embodiments, at least 90% of an area of the continuous portion of the surface is covered by a first layer of the first therapeutically active agent. In some such embodiments, at least 95% of an area of the continuous portion of the surface is covered by a first layer of the first therapeutically active agent. In some such embodiments, at least 98% of an area of the continuous portion of the surface is covered by a first layer of the first therapeutically active agent. In some such embodiments, at least 99% of an area of the continuous portion of the surface is covered by a first layer of the first therapeutically active agent.

In some embodiments of any of the embodiments described herein, an average density of the first therapeutically active agent on the continuous portion of the surface is no more than 4 $\mu g/mm^2$. In some such embodiments, at least 50% of an area of the continuous portion of the surface is covered by a first layer of the first therapeutically active agent. In some such embodiments, at least 60% of an area of the continuous portion of the surface is covered by a first layer of the first therapeutically active agent. In some such embodiments, at least 70% of an area of the continuous portion of the surface is covered by a first layer of the first therapeutically active agent. In some such embodiments, at least 80% of an area of the continuous portion of the surface is covered by a first layer of the first therapeutically active agent. In some such embodiments, at least 90% of an area of the continuous portion of the surface is covered by a first layer of the first therapeutically active agent. In some such embodiments, at least 95% of an area of the continuous portion of the surface is covered by a first layer of the first therapeutically active agent. In some such embodiments, at least 98% of an area of the continuous portion of the surface is covered by a first layer of the first therapeutically active agent. In some such embodiments, at least 99% of an area of the continuous portion of the surface is covered by a first layer of the first therapeutically active agent.

In some embodiments of any of the embodiments described herein, an average density of the first therapeutically active agent on the continuous portion of the surface is no more than 3 $\mu g/mm^2$. In some such embodiments, at least 50% of an area of the continuous portion of the surface is covered by a first layer of the first therapeutically active agent. In some such embodiments, at least 60% of an area of the continuous portion of the surface is covered by a first layer of the first therapeutically active agent. In some such embodiments, at least 70% of an area of the continuous portion of the surface is covered by a first layer of the first therapeutically active agent. In some such embodiments, at least 80% of an area of the continuous portion of the surface is covered by a first layer of the first therapeutically active agent. In some such embodiments, at least 90% of an area of the continuous portion of the surface is covered by a first layer of the first therapeutically active agent. In some such embodiments, at least 95% of an area of the continuous portion of the surface is covered by a first layer of the first therapeutically active agent. In some such embodiments, at least 98% of an area of the continuous portion of the surface is covered by a first layer of the first therapeutically active agent. In some such embodiments, at least 99% of an area of the continuous portion of the surface is covered by a first layer of the first therapeutically active agent.

In some embodiments of any of the embodiments described herein, an average density of the first therapeutically active agent on the continuous portion of the surface is no more than 1 μg/mm$^2$. In some such embodiments, at least 50% of an area of the continuous portion of the surface is covered by a first layer of the first therapeutically active agent. In some such embodiments, at least 60% of an area of the continuous portion of the surface is covered by a first layer of the first therapeutically active agent. In some such embodiments, at least 70% of an area of the continuous portion of the surface is covered by a first layer of the first therapeutically active agent. In some such embodiments, at least 80% of an area of the continuous portion of the surface is covered by a first layer of the first therapeutically active agent. In some such embodiments, at least 90% of an area of the continuous portion of the surface is covered by a first layer of the first therapeutically active agent. In some such embodiments, at least 95% of an area of the continuous portion of the surface is covered by a first layer of the first therapeutically active agent. In some such embodiments, at least 98% of an area of the continuous portion of the surface is covered by a first layer of the first therapeutically active agent. In some such embodiments, at least 99% of an area of the continuous portion of the surface is covered by a first layer of the first therapeutically active agent.

In some embodiments of any of the embodiments described herein, the crystalline form of the first therapeutically active agent in the first layer comprises crystals having an average diameter in a range of from 200 nm to 5 μm. In some embodiments, the average diameter is in a range of from 400 nm to 5 μm. In some embodiments, the average diameter is in a range of from 1 to 5 μm. In some embodiments, the average diameter is in a range of from 2 to 5 μm.

Herein throughout, an "average diameter" refers to a median diameter of particles (e.g., crystals), the diameter of each particle being the length of a particle (i.e., the longest dimension) as viewed by microscopy (e.g., scanning electron microscopy).

Additional Layers Comprising a Therapeutically Active Agent:

In some embodiments of any of the embodiments described herein, a surface (e.g., a surface of an object of an article-of-manufacture) according to any of the embodiments described herein comprises one or more additional layers comprising a therapeutically active agent, the additional layer(s) being deposited onto at least a portion of a continuous portion of the surface on which a first layer is deposited, such that a first layer overlies one or more additional layer and/or one or more additional layer overlies a first layer (i.e., one of the aforementioned layers overlies the other(s)). In embodiments relating to two or more additional layers, the additional layers may include layers having the same composition (e.g., are composed of the same compound(s) in the same proportions) and/or layers having different compositions (e.g., are composed of the different compound(s) and/or in different proportions of compounds).

Herein, the terms "overlie" and "overlying" refer to a layer (the overlying layer) having one or more other layers (the layer(s) being overlain, also referred to herein as "underlying") between it and a surface, such that the overlying layer is distal to the surface.

In some embodiments of any of the embodiments described herein, each of the one or more addition layers (according to any of the respective embodiments described herein). The first layer may optionally be in direct contact with the surface or with a base layer (according to any of the respective embodiments described herein) on the surface.

In some embodiments of any of the embodiments described herein, a first layer (according to any of the respective embodiments described herein) overlies each of the one or more addition layers (according to any of the respective embodiments described herein). The lowermost additional layer may optionally be in direct contact with the surface or with a base layer (according to any of the respective embodiments described herein) on the surface.

In some embodiments of any of the embodiments described herein, at least one additional layer (according to any of the respective embodiments described herein) overlies a first layer (according to any of the respective embodiments described herein), and the first layer overlies at least one other additional layer (according to any of the respective embodiments described herein). The lowermost additional layer may optionally be in direct contact with the surface or with a base layer (according to any of the respective embodiments described herein) on the surface.

In some embodiments of any of the embodiments described herein, at least one additional layer is different than the first layer according to any of the respective embodiments described herein, that is, at least two types of a layer comprising a therapeutically active agent are present (e.g., a first layer and an additional layer).

In some embodiments of any of the embodiments described herein, at least one additional layer is a first layer according to any of the respective embodiments described herein, that is, at least two first layers are present. In some such embodiments, at least one additional layer is different than the first layers.

In some embodiments of any of the embodiments described herein, at least one additional layer differs from a first layer (according to any of the respective embodiments described herein) in that a therapeutically active agent in the additional layer(s) (referred to herein as a "second therapeutically active agent") differs from the first therapeutically active agent in the first layer.

In some embodiments, the second therapeutically active agent is the same agent as the first therapeutically active agent, but in a different form than the first therapeutically active agent. In some embodiments, the second therapeutically active agent is in an amorphous form (as opposed to the crystalline form in the first layer). In some embodiments, the second therapeutically active agent is in a crystalline form which is different than the crystalline form in the first layer (also referred to herein as the "first crystalline form").

Different crystalline forms of a therapeutically active agent may comprise, for example, different polymorphs. In some embodiments of any of the embodiments described herein wherein the first therapeutically active agent is rapamycin, the first therapeutically active agent comprises crystalline rapamycin primarily (at least 50%) as polymorph II (e.g., having cell unit parameters of about a=34.9; b=13.1; c=12.3 angstrom), and the second therapeutically active agent is amorphous rapamycin or rapamycin in a crystalline form other than polymorph II.

Top Coat:

In some embodiments of any of the embodiments described herein, a surface (e.g., a surface of an object of an article-of-manufacture) according to any of the embodiments described herein further comprises a top coat (also referred to herein interchangeably as a "coat layer" which coats at least a portion of the first layer (according to any of the respective embodiments described herein). The top coat may optionally directly contact the first layer and/or be separated from the first layer by an intervening substance (e.g., one or more additional layers described herein according to any of the respective embodiments).

A top coat may consist essentially of a single layer or comprise multiple layers, which may be the same as and/or different from each other.

In some embodiments of any of the embodiments described herein, the top coat comprises a water-soluble material, for example, in order to facilitate its removal shortly after it is placed in a physiological environment. In some embodiments, at least 20 weight percents of the top coat (by dry weight) is water-soluble material. In some embodiments, at least 30 weight percents of the top coat (by dry weight) is water-soluble material. In some embodiments, at least 40 weight percents of the top coat (by dry weight) is water-soluble material. In some embodiments, at least 50 weight percents of the top coat (by dry weight) is water-soluble material. In some embodiments, at least 60 weight percents of the top coat (by dry weight) is water-soluble material. In some embodiments, at least 70 weight percents of the top coat (by dry weight) is water-soluble material. In some embodiments, at least 80 weight percents of the top coat (by dry weight) is water-soluble material. In some embodiments, at least 90 weight percents of the top coat (by dry weight) is water-soluble material. In some embodiments, the top coat essentially consists of a water-soluble material.

A top coat comprising a water-soluble material can serve as protection against forces associated with preparation (e.g., crimping processes), packaging, shipping and/or use of an object (e.g., a medical device), but dissolve after a brief period of time in an aqueous environment. Water-soluble gels (e.g., hydrogels) are exemplary water-soluble materials that can be used as a top layer, according to some embodiments of the invention.

The optimal rate of dissolution in an aqueous environment will depend on the particular use of the object. Optionally, for an object used in physiological conditions (e.g., a medical device or an implantable medical device) at least 20% (by dry weight) of the top coat is dissolved after 1 hour under physiological conditions. Optionally, the percentage of top coat which dissolves after 1 hour under physiological conditions is in a range of 20% to 90%, optionally 30% to 70%, and optionally 40% to 60% (by dry weight).

A top coat should typically have some elasticity and lack stickiness. For devices which are used at temperatures other than room temperature (e.g., implantable medical devices used in the body), the top layer may be more resilient and less elastic at room temperature in order to more effectively protect the object before use, and more elastic and less resilient at the temperature at which the object is used (e.g., 37° C.) in order to ease the use of the object and facilitate the removal of the top coat after it is no longer needed.

One of ordinary skill in the art will be capable of selecting a material for forming a top coat with the appropriate chemical properties discussed hereinabove.

The top coat can be formed from, for example, biodegradable, hydrophobic, amphiphilic or hydrophilic polymers, from organic compounds such as fatty acids and glycerol, from surfactants such as TWEENs, and from any combination thereof.

In some embodiments of any of the embodiments described herein, the top coat comprises a polymeric substance. In some embodiments, the dry weight of the top coat essentially consists of a polymeric substance.

Herein, the term "polymeric substance" refers to a substance which consists primarily of one or more polymers, that is, at least 50 weight percents of the substance (by dry weight) consists of one or more polymers.

In some embodiments of any of the embodiments described herein, the top coat comprises a polysaccharide or an oligosaccharide, optionally a water-soluble polysaccharide or oligosaccharide. In some embodiments, at least 20 weight percents of the top coat (by dry weight) consists of a polysaccharide or an oligosaccharide, optionally a water-soluble polysaccharide or oligosaccharide. In some embodiments, at least 30 weight percents of the top coat (by dry weight) consists of a polysaccharide, optionally a water-soluble polysaccharide. In some embodiments, at least 40 weight percents of the top coat (by dry weight) consists of a polysaccharide, optionally a water-soluble polysaccharide. In some embodiments, at least 50 weight percents of the top coat (by dry weight) consists of a polysaccharide, optionally a water-soluble polysaccharide. In some embodiments, at least 60 weight percents of the top coat (by dry weight) consists of a polysaccharide, optionally a water-soluble polysaccharide. In some embodiments, at least 70 weight percents of the top coat (by dry weight) consists of a polysaccharide, optionally a water-soluble polysaccharide. In some embodiments, at least 80 weight percents of the top coat (by dry weight) consists of a polysaccharide, optionally a water-soluble polysaccharide. In some embodiments, at least 90 weight percents of the top coat (by dry weight) consists of a polysaccharide, optionally a water-soluble polysaccharide. In some embodiments, the top coat (by dry weight) essentially consists of a polysaccharide, optionally a water-soluble polysaccharide.

Examples of polysaccharides or oligosaccharides which may optionally be used for forming the top coat include, without limitation, hyaluronic acid, cellulose derivatives (e.g., carboxymethylcellulose), dextran, chitosan, alginate and arabinogalactan, and copolymers and/or mixtures thereof.

As exemplified herein, hyaluronic acid is a particularly suitable substance for forming a top coat.

In some embodiments of any of the embodiments described herein, at least 20 weight percents of the top coat (by dry weight) consists of hyaluronic acid. In some embodiments, at least 30 weight percents of the top coat (by dry weight) consists of hyaluronic acid. In some embodiments, at least 40 weight percents of the top coat (by dry weight) consists of hyaluronic acid. In some embodiments, at least 50 weight percents of the top coat (by dry weight) consists of hyaluronic acid. In some embodiments, at least 60 weight percents of the top coat (by dry weight) consists of hyaluronic acid. In some embodiments, at least 70 weight percents of the top coat (by dry weight) consists of hyaluronic acid. In some embodiments, at least 80 weight percents of the top coat (by dry weight) consists of hyaluronic acid. In some embodiments, at least 90 weight percents of the top coat (by dry weight) consists of hyaluronic acid. In some embodiments, the top coat (by dry weight) essentially consists of hyaluronic acid.

In some embodiments of any of the embodiments described herein, at least 20 weight percents of the water-soluble material in the top coat (by dry weight) consists of hyaluronic acid. In some embodiments, at least 30 weight percents of the water-soluble material in the top coat (by dry weight) consists of hyaluronic acid. In some embodiments, at least 40 weight percents of the water-soluble material in the top coat (by dry weight) consists of hyaluronic acid. In some embodiments, at least 50 weight percents of the water-soluble material in the top coat (by dry weight) consists of hyaluronic acid. In some embodiments, at least 60 weight percents of the water-soluble material in the top coat (by dry weight) consists of hyaluronic acid. In some embodiments, at least 70 weight percents of the water-soluble material in the top coat (by dry weight) consists of hyaluronic acid. In some embodiments, at least 80 weight percents of the water-soluble material in the top coat (by dry weight) consists of hyaluronic acid. In some embodiments, at least 90 weight percents of the water-soluble material in the top coat (by dry weight) consists of hyaluronic acid. In some embodiments, of the water-soluble material in the top coat (by dry weight) essentially consists of hyaluronic acid.

In some embodiments of any of the embodiments described herein, the polymeric substance (as defined herein) in the top coat is a mixture of a polymer and a plasticizer. In some embodiments, the polymer is a polysaccharide (e.g., according to any of the respective embodiments described herein). In some embodiments the polysaccharide is a polysaccharide other than hyaluronic acid. In some embodiments the polysaccharide is carboxymethylcellulose (CMC).

In some embodiments of any of the respective embodiments described herein, the plasticizer is a polyalkylene glycol. Examples of suitable polyalkylene glycols include polyethylene glycol, polypropylene glycol and copolymers thereof (e.g., poloxamers).

In some embodiments of any of the respective embodiments described herein, an average molecular weight (e.g., weight average molecular weight) of the polyalkylene glycol (e.g., polyethylene glycol) is in a range of from 0.5 to 30 kDa. In some embodiments, the average molecular weight (e.g., weight average molecular weight) is in a range of from 1 kDa to 15 kDa. In some embodiments, the average molecular weight (e.g., weight average molecular weight) is in a range of from 1 kDa to 10 kDa. In some embodiments, the average molecular weight (e.g., weight average molecular weight) is in a range of from 2 kDa to 7 kDa. In some embodiments, the average molecular weight (e.g., weight average molecular weight) is in a range of from 3 kDa to 6 kDa. In some exemplary embodiments, the average molecular weight (e.g., weight average molecular weight) is about 4.6 kDa.

In some embodiments of any of the respective embodiments described herein, the object is devoid of a water-insoluble polymeric carrier on said surface which envelops the first therapeutically active agent, e.g., such that the first therapeutically active agent is not enveloped by a water-insoluble polymeric material.

As used herein, the term "carrier" describes a substance, typically a solid or semi-solid substance, which is deposited on the object's surface, and in which a drug is dispersed, embedded or encapsulated. Carriers are typically used to promote adherence of the therapeutically active agent to the surface and/or to control (e.g., to slow) the release of the therapeutically active agent.

A "polymeric carrier" refers herein to a carrier that comprises a polymeric material.

As used herein, the term "envelop" encompasses covering (e.g., overlying), surrounding and encapsulating.

As used herein, the term "water-insoluble" refers to a solubility in water (at pH 7) of less than 10 grams/liter.

Herein throughout, the term "water-soluble" refers to a solubility in water (at pH 7) of at least 10 grams/liter.

In some embodiments of any of the embodiments described herein, the top coat comprises a therapeutically active agent, optionally a second therapeutically active agent (e.g., according to any of the respective embodiments described herein).

It is to be appreciated that a top coat comprising a therapeutically active agent may also be considered an additional layer (according to any of the respective embodiments described herein), or a plurality of additional layers if the top coat comprises multiple layers according to any of the respective embodiments described herein.

Release of Therapeutically Active Agent:

In some embodiments of any of the embodiments described herein, less than 20% (by weight) of the first therapeutically active agent on the object is released upon subjecting the object to physiological conditions for 24 hours. In some embodiments, less than 10% (by weight) of the first therapeutically active agent on the object is released upon subjecting the object to physiological conditions for 24 hours. In some embodiments, less than 5% (by weight) of the first therapeutically active agent on the object is released upon subjecting the object to physiological conditions for 24 hours. In some embodiments, less than 2.5% (by weight) of the first therapeutically active agent on the object is released upon subjecting the object to physiological conditions for 24 hours. In some embodiments, less than 1% (by weight) of the first therapeutically active agent on the object is released upon subjecting the object to physiological conditions for 24 hours.

Herein throughout, the phrase "physiological conditions" is optionally represented by exposure to aqueous phosphate buffer (optionally at a concentration of 0.1 M) at pH 7.4 and 37° C. (e.g., as exemplified herein).

In some embodiments of any of the embodiments described herein, less than 60% (by weight) of the first therapeutically active agent on the object is released upon subjecting the object to physiological conditions for 28 days. In some embodiments, less than 50% (by weight) of the first therapeutically active agent on the object is released upon subjecting the object to physiological conditions for 28 days. In some embodiments, less than 40% (by weight) of the first therapeutically active agent on the object is released upon subjecting the object to physiological conditions for 28 days. In some embodiments, less than 30% (by weight) of the first therapeutically active agent on the object is released upon subjecting the object to physiological conditions for 28 days. In some embodiments, less than 20% (by weight) of the first therapeutically active agent on the object is released upon subjecting the object to physiological conditions for 28 days. In some embodiments, less than 10% (by weight) of the first therapeutically active agent on the object is released upon subjecting the object to physiological conditions for 28 days.

In some embodiments of any of the embodiments described herein, less than 80% (by weight) of the first therapeutically active agent on the object is released upon subjecting the object to physiological conditions for 90 days. In some embodiments, less than 70% (by weight) of the first therapeutically active agent on the object is released upon subjecting the object to physiological conditions for 90 days. In some embodiments, less than 60% (by weight) of the first therapeutically active agent on the object is released upon subjecting the object to physiological conditions for 90 days. In some embodiments, less than 50% (by weight) of the first therapeutically active agent on the object is released upon subjecting the object to physiological conditions for 90 days. In some embodiments, less than 40% (by weight) of the first therapeutically active agent on the object is released upon subjecting the object to physiological conditions for 90 days. In some embodiments, less than 30% (by weight) of the first therapeutically active agent on the object is released upon subjecting the object to physiological conditions for 90 days.

As exemplified herein, drug release profiles of exemplary coated surfaces according to some embodiments are characterized by a relatively steady rate of drug release over time, as opposed to a profile wherein drug release is initially quite high and decreases considerably over time (e.g., due to depletion of the agent from the coated surface).

In some embodiments of any of the embodiments described herein, an amount of the first therapeutically active agent that is released upon subjecting said object to physiological conditions for 28 days is no more than 70% of an amount of the first therapeutically active agent that is released upon subjecting said object to physiological conditions for 90 days. In some embodiments, an amount of the first therapeutically active agent that is released upon subjecting the object to physiological conditions for 28 days is no more than 60% of an amount of the first therapeutically active agent that is released upon subjecting the object to physiological conditions for 90 days. In some embodiments, an amount of the first therapeutically active agent that is released upon subjecting the object to physiological conditions for 28 days is no more than 50% of an amount of the first therapeutically active agent that is released upon subjecting the object to physiological conditions for 90 days. In some embodiments, an amount of the first therapeutically active agent that is released upon subjecting the object to physiological conditions for 28 days is no more than 40% of an amount of the first therapeutically active agent that is released upon subjecting the object to physiological conditions for 90 days.

As exemplified herein, more rapid release and/or a more heterogeneous release profile (e.g., a combination of rapid release and slow release) may be obtained in a predictable manner by selecting suitable proportions of crystalline and amorphous therapeutically active agent, optionally in different layers.

Herein throughout, percentages of released therapeutically active agent are optionally determined by considering degraded (e.g., inactive) forms of the agent as part of the amounts of active agent.

As further exemplified herein, the crystalline form of a first therapeutically active agent enhances the chemical stability of the agent, thereby increasing a percentage of the agent which is released in its native (i.e., undegraded) form.

In some embodiments of any of the embodiments described herein, at least 10% of the first therapeutically active agent (according to any of the respective embodiments described herein) that is released upon subjecting the object to physiological conditions for 90 days is released in a native form. In some embodiments, at least 20% of the first therapeutically active agent that is released upon subjecting the object to physiological conditions for 90 days is released in a native form. In some embodiments, at least 30% of the first therapeutically active agent that is released upon subjecting the object to physiological conditions for 90 days is released in a native form. In some embodiments, at least 40% of the first therapeutically active agent that is released upon subjecting the object to physiological conditions for 90 days is released in a native form. In some embodiments, at least 50% of the first therapeutically active agent that is released upon subjecting the object to physiological conditions for 90 days is released in a native form. In some embodiments, at least 60% of the first therapeutically active agent that is released upon subjecting the object to physiological conditions for 90 days is released in a native form. In some embodiments, at least 70% of the first therapeutically active agent that is released upon subjecting the object to physiological conditions for 90 days is released in a native form. In some embodiments, at least 80% of the first therapeutically active agent that is released upon subjecting the object to physiological conditions for 90 days is released in a native form. In some embodiments, at least 90% of the first therapeutically active agent that is released upon subjecting the object to physiological conditions for 90 days is released in a native form. In some of any of the abovementioned embodiments, the first therapeutically active agent is rapamycin or a derivative thereof.

Base Layer:

In some embodiments of any of the embodiments described herein, a surface (e.g., a surface of an object of comprises by an article-of-manufacture) according to any of the respective embodiments described herein has a base layer applied onto at least a portion of the surface. In some embodiments, at least a portion of a first layer (according to any of the respective embodiments described herein) is deposited onto the base layer. In some such embodiments, the first layer is deposited directly onto the base layer.

In some embodiments of any of the embodiments described herein relating to a base layer, at least one nucleating agent is conjugated to the base layer, for example, by a covalent bond. In some embodiments, the at least one nucleating agent comprises a first therapeutically active agent (according to any of the respective embodiments described herein). In some embodiments, the nucleating agent described herein is a first therapeutically active agent (according to any of the respective embodiments described herein).

Herein, the term "nucleating agent" refers to a compound or moiety which enhances formation of crystals, for example, crystals of a first therapeutically active agent described herein.

Without being bound by any particular theory, it is believed that a given compound (e.g., a first therapeutically active agent described herein) is generally an effective nucleating agent with respect to nucleation of crystals of the given compound.

In some embodiments of any of the embodiments described herein, the surface is a conductive or semiconductive surface and the base layer comprises at least one moiety being electrochemically attached to said surface. Examples of moieties which may optionally be electrochemically attached to the surface include aryl moieties, which may optionally be covalently bound to a conductive or semi-conductive surface, and thiol moieties, which may optionally be complexed to a conductive or semi-conductive surface such as a surface comprising gold (e.g., as —S—Au).

In some embodiments of any of the respective embodiments described herein, a thiol described herein is an alkyl thiol substituted at least by a functional group which is conjugated to the nucleating agent. The alkyl thiol may comprise a linear or branched alkyl, and may optionally comprise from 1 to 20 carbon atoms, optionally 1 to 16 carbon atoms, optionally 1 to 12 carbon atoms, optionally 1 to 8 carbon atoms, and optionally 1 to 4 carbon atoms.

Examples of suitable functional groups include amine (e.g., —NH$_2$), hydroxy, carboxy (e.g., —C(=O)OH), amide (e.g., —C(=O)NH$_2$) and phosphonate (e.g., —P(=O)(OH)$_2$). For example, an amine group can be conjugated to a carbon atom of a nucleating agent to form an amine or amide moiety (e.g., —NH—R*, wherein R* is the nucleating agent moiety); a hydroxy group can be conjugated to a nucleating agent to form an ether or ester moiety —O—R* wherein R* is the nucleating agent moiety; a carboxy group can be conjugated to a nucleating agent to form an ester moiety —C(=O)O—R* or to an amine group of a nucleating agent to form an amide moiety —C(=O)—R* (wherein R* is the nucleating agent moiety); and a phosphonate group can be conjugated to a nucleating agent, e.g., to form —P(=O)(OH)O—R*, wherein R* is the nucleating agent moiety.

In some embodiments of any of the embodiments described herein, the base layer is a non-polymeric layer.

Therapeutically Active Agents:

Herein throughout, the terms "drug" and "therapeutically active agent", and simply an "agent" or an "active agent", are used herein interchangeably and describe a compound or composition that exhibits a beneficial therapeutic effect when administered to a subject. Thus, a therapeutically active agent is any agent known in the medical arts to have a therapeutic effect, and that is capable of treating or preventing, as these terms are defined herein, a medical condition.

Therapeutically active agents that are suitable for use as a first therapeutically active agent and/or second therapeutically active agent in the context of embodiments of the invention include, but are not limited to, anti-restenosis agents, anti-thrombogenic agents, anti-platelet agents, anti-coagulants, statins, toxins, antimicrobial agents, analgesics, anti-metabolic agents, vasoactive agents, vasodilators, prostaglandins, thrombin inhibitors, vitamins, cardiovascular agents, antibiotics, chemotherapeutic agents, antioxidants, phospholipids, anti-proliferative agents, paclitaxel, rapamycin, tacrolimus, cyclosporin A, and any combination thereof.

Additional agents include, but are not limited to, peptides, proteins, hormones, growth factors, enzymes, antibodies, nucleic acids, oligonucleotides, antisense molecules, and the like.

In general, the first therapeutically active agent is such that can adapt a crystalline form under common crystallization or re-crystallization conditions (e.g., dissolution and crystallization from a saturated or supersaturated solution of the active agent), whereby the crystalline form thereof is identifiable by common techniques, as delineated herein.

In some embodiments, the first and/or second therapeutically active agent is an anti-proliferative agent, such as, for example, those currently used in drug-eluting stents.

In some embodiments of any of the embodiments described herein, the first and/or second therapeutically active agent is a drug such as rapamycin, tacrolimus, cyclosporin A or paclitaxel, including derivatives and analogs thereof. In some embodiments, at least the first therapeutically active agent is rapamycin, tacrolimus, cyclosporin A or paclitaxel, including derivatives and analogs thereof.

In some embodiments of any of the embodiments described herein, the first and/or second therapeutically active agent is rapamycin, tacrolimus or paclitaxel, including derivatives and analogs thereof. In some embodiments, at least the first therapeutically active agent is rapamycin, tacrolimus or paclitaxel, including derivatives and analogs thereof.

In some embodiments of any of the embodiments described herein, the first and/or second therapeutically active agent is rapamycin or paclitaxel, including derivatives and analogs thereof. In some embodiments, at least the first therapeutically active agent is rapamycin or paclitaxel, including derivatives and analogs thereof.

In some embodiments of any of the embodiments described herein, the first and/or second therapeutically active agent is rapamycin. In some embodiments, at least the first therapeutically active agent is rapamycin.

The therapeutically active agent(s) selected will typically depend on the intended use of the object. Thus, for example, paclitaxel and rapamycin are particularly suitable for certain implantable medical devices (e.g., stents).

In some embodiments of any of the embodiments described herein, a first therapeutically active agent according to any of the respective embodiments described herein (optionally rapamycin) is mixed ("doped") with a small proportion of an additional compound. As exemplified herein, a crystal morphology and/or drug release profile of a first layer can be controlled by doping the first therapeutically active agent (e.g., a solution of the agent used first therapeutically active agent for effecting crystallization according to any of the respective embodiments described herein) with a suitably selected additional compound and concentration thereof (e.g., in a weight ratio in a range of from 1000:1 to 4:1, and optionally from 99:1 to 9:1 (first therapeutically active agent: additional therapeutically active agent).

In some embodiments of any of the embodiments described herein, the first therapeutically active agent is doped with another therapeutically active agent, optionally any of the therapeutically active agents described herein.

In some embodiments of any of the embodiments described herein, the first therapeutically active agent is rapamycin, and the rapamycin is doped with an additional therapeutically active agent. In some embodiments, the additional therapeutically active agent is tacrolimus, paclitaxel and/or cyclosporin A.

In some embodiments of any of the embodiments described herein, the first therapeutically active agent is tacrolimus, and the tacrolimus is doped with an additional therapeutically active agent. In some embodiments, the additional therapeutically active agent is rapamycin, paclitaxel and/or cyclosporin A.

In some embodiments of any of the embodiments described herein, the first therapeutically active agent is paclitaxel, and the paclitaxel is doped with an additional therapeutically active agent. In some embodiments, the additional therapeutically active agent is tacrolimus, rapamycin and/or cyclosporin A.

Processes:

According to an aspect of some embodiments of the invention, there is provided a process of depositing at least a first layer of a first therapeutically active agent (e.g., according to any of the embodiments described herein relating to a first layer) onto at least a continuous portion of a surface of an object, wherein at least 50 weight percents of said first layer is the first therapeutically active agent in a crystalline form.

The process comprises contacting the surface with a solution containing the first therapeutically active agent, so as to form a crystalline form of the first therapeutically active agent deposited on at least a portion of the surface.

In some embodiments of any of the embodiments described herein, the process comprises seeding the surface of the object (on at least a portion of the surface) with crystals of the first therapeutically active agent, so as to obtain a seeded surface comprising the crystals; and contacting the seeded surface with a solution containing the first therapeutically active agent, so as to form a crystalline form of the first therapeutically active agent deposited on at least a portion of the surface.

In some embodiments of any of the embodiments described herein relating to a process, process results in a coated surface according to any of the embodiments described herein relating to surface of an object (and/or an article-of-manufacture comprising such an object) coated by at least a first layer.

According to preferred embodiments of any of the embodiments described herein relating to a process, the surface is not cooled to a temperature below a temperature of the solution.

In some embodiments of any of the embodiments described herein, a temperature of the surface is not lower than 5° C. cooler than a temperature of the solution (e.g., after exposure to the solution for at least 10 seconds). In some embodiments, a temperature of the surface is not lower than 2° C. cooler than a temperature of the solution (e.g., after exposure to the solution for at least 10 seconds). In some embodiments, a temperature of the surface is not lower than 1° C. cooler than a temperature of the solution (e.g., after exposure to the solution for at least 10 seconds). In some embodiments, a temperature of the surface is within 1° C. of a temperature of the solution (e.g., after exposure to the solution for at least 10 seconds).

In some embodiments of any of the embodiments described herein, a temperature of the solution is in a range of from 0° C. to 50° C. In some embodiments, a temperature of the solution is in a range of from 10° C. to 40° C. In some embodiments, a temperature of the solution is in a range of from 20° C. to 30° C. In some embodiments, a temperature of the solution is about 25° C. (e.g., 25±1° C.).

In some embodiments of any of the embodiments described herein, the process further comprising depositing at least one additional layer comprising a second therapeutically active agent (according to any of the embodiments described herein relating to an additional layer and/or second therapeutically active agent) onto the surface, such that one of the first layer and the additional layer overlies the other (e.g., according to any of the respective embodiments described herein). In some embodiments, the process comprises forming the additional layer(s) prior to the seeding (e.g., to thereby form one or more additional layers underlying the first layer, whereby a surface of an additional layer is seeded during the seeding procedure described herein) and/or subsequent to contacting the seeded surface with said solution (e.g., to thereby form one or more additional layers overlying the first layer).

In some embodiments of any of the embodiments described herein, seeding s performed such that the crystals in the seeded surface have an average diameter (as defined herein) of less than 1 µm. In some embodiments, the average diameter is in a range of from 200 to 400 nm.

In some embodiments of any of the embodiments described herein, seeding a surface comprises contacting a surface with a dispersion of crystals of the first therapeutically active agent. The dispersion may optionally comprise crystals characterized by a size distribution desired for the seeded surface (e.g., wherein an average diameter of less than 1 µm, as described herein).

In some embodiments of any of the embodiments described herein, seeding further comprises subjecting the dispersion to sonication, prior to and/or subsequent to contact with the surface to be seeded.

Without being bound by any particular theory, it is believed that sonication is particularly suitable for dispersing small crystals in a liquid in a relatively even manner, and (when applied to a dispersion which is in contact with a surface) is particularly effective at promoting a relatively homogeneous distribution of crystals for seeding on a surface.

Examples of suitable frequencies for sonication include, without limitation, a range of from 20 to 180 kHz, optionally from 40 to 120 kHz, and optionally from 60 to 100 kHz.

In some embodiments, sonication according to any of the respective embodiments described herein may optionally be effected for at least one minute, optionally from 1 to 50 minutes.

In some embodiments, sonication according to any of the respective embodiments described herein may optionally be effected for at least 2.5 minutes, optionally from 2.5 to 20 minutes.

In some embodiments, sonication according to any of the respective embodiments described herein may optionally be effected for at least 5 minutes, optionally from 5 to 10 minutes.

In some embodiments of any of the embodiments described herein, seeding is performed so as to obtain a seeded surface comprising crystals at a desired density, for example, a density in a range of from 0.03 µg/mm$^2$ to 3 µg/mm$^2$. In such embodiments, a desired density may be contained by selecting a suitable concentration of therapeutically active agent in a dispersion used for seeding, a suitable time of contact with the dispersion, and/or a suitable duration, frequency and/or intensity of sonication. In some embodiments, seeding is performed so as to obtain a seeded surface comprising crystals at a density in a range of from 0.1 µg/mm$^2$ to 1 µg/mm$^2$.

In some embodiments of any of the embodiments described herein, the solution containing the first therapeutically active agent contains a mixture of a solvent the first therapeutically active agent (i.e., a liquid in which the agent is soluble) and anti-solvent of the first therapeutically active agent.

As used herein, the term "anti-solvent" describes a compound or mixture of compounds which, when added to a solution containing the agent, reduces the solubility of the agent in the solution.

Ethyl acetate is an exemplary solvent of a therapeutically active agent, including for example, rapamycin, tacrolimus and paclitaxel.

Hexane (e.g., n-hexane) is an exemplary anti-solvent of a therapeutically active agent, including for example, rapamycin, tacrolimus and paclitaxel.

In some embodiments of any of the embodiments described herein, solution containing the first therapeutically active agent is saturated or supersaturated with the first therapeutically active agent.

As used herein, the term "saturated", with respect to the solution, describes the most concentrated solution possible at a given temperature.

The term "supersaturated" describes a solution that is more concentrated than normally possible and which therefore is not in equilibrium (a metastable solution).

A concentration of solute in a supersaturated solution is preferably sufficiently low so as to substantially reduce the likelihood of spontaneous precipitation (i.e., precipitation in the absence of a seeded surface) of the solute (which may optionally, but not necessarily, precipitate in crystalline form).

In some embodiments, however, a supersaturated solution is optionally prepared in order to form a dispersion of a therapeutically active agent (according to any of the embodiments described herein), e.g., as exemplified herein. In such embodiments, a higher degree of supersaturation may optionally be used (e.g., by using a higher concentration for solute and/or a lower ratio of solvent to anti-solvent), as spontaneous crystallization to form a dispersion is intended.

A saturated or supersaturated solution may conveniently be prepared by adding thereto an anti-solvent of the agent, e.g., so as to obtain a mixture of a solvent and anti-solvent of the first therapeutically active agent, as described herein. Proportions of solvent and anti-solvent suitable for forming a saturated or supersaturated solution can be determined readily by a skilled artisan without undue experimentation.

In some embodiments of any of the embodiments described herein, contacting the seeded surface with a solution containing of the first therapeutically active agent (according to any of the respective embodiments described herein) is effected for at least one minute, optionally from 1 to 50 minutes, optionally from 1 to 30 minutes, optionally from 1 to 20 minutes, and optionally from 1 to 10 minutes.

In some embodiments of any of the embodiments described herein, contacting the seeded surface with a solution containing the first therapeutically active agent (according to any of the respective embodiments described herein) is effected for at least 2.5 minutes, optionally from 2.5 to 50 minutes, optionally from 2.5 to 30 minutes, optionally from 2.5 to 20 minutes, and optionally from 2.5 to 10 minutes.

In some embodiments of any of the embodiments described herein, contacting the seeded surface with a solution containing the first therapeutically active agent (according to any of the respective embodiments described herein) is effected for at least 5 minutes, optionally from 5 to 50 minutes optionally from 5 to 30 minutes optionally from 5 to 20 minutes, optionally from 5 to 15 minutes, and optionally from 5 to 10 minutes.

In some embodiments of any of the embodiments described herein. The process further comprises masking a portion of the surface, to thereby obtain a masked portion of said surface, such that the first therapeutically active agent is absent from a portion of the surface. For example, in some embodiments wherein the object comprises a stent, an inner surface of the stent is masked, for example, by mounting the stent on a rod which contacts the inner surface. In some such embodiments, the rod swells upon contact with the solution described herein, thereby facilitating mounting while providing effective masking.

In some embodiments of any of the embodiments described herein, the process further comprises applying a top coat according to any of the respective embodiments described herein onto a surface having the first layer deposited thereon. In some such embodiments, the top coat comprises a polysaccharide (e.g., according to any of the respective embodiments described herein). In some embodiments, the top coat comprises hyaluronic acid according to any of the respective embodiments described herein.

In some embodiments, applying the top coat is effected by spray coating (e.g., according to any of the respective embodiments described herein).

In some embodiments of any of the embodiments described herein, the process further comprises applying a base layer and at least one nucleating agent conjugated to said base layer (according to any of the respective embodiments described herein).

In some embodiments, applying the base layer is performed prior to seeding the surface.

In some embodiments in which a base layer is applied, seeding with crystals is not performed, for example, the base layer serves as an effective substrate for crystallization even in the absence of seeding with crystals. In such embodiments, the nucleating agent(s) (optionally a first therapeutically effective agent) in the base layer effectively serves as an equivalent of a crystal seed.

In some embodiments of any of the embodiments described herein, the surface is surface is a conductive or semi-conductive surface (according to any of the respective embodiments described herein), and applying a base layer comprises electrochemically attaching at least one aryl moiety and/or at least one thiol moiety (according to an of the respective embodiments described herein) to the surface.

Applications of Coated Object:

In some embodiments of any of the embodiments described herein, the object described herein is a medical device.

The medical device can be used for implantation, injection, or otherwise placed totally or partially within the body, and hence it is desirable that the device will be a drug-eluting device.

In some embodiments, the medical device is for transdermal and/or topical applications in a subject. Such medical device should cause minimal tissue irritation when used to treat a given tissue and hence the inclusion of drugs therewith is beneficial.

Exemplary devices which can be used for transdermal application include, without limitation, a suture, an adhesive plaster and a skin patch.

Exemplary devices which can be used for topical application include, without limitation, a suture, an adhesive strip, a bandage, an adhesive plaster, a wound dressing and a skin patch.

In some embodiments, the medical device is an implantable medical device, for being implanted in a bodily organ of a subject.

The phrase "implantable device" is used herein to describe any medical device that is placed within a bodily cavity for a prolonged (e.g., from a few hours, to a few years and even for lifetime) time period.

Exemplary implantable devices include, without limitation, a plate, a mesh, a screw, a pin, a tack, a rod, a suture anchor, aortic grafts, arterial tubing, artificial joints, blood oxygenator membranes, blood oxygenator tubing, bodily implants, catheters, dialysis membranes, drug delivery systems, endoprostheses, endotracheal tubes, guide wires, heart valves, intra-aortic balloons, pacemakers, pacemaker leads, stents, ultrafiltration membranes, vascular grafts, vascular tubing, venous tubing, wires, orthopedic implants, implantable diffusion pumps and injection ports.

Additional exemplary devices include an anastomosis clip or plug, a dental implant or device, an aortic aneurysm graft device, an atrioventricular shunt, a hemodialysis catheter, a bone-fracture healing device, a bone replacement device, a joint replacement device, a tissue regeneration device, a hemodialysis graft, an indwelling arterial catheter, an indwelling venous catheter, a needle, a patent foramen ovale septal closure device, a vascular stent, a tracheal stent, an esophageal stent, a urethral stent, a rectal stent, a stent graft, a suture, a thread, a tube, a vascular aneurysm occluder, a vascular clip, a vascular prosthetic filter, a vascular sheath and a drug delivery port, a venous valve and a wire.

Examples of bodily sites where a medical device can be implanted include, without limitation, skin, scalp, a dermal layer, an eye, an ear, a small intestines tissue, a large intestines tissue, a kidney, a pancreas, a liver, a digestive tract tissue or cavity, a respiratory tract tissue or cavity, a bone, a joint, a bone marrow tissue, a brain tissue or cavity, a mucosal membrane, a nasal membrane, the blood system, a blood vessel, a muscle, a pulmonary tissue or cavity, an abdominal tissue or cavity, an artery, a vein, a capillary, a heart, a heart cavity, a male reproductive organ, a female reproductive organ and a visceral organ.

In some embodiments of any of the respective embodiments described herein, the implantable medical device is a stent. The stent can be of various types, shapes and materials. Any commercially available stent, presently or in the future, can be used according to embodiments of the invention. Optionally, a stent particularly designed or modified for the purposes of the present embodiments, can be used.

Exemplary stents include, but are not limited to, the Z, Palmaz, Medivent, Strecker, Tantalum and Nitinol stents.

Further exemplary stents include, but are not limited to, YUKON® micropore stainless steel 316 LVM stent, by Translumina, a CrCo (L605) stent, a stent that serves for manufacturing CYPHER® drug-eluting stents, a bare stainless steel stent manufactured by Johnson & Johnson, Conor stent (J&J) with drug cavities, MULTI-LINK ULTRA Coronary Stent by Abbott Vascular, ABSOLUTE 0.035 Biliary Self-Expanding Stent System by Abbott Vascular, Dynamic™ (Y) Stent by Boston Scientific, WallFlex® Duodenal Stent by Boston Scientific, and currently developed bioresorbable stents such as, for example, a magnesium-based stent by Biotronix.

In cases where the object is a medical device, as described herein, the article-of-manufacturing may further comprise a packaging material in which the object (having the therapeutically active agent deposited on its surface) is packaged, and the article-of-manufacturing can be identified in print, in or on the packaging material, for use in the treatment of a medical condition treatable by the medical device, as detailed herein below.

As discussed herein, medical devices (e.g., implantable medical devices) prepared as described herein benefit from the advantageous properties of gradual release and controllable release profiles for a therapeutically active agent applied thereon, including (but not limited to), a first therapeutically active agent according to any of the respective embodiments described herein.

According to another aspect of the present invention, there is provided a method of treating a subject having a medical condition in which implanting a medical device (optionally a stent) is beneficial, which is effected by implanting a medical device according to any of the respective embodiments described herein within a desired bodily site of the subject.

Medical conditions suitable for being treated by the aforementioned method include, without limitation, a cardiovascular disease, atherosclerosis, thrombosis, stenosis, restenosis, a cardiologic disease, a peripheral vascular disease, an orthopedic condition, a proliferative disease, an infectious disease, a transplantation-related disease, a degenerative disease, a cerebrovascular disease, a gastrointestinal disease, a hepatic disease, a neurological disease, an autoimmune disease, and an implant-related disease.

The therapeutically active agent and the device are selected suitable for treating the medical condition.

Accordingly, there is provided a use of the medical device (according to any of the respective embodiments described herein) in the treatment of a medical condition as described herein.

It is expected that during the life of a patent maturing from this application many relevant therapeutically active agents will be developed and the scope of the term "therapeutically active agents" is intended to include all such new technologies a priori.

As used herein the term "about" refers to ±20%. In some embodiments of any of the embodiments described herein, the term "about" refers to ±10.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non-limiting fashion.

Materials and Methods

Materials:
Alginate was obtained from Sigma-Aldrich.
Calcium chloride was obtained from Sigma-Aldrich.
Carboxymethylcellulose was obtained from Sigma-Aldrich.
Chitosan was obtained from Sigma-Aldrich.
Ethyl acetate (AR) was obtained from Bio Lab Ltd. (Israel).
Glycerol was obtained from Bio Lab Ltd.
 n-Hexane (AR) was obtained from Bio Lab Ltd.
 Hyaluronic acid aqueous solution (Macrolane™ VRF20) was obtained from Q-Med AB (Sweden).
 Hydrochloric acid was obtained from Bio Lab Ltd.
 Methanol (HPLC grade) was obtained from J. T. Baker.
 Polyethylene Glycol (1,000-15,000 Da) was obtained from Sigma-Aldrich.
 Rapamycin was obtained from Alvimedica (Turkey).
 Sodium azide was obtained from Merck.
 Sodium carbonate was obtained from J. T. Baker.
 Sodium lauryl sulfate (SDS) was obtained from Sigma-Aldrich.
 Sodium hydrogen phosphate and sodium phosphate (monobasic) were obtained from J. T. Baker.
 Stainless steel CoCr stents (smooth and rough stents; 15 mm length) and Cypher® drug-eluting stents (18 mm) were obtained from Alvimedica (Turkey).
 Shrinkable tube (PVLF05J) was obtained from Shrink Sleeve Ltd. (UK).
 Stent Cleaning:
 10 stents were placed in 20 ml vials, 10 ml of acetonitrile was added, the vials were well-sealed and sonicated for 15 minutes at 25° C. to remove dirt and organic residues from the outer surface of the stents, and the stents were then dried completely over air flow for 1 hour.
 Stent Mounting:
 Stents were mounted onto a 21G needle coated with a shrinkable sleeve. The tube shrunk on the needle after being exposed to heat. A cleaned stent was placed on the center of the tube. When placed in hexane solution, the sleeve slightly swelled, thereby completely blocking the inner face of the stents. After the crystallization process, the sleeve was dried and returned to its original diameter, such that the stent could be easily removed.

Preparation of Rapamycin Seeds:
50.0 mg of commercial crystalline rapamycin was ground for 3 minutes by a mortar and pestle to form a fine powder. The crystals were stored at −20° C. The seeding crystal size interval was analyzed by scanning electron microscopy (SEM) and the melting point and melting point interval were determined.

Treatment of Stents:
Stents were typically subjected to a three-step process—seeding, crystallization and hyaluronic acid coating:
1.6 mg of ground rapamycin powder was added to a 5 ml glass vial containing 4 ml of n-hexane, and sonicated at 60 kHz for 15 minutes in a water bath. The mounted stent was placed in the rapamycin dispersion. The vials were incubated in an ultrasonic bath at 30° C. for 10 minutes and dried for 2 minutes at room temperature.

For preparing a set of 10 stents, 13 mg of ground rapamycin powder was placed in 60 ml hexane and sonicated for 5 minutes (60 kHz for 1.5 minutes and then for 3.5 minutes at 100 kHz) until a homogeneous dispersion was formed. To this dispersion, 10 clean stents mounted on shrinkable tube were placed in dispersion, and the vial was placed in an ultrasonic bath for 10 minutes at 30° C., and then dried for 5 minutes under room air.

For effecting crystallization, rapamycin (usually 50 mg) was dissolved in 3 ml ethyl acetate and mixed with 65 ml n-hexane to form a homogeneous solution. Stents were placed in this solution at 25° C. for a few minutes, in order to effect crystallization, and then allowed to dry under room air.

For forming a top coat on crystallized rapamycin, a 0.3% hyaluronic acid solution was prepared by dissolving 1 ml of Macrolane™ VRF20 20 mg/ml hyaluronic acid aqueous solution in 5.7 ml of double distilled water (DDW) and then mixing vigorously for 3 days. This solution was used for spray coating of the stent using an ultrasonic spray-coating machine (Sono-Tek) with a sprayed volume of 0.1 ml, solution flow 0.2 ml/minute, 10 W ultrasonic generator power and a 5 ml syringe (diameter 11.45 mm). Stents were then dried overnight in an active hood.

Amorphous Coated Stents:
An amorphous coating on stents was prepared by dipping the stent into 1% (w/v) rapamycin in ethyl acetate and then fast drying in an active hood or by spraying a drug solution using an ultrasonic spray-coating machine (Medical, Sono-Tek). Rapamycin solution was prepared by dissolving the drug in ethyl acetate (1% w/v). The solution was then spray-coated at a flow rate of 0.2 ml/minute; the ultrasonic generator power was set at 1.2 W. Control of coating load was achieved by the concentration and spraying conditions. Spray-coated samples were examined visually for their homogeneity and then weighed using a microbalance.

Rapamycin Extraction from Stents:
Rapamycin was easily extracted from crystalline or amorphous coated stents by incubation in 1 ml methanol and vigorous stirring for 30 minutes with a vortex. Then the obtained rapamycin solution was transferred into an HPLC vial and analyzed. For Cypher® coronary stents, the two polymer coatings, PEVA and PBMA, and rapamycin were dissolved in dimethylformamide (DMF). The stent was crushed, and 500 µl of DMF was added into the tube, which was then tightly screwed closed. The screwed tube was placed for 30 minutes into an ultrasonic bath at 25° C. DMF was then removed by evaporation with a nitrogen stream, and an exact amount of 250 µl chloroform was added. 1 ml of acetone was added to the 250 µl chloroform and put into the ultrasonic bath for a further 15 minutes. Subsequently, 4 ml diethyl ether was added to precipitate the polymer. The mixture was ultrasonicated for an additional 20 minutes and then centrifuged for 30 minutes at 4000 rpm. The polymer precipitated and the clear supernatant was pipetted into a new tube and evaporated with a nitrogen stream to dryness. The rapamycin residue in the tube was dissolved in 1 ml acetonitrile and the obtained rapamycin solution was transferred into a HPLC vial.

Stent Inflation:

Stents were inflated at room temperature prior to incubation. Stents with an initial diameter of 1.5 mm were mounted on a balloon catheter system (Bxsonic) and inflated with air. Using a 200 cc inflation device (Biometrics), the stents attained a diameter of 3 mm and a final pressure of 10 bar.

X-Ray Diffraction (XRD) Measurements:

X-ray powder diffraction measurements were performed using a D8 advance diffractometer (Bruker, AXS) with a goniometer radius of 217.5 nm, Gobel mirror parallel beam optics, 2° Sollers slits, and 0.2 mm receiving slit. The powder samples were placed on low background quartz sample holders. XRD patterns from 20° to 60° 2θ were recorded at room temperature using CuKα radiation ($\lambda$=0.15418 nm) with the following measurement conditions: tube voltage of 40 kV, tube current of 40 mA, step mode with size of 0.02° 2θ and a counting time of 1 second per step. The instrumental broadening was determined using $LaB_6$ powder (NIST SRM-660). Samples analysis was performed directly on the crystalline coated stents.

Melting Point Measurement:

The drug was inserted into a designated capillary that was heated at a rate of 10° C./minute. Melting point measurements were carried out using a conventional apparatus (Stuart SMP10, UK). Melting point interval was determined from the first liquid droplet formation until complete melting of the sample.

Scanning Electron Microscopy (SEM):

Samples were placed on conductive carbon paper and were coated with gold to a thickness of about 10 nm using a sputtering deposition machine (Polarone E5100). Samples were then imaged using a Quanta™ 2000 environmental scanning electron microscopy (E-SEM) device (FEI Co.) at an acceleration voltage of 30 kV.

At the end of an in vitro release study (90 days), one stent from each group (Crystalline, amorphous and Cypher) was terminated and stents were studied by E-SEM in order to assess the presence of crystalline drug on stents after in vitro release and morphology changes. The remaining rapamycin on stents was extracted and analyzed by HPLC.

Profilometry:

The thicknesses of crystalline rapamycin coating and its roughness were determined by a P-15 profilometer (KLA-Tencor Co., San Jose, Calif.). Specifically, the profiles were recorded across a notch in the coating, which was manually scratched by a wooden stick. Also roughness of the seeding layer and crystalline rapamycin top-coated with hyaluronic acid was determined in the same manner. Sample analysis was performed on cylindrical tubes prepared similarly to stents with crystalline rapamycin coating.

Atomic Force Microscopy (AFM):

Stent samples were fixed on glass slides by using melted polyethylene glycol (PEG) (20,000 Da). For these fixed stent samples, the topography was scanned with a Dimension 3100 scanning probe microscope with a Nanoscope-V controller (Bruker) by using tapping mode (TM). Stents surface topography was obtained by lightly tapping the surface with an oscillating Si probe (RTESP probe, Bruker) at f=300 kHz. The topography of bare metal stents, seeded and crystalline rapamycin coatings and after application of hyaluronic acid top coats was determined by AFM. Three different points on 3 stents were analyzed.

Differential Scanning Calorimetry (DSC):

Thermal analysis was determined using a TA 4000-DSC differential scanning calorimeter (Mettler), calibrated with zinc and indium standards, at a heating rate of 10° C./minute (typical sample weight was 10 mg) and using a Stuart Scientific melting point SMP1 heater. The samples were analyzed with heating interval of +20 until +240° C. Sample analysis was performed on cylindrical tubes prepared similarly to stents with crystalline rapamycin coatings. Powder of the crystals was collected from the tubes by using scalpel. An amorphous rapamycin coating was prepared by spray coating a drug solution as described herein, examined visually for their homogeneity, weighed using a microbalance, and then collected from the tubes by using scalpel.

Amorphous Coating for XRD and DSC Analysis:

To avoid possible self-crystallization of rapamycin, samples were analyzed immediately after sample preparation. 20 mg rapamycin was dissolved in a minimal volume of solvent, 250 µl of absolute ethanol or 200 µl ethyl acetate or 150 µl acetone, followed by filtration with PTFE filters (0.2 µm) and rapid solvent evaporation enhanced by N2 flow until complete dryness.

Example 1

Seeding Crystal Preparation and Size

Commercial rapamycin crystals (characterized by a crystal size of 5-300 µm) were ground with mortar and pestle for 3 minutes to form a fine powder.

As shown in FIGS. 1A and 1B, the grinding reduced the particle size mostly to within in a range of 400-1100 nm (although crystals larger than 1500 nm in size were also present), as determined by SEM analysis.

As shown in FIGS. 2A and 2B, further grinding resulted in particle size in the range of 200-400 nm.

Stents were then seeded with the finely ground rapamycin crystals, according to procedures described in the Materials and Methods section hereinabove.

As shown in FIG. 3, seeded stents exhibited a fine and homogeneous coverage by rapamycin crystals. The weight increase was 15±5 µg per stent.

Example 2

Crystalline Rapamycin Coating Formation on a Seeded Surface

Stents were then seeded with the rapamycin nanocrystals prepared as described in Example 1, using ultrasonication according to procedures described in the Materials and Methods section hereinabove.

The seeded stent surface was subjected to a crystallization process by incubating the stents in a 250 ml chamber at 25° C. in a solvent/anti solvent mixture prepared by dissolving a desired amount of rapamycin in 3 ml ethyl acetate and adding the solution to 65 ml n-hexane. The solution was preferably clear rather than milky in appearance. The chamber was equipped with an upper cover built to allow movement of the stent in/out of the drug solution to facilitate time processing studies. The upper cover was loaded with the seeded stents (prepared as described in Example 1) on a shrinkable tube without stirring. At the end of the process the stents were removed from the chamber and dried overnight.

The obtained crystalline layer was studied after using different incubation time periods, using light microscopy, scanning electron microscopy and an analytical microbalance.

As shown in FIG. 4, a uniform and continuous carpet of crystals was formed in a highly effective manner, wherein the crystals had a clearly defined parallelogram shape and were strongly attached one to another.

To study the effect of crystallization time, crystallization was performed with constant drug concentrations and temperatures.

Seeded stents were incubated for 30, 60 and 180 minutes with 70 mg or 140 mg rapamycin in a solution of ethyl acetate:hexane (3:65 ml), which resulted in crystal sizes of 15-100 μm or 20-130 μm respectively, whereas incubation in crystallization chamber for 5, 7.5 and 10 minutes with 50 mg rapamycin in the same solvent/anti solvent ratio resulted in low drug loads (~100 μg per stent) and 2-5 μm crystal sizes.

To study the effect of drug concentration on the final amount of drug loaded on stents, drug concentrations of 0.80, 1.11, and 2.22 mg/ml (50, 70 and 140 mg, respectively) were tested, while temperature and incubation time were kept constant for comparison. Drug concentration was correlated with amount of drug loaded on the stent and with crystals density.

The crystal size was about 200 nm-5 μm on stents with low drug loading (e.g., 50-150 μg/stent), about 10-20 μm on stents with medium drug loading (e.g., 200-750 μg/stent), and about 80-130 μm on stents with high drug loading (e.g., at least 750 μg/stent). At all drug loading levels, crystals were strongly attached one to another and to the stent surface.

Furthermore, a few micrograms (e.g., about 10 μg) of drug loaded on the stent was sufficient to result in a continuous crystalline carpet, indicating that a wide variety of doses can be loaded as a crystalline carpet.

These results indicate that this process is particularly suitable for preparation of crystalline coating which is homogeneous, continuous, uniform and easy to control, prepare and reproduce, and that the process is suitable for preparation of low (~100 μg) and high (~10 mg) drug loads on stents.

For comparison, rapamycin was crystallized onto stents directly without any prior seeding. The stents were dipped in the abovementioned solvent/anti solvent mixture of ethyl acetate:hexane (3:65 v/v) for time periods in a range of 5-30 minutes.

As shown in FIGS. 5A and 5B, in the absence of seeding, very large rapamycin crystals formed on the surface of the stent, without forming a continuous crystalline carpet.

In an alternative procedure for seeding using a dispersion of rapamycin crystals, a supersaturated solvent/anti-solvent mixture (ethyl acetate:hexane at a 1:65 volume/volume ratio) was prepared, which became turbid as rapamycin crystals formed therein and the solution became a dispersion. Stents were dipped in the solvent/anti-solvent mixture, resulting in uniform coverage of the stent with nanocrystals. This seeding was followed by a second step of dipping in a solvent/anti-solvent mixture (ethyl acetate:hexane 3:65 volume/volume ratio) for a specific time to promote crystallization, as described hereinabove. This process for coating preparation was effective in forming a uniform and continuous crystal layer, in which crystals were attached to one to another to a considerable degree, and strongly adhered to the stent surface.

In order to evaluate the effects of incubation times in the solutions for seeding and for crystallization, incubation times in the seeding solution were varied within a range of from 10 to 60 minutes (with total incubation time and incubation time after the seeding solution became turbid being both considered), and incubation time in the crystallization solution was varied in range of from 10 minutes to 1 hour.

As shown in FIGS. 6A-8B, the time during which the stent was incubated in the seeding solution after the solution became turbid (indicating formation of a dispersion) was correlated with the degree of coverage of the stent surface by crystals.

As shown in FIGS. 9-11, the time during which the stent was incubated in the crystallization solution for promoting crystallization was correlated with the degree of coverage of the stent surface by crystals.

These results further indicate that formation of crystalline drug layer following seeding by a dispersion of the drug is readily controlled according to seeding density and/or the time of incubation in a dispersion for seeding and/or in a solution for promoting crystallization.

These results suggest that the seeding procedure and crystalline coatings described herein can provide a continuous release profile—for a wide variety of drug doses—as a result of slow dissolution of the crystalline layer, as dissolution of the crystalline form is much slower than dissolution of the amorphous form, with the multilayer nature of the crystalline carpet prolonging drug release as the inner layers of drug crystals come into contact with medium only after the outer layers dissolve.

Example 3

Scaled Up Preparation of Crystalline Coating on Stents

The crystalline coating of stents as described in Example 2 was performed in a system designed for preparation of 10, 15 or 30 coated stents in parallel. Using the same technique, 100 coated stents or even more can be prepared in parallel.

Stents were placed onto a rod coated with a rubber sleeve that slightly swells in the drug solution and tightly blocked the inner side of the stent. These stents mounted onto rods were immersed vertically into rapamycin solution for the time period that allowed crystal formation onto the outer surface of the stent.

To form a crystalline coating containing about 100 μg drug per stent (50.53 $mm^2$ surface area per stent available for crystalline coating), the following procedure was developed: 13 mg of ground rapamycin (crystals seeds) was sonicated for 5 minutes in hexane, and 10 stents seeded by being placed in the dispersion in a 250 ml container, sonicated and dried, according to procedures described in the Materials and Methods section hereinabove. The dried, seeded stents were then subjected to a crystallization process in a clear solution of 50 mg rapamycin in a mixture of 3 ml ethyl acetate and 65 ml hexane, at 25° C. for 5 minutes, and then dried overnight in an active hood, as described hereinabove. The stent were then weighed with a microbalance to evaluate drug loading.

As shown in FIG. 12 the stents exhibited complete coating by crystals.

As shown in Table 1 below, stents coated by the scaled up process typically had a drug load in a range of about 1.8-2.2 µg/mm² (about 90-110 µg per stent).

Analytical validation for drug loading was performed by HPLC analysis. Three stents from each set were individually incubated in 3 ml methanol (HPLC grade) and mixed for 30 minutes, and then 20 µl was injected into an HPLC system. The results indicated a negligible difference of less than 1% between the microbalance and HPLC in quantification of total drug loading.

Crystalline coating was directed to the outer surface of the stent, and almost no crystalline coating was found on the inner surface due to the polymeric sleeve swelling and the resulting protection of the inner surface.

TABLE 1

Drug (rapamycin) loading by scaled up crystalline coating formation of 15 stents in parallel (in two batches of 15 stents)

| Stent no. | Drug per stent (µg) | Drug surface density (µg/mm²) |
|---|---|---|
| 1 | 113 | 2.24 |
| 2 | 98 | 1.94 |
| 3 | 113 | 2.24 |
| 4 | 108 | 2.14 |
| 5 | 99 | 1.96 |
| 6 | 118 | 2.34 |
| 7 | 117 | 2.32 |
| 8 | 109 | 2.16 |
| 9 | 100 | 1.98 |
| 10 | 84 | 1.66 |
| 11 | 90 | 1.78 |
| 12 | 100 | 1.98 |
| 13 | 97 | 1.92 |
| 14 | 104 | 2.06 |
| 15 | 98 | 1.94 |
| 16 | 95 | 1.88 |
| 17 | 100 | 1.98 |
| 18 | 104 | 2.06 |
| 19 | 119 | 2.36 |
| 20 | 112 | 2.22 |
| 21 | 100 | 1.98 |
| 22 | 118 | 2.34 |
| 23 | 92 | 1.82 |
| 24 | 93 | 1.84 |
| 25 | 103 | 2.04 |
| 26 | 99 | 1.96 |
| 27 | 107 | 2.12 |
| 28 | 105 | 2.08 |
| 29 | 103 | 2.04 |
| 30 | 100 | 1.98 |

Example 4

Comparison of Crystalline and Amorphous Coatings

The difference between the crystalline rapamycin coatings prepared as described herein and amorphous rapamycin coatings was studied using XRD analysis.

Amorphous coatings were prepared by solvent fast evaporation by dipping or spray coating described in the Materials and Methods section hereinabove, and were immediately tested in order to avoid possible self-crystallization. The process was studied in different solvents: ethanol, ethyl acetate and acetone.

As shown in FIG. 13, amorphous rapamycin coatings prepared using ethanol or ethyl acetate was entirely amorphous, exhibiting no significant peaks in the XRD spectra, whereas amorphous coatings prepared using acetone exhibited trace crystal patterns.

These results can be explained based on reports that acetone is a particularly good solvent for rapamycin, which can result in very small size crystals as was indicated by XRD of an individual peak [Gandhi & Murthy, Crystal Research and Technology 2010, 45:213-218].

As shown in FIG. 14, the crystalline rapamycin coatings exhibited unit cell parameters (a=34.883; b=13.075; c=12.253 Å) which are substantially the same as the theoretical values for polymorph II (a=34.850; b=13.080; c=12.250 Å), and the measured and theoretical spectra completely overlapped.

This result indicates that the crystalline coating was polymorph II of rapamycin, with difference in crystallite sizes.

The degree of crystallinity was calculated according to the method described by Shujun et al., [Ultrasonics, Ferroelectrics, and Frequency Control, IEEE Transactions, 2005 52:564-569], and was determined to be about 100%.

These results indicate that an essentially crystalline rapamycin coating can be obtained by the method described herein, which is considerably different than amorphous coatings obtained by techniques such as dipping or spray coating.

Example 5

Control Over Drug Loading and Crystal Size

In designing a controlled release system for a therapeutic agent it is advantageous to control different parameters affecting the release profile. The effect of incubation time and drug concentration in the crystallization mixture (prepared as described in Example 2) on the obtained crystalline coating was examined.

As shown in Table 2 below, different crystal sizes (as determined by SEM images at 3 sites per stent) in the range of 15-130 µm were obtained (with the same parallelogram morphology), wherein incubation times were positively correlated to crystal size as well as drug loading and density, whereas drug concentration in the crystallization chamber was strongly correlated to drug loading and density, and more weakly correlated to crystal size.

These results indicate that crystal size and drug loading can be controlled by selecting suitable incubation times and drug concentrations for crystallization.

TABLE 2

Effect of incubation time and drug concentration in crystallization solution on crystal size and drug loading

| Code | Amount of drug in crystallization solution | Incubation time in crystallization solution | Amount of drug loaded on stents | Density of drug on stent surfaces | Crystal size |
|---|---|---|---|---|---|
| A | 70 mg | 20 minutes | 1.624 mg | 32.1 µg/mm² | 20 µm |
| B | 70 mg | 1 hour | 2.825 mg | 55.9 µg/mm² | 40 µm |
| C | 70 mg | 3 hours | 3.844 mg | 76.1 µg/mm² | 100 µm |

TABLE 2-continued

Effect of incubation time and drug concentration in crystallization solution on crystal size and drug loading

| Code | Amount of drug in crystallization solution | Incubation time in crystallization solution | Amount of drug loaded on stents | Density of drug on stent surfaces | Crystal size |
|---|---|---|---|---|---|
| D | 140 mg | 20 minutes | 2.290 mg | 45.3 µg/mm$^2$ | 15-20 µm |
| E | 140 mg | 1 hour | 3.782 mg | 74.8 µg/mm$^2$ | 80-90 µm |
| F | 140 mg | 3 hours | 5.858 mg | 115.9 µg/mm$^2$ | 100-130 µm |

Example 6

Effect of Crystal Size on Initial Drug Release Profile

The initial drug release profiles of stents with crystalline coatings with different crystal size ranges, as described in Example 5, were evaluated by incubating the stents for 10 days in phosphate buffer pH 7.4, 37° C., stirring at 100 rpm, with 0.02% w/v sodium dodecyl sulfate (SDS) in order to maintain sink conditions for the drug.

As shown in FIG. 15, a slower drug release (as a percentage of loaded drug) over the course of 10 days was associated with increased crystal size, increased drug loading (e.g., 5.8 µg per stent rather than 1.6 µg per stent), and increased crystallization time (e.g., 3 hours rather than 20 minutes).

These results indicate that the drug release profile can be controlled by selecting suitable incubation times and drug concentrations for crystallization.

Example 7

Thermal Stability of Crystalline Rapamycin Layer

The thermal stability of rapamycin seeds prepared as described in Example 1 and crystalline and amorphous rapamycin coatings prepared as described in Examples 2-5 were evaluated using differential scanning calorimetry (DSC) analysis. The rapamycin coatings were peeled off from stents using a sharp scalpel and compared with commercial crystalline rapamycin by applying heating profile of (20-240° C. with heat flow of 10° C./minute. Amorphous coatings were shortly prior to the analysis to avoid possible self-crystallization of rapamycin.

As shown in FIG. 16, rapamycin crystals exhibited two close peaks, the first peak being identified as a melting peak, and the second peak as representing thermal degradation (Dp) of rapamycin.

The thermal degradation following crystal melting was also confirmed using a melting point apparatus, wherein white crystals melted, followed by an immediate color change to yellowish and then very rapidly to a brownish-black color and sample bubbling.

The difference in melting point between the commercial rapamycin (190.3° C.) to the rapamycin seeds (183.7° C.) shown in FIG. 16 was consistent with the effect of differences in crystal size (5-50 µm for commercial rapamycin versus 0.3-1.1 µm for the rapamycin seeds) on melting points of rapamycin and similar compounds, as reported by U.S. Patent Application Publication Nos. 2007/0128731 and 2011/0275798.

As further shown in FIG. 16, the crystalline layer of rapamycin on stents exhibited a melting point peak at 170.5° C. This may be due to the layer including a wide range of crystals sizes from 200 nm to 5 µm.

As further shown in FIG. 16, amorphous rapamycin did not exhibit a melting peak, confirming that it is essentially entirely amorphous, but did exhibit a glass transition temperature (Tg) 93.94±1.49° C. (n=3) with a ΔCp value of 0.134-0.192.

These results are consistent with those reported for amorphous rapamycin in U.S. Pat. No. 7,393,952 (Tg=93-95° C.).

As further shown in FIG. 16, a wide degradation peak was observed. The peak was confirmed to be a degradation peak by fast cooling with cooling flow of 30° C./minute after heating to 240° C., and heating again with a flow of 10° C./minute. No peak was observed in the repeat measurement (data not shown), confirming that the drug had degraded.

These results confirm that crystalline rapamycin layers are stable at physiologically relevant temperatures.

Example 8

Crystalline Coatings on Balloons/Catheters

The preparation of crystalline coating as described in Example 2 was also performed on a surface of a stent insertion balloon, on a plastic component on which the stent is supposed to rest. Balloons were first seeded with a seeding layer of rapamycin (0.2-0.6 µm crystals), followed by crystallization.

As shown in FIGS. 17A-17B and 18A-18B, a continuous crystalline coating exhibiting full coverage was formed on the balloon after 5-10 minutes, with a same drug-loading density of about 1.6-2.2 µg/mm$^2$.

Adhesion of the crystalline coating to the plastic surface was examined during balloon inflation via syringe.

As shown in FIGS. 18A-18C, the crystalline coating remained stably adhered to the balloon surface upon inflation of the balloon, and resulting expansion of the crystalline coating, with no apparent crystal loss, indicating that the crystals were strongly attached to the surface.

Example 9

Stents with Top Coat

Coating durability is an important property in a coated device such as a stent, particularly durability during device preparation, crimping, shipment, handling and deployment. In order to enhance the durability of the crystalline coating, a protective top coat was developed to coat the crystalline coating, and the crystalline coating was confined coating to the outer surface of the stent (as described hereinabove). The coating stability was evaluated using light microscopy, scanning electron microscopy, analytical weight measurements and HPLC analysis. The top coat was designed to absorb mechanical stress throughout the stent life until deployment in a patient, and to dissolve and/or erode rapidly after deployment. Advantageous characteristics which were sought for in a top coat include thinness, flexibility to allow adjustment (e.g., stretching) to new stent dimensions upon deployment, prevention of crystal detachment during changes in stent dimensions or due to mechanical stress, enhancement of stent biocompatibility, and absence of a significant effect on the drug release profile.

Carboxymethylcellulose (CMC) sodium salt, alginate, chitosan, hyaluronic acid, waxes, triglycerides, polyethylene glycol (PEG) and poloxamers were evaluated for use in a top coat. Glycerol or PEG (1000-15000 Da) were used as plasticizers. Stents were examined after inflation and the amount of drug remaining attached to the stent was determined by HPLC.

Top coats were formed by dip coating, wherein stents were dipped for 10 seconds into an aqueous solution of a substance (e.g., CMC, alginate chitosan) and dried in an active hood overnight. Two different concentrations were prepared, 0.5% and 2% w/v.

In addition, a milky acidic solution of CMC was prepared at pH=2 to make the final top coat less soluble. Similarly, in order to crosslink a layer of alginate, alginate coated stents were dipped in 0.1% or 0.5% calcium chloride solution.

The properties of the various top coats are presented in Table 3 below.

TABLE 3

Top coat weight obtained by dip coating in various solutions

| Coating material | Solution concentration (w/v) | Additional specifications | Weight of top coat per stent (µg) | Weight of top coat per stent length (µg/mm) |
|---|---|---|---|---|
| CMC | 0.5% | N.A. | 73 | 4.87 |
| CMC | 0.5% | pH = 2 | 266 | 17.73 |
| CMC | 2% | N.A. | 273 | 18.20 |
| CMC | 2% | pH = 2 | 211 | 14.07 |
| Alginate | 0.5% | N.A. | 40 | 2.67 |
| Alginate | 0.5% | With 0.1% CaCl$_2$ | 74 | 4.93 |
| Alginate | 2% | N.A. | 257 | 17.13 |
| Alginate | 2% | With 0.1% CaCl$_2$ | 352 | 23.47 |
| Alginate | 2% | With 0.5% CaCl$_2$ | 395 | 26.33 |
| Chitosan | 0.5% | N.A. | 153 | 10.20 |
| Chitosan | 2% | N.A. | 754 | 50.27 |

N.A. = not applicable

As shown in Table 3, the weights (per stent length) of top coats prepared by dip coating stents in 2% aqueous solution were about 15-18 µg/mm for CMC top coats, about 23-26 µg/mm for alginate top coats, and about 50 µg/mm for chitosan top coats.

Example 10

Stents with Multilayer Top Coat

Stents with a multilayer top coat were prepared and compared to stents with single-layer top coats. Multilayer top coats with three layers were prepared by preparing each layer in the top coat separately, by dip coating using a solution CMC, alginate or chitosan (as described in Example 9) and drying overnight in an active hood. When alginate was cross-linked with calcium chloride (as described in Example 9), only the top layer (third layer to be formed) was contacted with calcium chloride. The weights of various top coats are presented in Table 4 below.

As shown in Table 4, the multilayer top coats typically contained less material per layer than do single-layer top coats, suggesting that previously formed layers at least partially dissolve in the polymer solutions used subsequent dip coating steps.

These results indicate that single-layer top coats and/or use of concentrated polymer solutions are preferable for coating a crystalline layer with a top coat.

TABLE 4

Weight of single-layer and multilayer top coats obtained by dip coating in various solutions

| Coating material | Solution concentration (w/v) | Additional specifications | Number of layers in top coat | Weight of top coat per stent (µg) |
|---|---|---|---|---|
| CMC | 0.5% | N.A. | 1 | 593 |
| CMC | 0.5% | N.A. | 3 | 44 |
| CMC | 0.5% | pH = 2 | 1 | 478 |
| CMC | 0.5% | pH = 2 | 3 | 37 |
| CMC | 2% | N.A. | 1 | 329 |
| CMC | 2% | N.A. | 3 | 44 |
| CMC | 2% | pH = 2 | 1 | 258 |
| CMC | 2% | pH = 2 | 3 | 5 |
| Alginate | 0.5% | N.A. | 1 | 18 |
| Alginate | 0.5% | N.A. | 3 | 11 |
| Alginate | 0.5% | With 0.1% CaCl$_2$ | 1 | 149 |
| Alginate | 0.5% | With 0.1% CaCl$_2$ | 3 | 81 |
| Alginate | 2% | N.A. | 1 | 338 |
| Alginate | 2% | N.A. | 3 | 159 |
| Alginate | 2% | With 0.1% CaCl$_2$ | 1 | 361 |
| Alginate | 2% | With 0.1% CaCl$_2$ | 3 | 340 |
| Alginate | 2% | With 0.5% CaCl$_2$ | 1 | 218 |
| Alginate | 2% | With 0.5% CaCl$_2$ | 3 | 124 |
| Chitosan | 0.5% | N.A. | 1 | 414 |
| Chitosan | 0.5% | N.A. | 3 | 18 |
| Chitosan | 2% | N.A. | 1 | 94 |
| Chitosan | 2% | N.A. | 3 | 548 |

N.A. = not applicable

Example 11

Polymeric Films with Plasticizer

In order to assess characteristics of the polymer coating, including flexibility, stretching and rigidity, films were prepared from 0.5% and 2% w/v polymeric solutions as described in Example 9, in a 3.7 cm diameter plate with polytetrafluoroethylene-coated surface, solvent was evaporated in an active hood overnight, and overnight again in oven at 65° C. Each of the films was observed by light microscope and its capability of stretching was assessed.

CMC films formed with 0.5% or 2% CMC solutions were transparent and rigid.

Alginate films formed with 0.5% or 2% alginate solutions were yellowish and rigid.

Chitosan films formed with 0.5% or 2% chitosan solutions were transparent to yellowish (when formed with 0.5% solution) or yellowish (when formed with 2% solution), and highly rigid. Chitosan films were more rigid than alginate films, and alginate films were more rigid than CMC films.

These results indicate that CMC is more suitable than alginate and chitosan for forming flexible and stretchable top coats.

In order to enhance the suitability of each of the above-mentioned polymers for forming flexible and stretchable top coats, triethyl citrate (TEC) or polyethylene glycol (PEG) (1000 or 4600 Da) were included as plasticizers to CMC, alginate and chitosan films prepared from 2% solutions as described hereinabove. The plasticizers were included at weight ratios of 5 or 10% relative to the film-forming polymer.

As with films without plasticizer, films formed with CMC were more flexible than films formed with alginate, and chitosan films were the least flexible.

CMC films were then prepared with additional plasticizers and plasticizer concentrations. PEG with a molecular weight of 1000, 4600, 8000, 10000 or 15000 Da was tested as a plasticizer, at weight ratios of 10%, 20% or 30% relative to CMC.

4600 Da PEG at a weight ratio of 10% resulted in a particularly suitable film, with high flexibility and capability for stretching.

These results indicate that PEG having a molecular weight between 1000 and 8000 Da is a particularly suitable plasticizer, and that a weight ratio between 5% and 20% is a particularly suitable proportion of plasticizer, for the preparation of top coats.

The films with plasticizers prepared as described hereinabove are summarized in Table 5 below.

TABLE 5

Ingredients of exemplary films comprising polymer and plasticizer

| Polymer (% w/v in solution) | Plasticizer (% w/w relative to polymer) |
|---|---|
| CMC (2%) | TEC (5%) |
| | TEC (10%) |
| | PEG 1000 Da (5%) |
| | PEG 1000 Da (10%) |
| | PEG 4600 Da (10%) |
| Alginate (2%) | TEC (5%) |
| | TEC (10%) |
| | PEG 1000 Da (5%) |
| | PEG 1000 Da (10%) |
| | PEG 4600 Da (10%) |
| Chitosan (2%) | TEC (5%) |
| | TEC (10%) |
| | PEG 1000 Da (5%) |
| | PEG 1000 Da (10%) |
| | PEG 4600 Da (10%) |
| CMC (2%) | PEG 1000 Da (10%) |
| | PEG 1000 Da (20%) |
| | PEG 1000 Da (30%) |
| | PEG 4600 Da (10%) |
| | PEG 4600 Da (20%) |
| | PEG 4600 Da (30%) |
| | PEG 8000 Da (10%) |
| | PEG 8000 Da (20%) |
| | PEG 8000 Da (30%) |
| | PEG 10000 Da (10%) |
| | PEG 10000 Da (20%) |
| | PEG 10000 Da (30%) |
| | PEG 15000 Da (10%) |
| | PEG 15000 Da (20%) |
| | PEG 15000 Da (30%) |

Example 12

Application of Top Coats onto Bare Stents and Stents with Crystalline Drug Layer Top coats were prepared from CMC and hyaluronic acid (HA) of a high molecular weight (approximately 1,000,000 Da) on bare and crystalline rapamycin-coated stents. The coating process was performed by dipping the stents for 10 seconds into an aqueous solution of CMC (2% w/v; pH 1; with or without 10% PEG (4600 Da), as described in Example 11) or HA (0.5% or 1% w/v), and then drying the stents in an active hood overnight. The stents were examined by light microscopy and weighed by microbalance, before and after expansion of the stents by balloon inflation.

The use of 2% CMC without plasticizer to coat a bare stent gave poor results, with a broken coating after stent expansion, while the addition of 10% w/w plasticizer to the CMC improved the results dramatically. In addition, the use of 0.5% or 1% HA to coat a bare stent gave excellent results, with the HA top coat exhibiting particularly high flexibility.

Top coats were then applied on 15 mm stents with a crystalline rapamycin layer, having about 50 µg rapamycin per mm stent length (about 750 µg per stent), which were prepared by incubating seeded stents for 20 minutes in a solution of 70 mg rapamycin dissolved in 3 ml ethyl acetate with 65 ml n-hexane, according to procedures described in Examples 2, 3 and 5. Six stents were prepared for each type of top coat.

The polymer solutions used were as follows:

(1) 2% w/v CMC solution was prepared, the pH was adjusted to 1 by 37% hydrochloric acid 37% solution, and the day after, 10% w/w PEG 4600 was added to the milky viscous solution and stirred for 2 hours.

(2) 2% w/v HA solution was prepared by stirring overnight to complete dissolution.

The weight increase associated with the coating process (the weight of the top coat) was about 20-30 µg per mm stent. Coated tents were analyzed by light microscopy before and after the balloon inflation process, and representative stents were used to determine the amount of drug lost upon stent expansion, by HPLC.

Figure 19A:
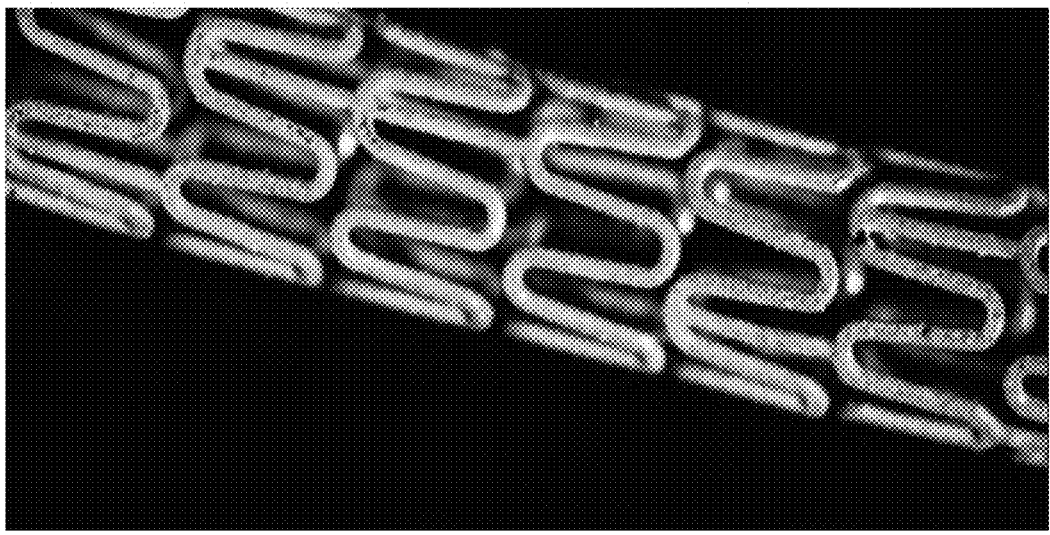
Figure 19B:
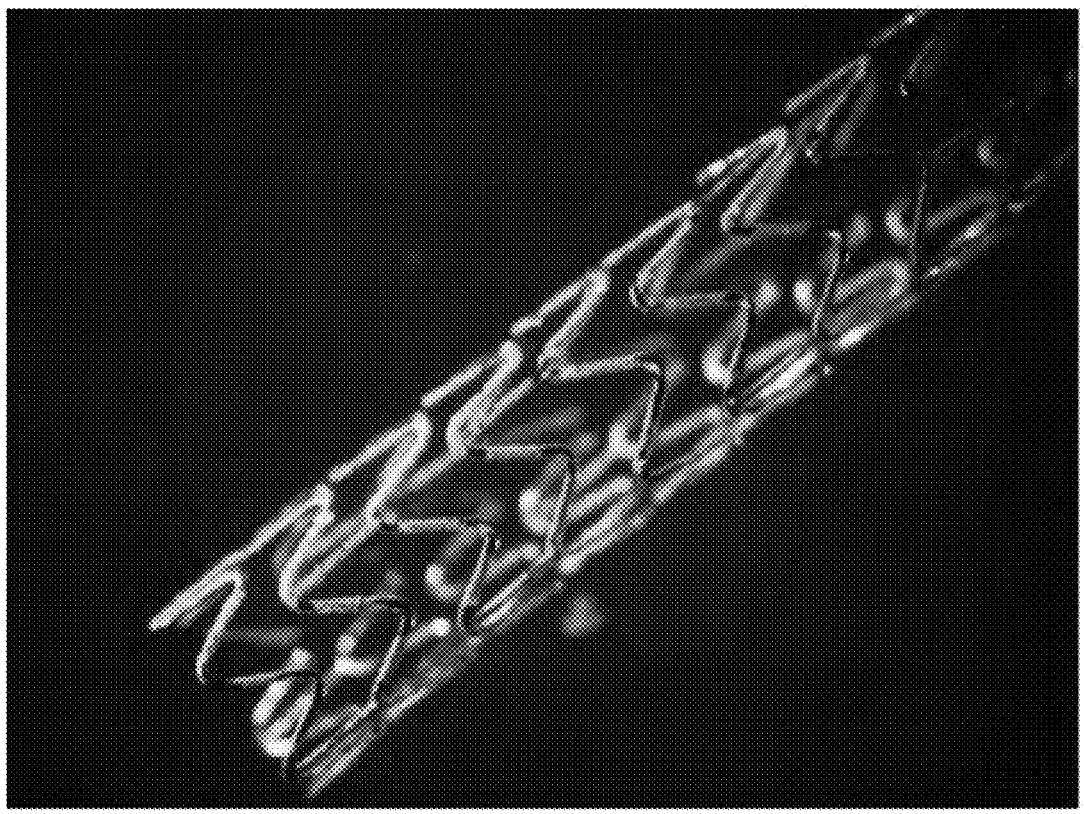
Figure 19C:
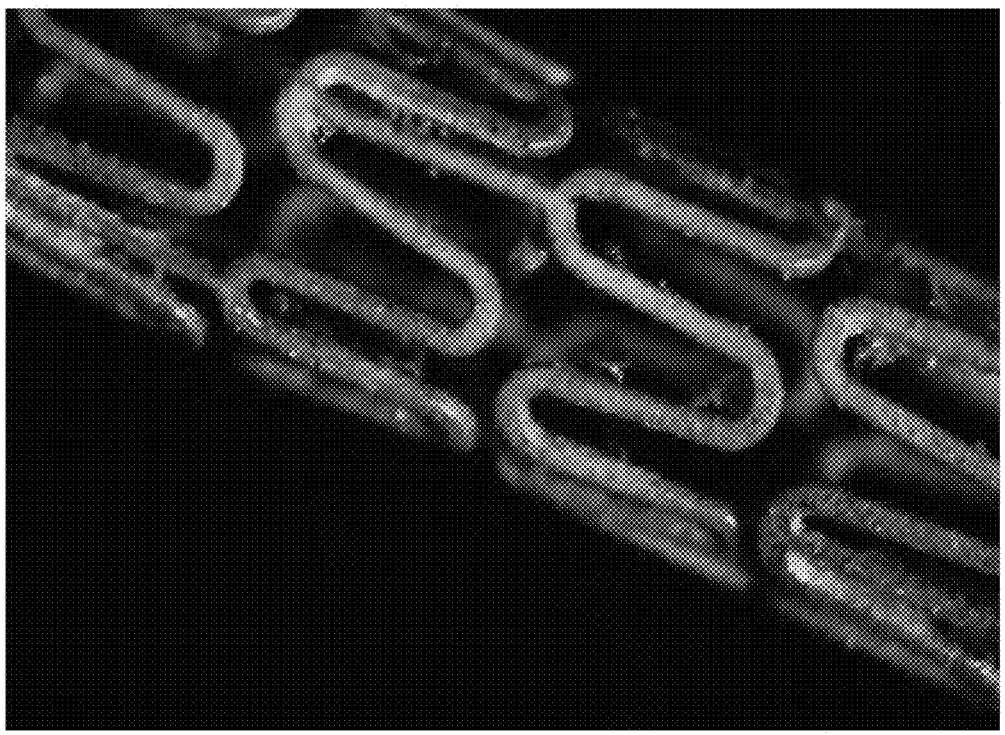
Figure 19D:
Figure 19E:
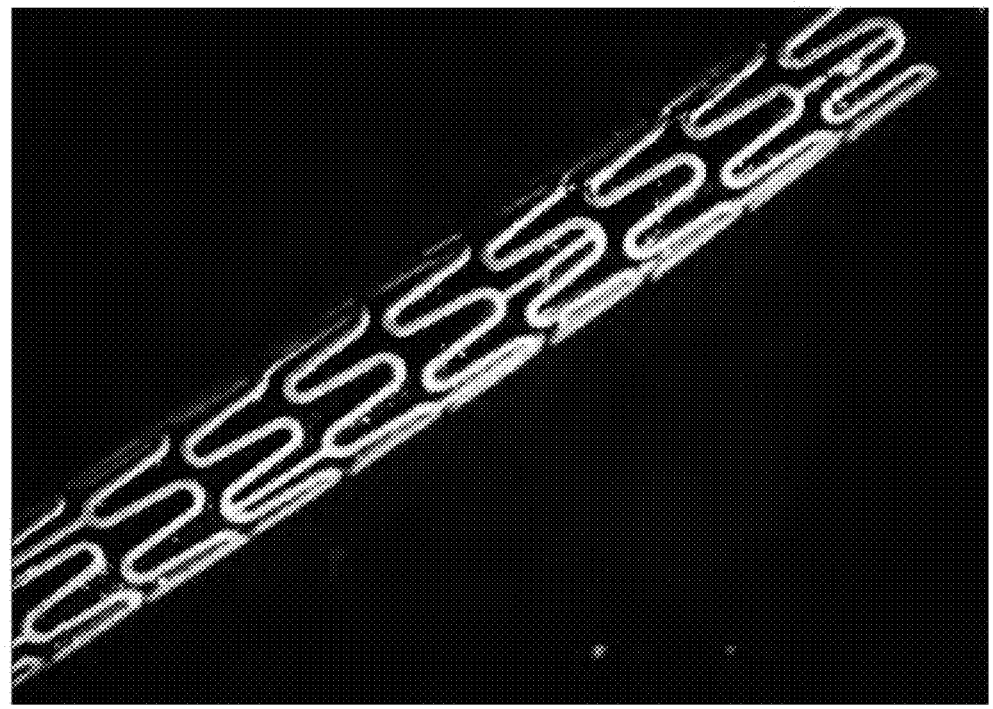
Figure 19F:
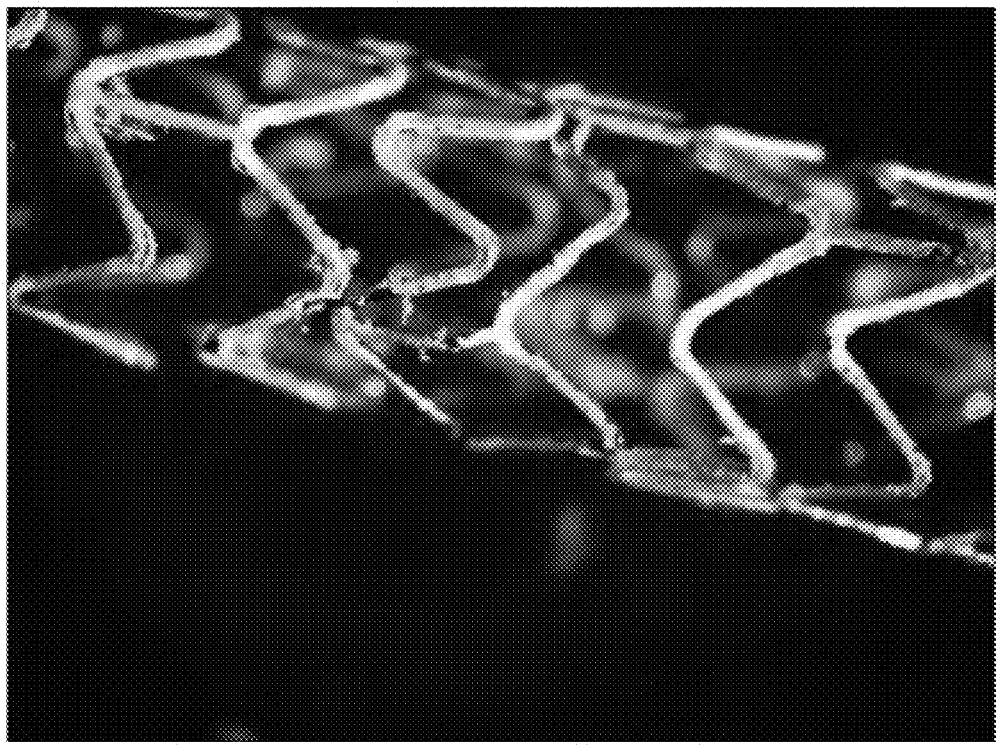

As shown in FIGS. 19A-19F, in the absence of a top coat, the initially homogeneous crystalline layer broke upon inflation, particularly in regions subjected to the most mechanical stress, such as bent regions and "Y regions" (FIGS. 19A and 17B), the CMC top coat partially protected the crystalline layer, but exhibited cracks in tears in regions subjected to mechanical stress (FIGS. 19C and 19D), and the HA top coat exhibited particularly effective protection of the crystalline layer, with sufficient flexibility to adapt to the new dimensions of the stent with little visible damage (FIGS. 19E and 19F).

These results were confirmed by HPLC analysis, which showed that in the absence of a top coat, drug loss upon inflation was about 20-30% of initial amount of loaded drug; with a CMC top coat, drug loss was reduced to about 10%; and with a HA top coat, drug loss was reduced to about 2-3%.

These results indicate that CMC and HA top coats considerably reduce drug loss, and that HA is particularly suitable for forming a durable top coat on a surface of an object which changes shape, such as a stent.

Example 13

Effect of Stent Expansion and Top Coat on In Vitro Drug Release

Stents with a top coat, prepared as described in Example 12, were subjected to an in vitro study of drug release, in order to assess the effect of top coat formation and stent expansion on initial drug release, that is, drug release during the first 3 days after contact with an aqueous environment. A constant reservoir system of release medium containing 40 ml of buffer was used. At each sampling time-point, a small aliquot of 2 ml was removed and replaced by fresh buffer. The release assay was carried out under physiological conditions (37° C., phosphate buffer 0.1 M, pH 7.4, stirring at 100 rpm). 0.02% sodium dodecyl sulfate (SDS) was added to the solution in order to sustain sink conditions. Sampling was performed at time points of 1 and 3 hours, and 1 and 3 days. 20 μl of each sample was injected into an HPLC system, and rapamycin was measured by reverse phase HPLC on a C-18 column with a mobile water-methanol phase (10:90 v/v), an isocratic mode set at a flow rate of 1 ml/minute and a wavelength of 277 nm.

As shown in FIGS. 20A and 20B, no significant difference was observed between the release profiles of stents with a top coat and stents without a top coat, with all of the stents exhibiting slow release of the drug. This result indicates that the top coat protects the crystalline layer without affecting the drug release profile.

As further shown therein, stents with an HA top coat exhibited moderately greater drug release after 1-3 hours than did stents with a CMC top coat.

Example 14

Spray Coated Top Coat of Hyaluronic Acid

As exemplified in the above Examples, hyaluronic acid (HA) forms top coats with excellent flexibility, stretching capability and protection of an underlying crystalline layer. However, a 1% hyaluronic acid solution is quite viscous.

As shown in FIGS. 21A and 21B, dip coating in a 1% HA solution resulted in a gummy layer on the stent with webbing between stent struts, which in some cases, can fill the spaces between the struts so as to form a cylinder.

In order to avoid webbing, a dilute solution of hyaluronic acid was applied using of spray coating machine (Sono-Tek). The relationship between concentration, number of layers and the amount of coating per stent was evaluated by spray coating bare stents, and determining weight increase by micro balance and top coat mechanical properties by light microscopy. The spray coating machine was used with the following parameters: generator power 12 watts, sprayed volume 0.1 ml, flow 0.2 ml/minute, semiautomatic rotation of 60 rpm, drying for 10 minutes in an active hood for multilayer top coat formation, and drying overnight at the end of the top coat formation. 10% w/w of glycerol was added to the sprayed solution to increase flexibility and streamline properties of the hyaluronic acid as coating material.

TABLE 6 weight of exemplary spray coated hyaluronic acid (HA) top coats

| Spray coated solution | No. of spray coated layers | Top coat weight (μg) |
| --- | --- | --- |
| 0.1% HA | 1 | 12 |
| 0.1% HA | 2 | 22 |
| 0.1% HA | 3 | 43 |
| 0.1% HA + glycerol (10:1 w/w HA:glycerol) | 1 | 17 |
| 0.1% HA + glycerol (10:1 w/w HA:glycerol) | 2 | 32 |
| 0.05% HA | 2 | 23 |
| 0.05% HA | 2 | 22 |

Tested solutions, number of layers formed by spray coating, and weight increase per stent are summarized in Table 6 herein.

As shown in Table 6, the weight per layer was consistent between spray coated single-layer and multilayer top coats, being about 12 μg per layer for 0.1% HA without glycerol, and about 17 μg per layer for 0.1% HA with 10% glycerol.

As shown in FIGS. 22A-22C, spray coating was effective at forming an HA top coat, with less webbing being formed than by dip coating.

It was further found that 0.3% hyaluronic acid (w/v) solution with 10% glycerol (w/w relative to HA concentration) was a particularly effective spray coating solution which resulted in particularly high stability, drug layer protection, flexibility and compatibility in a top coat for drug loaded stents. The following spray coating system parameters were used: generator power 10 watts, sprayed volume 0.1 ml, flow 0.2 ml/minute, semiautomatic rotation 60 rpm, and drying overnight in an active hood.

As shown in FIGS. 23A and 23B, no drug loss of damage to the drug coating or top coat was observed before or after stent expansion, and the top coat readily stretched without being torn. In addition, no webbing was formed.

These results demonstrate particular utility for spray coating in formation of a top coat.

Example 15

Scanning Electron Microscopy (SEM) Analysis of Exemplary Stents with Top Coats

Top coats were formed on stents by spray coating 0.3% hyaluronic acid (HA) solution, according to procedures described in Example 14, and examiner by SEM analysis. Top coats containing 1 or 2 layers were applied onto stents with smooth surfaces (a few nm deviation in surface height) or rough surfaces (>100 nm deviation in surface height), and examined before and after stent expansion. Stents without a top coat were also examiner for comparison.

The stents with smooth and rough surfaces were each 15 mm stainless steel CoCr stents with 50.53 mm$^2$ surface area. Representative bare surfaces of smooth and rough surfaces of stents are presented in FIGS. 24A and 24B.

As shown in FIGS. 25A-25D, 25M-25P and 26A-26B, no significant difference between smooth and rough surfaces upon seeding and crystallization (FIGS. 25A, 25B, 25M and 25N), but upon stent expansion (in the absence of a top coat), smooth surface stents exhibited weak crystal adhesion at the bents struts (FIGS. 25O, 25P and 26B), whereas for the rough surface only minimal changes were observed (FIGS. 25C, 25D and 26A).

In contrast, as shown in FIGS. 25E-25L, 25Q-25X and 27, hyaluronic acid top coats with either 1 or 2 layers effectively protected crystal coatings upon stent expansion on both smooth and rough surfaces, with little or no cracking of the crystal coatings being observed. As further shown in FIG. 27, the hyaluronic acid top coat protected in particular against crystal loss where cracks formed in a crystalline layer with low drug load (~100 μg per stent). As further shown in FIGS. 25E-25L and 25Q-25X, single-layer hyaluronic acid top coats were as effective as top coats with two layers at protecting a crystalline coating upon stent expansion.

These results indicate that a thin top coat is effective for protecting crystalline drug layers, especially on smooth surface stents in which the crystalline layers are more susceptible to damage.

As further shown in FIGS. 25A-27, the top coat smoothed the surface of the crystalline coating, resulting in blunter edges.

As further shown in FIGS. 25A-25X and 28A-28C, a 2-layer top coat (e.g., FIG. 28C) was more effective at smoothing a surface than a single-layer top coat (e.g., FIG. 28B). Multiple layers in a top coat also increased an amount of webbing.

Example 16

Thickness and Roughness of Crystalline Coatings

Stents with a continuous crystalline coating of ~100 μg rapamycin per stent were prepared with and without a single-layer HA top coat (with 10% w/w glycerol), as described hereinabove. The thickness of crystalline coatings were evaluated at several locations in a cross section SEM image of the coatings, as shown in FIGS. 29A and 29B. In addition, roughness of the coatings (with and without a top coat) and seeded surfaces were evaluated by profilometer analysis, as described in the Materials and Methods section, by applying the coatings onto cylindrical tubes. Roughness was defined as the standard deviation of height (along the z-axis).

As shown in Table 7 below, the thickness of the crystalline coatings were usually in the range 3-5 μm, and addition of a single-layer top coat increased the thickness by about 200-500 nm.

As further shown in Table 7, the roughness of surfaces was about 100 nm after seeding, increased to about 920 nm after formation of a crystalline layer, and decreased to about 500 nm upon application of a top coat.

TABLE 7

Thickness and roughness of exemplary seeded surfaces and coatings

| Sample no. | Surface type | Coating thickness (μm) | Roughness (nm) |
|---|---|---|---|
| 1 | Seeded surface | N.A. | 95 |
| 2 | Seeded surface | N.A | 105 |
| 3 | Seeded surface | N.A | 98 |
| 4 | Crystalline layer | 3.70-5.10 | 925 |
| 5 | Crystalline layer | 2.95-5.60 | 1030 |
| 6 | Crystalline layer | 4.30-4.95 | 780 |
| 7 | Crystalline layer + top coat | N.A | 409 |
| 8 | Crystalline layer + top coat | N.A | 433 |
| 9 | Crystalline layer + top coat | N.A | 666 |

N.A. = not applicable

Example 17

Effect of Webbing on Hyaluronic Acid Top Coat

As described hereinabove, multilayer top coats increase the likelihood of webbing formation in comparison to single-layer top coats. In order to assess the effect of webbing on a crystalline layer during expansion of a stent in a dry and/or aqueous environment, crystalline rapamycin-coated stents with an extra top coat were prepared (~200 μg top coat per stent) so as to form webbing.

Figures 30A, 30B:
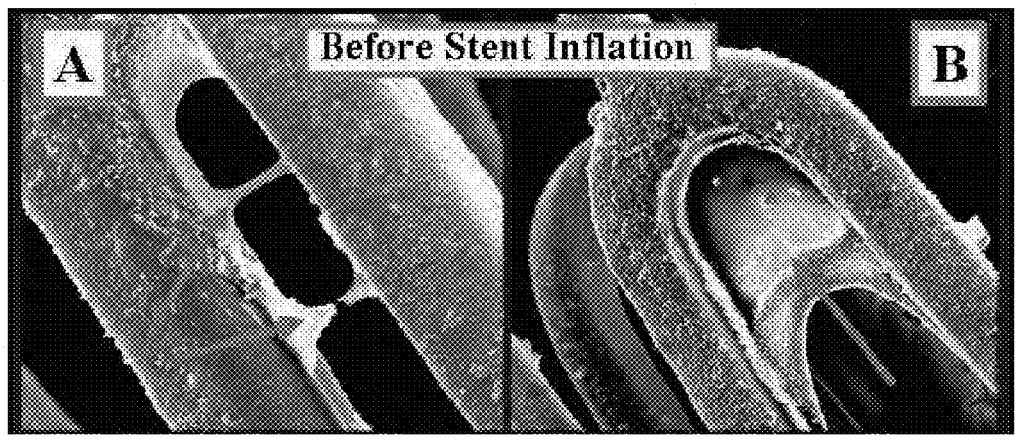
Figures 30C, 30D:
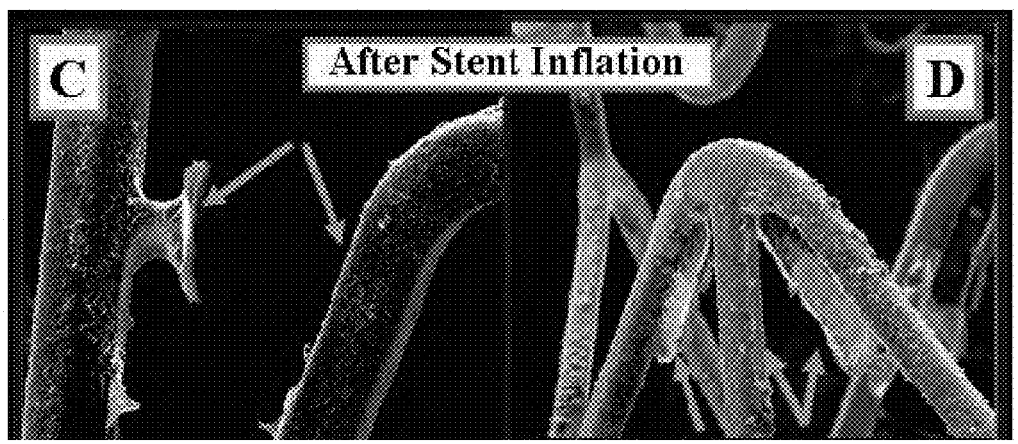
Figures 30E, 30F:
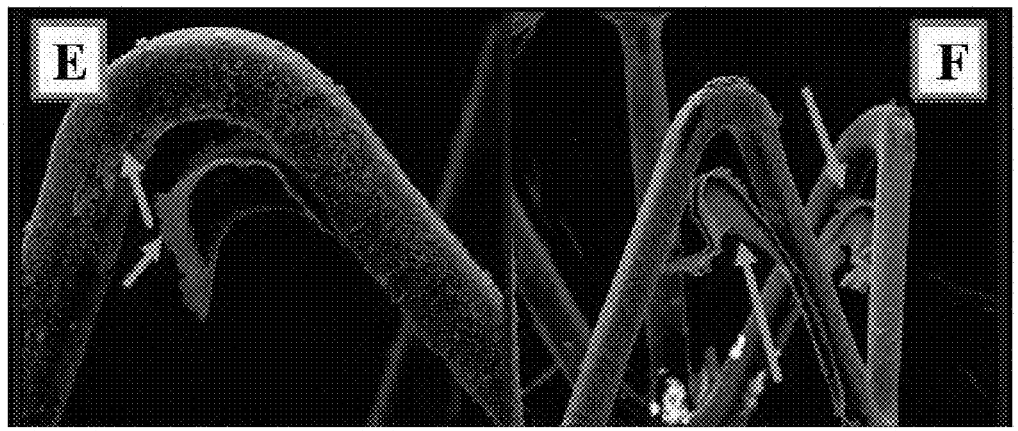

As shown in FIGS. 30A and 30B, various types of webbing were formed, including bridges (FIG. 30A) and space-filling webbings (FIG. 30B).

As described hereinabove, such webbing can be avoided by better spray coating while increasing rotation speed, and a single-layer top coat may provide sufficient protection of the crystalline layer.

However, as shown in FIGS. 30C-30F, even in the presence of webbing, a hyaluronic acid top coat does not crack the continuous crystalline layer or pull out parts of it upon stent expansion. Parts of the coating webbing easily pulled away from bent areas of the stent without damaging the crystalline layer.

Stent expansion in aqueous physiological medium increased the flexibility of the top coat even further, and no cracks in the crystalline layer were observed, similarly to the abovementioned results obtained by expansion of a dry stent.

These results indicate that top coats comprising a relatively large amount of hyaluronic acid, such as multilayer hyaluronic acid top coats, can be used advantageously.

Example 18

Effect of Drug Load on Crystalline Layer Integrity

Stents with a crystalline rapamycin layer characterized by a low drug load (about 100 μg per stent) were compared with those characterized by a high drug load (about 750 μg per stent).

As shown in FIGS. 31A and 31B, upon expansion of stents, breaking and cracking of the crystalline layer (primarily at bending sites) occurred considerably more frequently in stents with a high drug load than in stents with a drug load.

Similarly, measurement of drug loss showed that drug loss upon expansion of the stents with a high drug load was about 30%, but less than 5% upon expansion of the stents with a low drug load.

These results indicate that the crystalline layers described herein are particularly useful for stents with a drug load of less than 750 μg.

Example 19

Roughness of Exemplary Stents with and without Top Coats

The topography of a surface of an implant may be clinically significant, especially when implanted in blood vessels. The roughness of stent surfaces was therefore determined by atomic force microscopy (AFM) and scanning electron microscopy (SEM) profilometer analysis.

For SEM analysis of a continuous crystalline coating, cross sections of the crystalline layer were prepared using a sharp scalpel, and then the stents were coated with a thin layer of Au/Pd (10 nm) and analyzed by HRSEM, wherein sample insertion site was moved and tilted to get a clear view of the crystalline layer strata, including starting points (seeding crystals), crystalline layer development and accumulation, the coating thickness, and crystals protruding above the crystalline layer.

As shown in FIGS. 32A-32C, the crystalline coating thickness was in a range of from 3.0-5.5 μm.

Stent strut topography was determined by AFM for bare metal stents, seeded stents, crystalline rapamycin coatings on stents and single-layer hyaluronic acid (+10% w/w glycerol) top coats on stents. Representative images showing the upper crystal layer, the height of crystals protruding above the surface of the upper crystal layer, and height differences between the lowest and highest crystals on the outer surface of a continuous crystalline layer are presented in FIGS. 33A-33D.

As shown in FIGS. 33A-33D and 34, the roughness of bare metal stent surfaces was 10±2 nm (FIG. 33A), the roughness of seeded stent surfaces was 1115±212 nm (FIG. 33B), the roughness of surfaces of a crystalline rapamycin coating on stents was 0.8-1.5 µm (FIG. 33C), and the roughness of a hyaluronic acid top coat on stents was 139±21 nm (FIGS. 33D and 34).

These results indicate that the top coat as described herein greatly reduces the roughness of surfaces with a crystalline coating.

Example 20

Effects of Crimping, and Balloon Inflation and Deflation on Exemplary Stents

The mechanical properties of stents with a crystalline coating of about 100-130 µg per stent (prepared as described in Examples 2 and 3) were assessed by crimping, balloon inflation and balloon deflation tests, wherein some of the stents had a hyaluronic acid (+10% w/w glycerol) top coat of 80±10 µg prepared as described in Example 14. The weights of the drug and top coat on the tested stents are presented in Tables 8 and 9 below.

HPLC Analysis was used during analysis. Expanded stent coatings were dissolved in methanol and then analyzed. Crimped and nested stents were compared in terms of drug purity. For the cold crimp, drug purity was 97.5% for stents with a top coat, and 98.4% for stents without a top coat, whereas for the hot crimp, drug purity was 96.7% for stents with a top coat, and 98.1% for stents without a top coat.

As shown in FIG. 35, no crystalline coating defects were observed by light microscopy after stent crimping and/or expansion, for either smooth or rough stents, with or without a hyaluronic top coat.

These results indicate that the crystalline coatings described herein, particularly coatings with relatively low drug loads, are sufficiently stable so as to undergo crimping and expansion of stent surfaces without substantial damage, even in the absence of a top coat.

TABLE 8

Amounts of drug (rapamycin) on exemplary stents with crystalline rapamycin layer without a top coat

| Stent No. | Total drug load (µg) | Drug density (µg/mm$^2$) |
| --- | --- | --- |
| 1 | 134 | 1.98 |
| 2 | 133 | 1.97 |
| 3 | 131 | 1.94 |
| 4 | 119 | 1.76 |
| 5 | 95 | 1.41 |
| 6 | 135 | 2.00 |
| 7 | 91 | 1.35 |
| 8 | 100 | 1.48 |
| 9 | 91 | 1.35 |
| 10 | 118 | 1.75 |
| 11 | 128 | 1.89 |
| 12 | 103 | 1.52 |
| 13 | 137 | 2.03 |
| 14 | 130 | 1.92 |
| 15 | 101 | 1.49 |
| 16 | 135 | 2.00 |
| 17 | 138 | 2.04 |
| 18 | 138 | 2.04 |
| 19 | 102 | 1.51 |
| 20 | 110 | 1.63 |

TABLE 9

Amounts of drug (rapamycin) and top coat on exemplary stents crystalline rapamycin layer and top coat

| Stent No. | Total drug load (µg) | Drug density (µg/mm$^2$) | Top coat weight (µg) | Top coat density (µg/mm$^2$) |
| --- | --- | --- | --- | --- |
| 1 | 125 | 1.85 | 88 | 1.33 |
| 2 | 130 | 1.92 | 70 | 1.04 |
| 3 | 128 | 1.89 | 90 | 1.33 |
| 4 | 123 | 1.82 | 85 | 1.26 |
| 5 | 138 | 2.04 | 90 | 1.33 |
| 6 | 119 | 1.76 | 90 | 1.33 |
| 7 | 121 | 1.79 | 80 | 1.18 |
| 8 | 139 | 2.06 | 72 | 1.07 |
| 9 | 105 | 1.55 | 73 | 1.08 |
| 10 | 132 | 1.95 | 80 | 1.18 |
| 11 | 131 | 1.94 | 76 | 1.12 |
| 12 | 95 | 1.41 | 72 | 1.07 |
| 13 | 128 | 1.89 | 68 | 1.01 |
| 14 | 127 | 1.88 | 77 | 1.14 |
| 15 | 138 | 2.04 | 72 | 1.07 |
| 16 | 109 | 1.61 | 87 | 1.29 |
| 17 | 116 | 1.72 | 90 | 1.33 |
| 18 | 100 | 1.48 | 70 | 1.04 |
| 19 | 130 | 1.92 | 83 | 1.23 |
| 20 | 128 | 1.89 | 81 | 1.20 |

Example 21

In Vitro Release Profiles of Exemplary Crystalline-Coated Stents

Drug release kinetics were evaluated in vitro using a medium of phosphate buffer saline (PBS; pH 7.4) at 37° C., and then determining rapamycin concentrations in the medium by HPLC. Drug release was determined for stents with a crystalline rapamycin coating loaded with about 120 µg, prepared as described in Examples 2 and 3 herein). For comparison, stents coated with about 80 µg amorphous rapamycin and Cypher® drug-eluting stents containing about 150 µg rapamycin were also assayed. The stents coated with amorphous rapamycin were assayed shortly after preparation, so as to avoid self-crystallization. In Cypher® stents, rapamycin is incorporated in two non-erodible polymers (poly(ethylene-co-vinyl acetate) (PEVA) and poly(n-butyl methacrylate) (PBMA)) and the stent is coated with parylene C. Three stents of each type were incubated in the medium, two for 3 months (90 days) and one for 29 days.

Rapamycin can undergo hydrolysis in this medium so as to open the lactam ring, to give inactive forms of rapamycin and byproducts. The hydrolysis rate depends on the pH of the medium and the concentration of the buffer salts and the solubility of rapamycin in aqueous solution is very low. Considering the aforementioned properties of rapamycin, concentrations of both degraded and undegraded forms of rapamycin were determined by HPLC.

Figure 36A:
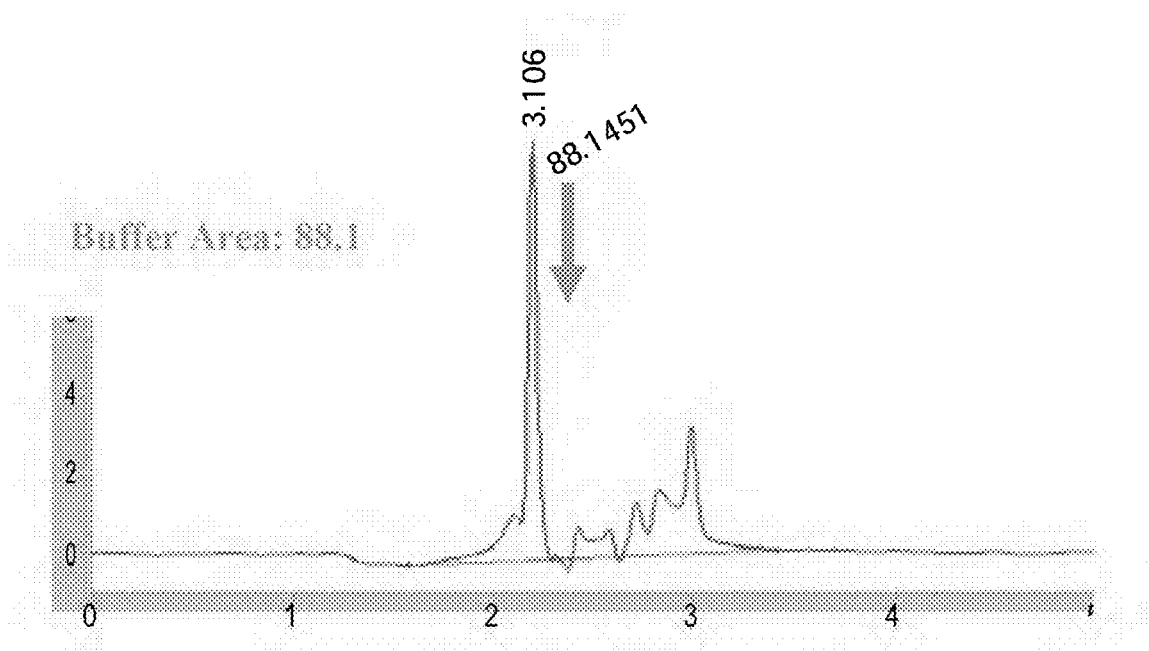
Figure 36B:
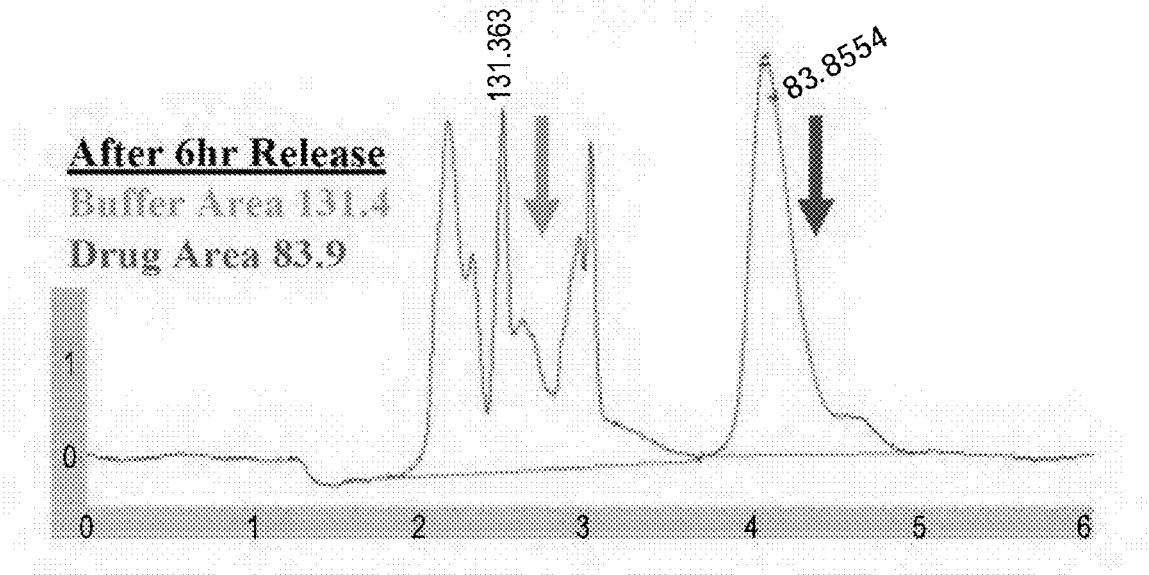
Figure 36C:
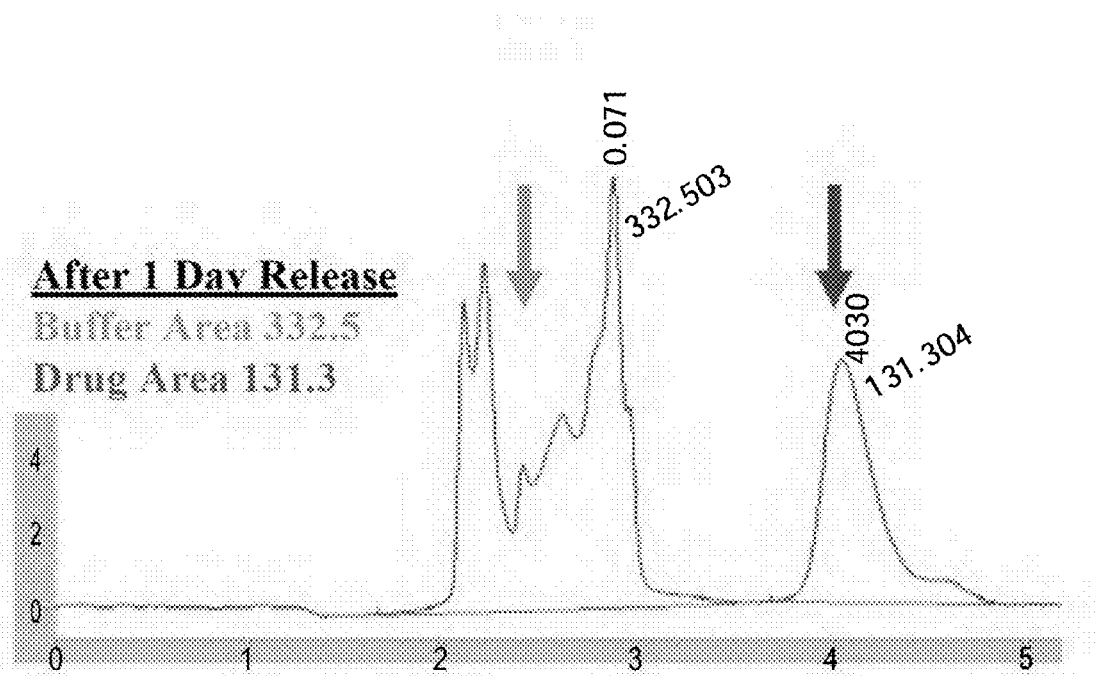
Figure 36D:
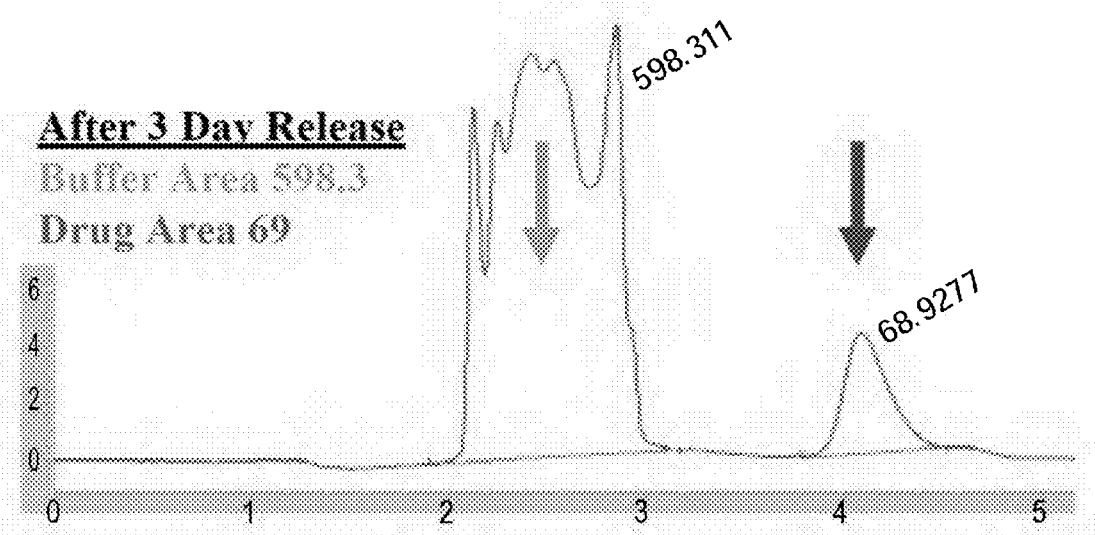
Figure 36E:
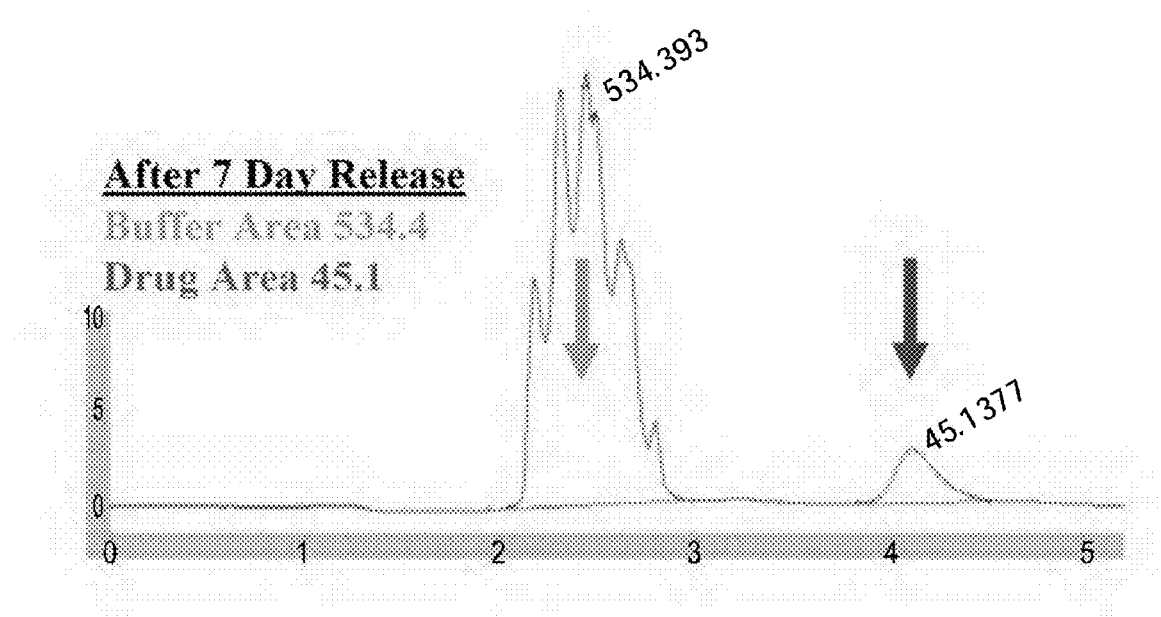

As shown in FIGS. 36A-36E, rapamycin was primarily in an undegraded form after 6 hours (FIG. 36B), but the proportion of degraded rapamycin gradually increased and was the dominant form of rapamycin after 1 to 7 days (FIGS. 36C-36E).

As shown in FIGS. 37A-37C and in Table 10 below, stents coated with a continuous crystalline layer of rapamycin gradually released about 45% (53 µg) of the rapamycin therein over the course of 90 days (FIG. 37C), whereas Cypher® stents released rapamycin more rapidly, such that about 75% (112 µg) was released over the same time period (FIG. 37B), and stents coated with amorphous rapamycin exhibited a burst release, releasing about 80% (60 µg) of the rapamycin in the first week (FIG. 37A). As further shown therein, the differences between the rate of release for stents coated with a continuous crystalline layer and Cypher® stents is even greater when the first 29 days are considered, after which the Cypher® stents exhibit a slower rate of release, possibly due to drug depletion.

The amorphous coating was prepared by spray coating of an ethanol solution of rapamycin which forms a predominantly amorphous drug layer. However, some rapamycin may crystallize upon drying and during the release process, which may be responsible for the 20% of drug in such samples which exhibited slow release after the first few days.

Furthermore, as shown in FIG. 43 and in Table 11 below, stents stored for one year at 37° C., 4-8° C. and −20° C. exhibited the same rapamycin release profiles. Similarly, as shown in FIGS. 44A-44C, stents stored for one year at 37° C., 4-8° C. and −20° C. released the same proportions of degraded and undegraded rapamycin.

As shown in FIG. 45, after one month at 37° C., 4-8° C. and −20° C. followed by two months of incubation in PBS, all of the stents exhibited a continuous crystalline layer over at least a portion of the surface, although in some regions separated crystal clusters were observed.

TABLE 10

Release of rapamycin from stents with crystalline or amorphous rapamycin coatings or from Cypher ® stents

| | After 29 days (n = 1) | | | After 3 months (n = 2) | | |
|---|---|---|---|---|---|---|
| Coating type | Crystalline | Amorphous | Cypher ® | Crystalline | Amorphous | Cypher ® |
| Drug load (µg) | 107 | 80 | 150 | 119 | 83 | 150 |
| Drug released (µg) | 23.5 | 68.3 | 91.1 | 53.8 ± 3.7 | 72.7 ± 7.3 | 111.1 ± 5.7 |
| Drug released (%) | 22.0 | 85.4 | 60.7 | 45.2 ± 0.0 | 88.0 ± 8.8 | 74.1 ± 0.0 |
| Drug remaining on stent (µg) | 83.5 | 11.7 | 58.9 | 57.2 ± 1.0 | 8.2 ± 3.5 | 47.2 ± 5.8 |
| Drug remaining on stent (%) | 78.0 | 14.6 | 39.3 | 48.1 ± 0.0 | 9.8 ± 4.2 | 31.5 ± 0.0 |
| Total mass balance (%) | 100.0 | 100.0 | 100.0 | 93.3 ± 0.3 | 98.0 ± 13.0 | 96.0 ± 4.8 |

As shown in FIGS. 38A-38C, the amorphous rapamycin coatings were confirmed by SEM imaging to be amorphous (FIG. 38A), whereas after 29 days, small amounts of semi-crystalline rapamycin was observed on the stent surface (FIGS. 38B and 38C).

As further shown in FIGS. 37A-37C, the percentage of released rapamycin which was in undegraded form was considerably higher for stents with a crystalline coating (about 30-35%) as compared with Cypher® stents (less than 10%).

Similarly, as shown in FIGS. 37A-37C and 39, the percentage of released rapamycin which was in undegraded form was considerably higher for stents with a crystalline coating as compared with stents with amorphous rapamycin.

These results indicate that stents with a continuous crystalline coating as described herein have a surprising and unique ability to both release a drug gradually as well as to enhance chemical stability of the drug.

Example 22

Stability of Crystalline and Amorphous Coatings Under Storage Conditions

The storage stability of rapamycin crystalline coating was determined for storage for 1 year at temperatures of 37° C., 4-8° C. and −20° C. At defined time points, the stents were analyzed by SEM and in measurement of in vitro rapamycin release over the course of two months.

As shown in FIGS. 40A-42F, no change in crystal integrity, morphology or topography was observed for crystalline coatings with or without a top coat after one year of storage at 37° C., 4-8° C. or −20° C.

As shown in Table 12 below, the crystalline coating content analyzed after 1 month of storage at 37° C., 4-8° C. and −20° C. contained no detectable degraded rapamycin, whereas after 12 months of storage 37° C., 4-8° C. and −20° C., only 2.76%, 2.46% and 2.33%, respectively, of the rapamycin was in degraded form.

These results indicate that the crystalline form in the coating is highly effective at inhibiting drug degradation at a wide variety of storage temperatures.

In comparison, as further shown in Table 12 below, after one month storage of stents with amorphous rapamycin coatings, about 20-25% of the loaded rapamycin was degraded upon storage at −20° C., and about 35-40% was degraded upon storage at 37° C.

As shown in FIGS. 46A-46C, storage of amorphous rapamycin coatings for one month at −20° C. resulted in the appearance of semi-crystalline rapamycin (FIG. 46B), whereas storage of amorphous rapamycin coatings for one month at 37° C. resulted in the appearance of fragile eroded areas (FIG. 46B), which indicate degradation of rapamycin.

As shown in FIGS. 47A-47C and in Table 11 below, stents with amorphous rapamycin coatings stored for one month at −20° C. exhibited a reduction in drug release over the course of two months. This result suggests that partial crystallization (e.g., as shown in FIG. 46B) affects the drug release profile.

As further shown in FIGS. 47B and 47C, stents with amorphous rapamycin coatings stored for one month at 37° C. (FIG. 47C) released a greater proportion of the drug in a degraded form than did the same type of stents stored for one month at −20° C. (FIG. 47B).

TABLE 11

Effect of stent storage duration and temperature on release of rapamycin upon incubation of stents with crystalline or amorphous rapamycin coatings for 1 month in PBS

| | 1 month storage | | | | | |
|---|---|---|---|---|---|---|
| | Coating type | | | | | |
| | Crystalline (n = 2) | | | Amorphous (n = 2) | | |
| | Storage temperature | | | | | |
| | 37° C. | 4-8° C. | −20° C. | 37° C. | 4-8° C. | −20° C. |
| Drug load (μg) | 95 | 91 | 102 | 138 | 144 | 131 |
| Drug released (μg) | 39.1 ± 2.5 | 37.4 ± 0.3 | 39.3 ± 1.2 | 84.6 ± 1.9 | 95.1 ± 0.8 | 79.7 ± 0.9 |
| Drug released (%) | 41.4 ± 0.0 | 41.1 ± 0.0 | 38.8 ± 0.0 | 61.3 ± 0.0 | 65.8 ± 0.0 | 60.8 ± 0.0 |
| Drug remaining on stent (μg) | 54.8 ± 7.7 | 51.8 ± 5.5 | 60.7 ± 13.4 | 42.1 ± 0.9 | 43.0 ± 0.1 | 43.0 ± 0.3 |
| Drug remaining on stent (%) | 58.0 ± 0.1 | 57.0 ± 0.1 | 59.8 ± 0.1 | 30.5 ± 0.0 | 29.8 ± 0.0 | 32.7 ± 1.5 |
| Total mass balance (%) | 99.3 ± 1.1 | 96.3 ± 5.2 | 94.4 ± 8.0 | 92.4 ± 10.6 | 95.8 ± 5.6 | 93.5 ± 3.1 |

| | 1 year storage | | |
|---|---|---|---|
| | Coating type | | |
| | Crystalline (n = 2) | | |
| | Storage temperature | | |
| | 37° C. | 4-8° C. | −20° C. |
| Drug load (μg) | 102 | 97 | 106 |
| Drug released (μg) | 45.8 ± 1.1 | 53.5 ± 6.8 | 52.6 ± 6.5 |
| Drug released (%) | 44.9 ± 0.0 | 55.1 ± 0.1 | 49.8 ± 0.1 |
| Drug remaining on stent (μg) | 64.4 ± 6.8 | 59.4 ± 2.5 | 59.3 ± 0.9 |
| Drug remaining on stent (%) | 63.2 ± 0.1 | 44.9 ± 0.0 | 56.2 ± 0.0 |
| Total mass balance (%) | 97.8 ± 3.1 | 100.0 ± 0.0 | 98.8 ± 1.7 |

TABLE 12

Effect of stent storage duration and temperature on proportions of degraded and undegraded rapamycin in stents with crystalline or amorphous rapamycin

1 month storage

| | Coating type | | | | | |
|---|---|---|---|---|---|---|
| | Crystalline (n = 2) | | | Amorphous (n = 1) | | |
| | Storage temperature | | | | | |
| | 37° C. | 4-8° C. | −20° C. | 37° C. | 4-8° C. | −20° C. |
| Drug load (μg) | 81 | 116 | 95 | 137 | N.D. | 142 |
| Degraded drug (μg) | 0 | 0 | 0 | 49.4 | N.D. | 34.8 |
| Degraded drug (%) | 0 | 0 | 0 | 36.0 | N.D. | 24.5 |

1 year storage

| | Coating type Crystalline (n = 2) Storage temperature | | |
|---|---|---|---|
| | 37° C. | 4-8° C. | −20° C. |
| Drug load (μg) | 126 | 123 | 126 |
| Degraded drug (μg) | 0.43 ± 0.00 | 0.42 ± 0.01 | 0.42 ± 0.01 |
| Degraded drug (%) | 2.76 ± 0.00 | 2.46 ± 1.74 | 2.33 ± 1.67 |

N.D. = not determined

Example 23

Effect of Co-Crystallized Compound on Crystalline Coatings

It was hypothesized that a less crystalline rapamycin coating may provide faster release in physiological medium. To test the hypothesis, two approaches were taken: a) co-crystallization of rapamycin with a foreign molecule which may result in a less crystalline coating, and b) spray coating amorphous rapamycin onto or under the crystalline layer.

For the first approach, a rapamycin derivative (tacrolimus (TR)) or other drug with a similar chemical structure to rapamycin (paclitaxel (PT), cyclosporine A (CS)) was added to the rapamycin crystallization solution at a concentration of 1%, 5% or 10% (w/w relative to amount of rapamycin), and crystallization was effected for 5 minutes, with other procedures, including seeding, time periods and solute/solution ratio, being as described in Examples 2 and 3. The weight of the crystalline coating was then determined by microanalytical balance.

As shown in Table 13 below, 1%, 5% and 10% paclitaxel and cyclosporine A reduced the degree of rapamycin crystallization in a concentration-dependent manner.

TABLE 13

Crystallization upon incubating a stent seeded with 15-17 μg rapamycin in a crystallization mixture for 5 minutes at 25° C.

| Crystallization mixture | Total drug load (μg) |
|---|---|
| Rapamycin:Paclitaxel (99:1) | 56 |
| Rapamycin:Paclitaxel (95:5) | 36 |

TABLE 13-continued

Crystallization upon incubating a stent seeded with 15-17 μg rapamycin in a crystallization mixture for 5 minutes at 25° C.

| Crystallization mixture | Total drug load (μg) |
|---|---|
| Rapamycin:Paclitaxel (90:10) | 24 |
| Rapamycin:cyclosporine A (99:1) | 82 |
| Rapamycin:cyclosporine A (95:5) | 43 |
| Rapamycin:cyclosporine A (90:10) | 32 |

As shown in FIGS. 48-54C, 1%, 5% and 10% paclitaxel and cyclosporin A reduced the integrity of the crystalline rapamycin layer, increased the degree of crystal aggregation, and altered the crystal morphology in a concentration-dependent manner.

These results indicate that the drug load, crystal morphology, and degree of coverage of a surface by a crystalline drug layer can be controlled by doping the primary drug with a small amount of another compound, which may optionally also be a drug.

Example 24

Effect of Co-Crystallized Compound on Degree of Crystallinity

Stents coated with crystalline rapamycin, alone or with a co-crystallized drug as described in Example 23, were analyzed in order to evaluate morphology and the degree of crystallinity using x-ray analysis, as described in the Materials and Methods section.

All coatings formed by co-crystallization exhibited changes in crystal morphology and/or packing, even when the concentration of co-crystallized agent was as low as 1%.

Example 25

Effect of Co-Crystallized Compound on Drug Release Profile

Stents coated with crystalline rapamycin, alone or with a co-crystallized drug as described in Example 23, were incubated in solution in vitro, in order to evaluate the effect of co-crystallization on the release profile. In order to obtain approximately 100 μg rapamycin per stent, stents undergoing co-crystallization were incubated in the crystallization mixture for 15 minutes instead of 5 minutes.

Coatings were prepared by co-crystallization of the following crystallization mixtures: (1) rapamycin doped with 5% paclitaxel, (2) rapamycin doped with 5% cyclosporine A, and (3) rapamycin doped with 1% tacrolimus.

Various types of pure rapamycin coatings were prepared as follows: (4) a bilayer having a crystalline layer of about 100 μg rapamycin coated with an amorphous layer of about 50 μg rapamycin (prepared by spray coating of 1% rapamycin in ethyl acetate), (5) a crystalline layer of about 100 μg rapamycin, and (6) an amorphous coating of about 100 μg rapamycin as a control.

As shown in FIGS. 55A and 55B, doping crystalline rapamycin with tacrolimus (1%) or paclitaxel (5%) increased the rate of drug release over the course of 28 days, whereas doping crystalline rapamycin with cyclosporine A (5%) reduced the rate of drug release.

As shown in FIGS. 55A and 55C, a crystalline rapamycin layer coated by an amorphous rapamycin layer exhibited a drug release profile characterized by a burst release phase followed by a slow release phase, wherein about 60% of the total drug load was released over the course of 28 days, in comparison with 18% for a crystalline layer alone, and 90% for an amorphous layer alone.

Coatings with different ratios between the amorphous layer and crystalline layer (50:50, 67:33 and 33:67) were also prepared and showed different release profiles.

As exemplified hereinabove, co-crystallization with a foreign molecule had a large impact on morphology and crystal architecture, but the changes in release profile were modest.

As shown in FIGS. 56A-56C, incubation of stents in PBS with 0.1% TWEEN 20 enhanced the difference between the release profiles of the different coatings by accelerating the release profile. In particular, crystalline rapamycin coating doped with 1% tacrolimus enhanced release to the greatest degree, in comparison with pure crystalline rapamycin coatings.

Example 26

Crystalline Tacrolimus Coating

A crystalline tacrolimus coating was prepared using the same procedures described in Examples 2 and 3 for rapamycin. The drug load for tacrolimus obtained using different crystallization times are presented in Table 14 below.

TABLE 13

Effect of crystallization time on tacrolimus drug load

| Process description | Total drug load per stent (μg) |
|---|---|
| Seeding only (10 minutes sonication, 30° C.) | 12 |
| Crystallization for 5 minutes (25° C.) | 23 |
| Crystallization for 10 minutes (25° C.) | 45 |
| Crystallization for 15 minutes (25° C.) | 70 |
| Crystallization for 20 minutes (25° C.) | 100 |

The crystalline nature of the tacrolimus coating was confirmed by scanning electron microscopy and XRD analysis.

The release profile of the crystalline tacrolimus-coated stents was determined as described hereinabove, and compared to the release profiles of stents with amorphous tacrolimus coatings prepared by spray coating. The crystalline tacrolimus coatings exhibited slow drug release, whereas the amorphous tacrolimus coatings exhibited rapid drug release (data not shown).

These results indicate that the properties of crystalline drug coatings in comparison to amorphous drug coatings, as described herein for rapamycin, are also exhibited by corresponding coatings of drugs other than rapamycin.

Example 27

Crystalline Paclitaxel Coating

A crystalline paclitaxel coating was prepared in the same manner used to prepare a crystalline rapamycin coating.

In preliminary studies, a non-continuous seeding layer was formed with large crystals of 0.5-2.5 μm in size, as shown in FIGS. 57A-57C. The seeded stents incubated for a prolonged time in order to examine various stages of paclitaxel crystal development by high resolution SEM.

As shown in FIGS. 58A-58C, crystals about 3.5 μm long and about 0.3 μm wide were formed upon crystallization for 5 minutes, crystals about 13 μm long and about 2 μm wide were formed upon crystallization for 60 minutes, and crystals about 25 μm long and about 3 μm wide were formed upon crystallization for 60 minutes, and the crystals formed a full, continuous carpet.

As shown in FIGS. 59A and 59B, extended crystallization time yielded multiple crystalline layers or clusters of crystals, which were strongly attached to the metallic surface.

Example 28

Controlled Crystalline Paclitaxel Coating Formation

In order to enhance control over the paclitaxel crystallization process, paclitaxel was ground to obtain paclitaxel crystal seeds 200-400 nm in size, which were suspended in anti-solvent. The crystals for used for seeding according to procedures described in Examples 2 and 3 herein, and upon subjecting the seeded surface to crystallization, resulted in a homogenous and continuous coating.

As shown in FIGS. 60A-64F, a homogenous and continuous crystalline coating with a paclitaxel drug load of about 100 μg was obtained upon crystallization for 15 minutes in a solution of ethyl acetate/hexane at a 7:65 v/v ratio (instead of 3:65 as used for rapamycin) (FIGS. 63A-63F). Crystallization times of 5 or 10 minutes yielded less coverage of the surface by the crystalline layer (FIGS. 60A-62D), whereas after 20 minutes of crystallization, bulky "star" or "snow ball" formations began to appear on the surface.

The effect of crystallization time on paclitaxel drug load is shown in Table 14 below.

TABLE 14

Effect of crystallization time on paclitaxel drug load

| Process description | Total drug load per stent (μg) |
|---|---|
| Seeding only (10 minutes sonication, 30° C.) | 26 |
| Crystallization for 5 minutes (25° C.) | 60 |
| Crystallization for 10 minutes (25° C.) | 79 |
| Crystallization for 15 minutes (25° C.) | 129 |
| Crystallization for 20 minutes (25° C.) | 135 |

Example 29

Controlled Crystalline Paclitaxel Coating Release Profile

The in vitro release of paclitaxel from coatings with about 100 μg in crystalline or amorphous form was determined over the course of 4 weeks in 2 ml medium according to procedures described hereinabove for rapamycin, with paclitaxel concentrations being determined by HPLC using a wavelength of 227 nm.

Crystalline stent coatings were prepared as described in Example 28 and amorphous stent coatings were prepared by spray coating using a Sono-Tek spray coating system with the following parameters: generator power 1.2 W, 1% paclitaxel solution in ethyl acetate, flow rate 0.2 ml/minute and 30 second coating process. Using the aforementioned procedures, 4 stents with a crystalline coating were prepared, having respective drug loads of 109, 112, 105 and 105 μg; and 4 stents with an amorphous coating were prepared, having respective drug loads of 95, 97, 121 and 110 μg. Representative images of the crystalline paclitaxel coatings are shown in FIGS. 65A-65F, and representative images of the amorphous paclitaxel coatings are shown in FIGS. 66A-66F. The crystallinity of the crystalline coatings was confirmed by x-ray analysis.

As shown in FIGS. 67A and 67B, crystalline paclitaxel coatings released paclitaxel more slowly than amorphous paclitaxel coatings in PBS, although release for both coatings was very slow.

The assay was repeated using PBS with 0.1% w/v TWEEN 20 in order to facilitate solubilization of paclitaxel.

As shown in FIG. 67B, the differences in release profiles of crystalline and amorphous coatings in PBS with TWEEN 20 was more pronounced than in PBS alone (similarly to results with rapamycin), with 52 µg paclitaxel being released after 28 days from the amorphous coating, as opposed to 10 µg paclitaxel being released after 28 days from the crystalline coating.

These results further indicate that the properties of crystalline drug coatings in comparison to amorphous drug coatings, as described herein for rapamycin and tacrolimus, are also exhibited by corresponding coatings of drugs other than rapamycin and tacrolimus.

Example 30

Expedited Drug Release Simulation

Rapamycin elution from crystalline rapamycin coating prepared as described in Examples 2 and 3 was studied using a sensitive and robust method for determination of the elution of rapamycin from drug-eluting coronary stents. The closed loop configuration of the elution apparatus and the small volume of eluent allow the low drug levels that elute from a single stent to be reproducibly monitored. The in vitro elution profile obtained over 24 hours mirrors the 30-day in vivo porcine profile, providing an in vitro release method that captures the entire in vivo release profile of the stent in a shorter time. Besides that, this method discriminates between common manufacturing and formulation product defects. The reported method employs an elution medium containing an organic solvent, which allowed the in vitro elution curve to be fit to the in vivo porcine profile. The method has been accepted by the U.S. FDA as a release method for evaluating elution of rapamycin from cardiovascular stents. The elution medium was prepared using 2% ultra-pure sodium dodecyl sulfate (SDS) in high-purity water with 10% gradient-grade acetonitrile (ACN), and buffered to pH 4.5 with phosphate. The mobile phase was a mixture of 55:45:0.02 (v/v) water/tetrahydrofuran(THF)/formic acid. Six stents (n=6) with crystalline coating were used for this study.

As shown in FIG. 68, rapamycin was eluted throughout the 24 hour period of study (24 hours), indicating controlled rapamycin release in an equivalent of an in vivo porcine model.

Example 31

Bioactive Top Coats

In order to combine rapid and slow drug release in a relatively simple coating, rapamycin and/or paclitaxel were incorporated into hyaluronic acid (HA) solution used to prepare a top coat, by mixing HA solution (in DDW) with a rapamycin and/or paclitaxel solution in methanol, and spray coating a bare stent with a crystalline drug coating. The top coat is intended to provide a burst release of the drug, which may be followed by slow release from an underlying crystalline coating.

The aqueous HA solution and methanol drug solution were mixed in a 1:1 ratio. Other alcoholic solvents were also tested and were found to be effective for coating preparation. A drug concentration of 10 mg/ml in methanol was found to be suitable, and to this solution, an aqueous solution of 0.3% hyaluronic acid (+glycerol 10% w/w) was added at a 1:1 ratio, and mixed vigorously for 1 hour. The spray coating process was according to the procedures described in Examples 14 and 15, briefly, using the parameters: generator power 10 watts, sprayed volume 0.1 ml, flow 0.2 ml/minute, semi-automatic rotation 60 rpm, with drying being reduced to 20 minutes in an active hood. Multilayer top coats were prepared by performed 2, 3 or 4 cycles of spray coating. In some samples, 0.3 ml was sprayed in a continuous manner. Coatings with rapamycin or paclitaxel were each prepared in duplicate. Drug loads were determined by microanalytical balance and validated by HPLC for representative stents, and are summarized in Tables 15 and 16 below.

TABLE 15 exemplary spray coated top coats with hyaluronic acid and rapamycin

| Stent No. | Top coat type | Total top coat weight per 15 mm stent (µg) (50% rapamycin, 50% hyaluronic acid) |
|---|---|---|
| 1 | 1 layer | 67 |
| 2 | 1 layer | 60 |
| 3 | 2 layers | 127 |
| 4 | 2 layers | 132 |
| 5 | 3 layers | 165 |
| 6 | 3 layers | 157 |
| 7 | 4 layers | 258 |
| 8 | 4 layers | 230 |
| 9 | Continuous spray coating of 300 µl | 180 |
| 10 | Continuous spray coating of 300 µl | 150 |

TABLE 16 exemplary spray coated top coats with hyaluronic acid and paclitaxel

| Stent No. | Top coat type | Total top coat weight per 15 mm stent (µg) (50% paclitaxel, 50% hyaluronic acid) |
|---|---|---|
| 1 | 1 layer | 50 |
| 2 | 1 layer | 58 |
| 3 | 2 layers | 120 |
| 4 | 2 layers | 140 |
| 5 | 3 layers | 153 |
| 6 | 3 layers | 168 |
| 7 | 4 layers | 255 |
| 8 | 4 layers | 307 |
| 9 | Continuous spray coating of 300 µl | 221 |
| 10 | Continuous spray coating of 300 µl | 198 |

As shown in Tables 15 and 16, the top coat weight (and amount of drug and hyaluronic acid in the top coat) was proportional to the volume of sprayed solution, for both multilayer top coats and top coats formed by one continuous spray coating process, and for both HA-rapamycin and HA-paclitaxel mixtures.

These results indicate that an amorphous can be included in controlled amounts in top coats described herein.

Example 32

Rapamycin Release from Top Coats

Coatings based on hyaluronic acid with rapamycin were prepared on bare stents as described in Example 31, and in Table 15 in particular. Immediately following coating preparation, an in vitro study in PBS was conducted.

As shown in FIGS. 69A-69C, the cumulative amount of rapamycin released from hyaluronic acid-based top coats was correlated with the number of coating cycles and drug load. As further shown therein, gradual rapamycin release continued for the duration of the study period (28 days), wherein 60-90% (25-75 μg) of the drug in the top coats was released in the first 72 hours. The percentage of drug released in the first 72 hours was inversely correlated to the number of coatings cycles and drug load.

The use of hyaluronic acid with 20% glycerol instead of 10% glycerol did not significantly affect the drug release profiles.

These results indicate that the relative degrees of slow release and burst release from top coats can be controlled by modulating the drug load in the top coat and the mass of the top coat, wherein thinner top coats have a relatively large burst release, whereas thicker top coats have a relatively lower burst release.

Example 33

Paclitaxel Release from Top Coats

Coatings based on hyaluronic acid with paclitaxel were prepared on bare stents as described in Example 31, and in Table 16 in particular. Immediately following coating preparation, an in vitro study in PBS was conducted.

As shown in FIGS. 70A-70C, the cumulative amount of paclitaxel released from hyaluronic acid-based top coats was correlated with the number of coating cycles and drug load. As further shown therein, gradual paclitaxel release continued for the duration of the study period (28 days), wherein 20-85% (35-55 μg) of the drug in the top coats was released in the first 72 hours. The percentage of drug released in the first 72 hours was inversely correlated to the number of coatings cycles and drug load. The use of hyaluronic acid with 20% glycerol instead of 10% glycerol did not significantly affect the drug release profiles.

These results further indicate that the relative degrees of slow release and burst release from top coats can be controlled by modulating the drug load in the top coat and the mass of the top coat, as described hereinabove.

Example 34

Control of Drug Release Profile Using Multilayer Coatings with Drug Incorporated in Top Coat Rapamycin or another drug was incorporated into a hyaluronic acid-based top coat applied by spray coating, as exemplified in Examples 32 and 33, in order to combine rapid and slow drug release, as described in Example 31. The procedures described in Examples 32 and 33 were applied to stents with a crystalline drug layer, in order to obtain a burst release from the top coat followed by slow release from the crystalline layer.

The types of coating applied to stents are summarized in Table 17 below. As shown in FIGS. 71A and 71B, a hyaluronic acid top coat without incorporated rapamycin did not affect the drug release profile, whereas a hyaluronic acid top coat with incorporated rapamycin exhibited a burst release which was more rapid than the burst release exhibited by amorphous rapamycin, followed by slow release associated with the underlying crystalline layer. As further shown therein, the combination of an amorphous rapamycin layer and crystalline rapamycin layer resulted in a release profile characterized by a combination of rapid and slow drug release.

The use of hyaluronic acid with 20% glycerol instead of 10% glycerol did not significantly affect the drug release profiles.

TABLE 17 exemplary stents with rapamycin in lower layer and/or in top coat

| Stent No. | Lower coating type | Top coat type | Rapamycin in top coat (μg) | Hyaluronic acid in top coat (μg) | Total rapamycin drug load (μg) |
|---|---|---|---|---|---|
| 1 | Crystalline rapamycin (173 μg) | None | N.A. | N.A. | 173 |
| 2 | Crystalline rapamycin (144 μg) | None | N.A. | N.A. | 144 |
| 3 | Crystalline rapamycin (166 μg) + hyaluronic acid (100 μg) | None | N.A. | N.A. | 166 |
| 4 | Crystalline rapamycin (155 μg) + hyaluronic acid (80 μg) | None | N.A. | N.A. | 155 |
| 5 | Crystalline rapamycin (138 μg) | 50% hyaluronic acid, 50% rapamycin (2 layers) | 69 | 69 | 207 |
| 6 | Crystalline rapamycin (109 μg) | 50% hyaluronic acid, 50% rapamycin (2 layers) | 54.5 | 54.5 | 163.5 |
| 7 | Crystalline rapamycin (114 μg) + hyaluronic acid (101 μg) | 50% hyaluronic acid, 50% rapamycin (2 layers) | 59.5 | 59.5 | 173.5 |
| 8 | Crystalline rapamycin (153 μg) + hyaluronic acid (95 μg) | 50% hyaluronic acid, 50% rapamycin (2 layers) | 53 | 53 | 206 |
| 9 | Crystalline rapamycin (180 μg) | Amorphous rapamycin | 108 | 0 | 288 |
| 10 | Crystalline rapamycin (188 μg) | Amorphous rapamycin | 69 | 0 | 257 |
| 11 | Amorphous rapamycin (117 μg) | None | N.A. | N.A. | 117 |
| 12 | Amorphous rapamycin (242 μg) | None | N.A. | N.A. | 242 |

N.A. = not applicable

Example 35

Enhanced of Adhesion of Drug Crystals to Modified Metal Surface

In order to improve adhesion of crystalline coating, a chemical adhering layer was applied.

As shown in FIG. 72, rapamycin was chemically bound to a metal strut by using an aryl diazonium salt with conjugated rapamycin in an electrocoating procedure, so as to obtain a uniform base layer covering the stents, wherein the layer contains rapamycin. Stents with this base layer were subjected to crystallization according to procedures described in Examples 2 and 3. A homogeneous and continuous crystalline coating resulted with improved adhesion proprieties, as determined by mechanical tests with no substantial change in the release profiles as compared to crystalline coatings described hereinabove.

As an alternative, nucleating agents other than rapamycin can be conjugated to the aryl diazonium.

Example 36

Enhanced of Adhesion of Drug Crystals Via Thiol-Gold Complexation

As depicted in FIG. 73A, stainless steel 304 or 316L or CoCr stents were furnished by vapor coating of a chromium layer with nanometric thickness, followed by vapor coating of a gold layer with nanometric thickness. Fixation of gold layer was enhanced by the chromium layer.

As shown in FIG. 73B, rapamycin was chemically conjugated to a thiol spacer molecule via rapamycin's hydroxyl, ether, ester, ketone, or amine group(s). A thiol spacer may optionally comprise a primary halocarbon (SH—R—X, wherein X=Cl, Br or I) wherein the halogen acts as leaving group during a nucleophilic reaction with a rapamycin hydroxyl groups, so as to result in an ether bond between the thiol spacer and rapamycin. The gold-coated stents are dipped at room temperature in a solution of the rapamycin-conjugated thiol spacer at low concentration, resulting in thiol-gold binding which forms a base layer on stent strut surfaces.

As shown in FIG. 73C, the conjugated rapamycin in the base layer serves as nucleating sites for rapamycin, upon subjecting the surface to crystallization according to procedures described in Examples 2 and 3. A homogeneous and continuous crystalline coating is obtained with improved adhesion proprieties, with no substantial change in the release profiles as compared to crystalline coatings described hereinabove.

Stents strut surfaces with different characteristics, including increased or reduced hydrophobicity or hydrophilicity are also prepared and tested. The thiol spacer is found to have direct effect on the final crystalline layer and its uniformity and to control aspects of crystal morphology and therapeutic drug loading density per targeted area of the surface.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A process of depositing at least a first layer of a first therapeutically active agent onto at least a continuous portion of a surface of an object, wherein at least 50 weight percents of said first layer is said first therapeutically active agent in a crystalline form, the process comprising:
    seeding said surface of said object with crystals of said first therapeutically active agent, so as to obtain a seeded surface comprising said crystals; and
    contacting said seeded surface with a solution containing said first therapeutically active agent for at least 5 minutes, so as to effect precipitation of said first therapeutically active agent onto said seeded surface in a crystalline form, thereby forming said crystalline form of said first therapeutically active agent deposited on at least said portion of said surface,
    wherein said surface is not cooled to a temperature below a temperature of said solution.

2. The process of claim 1, further comprising depositing at least one additional layer comprising a second therapeutically active agent onto said surface, wherein said second therapeutically active agent is said first therapeutically active agent in an amorphous form and/or in a different crystalline form than in said first layer, or said second therapeutically active agent is a different therapeutically active agent than said first therapeutically active agent.

3. The process of claim 1, wherein said seeding comprises contacting said surface with a dispersion of said crystals of said first therapeutically active agent.

4. The process of claim 1, wherein said seeded surface comprises said crystals at a density in a range of from 0.03 $\mu g/mm^2$ to 3 $\mu g/mm^2$.

5. The process of claim 1, wherein a concentration of said first therapeutically active agent in said solution contacted with said seeded surface is no more than 1 mg/ml.

6. The process of claim 1, further comprising applying a top coat onto said surface having said first layer deposited thereon.

7. The process of claim 1, wherein when said object further comprises a base layer applied onto at least a portion of said surface, and at least one nucleating agent conjugated to said base layer, the process further comprises, prior to seeding said surface, applying said base layer and said nucleating agent conjugated to said base layer onto said surface.

8. A process of depositing a first layer of a first therapeutically active agent onto at least a continuous portion of a surface of an object, wherein at least 50 weight percents of said first layer is said first therapeutically active agent in a crystalline form, the process comprising:
    seeding said surface of said object with crystals of said first therapeutically active agent, so as to obtain a seeded surface comprising said crystals;
    contacting said seeded surface with a solution containing said first therapeutically active agent for at least 5 minutes, so as to effect precipitation of said first therapeutically active agent onto said seeded surface in a crystalline form, thereby forming said crystalline form of said first therapeutically active agent deposited on at least said portion of said surface; and applying a top coat comprising hyaluronic acid onto said surface having said first therapeutically active agent deposited thereon.

* * * * *